US008815891B2

(12) United States Patent
Kim et al.

(10) Patent No.: US 8,815,891 B2
(45) Date of Patent: Aug. 26, 2014

(54) TRICYCLIC DERIVATIVE OR PHARMACEUTICALLY ACCEPTABLE SALTS THEREOF, PREPARATION METHOD THEREOF, AND PHARMACEUTICAL COMPOSITION CONTAINING THE SAME

(75) Inventors: Myung-Hwa Kim, Yongin-si (KR); Seung-Hyun Kim, Seoul (KR); Sae-Kwang Ku, Daegu (KR); Chun-Ho Park, Yongin-si (KR); Bo-Young Joe, Yongin-si (KR); Kwang-Woo Chun, Yongin-si (KR); In-Hae Ye, Yongin-si (KR); Jong-Hee Choi, Yongin-si (KR); Dong-Kyu Ryu, Yongin-si (KR); Ji-Seon Park, Yongin-si (KR); Han-Chang Lee, Yongin-si (KR); Ji-So Choi, Seoul (KR); Young-Chul Kim, Seongnam-si (KR)

(73) Assignee: Je Il Pharmaceutical Co., Ltd., Seoul (KR)

( * ) Notice: Subject to any disclaimer, the term of this patent is extended or adjusted under 35 U.S.C. 154(b) by 444 days.

(21) Appl. No.: 13/128,030

(22) PCT Filed: Nov. 11, 2009

(86) PCT No.: PCT/KR2009/006618
§ 371 (c)(1),
(2), (4) Date: May 6, 2011

(87) PCT Pub. No.: WO2010/056038
PCT Pub. Date: May 20, 2010

(65) Prior Publication Data
US 2011/0218193 A1   Sep. 8, 2011

(30) Foreign Application Priority Data
Nov. 11, 2008 (KR) ........................ 10-2008-0111808

(51) Int. Cl.
*C07D 471/06* (2006.01)
*A61K 31/4375* (2006.01)

(52) U.S. Cl.
USPC ............................................ 514/291; 546/81

(58) Field of Classification Search
USPC ........................................... 546/81; 514/291
See application file for complete search history.

(56) References Cited

U.S. PATENT DOCUMENTS

| 5,391,554 A | 2/1995 | Showalter |
| 2003/0105102 A1 | 6/2003 | Li et al. |
| 2005/0171101 A1 | 8/2005 | Yamamoto et al. |

FOREIGN PATENT DOCUMENTS

| EP | 1225173 | 7/2002 |
| JP | 2000-239273 | 9/2000 |
| WO | WO2005123687 | 12/2002 |
| WO | 2008/028168 A2 | 3/2008 |
| WO | WO2009/061131 A2 | 5/2009 |

OTHER PUBLICATIONS

Raffaella Ferraccioli et al, Synthesis of 6-Phenanthridinones and Their Heterocyclic Analogues through Palladium-Catalyzed Sequential Aryl-Aryl and N-Aryl Coupling , Oct. 2004.*
"Genentech raises stakes on PARP inhibitors," Nature Biotechnology, Oct. 2006, vol. 24, No. 10, pp. 1179-1180.
Fredric J. Vinick, et al., "A Simple Bis-Annelation Route to 3,4,5,6-Tetrahydropyrido[3,2-c]Quinolin-2-Ones", Tetrahedron Letters, 1989, vol. 30, No. 7, pp. 787-788.
Dana Ferraris, et al., "Design and Synthesis of Poly ADP-ribose Polymerase-1 Inhibitors, 2. Biological Evaluation of Aza-5[H]-phenanthridin-6-ones as Potent, Aqueous-Soluble Compounds for the Treatment of Ischemic Injuries", Journal of Medicina Chemistry, 2003, vol. 46, No. 14, pp. 3138-3151.
H. D. Hollis Showalter, "Ready Access to 7,8-Dihydro- and 1,2,3,4-Tetrahydro-1,6-Naphlhyridine-5(6H)-ones from Simple Pyridine Precursors", J. Heterocyclic Chem., 2006, vol. 43, pp. 1311-1317.

* cited by examiner

*Primary Examiner* — Rita Desai
(74) *Attorney, Agent, or Firm* — Lucas & Mercanti, LLP

(57) ABSTRACT

The present invention relates to a novel tricyclic derivative with efficient inhibitory activity against poly(ADP-ribose) polymerases (PARP) or pharmaceutically acceptable salts thereof, a preparation method thereof, and a pharmaceutical composition containing the same. The tricyclic derivative of the invention is useful for the prevention or treatment of diseases caused by excess PARP activity, especially neuropathic pain, neurodegenerative diseases, cardiovascular diseases, diabetic nephropathy, inflammatory diseases, osteoporosis, and cancer, by inhibiting the activity of poly(ADP-ribose)polymerases.

11 Claims, 2 Drawing Sheets

TRICYCLIC DERIVATIVE OR PHARMACEUTICALLY ACCEPTABLE SALTS THEREOF, PREPARATION METHOD THEREOF, AND PHARMACEUTICAL COMPOSITION CONTAINING THE SAME

CROSS-REFERENCE TO RELATED APPLICATIONS

This application is a 371 of PCT/KR2009/006618 filed on Nov. 11, 2009, which claims the benefit of Korean Patent Application No. 10-2008-0111808 filed Nov. 11, 2008, the contents of each of which are incorporated herein by reference.

TECHNICAL FIELD

The present invention relates to novel tricyclic derivative having superior Poly(ADP-ribose)polymerase inhibitory activity, or pharmaceutically acceptable salts thereof, a preparation method thereof, and a pharmaceutical composition containing the same.

BACKGROUND ART

Poly(ADP-ribose)polymerase (PARP) which is enzyme in the cell's nucleus, is found in most of eukaryotic cells, and catalyzes the transfer of ADP-ribose unit to nuclear receptor protein using nicotinamide adenine dinucleotide ($NAD^+$) as a substrate, and induces formation of homo-ADP-ribose polymer branched from protein-bound linear. PARP consists of 7 isozymes comprising PARP-1, PARP-2, PARP-3, PARP-4 (Vault-PARP), tankylase such as PARP-5 (TANK-I, TANK-2 and TANK-3), PARP-7, and PARP-10 [de la Lastra C A., et al., Curr Pharm Des., 13(9), 933~962, 2007]. Among the above, nucleus enzyme Poly(ADP-ribose)polymerase-1 (PARP-1) is the main enzyme, and occupies 97% of the Poly(ADP-ribose)polymerase made in the brain [Strosznajder R. P., et al. Mol Neurobiol., 31, (1-3), 149~167, 2005]. Among many functions of PARP, in particular PARP-1, the major function is to facilitate DNA repair by ADP-ribosylation and to regulate the number of DNA-repair proteins. The PARP activation in cells with huge scale of DNA damage results in significant decrease of $NDA^+$ concentration and considerable deficiency. PARP-1 is 116 kDa nucleoprotein that includes three domains which comprise a N-terminal DNA binding domain containing two zinc fingers, an automatic modification domain, and a C-terminal catalytic domain. The Poly(ADP-ribose)polymerase enzyme synthesizes poly(ADP-ribose) which is a polymer with branched structure may be consisted of 200 of more units of ADP-ribose. The poly(ADP-ribose) protein receptor may be included directly or indirectly maintaining DNA integrity. These include histone, topoisomerase, DNA and RNA polymerase, DNA ligase, and $Ca^{2+}$ and $Mg^{2+}$-dependent endonuclease. PARP proteins are expressed in many tissues, in particularly high concentration in immune system, heart, brain and microorganism cell strains. Although the PARP proteins have minimum PARP activity does exist under general biological conditions, the PARP activity increases up to 500 times greater when DNA is damaged.

PARP activation and formation of poly(ADP-ribose) reaction products are caused by the DNA decay after exposure of chemotherapy, ionizing radiation, oxygen free radical, or nitric oxidant (NO). In DNA damage induced by radiotherapy or chemotherapy, the transmission process of ADP-ribose of the cells may contribute to resistance that can occur in various types during cancer treatment since it is related to the repair of the damaged DNA. Therefore, PARP inhibition can deter repair of DNA damage in the cells and can enhance the anti-cancer effect of the cancer therapy. Furthermore, recently it has been reported that the tankyrase, which binds to telomere protein TRF-1, the negative control factor of the telomere length, has the catalytic domain with a significant homogeny with the PARP, and has in vitro PARP activity. In addition, it has been suggested that function of the telomere in human cells is adjusted by the poly(ADP-ribosyl)ation. The PARP inhibitor is useful as a means of study of function to regulate the length of the telomere in the adjustment of telomere activity by tankyrase [B A., et al., Int J Biochem Cell Biol., 37, 1043~1053, 2005]. For example, PARP inhibitor can be used for cancer treatment by shortening life cycle of immortalized cancer cells, or utilized as a cell life cycle regulator or an anti-aging medicine in view of the relationship between the length of the telomere and cell aging.

It has also been reported that the PARP inhibition can enhance the resistance in brain injury. Ischemic brain injury is generated by poly(ADP-ribose)polymerase activity-mediated exhaustion of $NAD^+$ and resulting in energy deficiency [Endres M., et al., J. Cereb Blood Flow Metab., 17(11), 1143~1151, 1997]. Regarding cerebral ischemia, activation of PARP according to DNA damage acts on apoptosis induced to seizure, brain damage and neurodegerative diseases. The apoptosis is considered to be generated as a result of energy decreases corresponding to $NAD^+$ consumption due to PARP reaction catalyzed by enzymes, and DNA damage occurs due to an excessive amount of nitric oxidant generated as the nitric oxidant synthetase is activated by the products initiated by the glutamic acid released from the depolarized nerve endings. Lack of oxygen in neurons causes stroke or ischemic brain damage, and then the neuron releases a large amount of glutamate. The excessive amount of glutamate causes hyperstimulation (exitotoxicity) of N-methyl-D-aspartate (NMDA), alpha-amino-3-hydroxy-5-methyl-4-isoxazole propionic acid (AMPA), kainite, and metabotropic glutamate receptor (MGR), which opens ion channel and thus allows unregulated ion flow (e.g., permitting $Ca^{2+}$ and $Na^+$ into cells, causing $K^+$ to release out of the cell), causing hyperstimulation of neurons. Hyperstimulated neurons causes more release of glutamate, generating feedback loop or domino effect and eventually causing cell damage or death through the generation of protease, lipase, and free radical. The over-activation of the glutamate receptors is related to a variety of neuropathic diseases including epilepsy, stroke, Alzheimer's disease, Parkinson's disease, amyotrophic lateral sclerosis (ALS), Huntington's disease, schizophrenia, chronic pain, ischemia, neuron damage after hypoxia, external injury, and neural damage.

The PARP inhibitor can be used for treatment of not only central nervous system disorders, but also disorders of peripheral nervous system such as neuropathic pain caused due to chronic constriction injury (CCI) of common sciatic nerve [Di Cesare Mannelli L., et al., Eur J Neurosci., 26(4), 820~827, 2007]. The exact mechanism for the potential of the PARP inhibitor in treatment for the neuropathic pain has not been explained fully yet, but considered positively.

The PARP inhibitor also acts on the treatment of inflammatory symptoms such as arthritis [Szab C., et al., Proc. Natl. Acid. Sci. USA 95(7), 3867~3872, 1998]. Poly(ADP-ribose) synthesis is included for induced expression of many genes which are essential for the inflammatory reactions. The PARP inhibitor inhibits formation of macrophagocyte, inducible nitric oxidant sythease (iNOS) from P-type selectin, and inter-cellular adhesion molecule-1 (ICAM-1) on endothelial cells. The above activity is a basis for the strong anti-inflammatory effect by the PARP inhibitor. Furthermore, the PARP inhibition can reduce necrosis by preventing translocation and infiltration of neutrophils into damaged tissues. Accordingly, the PARP inhibitor is useful for treatment of inflammatory symptoms.

The PARP inhibition is useful for protecting myocardinal ischemia [Szab C., Curr Vasc Pharmacol., 3(3), 301~303, 2005] and reperfusion injury [Zingarelli B., Cardiovascular Research, 36, 205-215, 1997]. It is considered that the main cause of damages to the tissues is to be follow-up formation of the free radical during the reperfusion. During ischemia and reperfusion, some of typical ATP decent in many organism can be related to $NAD^+$ deficiency which is derived from poly(ADP-ribos) conversion. Accordingly, PARP inhibition is expected to preserve cellular energy level, and subsequently to increase the survival of ischemic tissue after injury. Accordingly, PARP inhibitor is useful for treatment of cardiovascular diseases.

Recently, the potential of the PARP inhibitor for treatment of diabetic neuropathy has been suggested [Obrosova I G., Diabetes. 54(12), 3435-3441, 2005].

Until today, the development of the Poly(ADP-ribose) polymerase (PARPs) has been reported in below: INO-1001 (by Inotek Pharmaceuticals) is been developing cardiovascular indications and as a treatment of malignant melanoma. AG014699 (by Pfizer) is been developing as a treatment of malignant melanoma. BS-201 and Bs-401 (by Bipar Sciences) are been developing as a treat of cancer and pancreatic cancer, respectively. Additionally, AstraZeneca has been developing AZD2281 for treatment of breast cancer, and MGI Pharma has conducted a study of sensitizer for radiotherapy and chemotherapy [News, Nature biotechnology, 24(10), 1179~1180, 2006].

However, development of the Poly(ADP-ribose)polymerase (PARPs) inhibitors in connection with neurodegenerative diseases, which has not proceeded in the research until today, is demended acutely in consideration of increasing aging population and better life quality.

Accordingly, it is imperative to develop Poly(ADP-ribose) polymerase (PARP) inhibitor which can minimize side-effects, particularly in the current situation where no noticeable treatment has been developed for the above-mentioned diseases.

The present inventors have been researched low molecular weight PARP inhibitor which can be used for treatment of various diseases derived from over-activation of the Poly (ADP-ribose)polymerase (PARP), prepared novel tricyclic derivatives, confirmed the superior PARP inhibitory activity of said composition, and thus completed the present invention.

DISCLOSURE

Technical Problem

The objective of present invention is to provide novel tricyclic derivatives with superior Poly(ADP-ribose)polymerase inhibitory activity, or pharmaceutically acceptable salts thereof, a preparation method thereof, and a pharmaceutical composition containing the same.

Technical Solution

In order to achieve the object mentioned above, the present invention provides novel tricyclic derivatives or pharmaceutically acceptable salts thereof.

In addition, the present invention provides a preparation method of the novel tricyclic derivatives.

Further, the present invention provides a pharmaceutical composition containing the novel tricyclic derivatives or pharmaceutically acceptable salts thereof, as an active ingredient, for preventing or treating diseases derived from over-activation of Poly(ADP-ribose)polymerase.

Advantageous Effects

The tricyclic derivatives according to the present invention inhibit the activity of Poly(ADP-ribose)polymerase (PARP), thereby can be useful for prevention or treatment of diseases derived from over-activation of PARP, and in particular, neuropathic pain, neurodegeneration diseases, cardiovascular diseases, diabetic neuropathy, inflammatory disease, osteoporosis, and cancer.

BRIEF DESCRIPTIONS OF DRAWINGS

BEST MODE

Figure 1:
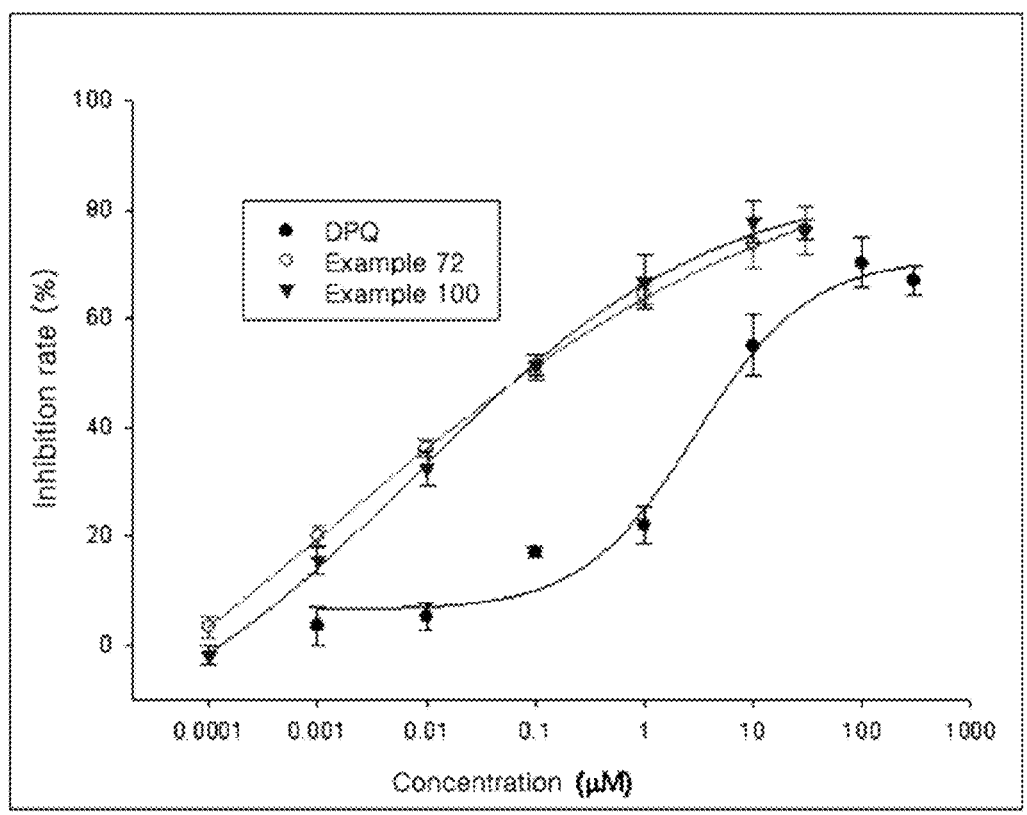
FIG. 1 is a graphical representation of the amount of NAD (P)H according to the concentration of compound of an embodiment of the present invention.

Hereinafter, the present invention will be explained in detail.

The present invention provides novel tricyclic derivatives or pharmaceutically acceptable salts thereof represented by chemical formula 1.

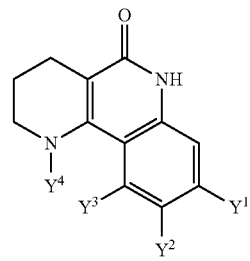

[Chemical formula 1]

wherein
$Y^1$, $Y^2$ and $Y^3$ are each independently H, $C_1$~$C_{10}$ straight or branched chain alkyl, hydroxy, $C_1$~$C_{10}$ alkoxy, —$COOR^1$, —$NR^2R^3$ or -A-B;
A is —O—, —$CH_2$—, —$CH(CH_3)$—, —CH=N— or —CONH—;
B is —$(CH_2)_{n_1}$-Z, —$(CH_2)_{n_2}$-$NR^2R^3$ or —$(CH_2)_{n_3}$-$OR^1$;
Z is $C_5$~$C_{20}$ aryl non-substituted or substituted with $R^5$ and selectively $R^6$, $C_3$~$C_{10}$ cycloalkyl non-substituted or substituted with $R^5$ and selectively $R^6$, $C_1$~$C_{20}$ heterocyclic compound non-substituted or substituted with $R^5$ and selectively $R^6$;
$R^1$ is H or $C_1$~$C_{10}$ straight or branched chain alkyl;
$R^2$ and $R^3$ are each independently H, $C_1$~$C_{10}$ straight or branched chain alkyl or —$(CH_2)_{n_4}R^7$;
$R^5$ is H, $C_1$~$C_{10}$ straight or branched chain alkyl, $C_5$~$C_{20}$ aryl or $C_1$~$C_{20}$ heterocyclic compound;
$R^6$ is H or $C_1$~$C_{10}$ straight or branched chain alkyl;

R⁷ is —NR⁸R⁹, —COOR¹, —OR¹, —CF₃, —CN, halogen or Z;

R⁸ and R⁹ are independently H or $C_1$~$C_{10}$ straight or branched chain alkyl;

$n_1$ to $n_4$ are integer between 0 and 15 respectively;

Y⁴ is H or $C_1$~$C_{10}$ straight or branched chain alkyl.

Preferably, the Y¹ and Y² are independently H, $C_1$~$C_5$ straight or branched chain alkyl, hydroxy, $C_1$~$C_5$ alkoxy, —COOR¹, —NR²R³ or -A-B;

wherein A is —O—, —CH₂—, —CH(CH₃)—, —CH═N— or —CONH—;

B is —(CH₂)$n_1$-Z, —(CH₂)$n_2$-NR²R³ or —(CH₂)$n_3$-OR¹;

Z is a group selected from the group consisting of the below structural formulae;

[Chemical structures depicting: piperidine with N-R⁵, piperidine-R⁵, piperazine with N-R⁵, phenyl-R⁵, morpholine-R⁵/R⁶, piperazinium N⁺R⁵R⁶, pyrrolidine, imidazole, pyrrole, piperidinone, piperidine=N-OR⁵, pyrroline, tetrazole, phenyl, cyclopentyl, tetrahydropyran, thiomorpholine, and maleimide with methyl]

wherein, R¹ is H or $C_1$~$C_5$ straight or branched chain alkyl;

R² and R³ are independently H, $C_1$~$C_5$ straight or branched chain alkyl or —(CH₂)$n_4$R⁷;

R⁵ is H, $C_1$~$C_5$ straight or branched chain alkyl, phenyl or morpholino;

R⁶ is H or $C_1$~$C_5$ straight or branched chain alkyl;

R⁷ is —NR⁸R⁹, —COOR¹, —OR¹, —CF₃, —CN, F, Cl or Z;

R⁸ and R⁹ are independently H or $C_1$~$C_5$ straight or branched chain alkyl;

$n_1$ to $n_4$ are integers of 0 to 10, respectively;

Y³ is H, hydroxy, $C_1$~$C_5$ alkoxy or —O(CH₂)$n_3$-OR¹;

Y⁴ is H or $C_1$~$C_5$ straight or branched chain alkyl.

More preferably, Y¹ and Y² are independently H, methyl, ethyl, hydroxy, methoxy, ethoxy, —COOR¹, —NR²R³ or -A-B;

wherein A is —O—, —CH₂—, —CH(CH₃)—, —CH═N— or —CONH—;

B is —(CH₂)$n_1$-Z, —(CH₂)$n_2$-NR²R³ or —(CH₂)$n_3$-OR¹;

Z is one base selected from the group consisting of the below structural formulae;

[Chemical structures depicting: piperidine with N-R⁵, piperidine-R⁵, piperazine with N-R⁵, phenyl-R⁵, morpholine-R⁵/R⁶, piperazinium N⁺R⁵R⁶, pyrrolidine, imidazole, pyrrole, piperidinone, piperidine=N-OR⁵, pyrroline, tetrazole, phenyl, cyclopentyl, tetrahydropyran, thiomorpholine, and maleimide with methyl]

R¹ is H, methyl, ethyl or isopropyl;

R² and R³ are independently H, methyl, ethyl, propyl, isopropyl, t-butyl or —(CH₂)$n_4$R⁷;

R⁵ is H, methyl, ethyl, propyl, phenyl or morpholino;

R⁶ is H, methyl or ethyl;

R⁷ is —NR⁸R⁹, —COOR¹, —OR¹, —CF₃, —CN, F, Cl or Z;

R⁸ and R⁹ are independently H or methyl;

$n_1$ to $n_4$ are respectively integer of 0 to 5;

Y³ is H, hydroxy, methoxy, ethoxy, propoxy or methoxyethoxy; and

Y⁴ is H, methyl, ethyl or propyl.

Preferably, the compound of tricyclic derivatives represented by chemical formula 1 of the present invention comprises:

1) 8-Methoxy-1,2,3,4-tetrahydrobenzo[h][1,6]naphthyridine-5(6H)-one;
2) 10-Methoxy-1,2,3,4-tetrahydrobenzo[h][1,6]naphthyridine-5(6H)-one;
3) 9-Methoxy-1,2,3,4-tetrahydrobenzo[h][1,6]naphthyridine-5(6H)-one;
4) 9-Methyl-1,2,3,4-tetrahydrobenzo[h][1,6]naphthyridine-5(6H)-one;
5) Ethyl 5-oxo-1,2,3,4,5,6-hexahydrobenzo[h][1,6]naphthyridine-9-carboxylate;
6) 9-Methoxy-1-propyl-1,2,3,4-tetrahydrobenzo[h][1,6]naphthyridine-5(6H)-one;
7) 1-Methyl-1,2,3,4-tetrahydrobenzo[h][1,6]naphthyridine-5(6H)-one;

8) 9-Methoxy-1-methyl-1,2,3,4-tetrahydrobenzo[h][1,6]naphthyridine-5(6H)-one;
9) 1-Ethyl-9-methoxy-1,2,3,4-tetrahydrobenzo[h][1,6]naphthyridine-5(6H)-one;
10) 1-Methyl-9-hydroxy-1,2,3,4-tetrahydrobenzo[h][1,6]naphthyridine-5(6H)-one;
11) 9-(1-Propylpiperidine-4-yloxy)-1,2,3,4-tetrahydrobenzo[h][1,6]naphthyridine-5(6H)-one;
12) 9-(1-Methylpiperidine-4-yloxy)-1,2,3,4-tetrahydrobenzo[h][1,6]naphthyridine-5(6H)-one;
13) 1-Methyl-9-(piperidine-4-yloxy)-1,2,3,4-tetrahydrobenzo[h][1,6]naphthyridine-5(6H)-one;
14) 1-Methyl-9-(1-methylpiperidine-4-yloxy)-1,2,3,4-tetrahydrobenzo[h][1,6]naphthyridine-5(6H)-one;
15) 5-Oxo-N-[2-(piperidine-1-yl)ethyl]-1,2,3,4,5,6-hexahydrobenzo[h][1,6]naphthyridine-9-carboxamide;
16) 9-[2-(Dimethylamino)ethoxy]-1,2,3,4-tetrahydrobenzo[h][1,6]naphthyridine-5(6H)-one;
17) 9-[2-(Piperidine-1-yl)ethoxy]-1,2,3,4-tetrahydrobenzo[h][1,6]naphthyridine-5(6H)-one;
18) 9-(2-Methoxyethoxy)-1,2,3,4-tetrahydrobenzo[h][1,6]naphthyridine-5(6H)-one;
19) 9-[2-(Piperazine-1-yl)ethoxy]-1,2,3,4-tetrahydrobenzo[h][1,6]naphthyridine-5(6H)-one;
20) 9-Ethoxy-1,2,3,4-tetrahydrobenzo[h][1,6]naphthyridine-5(6H)-one;
21) 9-[3-(Piperidine-1-yl)propoxy]-1,2,3,4-tetrahydrobenzo[h][1,6]naphthyridine-5(6H)-one;
22) 9-(2-Aminoethoxy)-1,2,3,4-tetrahydrobenzo[h][1,6]naphthyridine-5(6H)-one;
23) 9-[2-(4-Phenylpiperidine-1-yl)ethoxy]-1,2,3,4-tetrahydrobenzo[h][1,6]naphthyridine-5(6H)-one;
24) 9-(2-Hydroxyethoxy)-1,2,3,4-tetrahydrobenzo[h][1,6]naphthyridine-5(6H)-one;
25) 9-Penethoxy-1,2,3,4-tetrahydrobenzo[h][1,6]naphthyridine-5(6H)-one;
26) 9-[2-(Diethylamino)ethoxy]-1,2,3,4-tetrahydrobenzo[h][1,6]naphthyridine-5(6H)-one;
27) 9-(2-Morpholinoethoxy)-1,2,3,4-tetrahydrobenzo[h][1,6]naphthyridine-5(6H)-one;
28) 1,1-Diethyl-4-[2-(5-oxo-1,2,3,4,5,6-hexahydrobenzo[h][1,6]naphthyridine-9-yloxy]ethyl)piperazine-1-ium;
29) 9-[4-(Piperidine-1-yl)butoxy]-1,2,3,4-tetrahydrobenzo[h][1,6]naphthyridine-5(6H)-one;
30) 1-Methyl-9-[2-(piperidine-1yl)ethoxy]-1,2,3,4-tetrahydrobenzo[h][1,6]naphthyridine-5(6H)-one;
31) 9-[2-(Dimethylamino)ethyl]-1,2,3,4-tetrahydrobenzo[h][1,6]naphthyridine-5(6H)-one;
32) 8-[2-(Dimethylamino)ethoxy]-1,2,3,4,-tetrahydrobenzo[h][1,6]naphthyridine-5(6H)-one;
33) 9-[3-(Dimethylamino)propyl]-1,2,3,4-tetrahydrobenzo[h][1,6]naphthyridine-5(6H)-one;
34) 8-[2-(Dimethylamino)ethoxy]-1,2,3,4,5,6-hexahydrobenzo[h][1,6]naphthyridine-9-carboxamide;
35) 8-[2-(Piperidine-1-yl)ethoxy]-1,2,3,4-tetrahydrobenzo[h][1,6]naphthyridine-5(6H)-one;
36) 8-[3-(Dimethylamino)propoxy]-1,2,3,4-tetrahydrobenzo[h][1,6]naphthyridine-5(6H)-one;
37) 8-(Dimethylamino)-1,2,3,4-tetrahydrobenzo[h][1,6]naphthyridine-5(6H)-one;
38) 8-[1-(Dimethylamino)ethyl]-1,2,3,4-tetrahydrobenzo[h][1,6]naphthyridine-5(6H)-one;
39) 8-[1-(Methylamino)ethyl]-1,2,3,4-tetrahydrobenzo[h][1,6]naphthyridine-5(6H)-one;
40) 8-Ethyl-1,2,3,4-tetrahydrobenzo[h][1,6]naphthyridine-5(6H)-one;
41) 8-[(Dimethylamino)methyl]-1,2,3,4-tetrahydrobenzo[h][1,6]naphthyridine-5(6H)-one;
42) 8-[(Diethylamino)methyl]-1,2,3,4-tetrahydrobenzo[h][1,6]naphthyridine-5(6H)-one;
43) 8-[(Ethylamino)methyl]-1,2,3,4-tetrahydrobenzo[h][1,6]naphthyridine-5(6H)-one;
44) 8-(Pyrolidine-1-ylmethyl)-1,2,3,4-tetrahydrobenzo[h][1,6]naphthyridine-5(6H)-one;
45) 8-[(Isopropylamino)methyl]-1,2,3,4-tetrahydrobenzo[h][1,6]naphthyridine-5(6H)-one;
46) 8-[(Propylamino)methyl]-1,2,3,4-tetrahydrobenzo[h][1,6]naphthyridine-5(6H)-one;
47) 8-{[Ethyl(methyl)amino]methyl}-1,2,3,4-tetrahydrobenzo[h][1,6]naphthyridine-5(6H)-one;
48) 8-(Piperidine-1-ylmethyl)-1,2,3,4-tetrahydrobenzo[h][1,6]naphthyridine-5(6H)-one;
49) 8-(Morpholinomethyl)-1,2,3,4-tetrahydrobenzo[h][1,6]naphthyridine-5(6H)-one;
50) 9-[(Dimethylamino)methyl]-1,2,3,4-tetrahydrobenzo[h][1,6]naphthyridine-5(6H)-one;
51) 8-{[Benzyl(methyl)amino]methyl}-1,2,3,4-tetrahydrobenzo[h][1,6]naphthyridine-5(6H)-one;
52) 8-[(Methylamino)methyl]-1,2,3,4-tetrahydrobenzo[h][1,6]naphthyridine-5(6H)-one;
53) 8-{[(2-Hydroxyethyl)(methyl)amino]methyl}-1,2,3,4-tetrahydrobenzo[h][1,6]naphthyridine-5(6H)-one;
54) 8-{[(2-Dimethylaminoethyl)(methyl)amino]methyl}-1,2,3,4-tetrahydrobenzo[h][1,6]naphthyridine-5(6H)-one;
55) 8-[(4-Methylpiperazine-1-yl)methyl]-1,2,3,4-tetrahydrobenzo[h][1,6]naphthyridine-5(6H)-one;
56) 8-[(Methyl(propyl)amino)methyl]-1,2,3,4-tetrahydrobenzo[h][1,6]naphthyridine-5(6H)-one;
57) Ethyl-3-{methyl[(5-oxo-1,2,3,4,5,6-hexahydrobenzo[h][1,6]naphthyridine-8-yl)methyl]amino}propanoate;
58) 3-{Methyl[(5-oxo-1,2,3,4,5,6-hexahydrobenzo[h][1,6]naphthyridine-8yl)methyl]amino}propanoic acid;
59) 8-{[Isopropyl(methyl)amino]methyl}-1,2,3,4-tetrahydrobenzo[h][1,6]naphthyridine-5(6H)-one;
60) 8-{[(2-Methoxyethyl)(methyl)amino]methyl}-1,2,3,4-tetrahydrobenzo[h][1,6]naphthyridine-5(6H)-one;
61) Ethyl-3-[(5-oxo-1,2,3,4,5,6-hexahydrobenzo[h][1,6]naphthyridine-8yl)methylamino]propanoate;
62) 8-[(2,2,2-Trifluoroethylamino)methyl]-1,2,3,4-tetrahydrobenzo[h][1,6]naphthyridine-5(6H)-one;
63) 2-[(5-Oxo-1,2,3,4,5,6-hexahydrobenzo[h][1,6]naphthyridine-8yl)methylamino]acetonitrile;
64) 8-[(1H-Imidazole-1-yl)methyl]-1,2,3,4-tetrahydrobenzo[h][1,6]naphthyridine-5(6H)-one;
65) 8-[(1H-Pyrrole-1-yl)methyl]-1,2,3,4-tetrahydrobenzo[h][1,6]naphthyridine-5(6H)-one;
66) 8-[(Dimethylamino)methyl]-1-methyl-1,2,3,4-tetrahydrobenzo[h][1,6]naphthyridine-5(6H)-one;
67) 1-Methyl-8-(pyrolidine-1ylmethyl)-1,2,3,4-tetrahydrobenzo[h][1,6]naphthyridine-5(6H)-one;
68) 8-[(Diethylamino)methyl]-1-methyl-1,2,3,4-tetrahydrobenzo[h][1,6]naphthyridine-5(6H)-one;
69) 1-Methyl-8-(piperidine-1-ylmethyl)-1,2,3,4-tetrahydrobenzo[h][1,6]naphthyridine-5(6H)-one;
70) 1-Methyl-8-(morpholinomethyl)-1,2,3,4-tetrahydrobenzo[h][1,6]naphthyridine-5(6H)-one;
71) 8-{[Ethyl(methyl)amino]methyl}-1-methyl-1,2,3,4-tetrahydrobenzo[h][1,6]naphthyridine-5(6H)-one;
72) 8-[(Dimethylamino)methyl]-10-methoxy-1,2,3,4-tetrahydrobenzo[h][1,6]naphthyridine-5(6H)-one;
73) 10-Methoxy-8-[(methylamino)methyl]-1,2,3,4-tetrahydrobenzo[h][1,6]naphthyridine-5(6H)-one;

74) 10-Methoxy-8-(morpholinomethyl)-1,2,3,4-tetrahydrobenzo[h][1,6]naphthyridine-5(6H)-one;
75) 8-[(Ethylamino)methyl]-10-methoxy-1,2,3,4-tetrahydrobenzo[h][1,6]naphthyridine-5(6H)-one;
76) 8-{[Ethyl(methyl)amino]methyl}-10-methoxy-1,2,3,4-tetrahydrobenzo[h][1,6]naphthyridine-5(6H)-one;
77) 10-Methoxy-8-(pyrrolidine-1-ylmethyl)-1,2,3,4-tetrahydrobenzo[h][1,6]naphthyridine-5(6H)-one;
78) 10-Methoxy-8-[(4-oxopiperidine-1-yl)methyl]-1,2,3,4-tetrahydrobenzo[h][1,6]naphthyridine-5(6H)-one;
79) 8-{[4-(Hydroxyimino)piperidine-1-yl]methyl}-10-methoxy-1,2,3,4-tetrahydrobenzo[h][1,6]naphthyridine-5(6H)-one;
80) 10-Methoxy-8-[(4-(methoxyimino)piperidine-1-yl)methyl]-1,2,3,4-tetrahydrobenzo[h][1,6]naphthyridine-5(6H)-one;
81) 10-Methoxy-8-{[(2-methoxyethyl)(methyl)amino]methyl}-1,2,3,4-tetrahydrobenzo[h][1,6]naphthyridine-5(6H)-one;
82) 8-[(2,5-Dehydro-1H-pyrrole-1-yl)methyl]-10-methoxy-1,2,3,4-tetrahydrobenzo[h][1,6]naphthyridine-5(6H)-one;
83) 8-{[(2-Isopropoxyethyl)(methyl)amino]methyl}-10-methoxy-1,2,3,4-tetrahydrobenzo[h][1,6]naphthyridine-5(6H)-one;
84) 10-Methoxy-8-(piperidine-1-ylmethyl)-1,2,3,4-tetrahydrobenzo[h][1,6]naphthyridine-5(6H)-one;
85) 8-{[(2-Chloroethyl)(methyl)amino]methyl}-10-methoxy-1,2,3,4-tetrahydrobenzo[h][1,6]naphthyridine-5(6H)-one;
86) 8-[(Diethylamino)methyl]-10-methoxy-1,2,3,4-tetrahydrobenzo[h][1,6]naphthyridine-5(6H)-one;
87) 8-[(t-Butylamino)methyl]-10-methoxy-1,2,3,4-tetrahydrobenzo[h][1,6]naphthyridine-5(6H)-one;
88) 8-[(Isopropylamino)methyl]-10-methoxy-1,2,3,4-tetrahydrobenzo[h][1,6]naphthyridine-5(6H)-one;
89) 8-[(Cyclopentylamino)methyl]-10-methoxy-1,2,3,4-tetrahydrobenzo[h][1,6]naphthyridine-5(6H)-one;
90) 8-[(2,6-Dimethylmorpholino)methyl]-10-methoxy-1,2,3,4-tetrahydrobenzo[h][1,6]naphthyridine-5(6H)-one;
91) N-[(10-Methoxy-5-oxo-1,2,3,4,5,6-hexahydrobenzo[h][1,6]naphthyridine-8yl)methyl]-N,N-dimethylcyclopentane aminium chloride;
92) 8-{[Cyclopentyl(methyl)amino]methyl}-10-methoxy-1,2,3,4-tetrahydrobenzo[h][1,6]naphthyridine-5(6H)-one;
93) 8-{[Isopropyl(methyl)amino]methyl}-10-methoxy-1,2,3,4-tetrahydrobenzo[h][1,6]naphthyridine-5(6H)-one;
94) 8-{[(2-Fluoroethyl)(methyl)amino]methyl}-10-methoxy-1,2,3,4-tetrahydrobenzo[h][1,6]naphthyridine-5(6H)-one;
95) 8-[(1H-Tetrazol-5yl)methyl]-1,2,3,4-tetrahydrobenzo[h][1,6]naphthyridine-5(6H)-one;
96) 10-Methoxy-8-[(morpholinoamino)methyl]-1,2,3,4-tetrahydrobenzo[h][1,6]naphthyridine-5(6H)-one;
97) 10-Methoxy-8-{[methyl(morpholino)amino]methyl}-1,2,3,4-tetrahydrobenzo[h][1,6]naphthyridine-5(6H)-one;
98) (E)-10-Methoxy-8-[(morpholinoimino)methyl]-1,2,3,4-tetrahydrobenzo[h][1,6]naphthyridine-5(6H)-one;
99) 8-[(Dimethylamino)methyl]-10-hydroxy-1,2,3,4-tetrahydrobenzo[h][1,6]naphthyridine-5-(6H)-one;
100) 8-[(Dimethylamino)methyl]-10-ethoxy-1,2,3,4-tetrahydrobenzo[h][1,6]naphthyridine-5(6H)-one;
101) 10-Ethoxy-8-(morpholinomethyl)-1,2,3,4-tetrahydrobenzo[h][1,6]naphthyridine-5(6H)-one;
102) 10-Ethoxy-8-(piperidine-1-ylmethyl)-1,2,3,4-tetrahydrobenzo[h][1,6]naphthyridine-5(6H)-one;
103) 10-Ethoxy-8-[(methylamino)methyl]-1,2,3,4-tetrahydrobenzo[h][1,6]naphthyridine-5(6H)-one;
104) 10-Ethoxy-8-[(ethylamino)methyl]-1,2,3,4-tetrahydrobenzo[h][1,6]naphthyridine-5(6H)-one;
105) 8-(Hydroxymethyl)-10-methoxy-1,2,3,4-tetrahydrobenzo[h][1,6]naphthyridine-5(6H)-one;
106) 10-Methoxy-8-(thiomorpholinomethyl)-1,2,3,4-tetrahydrobenzo[h][1,6]naphthyridine-5(6H)-one;
107) 10-Methoxy-8-[(2-morpholinoethylamino)methyl]-1,2,3,4-tetrahydrobenzo[h][1,6]naphthyridine-5(6H)-one;
108) 10-Methoxy-8-[(4-morpholinopiperidine-1yl)methyl]-1,2,3,4-tetrahydrobenzo[h][1,6]naphthyridine-5(6H)-one;
109) 8-(Aminomethyl)-10-methoxy-1,2,3,4-tetrahydrobenzo[h][1,6]naphthyridine-5(6H)-one;
110) 8-[(Dimethylamino)methyl)]-10-propoxy-1,2,3,4-tetrahydrobenzo[h][1,6]naphthyridine-5(6H)-one;
111) 8-(Morpholinomethyl)-10-propoxy-1,2,3,4-tetrahydrobenzo[h][1,6]naphthyridine-5(6H)-one;
112) 8-(Aminomethyl)-1,2,3,4-tetrahydrobenzo[h][1,6]naphthyridine-5(6H)-one;
113) 8-(Aminomethyl)-10-ethoxy-1,2,3,4-tetrahydrobenzo[h][1,6]naphthyridine-5(6H)-one;
114) 8-(Aminomethyl)-10-propoxy-1,2,3,4-tetrahydrobenzo[h][1,6]naphthyridine-5(6H)-one;
115) 10-Methoxy-8-{[methyl(tetrahydro-2H-pyran-4-yl)amino]methyl}-1,2,3,4-tetrahydrobenzo[h][1,6]naphthyridine-5(6H)-one;
116) 8-[(Dimethylamino)methyl]-10-(2-methoxyethoxy)-1,2,3,4-tetrahydrobenzo[h][1,6]naphthyridine-5(6H)-one;
117) 10-(2-Methoxyethoxy)-8-(morpholinomethyl)-1,2,3,4-tetrahydrobenzo[h][1,6]naphthyridine-5(6H)-one; and
118) 1-[(10-Methoxy-5-oxo-1,2,3,4,5,6-hexahydrobenzo[h][1,6]naphthyridine-8-yl)methylamino]-1H-pyrrole-2,5-dione.

The present invention provides a preparation method of the compound represented by chemical formula 1.

The present invention provides a preparation method of tricyclic derivatives expressed by the chemical formula 1. Preferably, the compound of chemical formula 1 may be prepared by the reaction formulas disclosed below but not limited thereto. Accordingly, those skilled in the art may fully understand that the compound of chemical formula 1 of the present invention may be prepared with various methods of known technologies.

The following reaction formulas relate to preparation stages of the method for preparing representative compounds of the present invention in order, and various compounds of the present invention may be prepared by changing or modifying reagent, solvent or sequences of reactions used during the preparation process. Some of the compounds of the present invention were prepared by the processes which are not included within the scope of the reaction formulas disclosed below, and specific preparation processes of such compounds are described respectively in each of the examples explained below.

Preparation Method 1

In one embodiment, tricyclic derivatives or pharmaceutically acceptable salts thereof according to the present invention may be prepared by a method represented by reaction formula 1 below, the method comprising steps of:

1) converting carboxylic acid of 2-chloronicotinic acid expressed by chemical formula 2 into carboxylic acid chloride expressed by chemical formula 3 (step 1);

2) preparing compound of chemical formula 5 by amidation reaction of carboxylic acid chloride of chemical formula 3 prepared in step 1 with aniline of chemical formula 4 substituted at meta and/or para position (step 2);

3) introducing protection group in the compound of chemical formula 5 prepared in step 2 to obtain N-protected compound of chemical formula 6 (step 3);

4) preparing compound of chemical formula 7 by cyclization of the compound of chemical formula 6 prepared in step 3 under metal-catalyst (step 4);

5) preparing compound of chemical formula 8 by aromatic ring reduction of compound of chemical formula 7 prepared in step 4 under hydrogen gas and palladium (Pd) catalyst, or by aromatic ring reduction of compound of chemical formula 7 prepared in step 4 under hydrogen gas and palladium (Pd) catalyst, and then by reaction of alkyl halide compound or aryl halide compound and a base (step 5); and 6) deprotecting the compound of chemical formula 8 prepared in step 5 to obtain tricyclic compound of chemical formula 1 (step 6).

[Reaction formula 1]

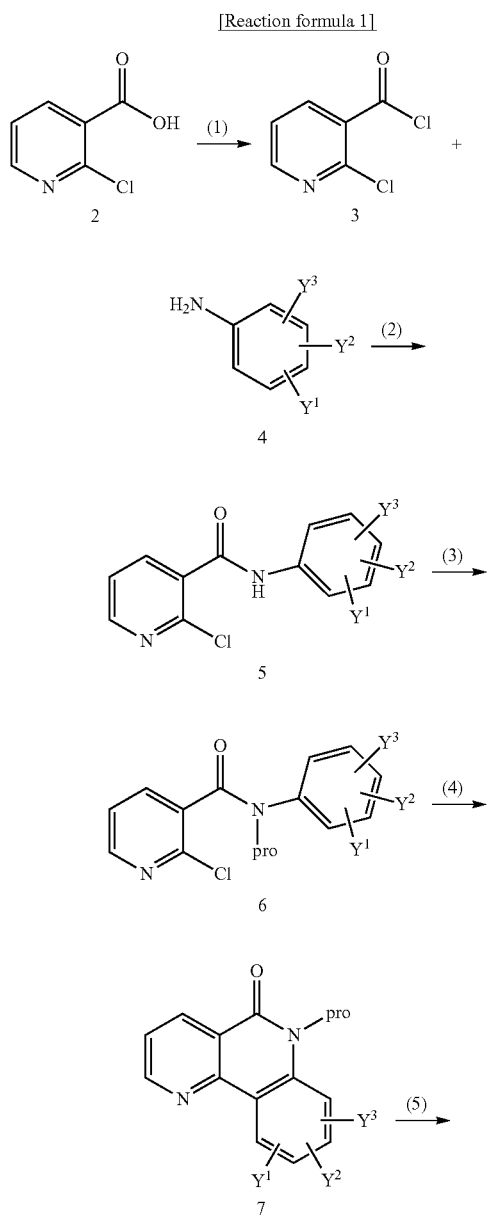

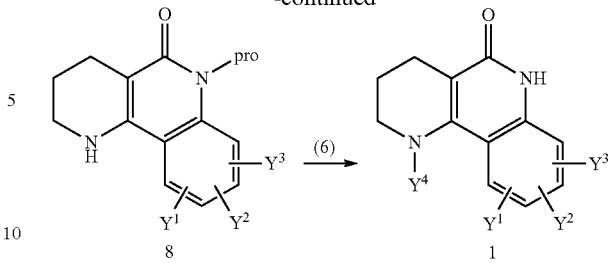

wherein, $Y^1$ to $Y^4$ are as defined in formula 1, and 'pro' represents protection group such as aryl group, benzyl group, benzyloxymethyl group, para-methoxybenzyl group, or methoxymethyl group, preferably para-methoxybenzyl group or methoxymethyl group.

Each step will be explained in greater detail below.

In step 1, acid chloride (3) is prepared by converting commercially available 2-chloronicotinic acid (2) into acid chloride using reagent such as thionyl chloride or oxalyl chloride. For the reaction of step 1, solvent is not used or solvent such as dichloromethane, chloroform, or toluene, which has no negative effect on the reaction, is used. Reacting temperature is not specially limited but in general, the reaction is performed under room temperature to elevated temperature, and desirably under elevated temperature.

In step 2, the compound of chemical formula 5 is prepared by amidation reaction of acid chloride of chemical formula 3 and aniline of chemical formula 4 substituted at meta and/or para position. In this step, the reaction is carried out without a base or in the presence of organic amine such as pyridine, triethylamine, diethylisopropylamine which is generally used for amidation reaction using dichloromethane, chloroform, tetrahydrofuran, diethylether, toluene, or N,N-dimethylformamide which has no negative effect on the reaction. The reaction temperature is not specifically limited, but generally, the reaction is performed under cold temperature to room temperature.

In step 3, protection group is introduced into the compound of chemical formula 5 prepared in step 2 so that N-protected amide intermediate product of chemical formula 6 is synthesized. The introduced protection group may include alkoxy methyl including methoxymethyl (MOM), benzyloxymethyl (BOM), or benzyl (Bn) or p-methoxybenzyl (PMB). A base used in the reaction may be sodium hydride, potassium t-butoxide, potassium carbonate, and solvent may be tetrahydrofuran, N,N-dimethylformamide, acetonitrile, or toluene which has no negative effect on the reaction. The reaction temperature is not specifically limited, but generally, the reaction is preferably performed under cold temperature to elevated temperature, and more preferably, under cold temperature.

In step 4, lactam of chemical formula 7 is prepared by cyclizations of N-protected amide intermediate product prepared in step 3 under metal-catalyst. In this step, palladium(0) is conventionally used as metal-catalyst, and tetrakis triphenylphosphine palladium(0) ((PPh$_3$)$_4$Pd), palladium acetate (II) (Pd(OAc)$_2$), tris(dibenzyllideneacetone)dipalladium(0) (Pd$_2$dba$_3$) and bis(triphenylphosphine)palladium(II)dichloride (PdCl$_2$(PPh$_3$)$_2$) may be used individually, or in combination with tributylphosphine (Bu$_3$P). The reaction may be performed without ligand or with ligand generally used for cyclization under metal-catalyst including, for instance, triphenylphosphine ((PPh$_3$)$_4$), 1,2-bis(diphenylphosphino) propane (DPPP), (R)-2,2'-bis(diphenylphosphino)-1,1'-binaphthyl ((R)-BiNAP). A base including potassium carbonate, sodium carbonate, silver carbonate, or diethylisopropylamine may be used for the reaction, and the reaction is performed using a solvent including N,N-dimethylformamide, benzene, xylene, or acetonitrile which has no negative effect on the reaction. The reaction temperature is not specifically limited, but the reaction is generally performed under room temperature to elevated temperature, and preferably under elevated temperature.

In step 5, piperidine-lactam (8) is prepared by aromatic ring reduction of pyridine-lactam (7) prepared in step 4 under hydrogen gas and palladium (Pd) catalyst. In this step, organic solvent including alcohol, chloroform, dichloromethane, or ethyl acetate which has no negative effect on the reaction, or a mixture thereof may be used. The reaction temperature is not specifically limited, but the reaction is performed generally under room temperature.

Further, the prepared piperidine-lactam (8) and alkyl halide compound or aryl halide compound may be additionally reacted in the presence of a base such as potassium carbonate to prepare N-substituted piperidine-lactam ($Y^4$=alkyl, or aryl). The reaction is performed in the presence of a base which is used in general alkylation or alylation of amine compound and alkyl halide or aryl halide. The base may be one of sodium hydride, potassium carbonate, sodium carbonate, cesium carbonate, sodium or potassium alkoxide. Further, the reaction may be desirably performed in the presence of solvent which has no negative effect on the reaction, and solvent may include dichloromethane, chloroform, tetrahydrofuran, diethylether, toluene, N,N-dimethylformamide or acetonitrile. The reaction temperature is not specifically limited, but the reaction is generally performed under cold temperature to elevated temperature, and preferably, under room temperature.

In step 6, tricyclic compound of chemical formula 1 is prepared by deprotection of piperidine-lactam (8) prepared in step 5 with the method of generally known in organic synthetic field.

Preparation Method 2

In one embodiment, tricyclic derivatives or pharmaceutically acceptable salts thereof may be prepared by a method as represented by reaction formula 2 below, the method comprising steps of:

1) demethylating the compound (7a) prepared in step 4 of the reaction formula 1 with boron tribromide to obtain hydroxyl compound (7a-1) (step 1);

2) reacting the hydroxyl compound (7a-1) prepared in step 1 with alkyl halide compound including 4-bromopiperidine, or 2-chloroethyl piperidine in the presence of a base including potassium carbonate and a catalytic amount of sodium iodide to obtain alkoxy compound (7a-2) (step 2);

3) preparing piperidine-lactam (8a) by aromatic ring reduction of the pyridine-lactam compound (7a-2) prepared in step 2 under hydrogen gas and palladium (Pd) catalyst (step 3); and 4) deprotecting the compound (8a) prepared in step 3 under acidic condition such as hydrochloric acid to obtain compound of chemical formula (1a) (step 4).

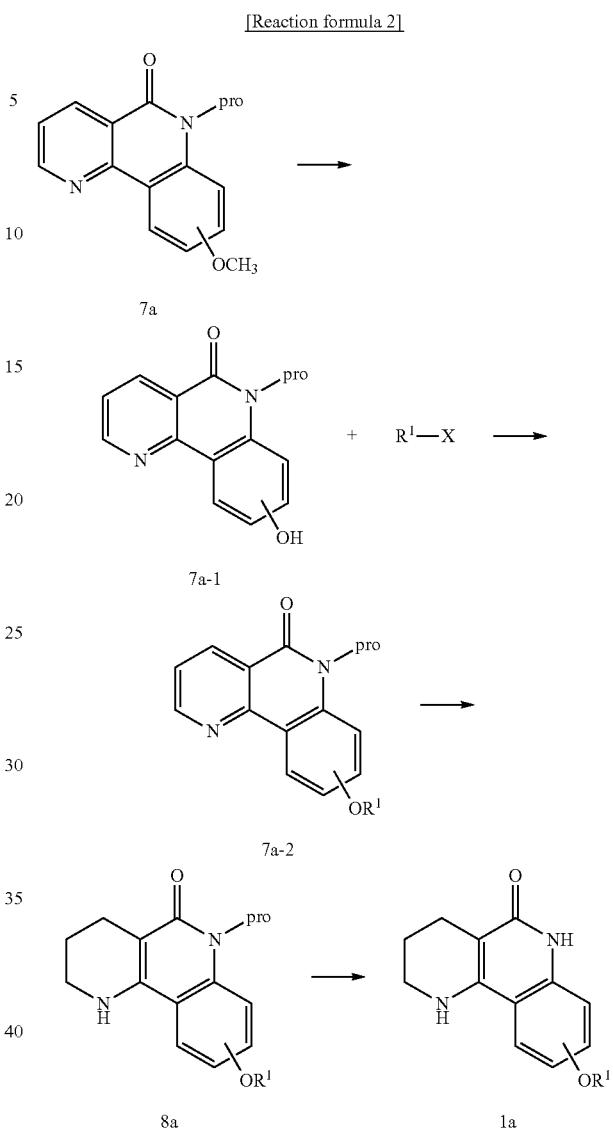

[Reaction formula 2]

wherein, 'pro' represents methoxymethyl (MOM) group, benzyl group, para-methoxybenzyl (PMB) group, $R^1$ is as defined in chemical formula 1, X denotes leaving group including halogen, methanesulfonyl group, p-toluenesulfonyl group, or trifluoromethanesulfonyl group, and preferably, halogen (chloro, bromo, iodo) or methanesulfonyl group, and formula 1a is included in the chemical formula 1 of the present invention.

According to reaction formula 2 of the present invention to prepare the compound of chemical formula (1a), first, in step 1, demethylated hydroxyl compound (7a-1) is prepared by using compound (7a) prepared in step 4 of the reaction formula 1 using boron tribromide. The organic solvent such as dichloromethane, or chloroform which has no negative effect on the reaction, may be used. The reaction temperature is not specifically limited, but the reaction is generally performed under cold temperature to elevated temperature, and preferably under room temperature.

In step 2, alkoxy compound (7a-2) is prepared by adding a catalytic amount of sodium iodide to hydroxy compound (7a-1) prepared in step 1 and alkyl halide compound such as 4-bromopiperidine, or 2-chloroethyl piperidine in the presence of a base such as potassium carbonate. The above reaction is generally an etherification between alcohol compound and alkyl halide and carried out in the presence of a base which can be used for the etherification. The base used in the above reaction may include sodium hydride, potassium carbonate, sodium carbonate, cesium carbonate, or sodium or potassium alkoxide. Solvent having no negative effect on the reaction such as dichloromethane, chloroform, tetrahydrofuran, diethylether, toluene, N,N-dimethylformamide or acetonitrile may be used in the reaction. The reaction temperature is not specifically limited, but the reaction is generally performed under cold temperature to elevated temperature, and preferably under room temperature to elevated temperature.

In step 3, piperidine-lactam (8a) is prepared by aromatic ring reduction of pyridine-lactam (7a-2) prepared in step 2 under hydrogen gas and palladium (Pd) catalyst. The above reaction is performed under the same conditions as the condition for the aromatic ring reduction to convert the compound of chemical formula 7 into the compound of chemical formula 8 in the reaction formula 1.

In step 4, compound of chemical formula (1a) was synthesized by performing deprotection reaction of the compound (8a) prepared in step 3 under the acidic condition such as hydrochloric acid.

Preparation Method 3

In one embodiment, tricyclic derivatives or pharmaceutically acceptable salts thereof may be prepared by a method as represented by the reaction formula 3 below, the method comprising steps of:

1) hydrolyzing the compound (7b) prepared in step 4 of the reaction formula 1 by slowly dropwise adding potassium hydroxide or sodium hydroxide aqueous solution into the compound (7b) to obtain the carboxyl acid compound (7b-1) (step 1);

2) Amidating the carboxyl acid compound (7b-1) prepared in step 1 with amines using coupling reagent to obtain the compound of chemical formula (7b-2) (step 2);

3) preparing piperidine-lactam (8b) by aromatic ring reduction of pyridine-lactam (7b-2) prepared in step 2 under hydrogen gas and palladium (Pd) catalyst (step 3); and 4) deprotecting the compound (8b) prepared in step 3 under acidic condition such as hydrochloric acid to obtain the compound of chemical formula (1b) (step 4).

[Reaction formula 3]

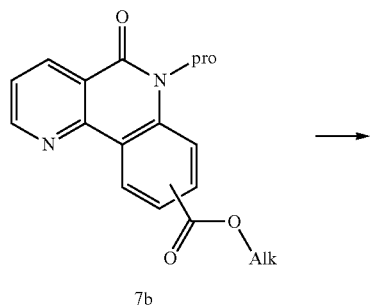

7b

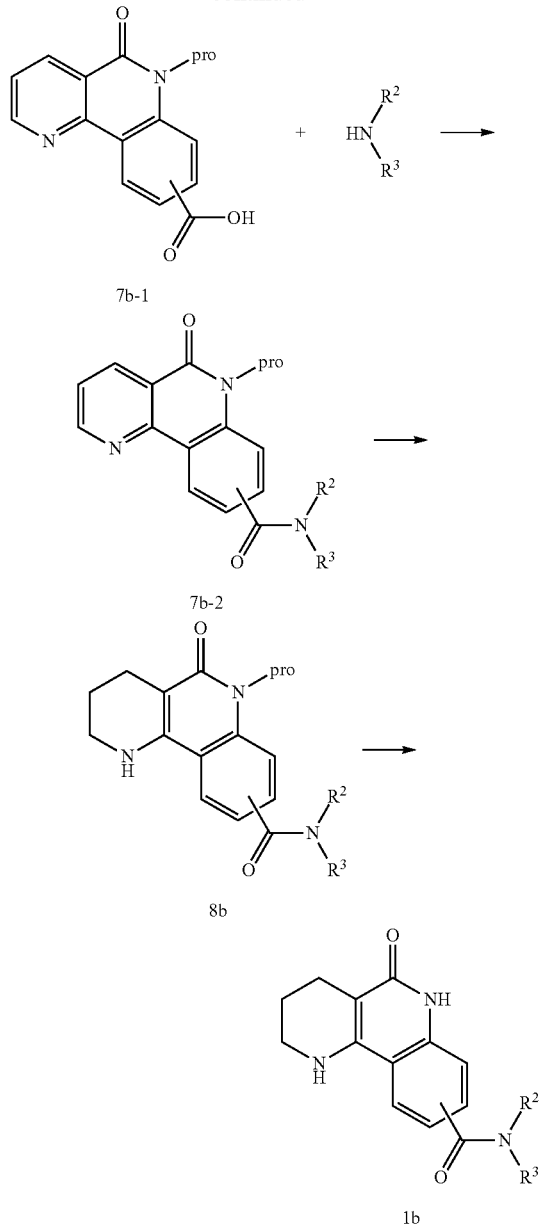

wherein, 'Alk' represents $C_1$~$C_{10}$ straight or branched chain alkyl, 'pro' represents methoxymethyl (MOM) group, benzyl group, or para-methoxybenzyl (PMB) group, $R^2$ and $R^3$ are as defined in chemical formula 1, and chemical formula 1b is included in chemical formula 1 of the present invention.

According to reaction formula 3 to prepare the compound of chemical formula (1b) according to the present invention, in step 1, carboxyl acid compound (7b-1) is prepared which is hydrolyzed by slowly dropwise adding potassium hydroxide or sodium hydroxide aqueous solution into the compound (7b) prepared in step 4 of the reaction formula 1. The reaction is performed in the presence of alcohol solvent such as methanol or ethanol which has no negative effect on the reaction. The reaction temperature is not specifically limited, but the reaction is performed generally under cold temperature to elevated temperature, and preferably, under room temperature to elevated temperature. The reaction may be performed under the general hydrolysis condition of ester.

In step 2, the compound of chemical formula (7b-2) is prepared by general amidation reaction in which the carboxyl acid compound (7b-1) prepared in step 1 and amine compound are reacted with each other by a coupling reagent. Generally, the coupling reagent may be commercially available (1-(3-dimethylaminopropyl)-3-ethylcarbodiimide (EDCI), 1,3-dicyclohexylcarbodiimide (DCC), 1,1-carbonyldiimidazole. The reaction of step 2 may be performed without using a base, or in the presence of a base which may be generally used in amidation reaction such as 4-dimethylaminopyridine, pyridine, triethylamine, diethylisopropylamine, N-methylmorpholine or dimethylphenylamine, using a solvent has no negative effect on the reaction, such as acetonitrile, dimethylformamide, or dichloromethane. The reaction temperature is not specifically limited, but the reaction is performed under cold temperature to elevated temperature, and preferably under cold temperature to room temperature.

In step 3, piperidine-lactam (8b) is prepared by aromatic ring reduction of pyridine-lactam (7b-2) prepared in step 2 under hydrogen gas and palladium (Pd) catalyst.

The reaction is generally performed under the same condition as aromatic ring reduction reaction which converts the compound of chemical formula 7 of reaction formula 1 into the compound of chemical formula 8.

In step 4, the compound (8b) prepared in step 3 is synthesized into the compound of chemical formula (1b) by deprotection reaction under the acidic condition including hydrochloric acid.

Preparation Method 4

In one embodiment, tricyclic derivatives or pharmaceutically acceptable salts thereof according to the present invention may be prepared by a method as represented reaction formula 4 below, the method comprising steps of:

1) reducing the lactam compound (8c) prepared in step 6 of the reaction formula 1 into corresponding alcohol (8c-1) by using a reducing agent including lithium aluminum hydride (LAH) (step 1);

2) preparing diamino-lactam compound (8c-2) by halogenation and amination of the alcohol compound (8c-1) prepared in step 1 (step 2); and 3) deprotecting the compound (8c-2) prepared in step 2 under acidic condition such as hydrochloric acid to obtain tricyclic compound of chemical formula (1c) (step 3).

[Reaction formula 4]

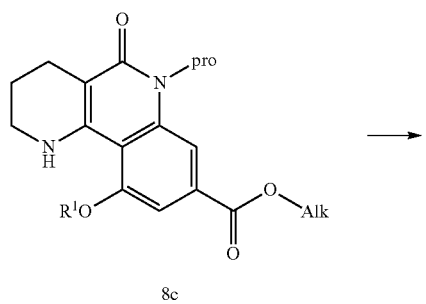

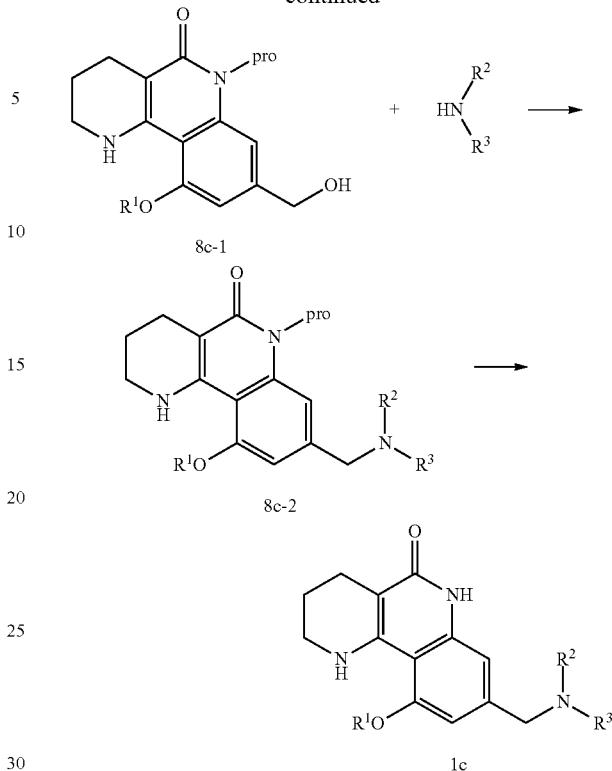

wherein, 'Alk' represents $C_1$~$C_{10}$ straight or branched chain alkyl, 'pro' is methoxymethyl (MOM) group, benzyl group, para-methoxybenzyl (PMB) group, $R^1$ to $R^3$ are as defined in the chemical formula 1, and chemical formula 1c is included in chemical formula 1 of the present invention.

According to reaction formula 4 to prepare the compound of chemical formula (1c) of the present invention, in step 1, the lactam compound (8c) prepared in step 6 of the reaction formula 1 is reduced to corresponding alcohol (8c-1) by using a reducing agent such as lithium aluminum hydride (LAH). Generally, a commercially-available reducing agent may be used, including, for example, lithium aluminum hydride (LAH), sodium borohydride ($NaBH_4$), or diisobutyl aluminum hydride (DIBAL-H). The reaction may be performed in the presence of solvent which has no negative effect on the reaction, such as tetrahydrofuran, diethylether, or alcohol. The reaction temperature is not specifically limited, but the reaction is performed generally under cold temperature to elevated temperature, and preferably, under cold temperature.

In step 2, diamino-lactam compound (8c-2) is prepared by halogenation and amination of the alcohol compound (8c-1) prepared in step 1. The conversion into halogen compound is performed using phosphorus tribromide, tetrabromomethane, or thionyl chloride which generally converts hydroxyl group into halogen, in the presence of solvent such as chloroform, acetonitrile, or dichloromethane which has no negative effect on the reaction. The reaction temperature is not specifically limited, but the reaction is generally performed under cold temperature to room temperature. Further, the conversion of the halogen compound into diamino-lactam compound (8c-2) may be performed by general amination reaction. The reaction is generally performed in the presence of organic amine such as pyridine, triethylamine, or diethylisopropylamine or potassium carbonate which is the base generally applicable in the amination reaction, using alcohol such as methanol or ethanol, dichloromethane, chloroform, tetrahydrofuran, diethyl ether, toluene, or N,N-dimethylformamide which has no negative effect on the reaction. The reaction temperature is not specifically limited, but the reaction is generally performed under cold temperature to elevated temperature, and preferably under room temperature to elevated temperature.

In step 3, the tricyclic compound of chemical formula (1c) is prepared by deprotection reaction of the compound (8c-2) prepared in step 2 under the acidic condition such as hydrochloric acid.

Preparation Method 5

In one embodiment, tricyclic derivatives or pharmaceutically acceptable salt thereof may be prepared by a method represented by reaction formula 5 below, the method comprising steps of:

1) preparing amino-lactam compound of chemical formula (8d-1) by general amination reaction of lactam compound (8d) of reaction formula 1 prepared in step 5 and substituted-amine; and 2) preparing tricyclic compound of chemical formula (1d) by deprotection reaction of the compound (8d-1) prepared in step 1 under acidic condition such as hydrochloric acid.

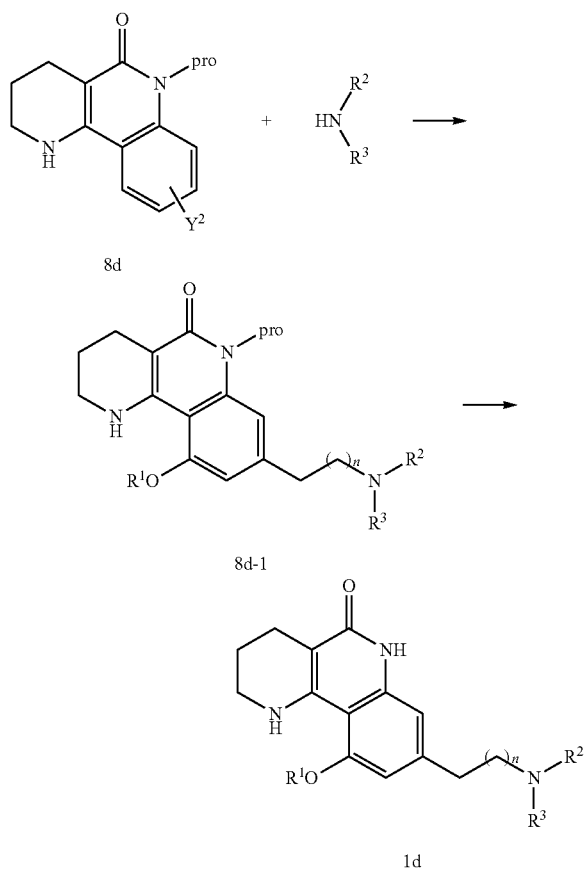

[Reaction formula 5]

8d 8d-1

1d wherein, $R^2$ is H or —$(CH_2)n$-X, 'pro' is methoxymethyl (MOM) group, benzyl group, para-methoxybenzyl (PMB) group, $R^2$, $R^3$ and n are defined as in chemical formula 1, and chemical formula 1d is included in chemical formula 1 of the present invention.

According to reaction formula 5 to prepare the compound of chemical formula (1d) of the present invention, in step 1, amino-lactam compound of chemical formula (8d-1) is prepared by general amination reaction of the lactam compound (8d) prepared in step 5 of the reaction formula 1 with substituted-amine. The reaction of step 1 is performed under the same condition of amination reaction as that of step 2 of reaction formula 4 of step 2 which converts the halogen compound of chemical formula (8c-1) into the compound of chemical formula (8c-2).

In step 2, tricyclic compound of chemical formula (1d) is prepared by deprotection reaction of the compound (8d-1) prepared in step 1 under acidic condition such as hydrochloric acid.

The target compounds generated in the reaction formulae may be purified by conventional methods such as, for example, column chromatography or re-crystallization.

The compound of chemical formula 1 of the present invention may be prepared into pharmaceutically acceptable salt and solvates by conventional methods as known in the art.

An acid addition salt, which is formed by pharmaceutically acceptable free acid, may be effectively used. The acid addition salt may be prepared by a conventional method, for example, dissolving a compound in an excessive amount of acid aqueous solution, and settling the compound with water-soluble organic solvent including methanol, ethanol, acetone or acetonitrile. The same amount of the compound and acid in water or alcohol (e.g., glycolmonomethylether) is heated, and the mixture is evaporated to dry or the salt extracted from the mixture may be suctioned and filtered.

Free acid may be organic acid and non-organic acid. Non-organic acid may be hydrochloric acid, phosphoric acid, sulfuric acid, or nitric acid, and organic acid may be methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycollic acid, gluconic acid, galacturonic acid, glutamic acid, glutaric acid, glucuronic acid, aspartic acid, ascorbic acid, carboxylic acid, vanillic acid, or hydroiodic acid, but not limited thereto.

Further, pharmaceutically acceptable metal salt may be prepared using a base. Alkali metal or alkaline earth metal salt may be obtained by dissolving a compound in an excessive amount of alkali metal hydroxide or alkali earth metal hydroxide aqueous solution, filtering non-soluble compound salt, and evaporating and drying the remaining solvent.

The metal salt may preferably be sodium, potassium or calcium salt which is suitable for pharmaceutical preparation, but not limited thereto. Further, a corresponding silver salt may be obtained by the reaction of alkali metal or alkaline earth metal salts with appropriate silver salt (e.g., silver nitrate).

The pharmaceutically acceptable salt of the compound of chemical formula 1 includes, unless otherwise specified, a salt of acid or alkali group which may be included in the compound of chemical formula 1. For example, the pharmaceutically acceptable salt may include sodium, calcium and potassium salt of hydroxyl group, and the other pharmaceutically acceptable salt of amino group may include hydrobromide, sulphate, hydrogen sulphate, phosphate, hydrogen phosphate, dihydrogen phosphate, acetate, succinate, citrate, tartrate, lactate, mandelate, methane sulfonate (mesilate) or p-toluene sulfonate (tosylate), and these may be prepared by the salt preparation methods known in the art.

In one embodiment, the pharmaceutically acceptable salt of tricyclic derivatives of formula 1 comprises:

1) 8-Methoxy-1,2,3,4-tetrahydrobenzo[h][1,6]naphthyridine-5(6H)-one hydrochloride;

2) 10-Methoxy-1,2,3,4-tetrahydrobenzo[h][1,6]naphthyridine-5(6H)-one hydrochloride;
3) 9-Methoxy-1,2,3,4-tetrahydrobenzo[h][1,6]naphthyridine-5(6H)-one hydrochloride;
4) 9-Methyl-1,2,3,4-tetrahydrobenzo[h][1,6]naphthyridine-5(6H)-one hydrochloride;
5) Ethyl 5-oxo-1,2,3,4,5,6-hexahydrobenzo[h][1,6]naphthyridine-9-carboxylate hydrochloride;
6) 9-Methoxy-1-propyl-1,2,3,4-tetrahydrobenzo[h][1,6]naphthyridine-5(6H)-one hydrochloride;
7) 1-Methyl-1,2,3,4-tetrahydrobenzo[h][1,6]naphthyridine-5(6H)-one hydrochloride;
8) 9-Methoxy-1-methyl-1,2,3,4-tetrahydrobenzo[h][1,6]naphthyridine-5(6H)-one hydrochloride;
9) 1-Ethyl-9-methoxy-1,2,3,4-tetrahydrobenzo[h][1,6]naphthyridine-5(6H)-one hydrochloride;
10) 1-Methyl-9-hydroxy-1,2,3,4-tetrahydrobenzo[h][1,6]naphthyridine-5(6H)-one hydrochloride;
11) 9-(1-Propylpiperidine-4-yloxy)-1,2,3,4-tetrahydrobenzo[h][1,6]naphthyridine-5(6H)-one dihydrochloride;
12) 9-(1-Methylpiperidine-4-yloxy)-1,2,3,4-tetrahydrobenzo[h][1,6]naphthyridine-5(6H)-one dihydrochloride;
13) 1-Methyl-9-(piperidine-4-yloxy)-1,2,3,4-tetrahydrobenzo[h][1,6]naphthyridine-5(6H)-one dihydrochloride;
14) 1-Methyl-9-(1-methylpiperidine-4-yloxy)-1,2,3,4-tetrahydrobenzo[h][1,6]naphthyridine-5(6H)-one dihydrochloride;
15) 5-Oxo-N-[2-(piperidine-1-yl)ethyl]-1,2,3,4,5,6-hexahydrobenzo[h][1,6]naphthyridine-9-carboxamide dihydrochloride;
16) 9-[2-(Dimethylamino)ethoxy]-1,2,3,4-tetrahydrobenzo[h][1,6]naphthyridine-5(6H)-one dihydrochloride;
17) 9-[2-(Piperidine-1-yl)ethoxy]-1,2,3,4-tetrahydrobenzo[h][1,6]naphthyridine-5(6H)-one dihydrochloride;
18) 9-(2-Methoxyethoxy)-1,2,3,4-tetrahydrobenzo[h][1,6]naphthyridine-5(6H)-one hydrochloride;
19) 9-[2-(Piperazine-1-yl)ethoxy]-1,2,3,4-tetrahydrobenzo[h][1,6]naphthyridine-5(6H)-one trihydrochloride;
20) 9-Ethoxy-1,2,3,4-tetrahydrobenzo[h][1,6]naphthyridine-5(6H)-one hydrochloride;
21) 9-[3-(Piperidine-1-yl)propoxy]-1,2,3,4-tetrahydrobenzo[h][1,6]naphthyridine-5(6H)-one dihydrochloride;
22) 9-(2-Aminoethoxy)-1,2,3,4-tetrahydrobenzo[h][1,6]naphthyridine-5(6H)-one dihydrochloride;
23) 9-[2-(4-Phenylpiperidine-1-yl)ethoxy]-1,2,3,4-tetrahydrobenzo[h][1,6]naphthyridine-5(6H)-one dihydrochloride;
24) 9-(2-Hydroxyethoxy)-1,2,3,4-tetrahydrobenzo[h][1,6]naphthyridine-5(6H)-one hydrochloride;
25) 9-Penethoxy-1,2,3,4-tetrahydrobenzo[h][1,6]naphthyridine-5(6H)-one hydrochloride;
26) 9-[2-(Diethylamino)ethoxy]-1,2,3,4-tetrahydrobenzo[h][1,6]naphthyridine-5(6H)-one dihydrochloride;
27) 9-(2-Morpholinoethoxy)-1,2,3,4-tetrahydrobenzo[h][1,6]naphthyridine-5(6H)-one dihydrochloride;
28) 1,1-Diethyl-4-[2-(5-oxo-1,2,3,4,5,6-hexahydrobenzo[h][1,6]naphthyridine-9-yloxy]ethyl)piperazine-1-ium dihydrochloride;
29) 9-[4-(Piperidine-1-yl)butoxy]-1,2,3,4-tetrahydrobenzo[h][1,6]naphthyridine-5(6H)-one dihydrochloride;
30) 1-Methyl-9-[2-(piperidine-1-yl)ethoxy]-1,2,3,4-tetrahydrobenzo[h][1,6]naphthyridine-5(6H)-one dihydrochloride;
31) 9-[2-(Dimethylamino)ethyl]-1,2,3,4-tetrahydrobenzo[h][1,6]naphthyridine-5(6H)-one dihydrochloride;
32) 8-[2-(Dimethylamino)ethoxy]-1,2,3,4,-tetrahydrobenzo[h][1,6]naphthyridine-5(6H)-one dihydrochloride;
33) 9-[3-(Dimethylamino)propyl]-1,2,3,4-tetrahydrobenzo[h][1,6]naphthyridine-5(6H)-one dihydrochloride;
34) 8-[2-(Dimethylamino)ethoxy]-1,2,3,4,5,6-hexahydrobenzo[h][1,6]naphthyridine-9-carboxamide dihydrochloride;
35) 8-[2-(Piperidine-1-yl)ethoxy]-1,2,3,4-tetrahydrobenzo[h][1,6]naphthyridine-5(6H)-one dihydrochloride;
36) 8-[3-(Dimethylamino)propoxy]-1,2,3,4-tetrahydrobenzo[h][1,6]naphthyridine-5(6H)-one dihydrochloride;
37) 8-(Dimethylamino)-1,2,3,4-tetrahydrobenzo[h][1,6]naphthyridine-5(6H)-one hydrochloride;
38) 8-[1-(Dimethylamino)ethyl]-1,2,3,4-tetrahydrobenzo[h][1,6]naphthyridine-5(6H)-one dihydrochloride;
39) 8-[1-(Methylamino)ethyl]-1,2,3,4-tetrahydrobenzo[h][1,6]naphthyridine-5(6H)-one dihydrochloride;
40) 8-Ethyl-1,2,3,4-tetrahydrobenzo[h][1,6]naphthyridine-5(6H)-one hydrochloride;
41) 8-[(Dimethylamino)methyl]-1,2,3,4-tetrahydrobenzo[h][1,6]naphthyridine-5(6H)-one dihydrochloride;
42) 8-[(Diethylamino)methyl]-1,2,3,4-tetrahydrobenzo[h][1,6]naphthyridine-5(6H)-one dihydrochloride;
43) 8-[(Ethylamino)methyl]-1,2,3,4-tetrahydrobenzo[h][1,6]naphthyridine-5(6H)-one dihydrochloride;
44) 8-(Pyrolidine-1-ylmethyl)-1,2,3,4-tetrahydrobenzo[h][1,6]naphthyridine-5(6H)-one dihydrochloride;
45) 8-[(Isopropylamino)methyl]-1,2,3,4-tetrahydrobenzo[h][1,6]naphthyridine-5(6H)-one dihydrochloride;
46) 8-[(Propylamino)methyl]-1,2,3,4-tetrahydrobenzo[h][1,6]naphthyridine-5(6H)-one dihydrochloride;
47) 8-{[Ethyl(methyl)amino]methyl}-1,2,3,4-tetrahydrobenzo[h][1,6]naphthyridine-5(6H)-one dihydrochloride;
48) 8-(Piperidine-1-ylmethyl)-1,2,3,4-tetrahydrobenzo[h][1,6]naphthyridine-5(6H)-one dihydrochloride;
49) 8-(Morpholinomethyl)-1,2,3,4-tetrahydrobenzo[h][1,6]naphthyridine-5(6H)-one dihydrochloride;
50) 9-[(Dimethylamino)methyl]-1,2,3,4-tetrahydrobenzo[h][1,6]naphthyridine-5(6H)-one dihydrochloride;
51) 8-{[Benzyl(methyl)amino]methyl}-1,2,3,4-tetrahydrobenzo[h][1,6]naphthyridine-5(6H)-one dihydrochloride;
52) 8-[(Methylamino)methyl]-1,2,3,4-tetrahydrobenzo[h][1,6]naphthyridine-5(6H)-one dihydrochloride;
53) 8-{[(2-Hydroxyethyl)(methyl)amino]methyl}-1,2,3,4-tetrahydrobenzo[h][1,6]naphthyridine-5(6H)-one dihydrochloride;
54) 8-{[(2-Dimethylaminoethyl)(methyl)amino]methyl}-1,2,3,4-tetrahydrobenzo[h][1,6]naphthyridine-5(6H)-one trihydrochloride;
55) 8-[(4-Methylpiperazine-1-yl)methyl]-1,2,3,4-tetrahydrobenzo[h][1,6]naphthyridine-5(6H)-one trihydrochloride;
56) 8-[(Methyl(propyl)amino]methyl]-1,2,3,4-tetrahydrobenzo[h][1,6]naphthyridine-5(6H)-one dihydrochloride;
57) Ethyl-3-{methyl[(5-oxo-1,2,3,4,5,6-hexahydrobenzo[h][1,6]naphthyridine-8-yl)methyl]amino}propanoate dihydrochloride;
58) 3-{Methyl[(5-oxo-1,2,3,4,5,6-hexahydrobenzo[h][1,6]naphthyridine-8 yl)methyl]amino}propanoic acid dihydrochloride;
59) 8-{[Isopropyl(methyl)amino]methyl}-1,2,3,4-tetrahydrobenzo[h][1,6]naphthyridine-5(6H)-one dihydrochloride;

60) 8-{[(2-Methoxyethyl)(methyl)amino]methyl}-1,2,3,4-tetrahydrobenzo[h][1,6]naphthyridine-5(6H)-one dihydrochloride;
61) Ethyl-3-[(5-oxo-1,2,3,4,5,6-hexahydrobenzo[h][1,6]naphthyridine-8yl)methylamino]propanoate dihydrochloride;
62) 8-[(2,2,2-Trifluoroethylamino)methyl]-1,2,3,4-tetrahydrobenzo[h][1,6]naphthyridine-5(6H)-one dihydrochloride;
63) 2-[(5-Oxo-1,2,3,4,5,6-hexahydrobenzo[h][1,6]naphthyridine-8yl)methylamino]acetonitrile dihydrochloride;
64) 8-[(1H-Imidazole-1-yl)methyl]-1,2,3,4-tetrahydrobenzo[h][1,6]naphthyridine-5(6H)-one hydrochloride;
65) 8-[(1H-Pyrrole-1-yl)methyl]-1,2,3,4-tetrahydrobenzo[h][1,6]naphthyridine-5(6H)-one hydrochloride;
66) 8-[(Dimethylamino)methyl]-1-methyl-1,2,3,4-tetrahydrobenzo[h][1,6]naphthyridine-5(6H)-one dihydrochloride;
67) 1-Methyl-8-(pyrolidine-1ylmethyl)-1,2,3,4-tetrahydrobenzo[h][1,6]naphthyridine-5(6H)-one dihydrochloride;
68) 8-[(Diethylamino)methyl]-1-methyl-1,2,3,4-tetrahydrobenzo[h][1,6]naphthyridine-5(6H)-one dihydrochloride;
69) 1-Methyl-8-(piperidine-1-ylmethyl)-1,2,3,4-tetrahydrobenzo[h][1,6]naphthyridine-5(6H)-one dihydrochloride;
70) 1-Methyl-8-(morpholinomethyl)-1,2,3,4-tetrahydrobenzo[h][1,6]naphthyridine-5(6H)-one dihydrochloride;
71) 8-{[Ethyl(methyl)amino]methyl}-1-methyl-1,2,3,4-tetrahydrobenzo[h][1,6]naphthyridine-5(6H)-one dihydrochloride;
72) 8-[(Dimethylamino)methyl]-10-methoxy-1,2,3,4-tetrahydrobenzo[h][1,6]naphthyridine-5(6H)-one dihydrochloride;
73) 10-Methoxy-8-[(methylamino)methyl]-1,2,3,4-tetrahydrobenzo[h][1,6]naphthyridine-5(6H)-one dihydrochloride;
74) 10-Methoxy-8-(morpholinomethyl)-1,2,3,4-tetrahydrobenzo[h][1,6]naphthyridine-5(6H)-one dihydrochloride;
75) 8-[(Ethylamino)methyl]-10-methoxy-1,2,3,4-tetrahydrobenzo[h][1,6]naphthyridine-5(6H)-one dihydrochloride;
76) 8-{[Ethyl(methyl)amino]methyl}-10-methoxy-1,2,3,4-tetrahydrobenzo[h][1,6]naphthyridine-5(6H)-one;
77) 10-Methoxy-8-(pyrrolidine-1-ylmethyl)-1,2,3,4-tetrahydrobenzo[h][1,6]naphthyridine-5(6H)-one dihydrochloride;
78) 10-Methoxy-8-[(4-oxopiperidine-1-yl)methyl]-1,2,3,4-tetrahydrobenzo[h][1,6]naphthyridine-5(6H)-one dihydrochloride;
79) 8-{[4-(Hydroxyimino)piperidine-1-yl]methyl}-10-methoxy-1,2,3,4-tetrahydrobenzo[h][1,6]naphthyridine-5(6H)-one trihydrochloride;
80) 10-Methoxy-8-[(4-(methoxyimino)piperidine-1-yl)methyl]-1,2,3,4-tetrahydrobenzo[h][1,6]naphthyridine-5(6H)-one trihydrochloride;
81) 10-Methoxy-8-{[(2-methoxyethyl)(methyl)amino]methyl}-1,2,3,4-tetrahydrobenzo[h][1,6]naphthyridine-5(6H)-one dihydrochloride;
82) 8-[(2,5-Dehydro-1H-pyrrole-1-yl)methyl]-10-methoxy-1,2,3,4-tetrahydrobenzo[h][1,6]naphthyridine-5(6H)-one dihydrochloride;
83) 8-{[(2-Isopropoxyethyl)(methyl)amino]methyl}-10-methoxy-1,2,3,4-tetrahydrobenzo[h][1,6]naphthyridine-5(6H)-one dihydrochloride;
84) 10-Methoxy-8-(piperidine-1-ylmethyl)-1,2,3,4-tetrahydrobenzo[h][1,6]naphthyridine-5(6H)-one dihydrochloride;
85) 8-{[(2-Chloroethyl)(methyl)amino]methyl}-10-methoxy-1,2,3,4-tetrahydrobenzo[h][1,6]naphthyridine-5(6H)-one dihydrochloride;
86) 8-[(Diethylamino)methyl]-10-methoxy-1,2,3,4-tetrahydrobenzo[h][1,6]naphthyridine-5(6H)-one dihydrochloride;
87) 8-[(t-Butylamino)methyl]-10-methoxy-1,2,3,4-tetrahydrobenzo[h][1,6]naphthyridine-5(6H)-one dihydrochloride;
88) 8-[(Isopropylamino)methyl]-10-methoxy-1,2,3,4-tetrahydrobenzo[h][1,6]naphthyridine-5(6H)-one dihydrochloride;
89) 8-[(Cyclopentylamino)methyl]-10-methoxy-1,2,3,4-tetrahydrobenzo[h][1,6]naphthyridine-5(6H)-one dihydrochloride;
90) 8-[(2,6-Dimethylmorpholino)methyl]-10-methoxy-1,2,3,4-tetrahydrobenzo[h][1,6]naphthyridine-5(6H)-one dihydrochloride;
91) N-[(10-Methoxy-5-oxo-1,2,3,4,5,6-hexahydrobenzo[h][1,6]naphthyridine-8yl)methyl]-N,N-dimethylcyclopentane aminium chloride hydrochloride;
92) 8-{[Cyclopentyl(methyl)amino]methyl}-10-methoxy-1,2,3,4-tetrahydrobenzo[h][1,6]naphthyridine-5(6H)-one dihydrochloride;
93) 8-{[Isopropyl(methyl)amino]methyl}-10-methoxy-1,2,3,4-tetrahydrobenzo[h][1,6]naphthyridine-5(6H)-one dihydrochloride;
94) 8-{[(2-Fluoroethyl)(methyl)amino]methyl}-10-methoxy-1,2,3,4-tetrahydrobenzo[h][1,6]naphthyridine-5(6H)-one dihydrochloride;
95) 8-[(1H-Tetrazol-5yl)methyl]-1,2,3,4-tetrahydrobenzo[h][1,6]naphthyridine-5(6H)-one hydrochloride;
96) 10-Methoxy-8-[(morpholinoamino)methyl]-1,2,3,4-tetrahydrobenzo[h][1,6]naphthyridine-5(6H)-one trihydrochloride;
97) 10-Methoxy-8-{[methyl(morpholino)amino]methyl}-1,2,3,4-tetrahydrobenzo[h][1,6]naphthyridine-5(6H)-one trihydrochloride;
98) (E)-10-Methoxy-8-[(morpholinoimino)methyl]-1,2,3,4-tetrahydrobenzo[h][1,6]naphthyridine-5(6H)-one trihydrochloride;
99) 8-[(Dimethylamino)methyl]-10-hydroxy-1,2,3,4-tetrahydrobenzo[h][1,6]naphthyridine-5-(6H)-one dihydrochloride;
100) 8-[(Dimethylamino)methyl]-10-ethoxy-1,2,3,4-tetrahydrobenzo[h][1,6]naphthyridine-5(6H)-one dihydrochloride;
101) 10-Ethoxy-8-(morpholinomethyl)-1,2,3,4-tetrahydrobenzo[h][1,6]naphthyridine-5(6H)-one dihydrochloride;
102) 10-Ethoxy-8-(piperidine-1-ylmethyl)-1,2,3,4-tetrahydrobenzo[h][1,6]naphthyridine-5(6H)-one dihydrochloride;
103) 10-Ethoxy-8-[(methylamino)methyl]-1,2,3,4-tetrahydrobenzo[h][1,6]naphthyridine-5(6H)-one dihydrochloride;
104) 10-Ethoxy-8-[(ethylamino)methyl]-1,2,3,4-tetrahydrobenzo[h][1,6]naphthyridine-5(6H)-one dihydrochloride;
105) 8-(Hydroxymethyl)-10-methoxy-1,2,3,4-tetrahydrobenzo[h][1,6]naphthyridine-5(6H)-one hydrochloride;

106) 10-Methoxy-8-(thiomorpholinomethyl)-1,2,3,4-tetrahydrobenzo[h][1,6]naphthyridine-5(6H)-one dihydrochloride;
107) 10-Methoxy-8-[(2-morpholinoethylamino)methyl)-1,2,3,4-tetrahydrobenzo[h][1,6]naphthyridine-5(6H)-one trihydrochloride;
108) 10-Methoxy-8-[(4-morpholinopiperidine-1-yl)methyl]-1,2,3,4-tetrahydrobenzo[h][1,6]naphthyridine-5(6H)-one trihydrochloride;
109) 8-(Aminomethyl)-10-methoxy-1,2,3,4-tetrahydrobenzo[h][1,6]naphthyridine-5(6H)-one dihydrochloride;
110) 8-[(Dimethylamino)methyl)]-10-propoxy-1,2,3,4-tetrahydrobenzo[h][1,6]naphthyridine-5(6H)-one dihydrochloride;
111) 8-(Morpholinomethyl)-10-propoxy-1,2,3,4-tetrahydrobenzo[h][1,6]naphthyridine-5(6H)-one dihydrochloride;
112) 8-(Aminomethyl)-1,2,3,4-tetrahydrobenzo[h][1,6]naphthyridine-5(6H)-one dihydrochloride;
113) 8-(Aminomethyl)-10-ethoxy-1,2,3,4-tetrahydrobenzo[h][1,6]naphthyridine-5(6H)-one dihydrochloride;
114) 8-(Aminomethyl)-10-propoxy-1,2,3,4-tetrahydrobenzo[h][1,6]naphthyridine-5(6H)-one dihydrochloride;
115) 10-Methoxy-8-{[methyl(tetrahydro-2H-pyran-4-yl)amino]methyl}-1,2,3,4-tetrahydrobenzo[h][1,6]naphthyridine-5(6H)-one dihydrochloride;
116) 8-[(Dimethylamino)methyl]-10-(2-methoxyethoxy)-1,2,3,4-tetrahydrobenzo[h][1,6]naphthyridine-5(6H)-one dihydrochloride;
117) 10-(2-Methoxyethoxy)-8-(morpholinomethyl)-1,2,3,4-tetrahydrobenzo[h][1,6]naphthyridine-5(6H)-one dihydrochloride; and
118) 1-[(10-Methoxy-5-oxo-1,2,3,4,5,6-hexahydrobenzo[h][1,6]naphthyridine-8-yl)methylamino]-1H-pyrrole-2,5-dione dihydrochloride.

Further, since the compound of chemical formula 1 has asymmetric center, the compound may exist as different mirror-image isomer forms, and all the optical isomers of the compound of chemical formula 1 and R or S type stereomer and mixtures thereof are also included in the scope of the invention. The invention includes use of racemic forms, one or more mirror image isomer forms, one or more diastereomer forms or mixtures thereof, and also includes the known methods for separating or process for preparing the isomers.

Furthermore, the present invention provides a pharmaceutical composition for prevention or treatment of diseases derived from over-activation of PARP, which comprise the tricyclic derivatives of chemical formula 1 or pharmaceutically acceptable salt thereof.

The diseases derived from over-activation of PARP may include neuropathic pain; neurodegeneration diseases including epilepsy, stroke, Alzheimer's disease, Parkinson's disease, amyotrophic lateral sclerosis (ALS), Huntington's disease, schizophrenia, chronic and acute pain, ischemia, neuron damage after hypoxia, external injury, and neural damage; cardiovascular diseases including atherosclerosis, hyperlipidemia, cardiac tissue damage, coronary-artery disease, myocardial infarction, angina, cardiogenic shock; diabetic neuropathy; inflammatory disease such as oatarthritis, osteoporosis, or cancer.

The tricyclic derivative of the present invention inhibits the activities of Poly(ADP-ribose)polymerase and can be used for prevention or treatment of diseases caused due to over-activation of PARP, and especially, neuropathic pain, neurodegenerative disease, cardiovascular disease, diabetic neuropathy, inflammatory disease, osteoporosis or cancer.

The pharmaceutical composition comprising the compound according to an embodiment may additionally include appropriate carrier, excipient or diluents suitable for use for methods known in the art. The carrier, excipient and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, micro-crystalline cellulose, polyvinyl pyrrolidon, water, methylhydroxybenzoate, propylhydroxybenzoate, talc, magnesium stearate, or mineral oil.

The composition comprising the compound according to an embodiment may be prepared into a dosage form including, for example, an oral preparation including powder, granules, tablet, capsule, suspension, emulsion, syrup, or aerosol, an external preparation, suppository, or sterile solution for injection.

To be specific, the composition according to an embodiment may be prepared into a dosage form using diluents or excipient such as filler, extender, binder, wetting agent, disintegrating agent, or surfactant. The solid dosage form may be prepared by mixing the compound with at least one or more of excipients such as, for example, starch, calciumcarbonate, sucrose, lactose, or gelatin. Further, a lubricant such as magnesium stearate, or talc may be used in addition to simple excipients. The liquid dosage form for oral administration may include suspension, liquid for internal use, emulsion, or syrup, and this may include various excipients other than simple diluents such as water, or liquid paraffin, such as, for example, wetting agent, sweetening agent, perfume, or preservative. The liquid dosage form for non-oral administration may include sterile aqueous solution, nonaqueous solvent, suspension, emulsion, freeze-dried formulation, and suppository. The non-aqueous solvent and suspension may include vegetable oil such as propylene glycol, polyethylene glycol, or olive oil, or ester for injectable use such as ethyl oleate. Witepsol, macrogol, tween 61, cacao oil, laurinum or glycerol-gelatin may be used as the suppository base.

Although doses of the compound of the present invention may vary depending on the state or weight of patient, seriousness of illness, dosage form, route or period of administration, the doses may be selected appropriately by those skilled in the art. However, for desirable effect, the compound of chemical formula 1 of the present invention may be administered by 0.000~11000 mg/kg, or desirably, 0.01~500 mg/kg one to several times a day. In one embodiment, the compound of chemical formula 1 may be mixed by 0.0001~50 weight % with respect to total amount of the composition.

Further, the pharmaceutical form for administration of the compound of the present invention may include pharmaceutically acceptable salt of the compound, and use of the compound alone or in combination with other pharmaceutically active compounds.

The pharmaceutical composition of the present invention may be administered to mammal including mouse, domestic animals, or human in various routes. All the administration methods are predictable, which may include peroral, rectal or intravenous, intramuscular, hypodermic, intrauterine epidural or intracerebrovascular injection.

MODE FOR INVENTION

The present inventive technical concept will be explained in greater detail below based on the examples and experimental datas which are not to be construed as limiting the present inventive concept.

Example 1

Synthesis of 8-Methoxy-1,2,3,4-tetrahydrobenzo[h][1,6]naphthyridine-5(6H)-one hydrochloride Step 1: Synthesis of 2-Chloro-N-(3-methoxyphenyl)nicotine amide

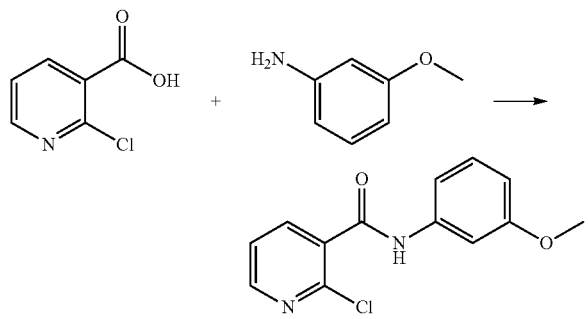

To a stirred solution of 2-chloronicotinic acid (500 mg, 3.17 mmol) in anhydrous dichloromethane (10 ml) was added dropwise oxalyl chloride (0.407 ml, 4.76 mmol) at a room temperature. A drop of anhydrous N,N-dimethylformamide was added and the reaction mixture stirred for 2 hours at a room temperature. Once the reaction was completed, intermediate product, i.e., 2-chloronicotinyl chloride was obtained with vacuum-concentration. Anhydrous dichloromethane (10 ml) was added, and then 3-anisidine (0.390 ml, 3.49 mmol) in anhydrous dichloromethane (5 ml) was added dropwise at 0° C. to a solution of the above mixture. Triethylamine (0.885 ml, 6.347 mmol) was added and the mixture was stirred for one hour at 0° C. Once the reaction was completed, water was added and the resultant mixture was extracted with dichloromethane. The separated organic layer was dried over anhydrous magnesium sulfate, and the solvent was concentrated under reduced pressure to obtain the title compound (970 mg, ivory oil).

$^1$H NMR (400 MHz, CDCl$_3$); δ 8.49 (dd, J=2.0 Hz, 4.8 Hz, 1H), 8.26 (s, 1H), 8.14 (dd, J=1.6 Hz, 7.2 Hz, 1H), 7.40 (s, 1H), 7.41-7.37 (m, 1H), 7.28 (t, J=8.0 Hz, 1H), 7.13-7.10 (m, 1H), 6.75 (dd, J=2.4 Hz, 8.4 Hz, 1H), 3.84 (s, 3H)

Step 2: Synthesis of 2-Chloro-N-(4-methoxybenzyl)-N-(3-methoxyphenyl)nicotine amide

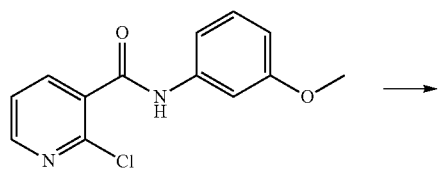

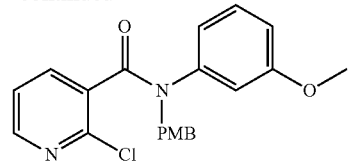

N,N-Dimethylformamide was added to the compound (972.4 mg, 3.1736 mmol) prepared in step 1 and the mixture was cooled to 0° C. Sodium hydride (380 mg, 9.52 mmol) was slowly added and the resulting mixture stirred at 0° C. for 20 minutes. p-Methoxybenzyl chloride (0.646 ml, 4.76 mmol) was added at 0° C. and the mixture stirred for 3 hours at room temperature. Once the reaction was completed, dichloromethane and water was added, the organic layer was dried over magnesium sulfate, and the solvent was concentrated under reduced pressure. The residue was purified by flash column chromatography (hexane:ethyl acetate=2.5:1) to obtain the title compound (1.01 g, yield: 84%, ivory oil).

$^1$H NMR (400 MHz, CDCl$_3$); δ 8.20 (dd, J=1.6 Hz, 4.4 Hz, 1H), 7.44 (dd, J=1.6 Hz, 7.6 Hz, 1H), 7.25 (d, J=8.8 Hz, 2H), 7.05 (dd, J=4.8 Hz, 7.2 Hz, 1H), 7.01 (t, J=7.6 Hz, 1H), 6.84 (d, J=8.8 Hz, 2H), 6.64 (dd, J=2.8 Hz, 8.4 Hz, 1H), 6.55-6.53 (m, 1H), 6.50 (s, 1H), 5.03 (s, 2H), 3.80 (s, 3H), 3.61 (s, 3H)

Step 3: Synthesis of 8-Methoxy-6-(4-methoxybenzyl)benzo[h][1,6]naphthyridine-5(6H)-one

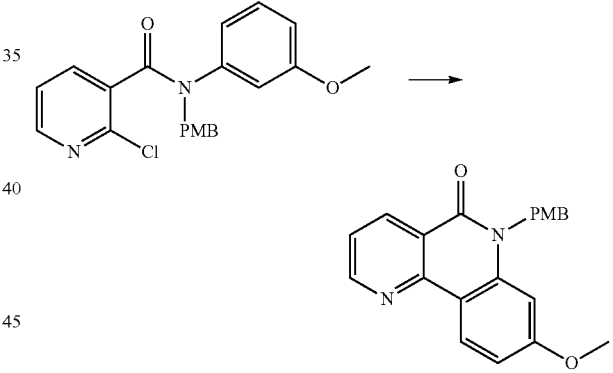

To a stirred solution of the compound (873 mg, 2.28 mmol) prepared in step 2 in N,N-dimethylformamide (6.0 ml), were added sequently palladium(II) acetate (153.6 mg, 0.684 mmol), 1,3-bis(diphenylphosphino)propane (282 mg, 0.684 mmol), tributylphosphine (0.563 ml, 2.28 mmol), and potassium carbonate (630 mg, 4.56 mmol) and the mixture was refluxed for four hours at 120° C. Once the reaction was completed, the reaction mixture was cooled to a room temperature and extracted with dichloromethane. The organic layer was dried over anhydrous magnesium sulfate and concentrated under reduced pressure. The residue was purified by flash column chromatography (hexane:ethyl acetate:dichloromethane=1:1:1) to obtain the title compound (192.4 mg, yield: 24%, white solid).

$^1$H NMR (400 MHz, CDCl$_3$); δ 8.96 (dd, J=1.6 Hz, 4.4 Hz, 1H), 8.771 (d, J=8.8 Hz, 1H), 8.767 (d, J=8.0 Hz, 1H), 7.46 (dd, J=4.4 Hz, 8.4 Hz, 1H), 7.24 (d, J=8.8 Hz, 2H), 6.91 (dd, J=2.0 Hz, 8.8 Hz, 1H), 6.85 (s, 1H), 6.84 (d, J=8.8 Hz, 2H), 5.55 (s, 2H), 3.81 (s, 3H), 3.76 (s, 3H)

In the reaction, 10-methoxy-6-(4-methoxybenzyl)benzo[h][1,6]naphthyridine-5(6H)-one (243.8 mg, yield: 31%, white solid) was obtained as a byproduct.

$^1$H NMR (400 MHz, CDCl$_3$); δ 9.15 (m, 1H), 8.88 (m, 1H), 7.53 (m, 1H), 7.43 (t, J=8.4 Hz, 1H), 7.20 (d, J=8.4 Hz, 2H), 7.05 (d, J=8.4 Hz, 1H), 6.92 (d, J=8.4 Hz, 1H), 6.84 (d, J=8.4 Hz, 2H), 5.55 (s, 2H), 4.10 (s, 3H), 3.76 (s, 3H)

Step 4: Synthesis of 8-Methoxy-6-(4-methoxybenzyl)-1,2,3,4-tetrahydrobenzo[h][1,6]naphthyridine-5(6H)-one

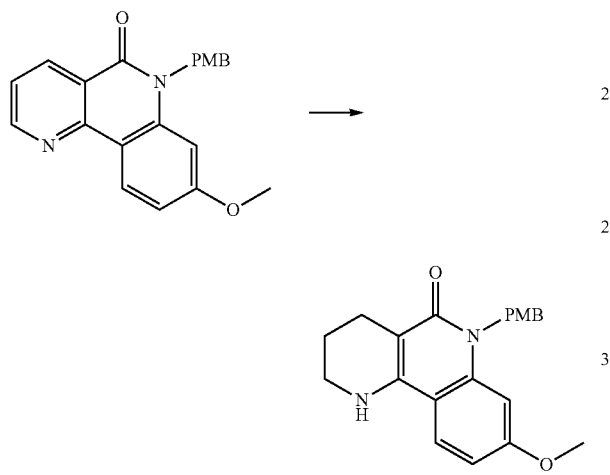

To a stirred solution of the compound of 8-methoxy-6-(4-methoxybenzyl)benzo[h][1,6]naphthyridine-5(6H)-one (192.4 mg, 0.555 mmol) prepared in step 3 in ethyl acetate/dichloromethane/methanol, was added 10%-palladium (Pd) (20 mg) and the mixture was stirred for 18 hours under hydrogen gas. Once the reaction was completed, 10%-palladium (Pd) was filtered out, and the filtrate was concentrated under reduced pressure to obtain the title compound (192.7 mg, yield: 99%, ivory solid).

$^1$H NMR (400 MHz, CDCl$_3$); δ 7.40 (d, J=8.4 Hz, 1H), 7.09 (d, J=8.8 Hz, 2H), 6.72 (d, J=8.8 Hz, 2H), 6.63 (s, 1H), 6.62 (d, J=8.4 Hz, 1H), 5.37 (s, 2H), 3.66 (s, 3H), 3.65 (s, 3H), 3.39-3.34 (m, 2H), 2.68-2.65 (m, 2H), 1.90-1.87 (m, 2H)

Step 5: Synthesis of 8-Methoxy-1,2,3,4-tetrahydrobenzo[h][1,6]naphthyridine-5(6H)-one

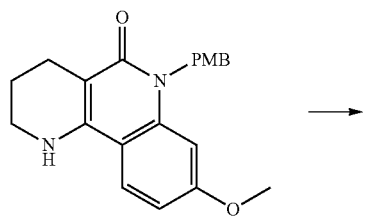

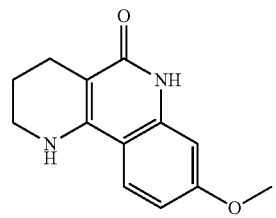

Trifluoroacetic acid (2 ml) was added to the compound (102.9 mg, 0.294 mmol) prepared in step 4 and the mixture was stirred in sealed-tube for 20 hours at 100° C. Once the reaction was completed, the reaction mixture was cooled to a room temperature and extracted with dichloromethane. The organic layer was washed with sodium bicarbonate aqueous solution, dried over anhydrous magnesium sulfate, and concentrated under reduced pressure. The residue was stirred in ethylacetate/hexane/diethylether and the resulting solid was filtered. The filtered solid was washed with diethylether and dried in vacuo to obtain the title compound (57.8 mg, yield: 85.5%, ivory solid).

$^1$H NMR (400 MHz, DMSO-d$_6$); δ 10.65 (s, 1H), 7.69 (d, J=9.6 Hz, 1H), 6.85 (s, 1H), 6.70 (s, 1H), 6.70-6.68 (m, 1H), 3.76 (s, 3H), 3.27 (m, 2H), 2.40-2.36 (m, 2H), 1.78-1.75 (m, 2H)

Step 6: Synthesis of 8-Methoxy-1,2,3,4-tetrahydrobenzo[h][1,6]naphthyridine-5(6H)-one hydrochloride

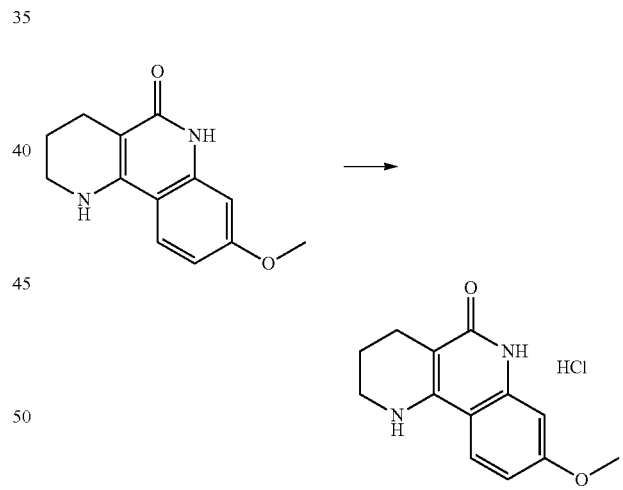

The compound (57.8 mg, 0.251 mmol) prepared in step 5 was dissolved in 1,4-dioxane (1 ml), added with 3.6N hydrochloric acid 1,4-dioxane solution (1 ml) and then stirred for 24 hours. Once the reaction was completed, the solvent was removed under reduced pressure and accordingly obtained residue was stirred for 30 minutes in ethyl acetate/diethyl ether. The resultant solid was filtered and washed with diethyl ether to obtain the title compound (38.1 mg, yield: 56.9%, green solid).

1H NMR (400 MHz, DMSO-d6); δ 11.78 (s, 1H), 7.95 (d, J=8.8 Hz, 1H), 6.93 (s, 1H), 6.94-6.90 (m, 1H), 3.82 (s, 3H), 3.37-3.35 (m, 2H), 2.55-2.52 (m, 2H), 1.83-1.80 (m, 2H)

Example 2

Synthesis of 10-Methoxy-1,2,3,4-tetrahydrobenzo[h][1,6]naphthyridine-5(6H)-one hydrochloride

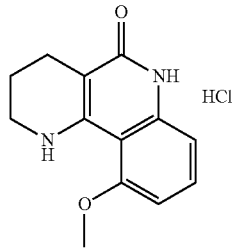 [SMILES: COc1cccc2[nH]c(=O)c3c(c12)NCCC3 ; Cl]

10-methoxy-6-(4-methoxybenzyl)benzo[h][1,6]naphthylidine-5(6H)-one (244 mg, 0.70 mmol) prepared in step 3 of Example 1 was reacted in the same manner as that of steps 4 to 6 of Example 1 to obtain the title compound (115 mg, yield: 61%, white solid).

$^1$H NMR (400 MHz, DMSO-$d_6$); δ 12.02 (s, 1H), 8.46 (br, 1H), 7.48 (t, J=8.0 Hz, 1H), 7.05 (dd, J=0.8 Hz, 8.4 Hz, 1H), 6.84 (dd, J=0.8 Hz, 8.4 Hz, 1H), 3.94 (s, 3H), 3.42-3.40 (m, 2H), 2.57-2.54 (m, 2H), 1.80-1.77 (m, 2H)

Example 3

Synthesis of 9-Methoxy-1,2,3,4-tetrahydrobenzo[h][1,6]naphthyridine-5(6H)-one hydrochloride

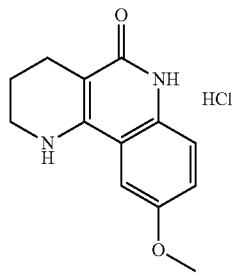 [SMILES: COc1ccc2[nH]c(=O)c3c(c2c1)NCCC3 ; Cl]

Except that 4-anisidine was used instead of 3-anisidine in step 1, the same manner as in Example 1 was applied to obtain the title compound.

$^1$H NMR (400 MHz, DMSO-$d_6$); δ 11.76 (s, 1H), 7.83 (br, 2H), 7.50 (d, J=2.0 Hz, 1H), 7.36 (d, J=8.8 Hz, 1H), 7.20 (dd, J=9.2 Hz, 2.4 Hz, 1H), 3.81 (s, 3H), 3.90 (t, J=5.2 Hz, 2H), 2.55 (t, J=5.6 Hz, 2H), 1.84-1.81 (m, 2H)

Example 4

Synthesis of 9-Methyl-1,2,3,4-tetrahydrobenzo[h][1,6]naphthyridine-5(6H)-one hydrochloride

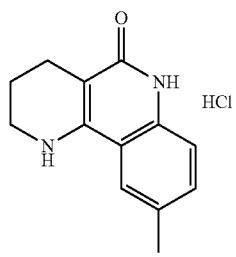 [SMILES: Cc1ccc2[nH]c(=O)c3c(c2c1)NCCC3 ; Cl]

Except that methoxymethylchloride (MOM-Cl) was used instead of p-methoxybenzylchloride in step 2, the same manner as in Example 1 was used to obtain the title compound.

$^1$H NMR (400 MHz, DMSO-$d_6$); δ 11.72 (s, 1H), 7.79 (s, 1H), 7.36 (d, J=8.4 Hz, 1H), 7.30 (d, J=8.4 Hz, 1H), 3.34 (t, J=5.6 Hz, 2H), 2.52 (t, J=6.0 Hz, 2H), 2.53 (s, 3H), 1.80 (t, J=5.2 Hz, 2H)

Example 5

Synthesis of Ethyl 5-oxo-1,2,3,4,5,6-hexahydrobenzo[h][1,6]naphthyridine-9-carboxylate hydrochloride

Step 1: Synthesis of Ethyl 4-(2-chloronicotineamido)benzoate

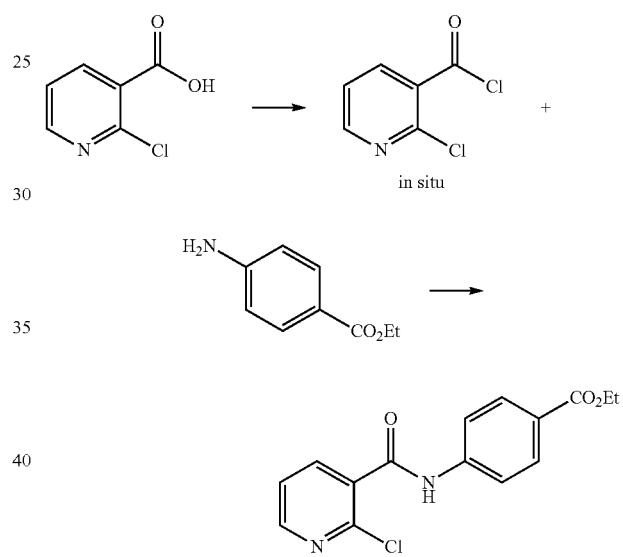

2-chloronicotinic acid (500 mg, 3.17 mmol) was dissolved in dichloromethane (10 ml), added with oxalylchloride (0.41 ml, 4.76 mmol) and N,N-dimethylformamide (cat. 1 drop) in order, and then stirred for 3 hours at room temperature. The reaction mixture was concentrated under reduced pressure and the residue was dissolved in dichloromethane (5 ml). Ethyl 4-aminobenzoate (576 mg, 3.48 mmol) and triethylamine (0.88 ml, 6.34 mmol) was added at room temperature and then the mixture was stirred for one hour. The mixture was poured into ice water, extracted with dichloromethane, and then washed with brine. The organic layer was dried over anhydrous sodium sulfate, filtered, and concentrated under reduced pressure. The residue was purified by flash column chromatography (hexane:ethyl acetate=1:1) to obtain the title compound (1.04 g, yield: quantitative yield, white solid).

$^1$H NMR (400 MHz, CDCl$_3$); δ 8.54~8.53 (m, 1H), 8.40 (brs, 1H), 8.23 (m, 1H), 8.09 (d, J=8.8 Hz, 2H), 7.75 (d, J=8.4 Hz, 2H), 7.44~7.41 (m, 1H), 4.40~4.35 (m, 2H), 1.40 (t, J=7.1 Hz, 3H)

Step 2: Synthesis of Ethyl 4-[2-chloro-N-(4-methoxybenzyl)aminonicotinamido]benzoate

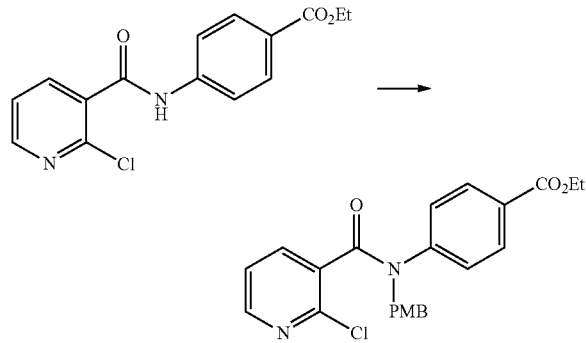

To a stirred solution of the compound (800 mg, 2.62 mmol) prepared in step 1 in N,N-dimethylformamide (10 ml), was added potassium carbonate (1.09 g, 7.87 mmol) and 4-methoxybenzyl chloride (0.43 ml, 3.15 mmol) at room temperature. The mixture was heated at 90° C. overnight. The mixture was poured into ice water and extracted with chloroform. The organic layer was washed with brine, dried over anhydrous sodium sulfate, and concentrated under reduced pressure. The residue was purified by flash column chromatography (hexane:ethyl acetate=1:1) to obtain the title compound (990 mg, yield: 89%, white solid).

$^1$H NMR (400 MHz, CDCl$_3$); δ 8.21 (m, 1H), 7.81 (d, J=8.4 Hz, 2H), 7.47~7.43 (m, 1H), 7.27~7.19 (m, 2H), 7.03~7.00 (m, 3H), 6.83 (d, J=8.4 Hz, 2H), 5.07 (brs, 2H), 4.30~4.24 (m, 2H), 3.79 (s, 3H), 1.33 (t, J=7.1 Hz, 3H)

Step 3: Synthesis of Ethyl 6-(4-methoxybenzyl)-5-oxo-5,6-dihydrobenzo[h][1,6]naphthyridine-9-carboxylate

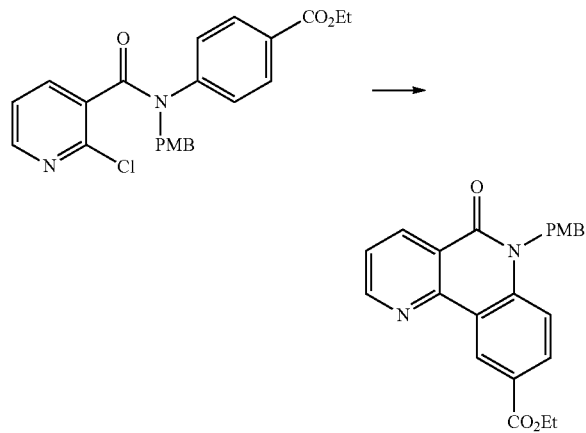

The compound (45 mg, 0.10 mmol) prepared in step 2 was dissolved in N,N-dimethylformamide (10 ml), and added with 1,3-bis(diphenylphosphino)propane (13 mg, 0.031 mmol), palladium(II) acetate (7 mg, 0.031 mmol), tributylphosphine (26 μl, 0.10 mmol), and potassium carbonate (29 mg, 0.21 mmol). The mixture was stirred for one hour at 140° C. The mixture was poured into ice water and extracted with chloroform. The organic layer was washed with brine, dried over anhydrous sodium sulfate, and concentrated under reduced pressure. The residue was purified by flash column chromatography (hexane:ethyl acetate=2:1) to obtain the title compound (34.7 mg, yield: 89%, white solid).

$^1$H NMR (400 MHz, CDCl$_3$); δ 9.56 (s, 1H), 9.09~9.08 (m, 1H), 8.84~8.81 (m, 1H), 8.18~8.16 (m, 1H), 7.61~7.58 (m, 1H), 7.44 (d, J=8.8 Hz, 1H), 7.22 (d, J=8.4 Hz, 2H), 6.85 (d, J=8.0 Hz, 2H), 5.62 (brs, 2H), 4.44 (q, J=7.3, 6.9 Hz, 2H), 3.76 (s, 3H), 1.43 (t, J=7.1 Hz, 3H)

Step 4: Synthesis of Ethyl 5-oxo-1,2,3,4,5,6-hexahydrobenzo[h][1,6]naphthyridine-9-carboxylate

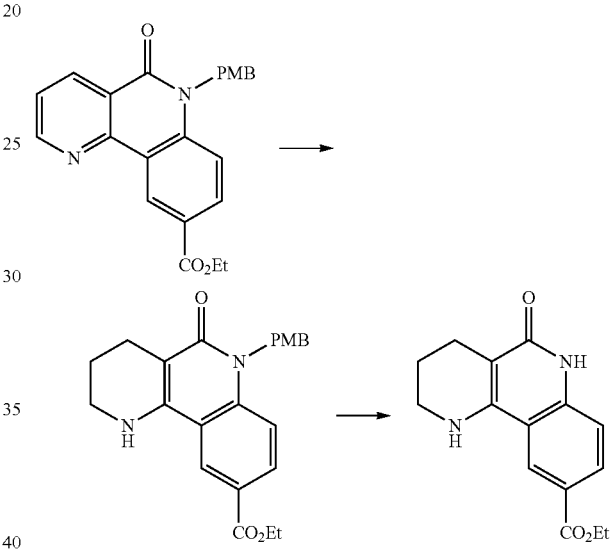

The compound (27 mg, 0.069 mmol) prepared in step 3 was dissolved in methanol (5 ml) and dichloromethane (5 ml), and added with 10%-palladium. The mixture was stirred for 18 hours at room temperature under hydrogen gas. Once the reaction was completed, 10%-palladium (Pd) was removed by celite filter and the filtrate was concentrated under reduced pressure. The residue was dissolved in trifluoroacetic acid (TFA, 2 ml), and the resultant mixture was added with anisol (0.64 ml, 0.58 mmol) and 12 N sulfuric acid aqueous solution (0.097 ml, 1.17 mmol). The reaction mixture was stirred for 18 hours at 100° C. The mixture was stirred for one hour at 140° C. The mixture was poured into a cold sodium bicarbonate aqueous solution and extracted with chloroform. The organic layer was dried over anhydrous sodium sulfate and concentrated under reduced pressure. The residue was purified by flash column chromatography (dichloromethane:methanol=7:1) to obtain the title compound (7.5 mg, yield: 47%, yellow solid).

$^1$H NMR (400 MHz, CDCl$_3$); δ 8.25 (s, 1H), 8.08 (d, J=8.4 Hz, 1H), 7.23 (d, J=8.8 Hz, 1H), 4.41 (q, J=7.3 Hz, 2H), 3.48 (t, 5.5 Hz, 2H), 2.67 (t, J=6.2 Hz, 2H), 2.00~1.94 (m, 2H), 1.42 (t, J=7.1 Hz, 3H)

Step 5: Synthesis of Ethyl 5-oxo-1,2,3,4,5,6-hexahydrobenzo[h][1,6]naphthyridine-9-carboxylate hydrochloride

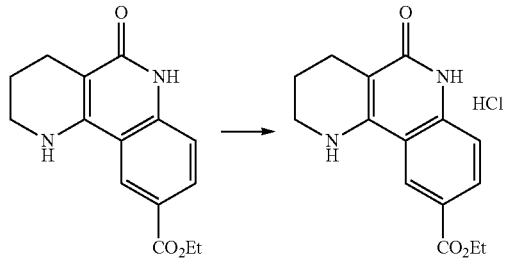 [SMILES: CCOC(=O)c1ccc2[nH]c(=O)c3c(c2c1)NCCC3 ; CCOC(=O)c1ccc2[nH]c(=O)c3c(c2c1)NCCC3 ; Cl]

The compound (7.5 mg, 0.027 mmol) prepared in step 4 was dissolved in 1,4-dioxane (1 ml), added with 3.7 N hydrochloric acid 1,4-dioxane solution (1 ml), and then stirred for 18 hours at room temperature. Once the reaction was completed, generated solid was filtered, washed with ethyl acetate, and dried in vacuo to obtain the title compound (4.5 mg, yield: 25%, white solid).

$^1$H NMR (400 MHz, DMSO-$d_6$); δ 11.17 (s, 1H), 8.48 (s, 1H), 7.95 (d, J=8.8 Hz, 1H), 7.26 (d, J=8.8 Hz, 1H), 4.35~4.29 (m, 2H), 3.31~3.28 (m, 2H), 2.46~2.44 (m, 2H), 1.81~1.74 (m, 2H), 1.35~1.32 (m, 3H)

Example 6

Synthesis of 9-Methoxy-1-propyl-1,2,3,4-tetrahydrobenzo[h][1,6]naphthyridine-5(6H)-one hydrochloride Step 1: Synthesis of 9-Methoxy-6-(4-methoxybenzyl)-1-propyl-1,2,3,4-tetrahydrobenzo[h][1,6]naphthyridine-5(6H)-one

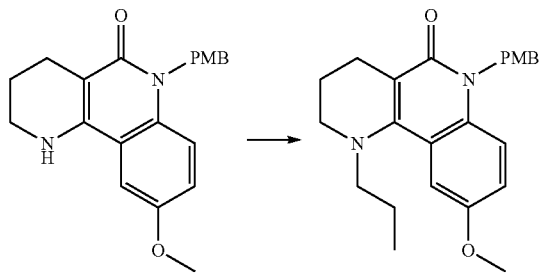

The compound of 9-methoxy-6-(4-methoxybenzyl)-1,2,3,4-tetrahydrobenzo[h][1,6]naphthyridine-5(6H)-one (100 mg, 0.285 mmol) prepared in step 4 of Example 3 was dissolved in N,N-dimethylformamide (5 ml), added with sodium hydride (17 mg, 0.428 mmol) at 0° C. The reaction mixture was stirred for 1 hour at room temperature. After that, 1-bromopropane (0.039 ml, 0.428 mmol) was added and the mixture was stirred for one more hour at room temperature. The mixture was poured into water extracted with chloroform. The organic layer was washed with saturated sodium bicarbonate aqueous solution, dried over anhydrous sodium sulfate, and concentrated under reduced pressure. The residue was purified by flash column chromatography (hexane:ethyl acetate=1:1) to obtain the title compound (56 mg, yield: 50%, yellow solid).

$^1$H NMR (400 MHz, CDCl$_3$); δ 7.26-7.14 (m, 4H), 6.98-6.95 (m, 1H), 6.82-6.81 (m, 2H), 5.45 (br, 2H), 3.83 (s, 3H), 3.75 (s, 3H), 3.17-3.15 (m, 2H), 3.01-2.97 (m, 2H), 2.71 (t, J=6.8 Hz, 2H), 1.94-1.85 (m, 4H), 0.981 (t, J=6.8 Hz, 3H)

Step 2: Synthesis of 9-Methoxy-1-propyl-1,2,3,4-tetrahydro[h][1,6]naphthyridine-5(6H)-one

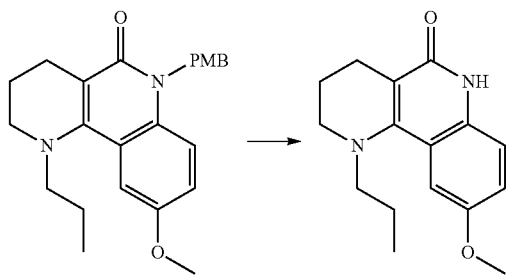

The compound (56 mg, 0.142 mmol) prepared in step 1 was dissolved in trifluoroacetic acid (3 ml) and the resulting mixture was stirred at 100° C. for one day. Once the reaction was completed, The mixture was concentrated under reduced pressure and the residue was purified by flash column chromatography (chloroform:methanol=15:1) to obtain the title compound (31 mg, yield: 82%, yellow solid).

$^1$H NMR (400 MHz, DMSO-$d_6$); δ 11.62 (s, 1H), 7.30 (d, J=4.4 Hz, 1H), 7.13 (s, 1H), 7.07-7.04 (m, 1H), 3.85 (s, 3H), 3.17-3.14 (m, 2H), 3.04-3.00 (m, 2H), 2.70 (t, J=6.8 Hz, 2H), 1.92-1.83 (m, 5H), 0.99 (t, J=7.2 Hz, 3H)

Step 3: Synthesis of 9-Methoxy-1-propyl-1,2,3-tetrahydrobenzo[h][1,6]naphthyridine-5(6H)-one hydrochloride

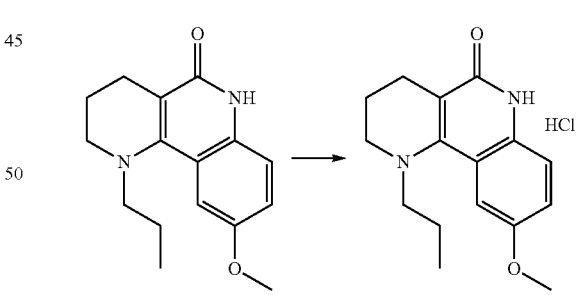

The compound (31 mg, 0.114 mmol) prepared in step 2 was dissolved in 1,4-dioxane (1 ml), added with 3.7 N hydrochloric acid 1,4-dioxane solution (1 ml), and then stirred for one day at room temperature. Once the reaction was completed, the mixture was concentrated under reduced pressure and washed with ethyl acetate to obtain the title compound (24 mg, yield: 70%, yellow solid).

$^1$H NMR (400 MHz, DMSO-$d_6$) δ 11.39 (s, 1H), 9.25-8.66 (br, 1H), 7.25 (d, J=8.8 Hz, 1H), 3.78 (s, 3H), 3.08 (m, 2H), 2.95 (t, J=7.6 Hz, 2H), 2.43 (t, J=6.8 Hz, 2H), 1.88-1.83 (m, 2H), 1.73 (m, 2H), 0.93 (t, J=7.6 Hz, 3H)

By the reaction of Example 6, the following compounds were prepared.

Example 7

1-Methyl-1,2,3,4-tetrahydrobenzo[h][1,6]naphthyridine-5(6H)-one hydrochloride

Example 8

9-Methoxy-1-methyl-1,2,3,4-tetrahydrobenzo[h][1,6]naphthyridine-5(6H)-one hydrochloride

Example 9

1-Ethyl-9-methoxy-1,2,3,4-tetrahydrobenzo[h][1,6]naphthyridine-5(6H)-one hydrochloride

Example 10

1-Methyl-9-hydroxy-1,2,3,4-tetrahydrobenzo[h][1,6]naphthyridine-5(6H)-one hydrochloride The compound prepared at Example 9 was dissolved in dichloromethane (2 ml) and 1M boron tribromide dichloromethane solution (4.2 ml). The mixture was stirred overnight at room temperature. The reaction mixture was poured into ice water and the precipitate was filtered to obtain the title compound.

| Ex. | Chemical structure | NMR spectrum data |
|---|---|---|
| 7 | 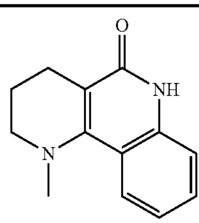 | $^1$H NMR (400 MHz, DMSO-$d_6$) δ 11.55 (s, 1H), 10.11 (br, 1H), 7.76 (d, J = 8.0 Hz, 1H), 7.41 (m, 1H), 7.29 (d, J = 8.4 Hz, 1H), 7.15 (m, 1H), 3.11 (m, 2H), 2.96 (s, 3H), 2.43 (t, J = 6.0 Hz, 2H), 1.76 (m, 2H) |
| 8 | 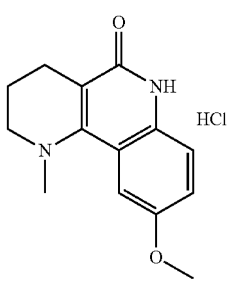 [SMILES: COc1ccc2[nH]c(=O)c3c(c2c1)N(C)CCC3 ; Cl] | $^1$H NMR (400 MHz, DMSO-$d_6$) δ 11.51 (s, 1H), 7.26 (d, J = 8.8 Hz, 1H), 7.19 (s, 1H), 7.11 (d, J = 8.8 Hz, 1H), 3.80 (s, 3H), 3.12 (m, 2H), 2.96 (s, 3H), 2.45 (t, J = 6.0 Hz, 2H), 1.76 (m, 2H) |
| 9 | 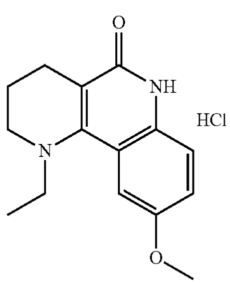 [SMILES: CCN1CCCc2c1c1cc(OC)ccc1[nH]c2=O ; Cl] | $^1$H NMR (400 MHz, DMSO-$d_6$) δ 11.38 (s, 1H), 7.24 (d, J = 8.8 Hz, 1H), 7.09 (d, J = 8.8 Hz, 1H), 7.02 (s, 1H), 3.79 (s, 3H), 3.06 (m, 4H), 2.42 (t, J = 6.0 Hz, 2H), 1.72 (m, 2H), 1.34 (t, J = 6.4 Hz, 3H) |
| 10 | 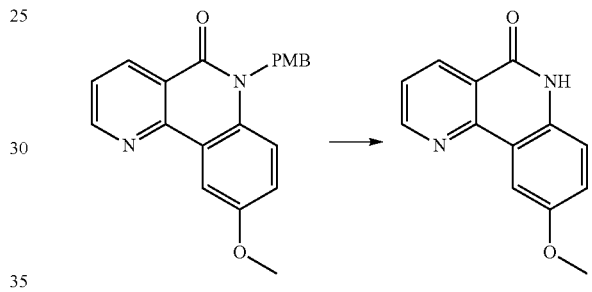 | $^1$H NMR (400 MHz, DMSO-$d_6$) δ 11.12 (s, 1H), 9.29 (s, 1H), 7.09 (d, J = 8.8 Hz, 1H), 7.07 (d, J = 2.4 Hz, 1H), 6.88 (dd, J = 8.8 Hz, 2.4 Hz, 1H), 3.05-3.02 (m, 2H), 2.85 (s, 3H), 2.39 (t, J = 6.4 Hz, 2H), 1.75-1.72 (m, 2H) |

Example 11

Synthesis of 9-(1-Propylpiperidine-4-yloxy)-1,2,3,4-tetrahydrobenzo[h][1,6]naphthyridine-5(6H)-one dihydrochloride Step 1: Synthesis of 9-Methoxybenzo[h][1,6]naphthyridine-5(6H)-one 9-Methoxy-6-(4-methoxybenzyl)benzo[h][1,6]naphthyridine-5(6H)-one (50 mg, 0.14 mmol) prepared in step 3 of Example 3 was dissolved in trifluoroacetic acid (5 ml), sequentially added with anisol (157 μl, 1.44 mmol) and 12N sulfuric acid (240 μl, 2.89 mmol). The mixture was stirred for one day at 90° C. The reaction mixture was cooled to room temperature and poured into a cold saturated sodium bicarbonate aqueous solution. After extraction with chloroform, the organic layer was washed with brine and dried over anhydrous sodium sulfate. After evaporation of the solvent, the residue was washed with ethyl acetate, filtered, and dried in vacuo to obtain the title compound (25 mg, yield: 77%, white solid).

$^1$H NMR (400 MHz, DMSO-$d_6$); δ 11.83 (s, 1H), 9.06 (d, J=6.0 Hz, 1H), 8.61 (dd, J=8.0 Hz, 2.8 Hz, 1H), 8.09 (d, J=2.4 Hz, 1H), 7.71-7.67 (m, 1H), 7.34 (d, J=8.8 Hz, 1H), 7.23 (dd, J=8.8 Hz, 2.4 Hz, 1H), 3.86 (s, 3H)

Step 2: Synthesis of 9-Hydroxybenzo[h][1,6]naphthyridine-5(6H)-one

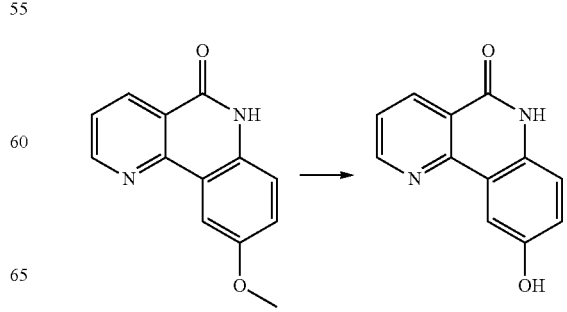

The compound (190 mg, 0.84 mmol) prepared in step 1 was dissolved in dichloromethane (2 ml), added with 1 M boron tribromide dichloromethane solution (4.2 ml). The mixture was stirred overnight at room temperature. The reaction mixture was poured into ice water and the precipitate was collected by filteration to obtain the title compound (125 mg, yield: 70%, yellow solid).

$^1$H NMR (400 MHz, DMSO-$d_6$); δ 11.70 (s, 1H), 9.56 (s, 1H), 9.03 (m, 1H), 8.58 (d, J=7.6 Hz, 1H), 7.99 (s, 1H), 7.65 (dd, J=7.6 Hz, 1.2 Hz, 1H), 7.24 (d, J=8.8 Hz, 1H), 7.05 (dd, J=8.8 Hz, 1.6 Hz, 1H)

Step 3: Synthesis of t-Butyl 4-(5-oxo-5,6-dihydrobenzo[h][1,6]naphthyridine-9-yloxy)piperidine-1-carboxylate

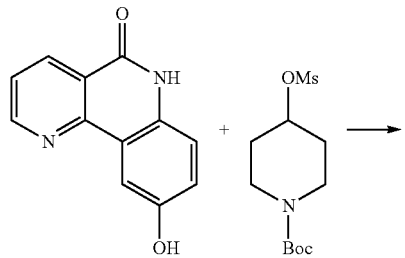

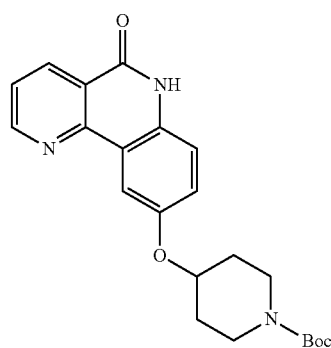

The compound (60 mg, 0.28 mmol) prepared in step 2 and potassium carbonate (120 mg, 0.85 mmol) were dissolved in acetonitrile (6 ml)/N,N-dimethylformamide (3 ml), added with t-butyl 4-(methylsulfonyloxy)piperidine-1-carboxylate (240 mg, 0.85 mmol). The resulting mixture was stirred for 3 days at 100~110° C. and cooled to room temperature. After extraction with chloroform, the reaction mixture was washed with brine and dried over anhydrous sodium sulfate. The solvent was removed under reduced pressure and the residue was purified by flash column chromatography (chloroform:methanol=10:1) to obtain the title compound (65 mg, yield: 58%, white solid).

$^1$H NMR (400 MHz, CDCl$_3$); δ 11.06 (s, 1H), 9.03 (m, 1H), 8.80 (d, J=7.6 Hz, 1H), 8.27 (d, J=2.4 Hz, 1H), 7.56 (m, 1H), 7.34 (d, J=8.8 Hz, 1H), 7.20 (dd, J=8.8 Hz, 2.4 Hz, 1H), 4.67 (m, 1H), 3.75-3.70 (m, 2H), 3.42-3.36 (m, 2H), 1.98-1.97 (m, 2H), 1.83-1.81 (m, 2H), 1.47 (s, 9H)

Step 4: Synthesis of 9-(Piperidine-4-yloxy)benzo[h][1,6]naphthyridine-5(6H)-one

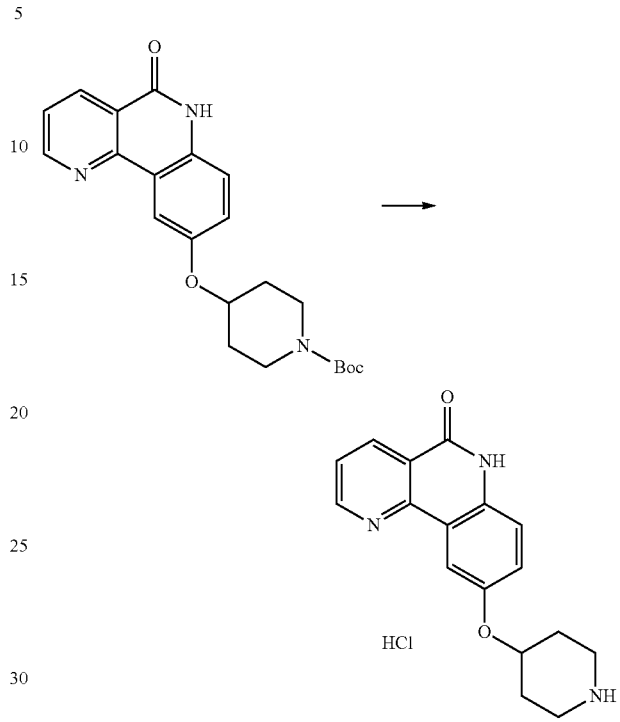

The compound (110 mg, 0.28 mmol) prepared in step 3 was dissolved in 1,4-dioxane, added with 3.7 N hydrochloric acid 1,4-dioxane solution. The resulting mixture was stirred overnight at room temperature and the precipitate was collected by filtration to obtain the title compound (90 mg, yield: 98%, yellow solid).

$^1$H NMR (400 MHz, DMSO-$d_6$); δ 11.89 (s, 1H), 9.10 (br, 2H), 9.06 (m, 1H), 8.64 (dd, J=8.0 Hz, 1.6 Hz, 1H), 8.20 (s, 1H), 7.71 (dd, J=7.6 Hz, 4.0 Hz, 1H), 7.37 (d, J=8.8 Hz, 1H), 7.31 (dd, J=8.8 Hz, 3.2 Hz, 1H), 4.78-4.76 (m, 1H), 3.24-3.23 (m, 2H), 3.12-3.10 (m, 2H), 2.16-2.12 (m, 2H), 1.93-1.88 (m, 2H)

Step 5: Synthesis of 9-(1-Propylpiperidine-4-yloxy)benzo[h][1,6]naphthyridine-5(6H)-one

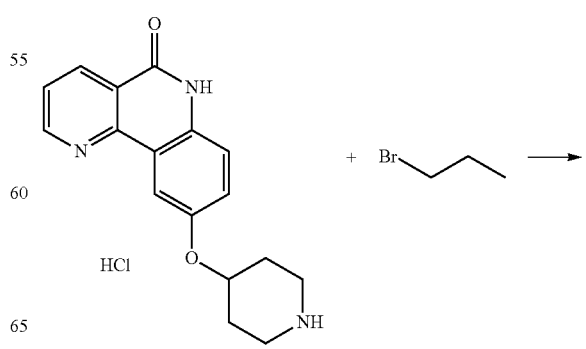

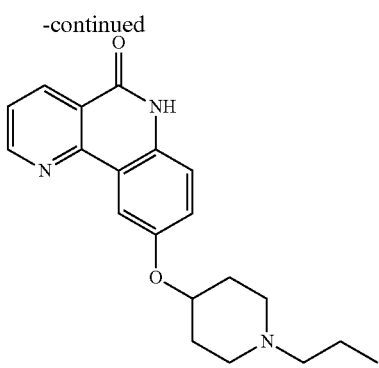

Compound (55 mg, 0.17 mmol) prepared in step 4 and potassium carbonate (70 mg, 0.50 mmol) were dissolved in acetonitrile (10 ml), added with 1-bromopropane (53 μl, 0.058 mol) at room temperature. The resulting mixture was stirred overnight at 60° C. and extracted with chloroform. The organic layer was washed with brine, dried over anhydrous sodium sulfate, and concentrated under reduced pressure. The residue was then purified by flash column chromatography (chloroform:methanol=5:1) to obtain the title compound (34 mg, yield: 61%, white solid).

$^1$H NMR (400 MHz, CDCl$_3$); δ 10.59 (s, 1H), 9.04 (m, 1H), 8.80 (dd, J=8.0 Hz, 2.0 Hz, 1H), 8.27 (d, J=2.4 Hz, 1H), 7.56 (dd, J=8.0 Hz, 4.8 Hz, 1H), 7.29 (d, J=8.8 Hz, 1H), 7.21 (dd, J=8.8 Hz, 2.4 Hz, 1H), 4.56 (m, 1H), 2.82 (m, 2H), 2.41 (m, 4H), 2.14 (m, 2H), 1.95 (m, 2H), 1.58 (m, 2H), 0.93 (t, J=7.2 Hz, 3H)

Step 6: Synthesis of 9-(1-Propylpiperidine-4-yloxy)-1,2,3,4-tetrahydrobenzo[h][1,6]naphthyridine-5(6H)-one

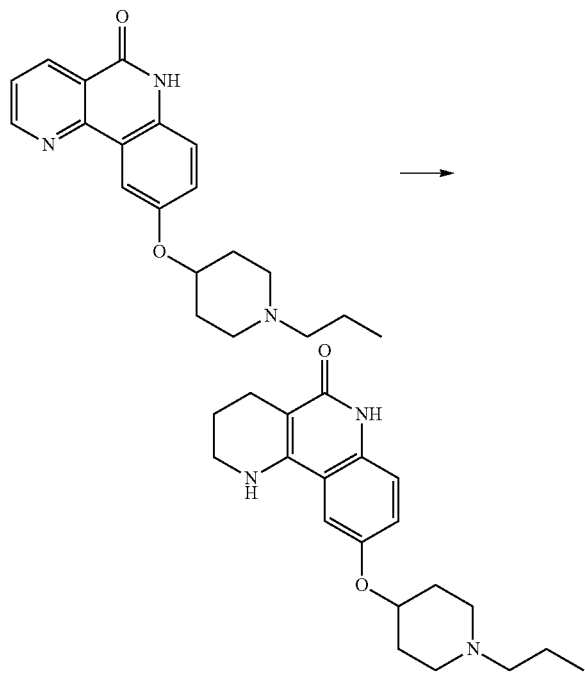

The compound (30 mg, 0.09 mmol) prepared in step 5 was dissolved in ethanol (4 ml)/dichloromethane (2 ml), added with 10%-palladium (Pd) (6 mg) at room temperature. The resulting mixture was stirred for one day under hydrogen gas. By using celite, 10%-palladium (Pd) was removed and the filtrate was concentrated under reduced pressure. Elthyl acetate was added and the precipitate was collected by filtration to obtain the title compound (28 mg, yield: 92%, white solid).

$^1$H NMR (400 MHz, CDCl$_3$+CD$_3$OD); δ 7.18-7.14 (m, 2H), 7.05 (d J=8.8 Hz, 1H), 4.64 (m, 1H), 3.44 (m, 2H), 2.66 (m, 2H), 2.35 (m, 2H), 2.12-2.09 (m, 2H), 1.98-1.92 (m, 2H), 1.80 (m, 2H), 1.00 (t, J=7.2 Hz, 3H)

Step 7: Synthesis of 9-(1-Propylpiperidine-4-yloxy)-1,2,3,4-tetrahydrobenzo[h][1,6]naphthyridine-5(6H)-one dihydrochloride

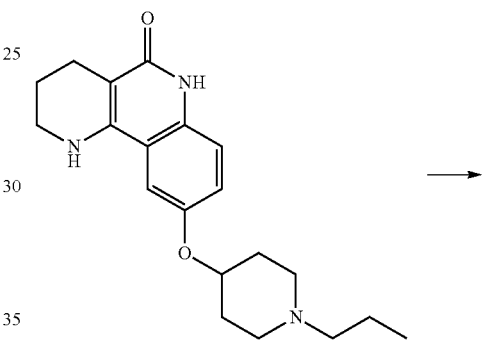

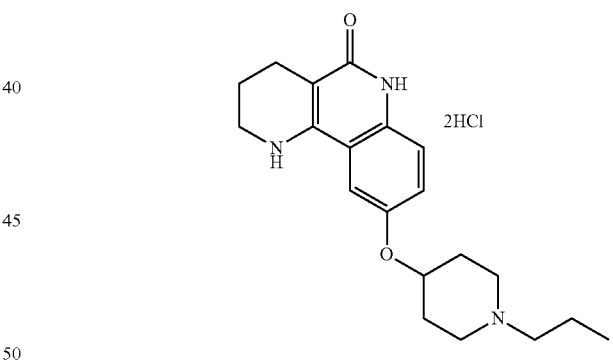

The compound (28 mg, 0.08 mmol) prepared in step 6 was dissolved in ethanol/1,4-dioxane, added with 3.7 N hydrochloric acid 1,4-dioxane solution. The resulting mixture was stirred overnight at room temperature. Once the reaction was completed, the mixture was concentrated under reduced pressure and washed with ethyl acetate. The organic layer was dried over anhydrous sodium sulfate and concentrated under reduced pressure to obtain the title compound (27 mg, yield: 79%, yellow solid).

$^1$H NMR (400 MHz, DMSO-d$_6$); δ 11.77 (m, 1H), 10.73 (br, 2H), 7.75 (m, 1H), 7.39-7.36 (m, 1H), 7.27-7.23 (m, 1H), 4.81-4.69 (m, 1H), 3.53 (m, 2H), 3.38 (m, 2H), 3.15-3.05 (m, 4H), 2.54 (m, 2H), 2.23-2.19 (m, 2H), 2.08-2.00 (m, 2H), 1.82 (m, 2H), 1.73 (m, 2H), 0.91 (t, J=7.2 Hz, 3H)

Example 12

Synthesis of 9-(1-Methylpiperidine-4-yloxy)-1,2,3,4-tetrahydrobenzo[h][1,6]naphthyridine-5(6H)-one dihydrochloride

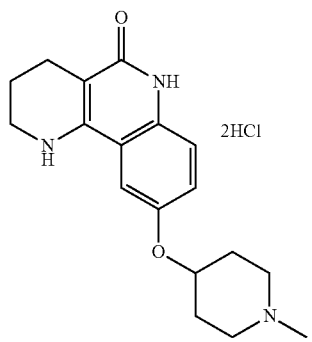 [SMILES: CN1CCC(Oc2ccc3[nH]c(=O)c4c(c3c2)NCCC4)CC1]

Except that 1-bromomethane was used instead of bromopropane in step 5 of Example 11, the same manner as in Example 11 was performed to obtain the title compound.

$^1$H NMR (400 MHz, DMSO-$d_6$); δ 11.52 (d, J=12.0 Hz, 1H), 10.60 (s, 1H), 7.65 (s, 1H), 7.34-7.31 (m, 1H), 7.25-7.20 (m, 1H), 4.76-4.59 (m, 1H), 3.50-3.29 (m, 4H), 3.15-3.06 (m, 2H), 2.67 (m, 4H), 2.23-2.04 (m, 3H), 1.88-1.80 (m, 4H)

Example 13

Synthesis of 1-Methyl-9-(piperidine-4-yloxy)-1,2,3,4-tetrahydrobenzo[h][1,6]naphthyridine-5(6H)-one dihydrochloride

Step 1: Synthesis of t-Butyl 4-(1-methyl-5-oxo-1,2,3,4,5,6-hexahydrobenzo[h][1,6]naphthyridine-9-yloxy)piperidine-1-carboxylate

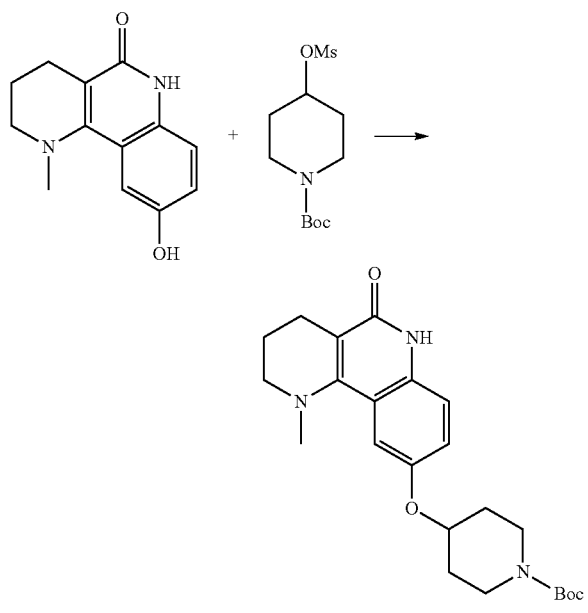

9-Hydroxy-1-methyl-1,2,3,4-tetrahydrobenzo[h][1,6]naphthyridine-5(6H)-one (60 mg, 0.26 mmol) prepared at Example 10 was dissolved in acetonitrile (8 ml)/N,N-dimethylformamide (4 ml), added with t-butyl 4-(methylsulfonyloxy)piperidine-1-carboxylate (220 mg, 0.78 mmol) at room temperature. The resulting mixture was stirred for four days at 90~100° C. and extracted with chloroform. The organic layer was washed with brine, dried over anhydrous sodium sulfate, concentrated under reduced pressure. The residue was then purified with flash column chromatography (chloroform:methanol=20:1) to obtain the title compound (70 mg, yield: 65%, brown oil).

$^1$H NMR (400 MHz, CDCl$^3$); δ 11.35 (s, 1H), 7.27 (m, 2H), 7.06 (dd, J=8.8 Hz, 3.2 Hz, 1H), 4.49-4.44 (m, 1H), 3.75-3.68 (m, 2H), 3.38-3.31 (m, 2H), 3.17-3.15 (m, 2H), 2.98 (s, 3H), 2.69 (t, J=6.4 Hz, 2H), 1.95-1.75 (m, 6H), 1.47 (s, 9H)

Step 2: Synthesis of 1-Methyl-9-(piperidine-4-yloxy)-1,2,3,4-tetrahydrobenzo[h][1,6]naphthyridine-5(6H)-one

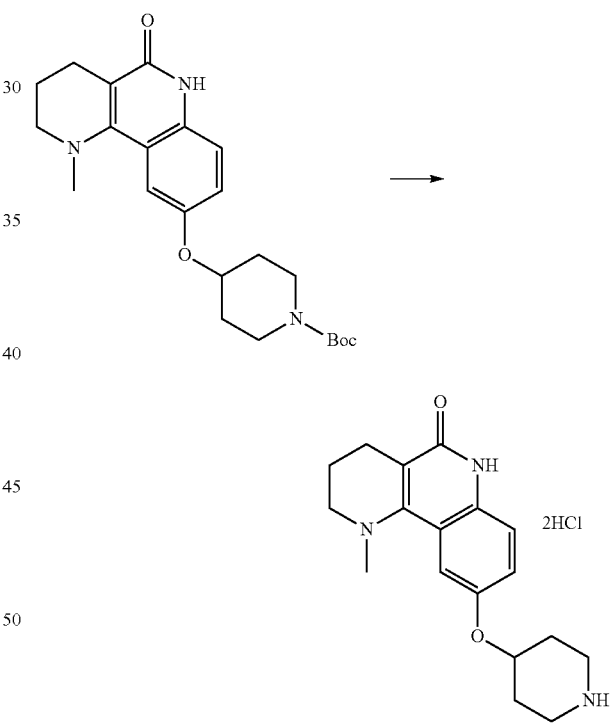

The compound (70 mg, 0.17 mmol) prepared in step 1 was dissolved in 1,4-dioxane (3 ml), added with 3.7 N hydrochloric acid 1,4-dioxane solution. The resulting mixture was stirred overnight at room temperature and the precipitate was collected by filtration to obtain the title compound (56 mg, yield: 86%, brown solid).

$^1$H NMR (400 MHz, DMSO-$d_6$); δ 11.35 (s, 1H), 8.97-8.83 (m, 2H), 7.24-7.22 (m, 2H), 7.15 (d, J=8.8 Hz, 1H), 4.64 (m, 1H), 3.20 (m, 2H), 3.07 (m, 4H), 2.90 (s, 3H), 2.42 (t, J=6.4 Hz, 2H), 2.08 (m, 2H), 1.86-1.77 (m, 4H)

Example 14

Synthesis of 1-Methyl-9-(1-methylpiperidine-4-yloxy)-1,2,3,4-tetrahydrobenzo[h][1,6]naphthyridine-5(6H)-one dihydrochloride

Step 1: Synthesis of 1-Methyl-9-(1-methylpiperidine-4-yloxy)-1,2,3,4-tetrahydrobenzo[h][1,6]naphthyridine-5(6H)-one

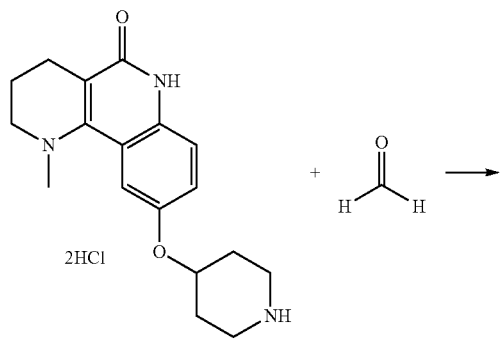

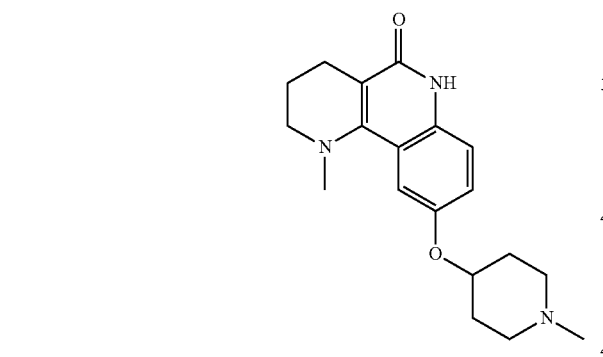

The compound (45 mg, 0.13 mmol) prepared in step 2 of Example 13 was dissolved in methanol (3 ml)/dichloromethane (3 ml), sequentially added with formaldehyde (29 μl, 0.38 mmol), acetic acid (12 μl, 0.22 mmol), and sodium triacetoxyborohydride (108 mg, 0.51 mmol) at room temperature. The resulting mixture was stirred overnight at room temperature and poured into cold 2 N sodium hydroxide aqueous solution. The mixture was extracted with chloroform and washed with brine. The organic layer was dried over anhydrous sodium sulfate and concentrated under reduced pressure. The residue was then by flash column chromatography (chloroform:methanol=5:1) to obtain the title compound (28 mg, yield: 66%, yellow oil).

$^1$H NMR (400 MHz, CDCl$_3$); δ 10.99 (s, 1H), 7.26-7.22 (m, 2H), 7.06 (dd, J=8.8 Hz, 2.0 Hz, 1H), 4.36 (m, 1H), 3.17-3.15 (m, 2H), 2.98 (s, 3H), 2.76 (m, 2H), 2.68 (t, J=6.4 Hz, 2H), 2.43-2.32 (m, 5H), 2.07 (m, 2H), 1.91-1.87 (m, 4H)

Step 2: Synthesis of 1-Methyl-9-(1-methylpiperidine-4-yloxy)-1,2,3,4-tetrahydrobenzo[h][1,6]naphthyridine-5(6H)-one dihydrochloride

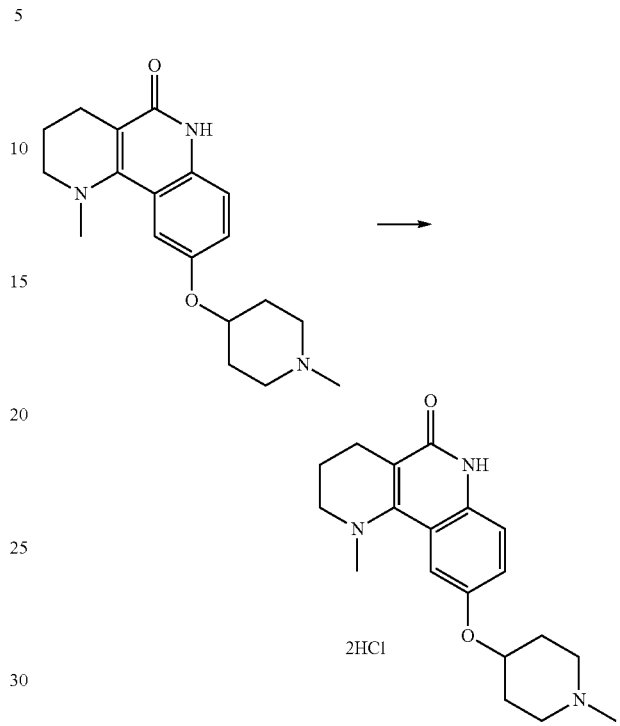

The compound (25 mg, 0.08 mmol) prepared in step 1 was dissolved in 1,4-dioxane (3 ml), added with 3.7 N hydrochloric acid 1,4-dioxane solution. The resulting mixture was stirred for 3 days at room temperature and the precipitate was collected by filtration to obtain the title compound (524 mg, yield: 79%, yellow solid).

$^1$H NMR (400 MHz, DMSO-d$_6$); δ 11.48 (s, 1H), 10.90 (m, 1H), 7.32-7.14 (m, 3H), 4.75-4.54 (m, 1H), 3.45-3.42 (m, 1H), 3.24-3.11 (m, 5H), 2.93 (s, 3H), 2.76-2.71 (m, 3H), 2.44 (m, 2H), 2.22-1.90 (m, 4H), 1.79 (m, 2H)

Example 15

Synthesis of 5-Oxo-N-[2-(piperidine-1yl)ethyl]-1,2,3,4,5,6-hexahydrobenzo[h][1,6]naphthyridine-9-carboxamide dihydrochloride

Step 1: Synthesis of 6-(4-Methoxybenzyl)-5-oxo-5,6-dihydrobenzo[h][1,6]naphthyridine-9-carboxylic acid

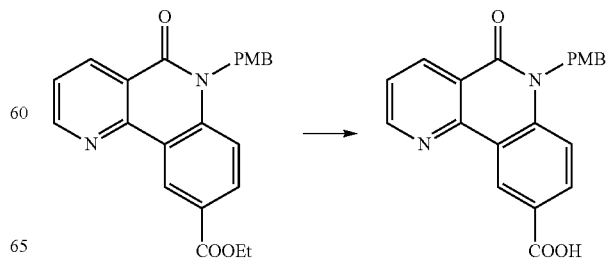

The compound (200 mg, 0.51 mmol) prepared in step 3 of Example 5 was dissolved in methanol, added with 1 N sodium hydroxide (5 ml). The resulting mixture was refluxed for 18 hours cooled to room temperature. The mixture was concentrated under reduced pressure and added with water. Water layer was acidified with 1 N hydrochloric acid and extracted with ethylacetat. The organic layer was dried over anhydrous magnesium sulfate and concentrated to dryness. With no separate purification process, title compound (140 mg, yield: 76%, white solid) was obtained.

$^1$H NMR (400 MHz, CDCl$^3$) δ 9.37 (s, 1H), 9.14-9.13 (m, 1H), 8.73 (d, J=8.0 Hz, 1H), 8.09 (d, J=8.0 Hz, 1H), 7.78~7.75 (m, 1H), 7.60 (d, J=8.4 Hz, 1H), 7.24 (d, J=7.7 Hz, 2H), 6.87 (d, J=7.3 Hz, 2H), 5.58 (brs, 2H), 3.69 (s, 3H)

Step 2: Synthesis of 6-(4-Methoxybenzyl)-5-oxo-N-[2-(piperidine-1yl)ethyl]-5,6-dihydrobenzo[h][1,6]naphthyridine-9-carboxamide

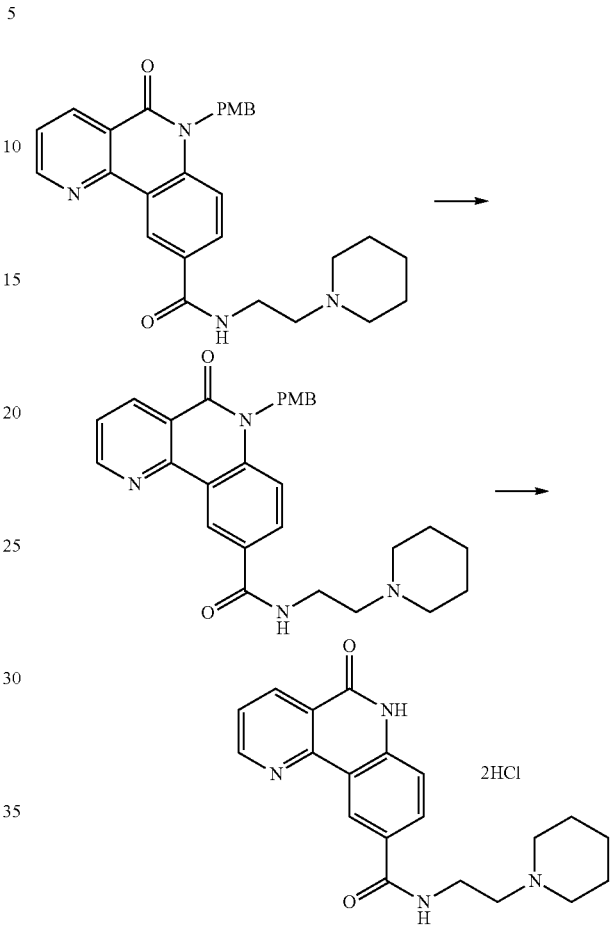

The compound (30 mg, 0.09 mmol) prepared in Step 1, 1-ethyl-3-(3-dimethylaminopropyl)-carbodiimide hydrochloride (EDC, 48 mg, 0.25 mmol), and 1-hydroxy-benzotriazole hydrate (HOBt, 34 mg, 0.25 mmol) were dissolved in N,N-dimethylformamide (5 ml) and added with 1-(2-aminoethyl)piperidine (0.033 ml, 0.23 mmol) at room temperature. The resulting mixture was stirred for 18 hours and poured into ice water. After extraction with chloroform, the organic layer was dried over anhydrous sodium sulfate and concentrated under reduced pressure. The residue was then purified by flash column chromatography (chloroform:methanol=7:1) to obtain the title compound (82 mg, yield: 92%, white solid).

$^1$H NMR (400 MHz, CDCl$_3$); δ 9.26 (s, 1H), 9.02~9.00 (m, 1H), 8.80~8.78 (m, 1H), 8.05~8.02 (m, 1H), 7.57~7.54 (m, 1H), 7.42 (d, J=8.8 Hz, 1H), 7.32 (brs, 1H), 7.21 (d, J=8.4 Hz, 2H), 6.84 (d, J=8.8 Hz, 2H), 5.58 (brs, 2H), 3.75 (s, 3H), 3.62~3.57 (m, 2H), 2.64 (t, J=6.2 Hz, 2H), 2.51 (brs, 4H), 1.68~1.62 (m, 4H), 1.49~1.48 (m, 2H)

Step 3: Synthesis of 5-Oxo-N-(2-(piperidine-1yl)ethyl)-1,2,3,4,5,6-hexahydro benzo[h][1,6]naphthyridine-9-carboxamide hydrochloride

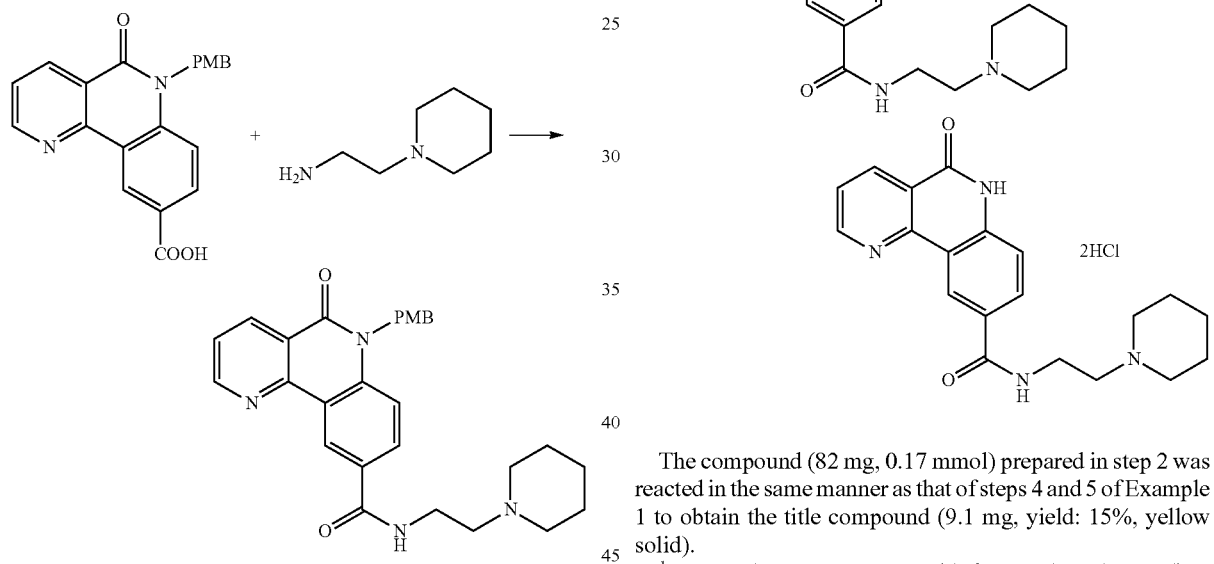

The compound (82 mg, 0.17 mmol) prepared in step 2 was reacted in the same manner as that of steps 4 and 5 of Example 1 to obtain the title compound (9.1 mg, yield: 15%, yellow solid).

$^1$H NMR (400 MHz, DMSO-d$_6$); δ 11.28 (s, 1H), 9.99 (brs, salt), 8.94~8.92 (m, 1H), 8.83 (s, 1H), 7.97 (d, J=8.4 Hz, 1H), 7.28 (d, J=8.8 hz, 1H), 3.70~3.68 (m, 2H), 3.56~3.53 (m, 2H), 3.33~3.25 (m, 4H), 2.92~2.87 (m, 2H), 2.47~2.45 (m, 2H), 1.82~1.78 (m, 6H), 1.71~1.68 (m, 1H), 1.39~1.36 (m, 1H)

Example 16

Synthesis of 9-[2-(Dimethylamino)ethoxy]-1,2,3,4-tetrahydrobenzo[h][1,6]naphthyridine-5(6H)-one dihydrochloride Step 1: Synthesis of 4-Aminophenyl t-butyl carbonate

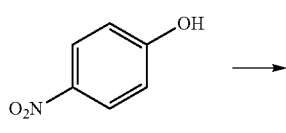

-continued

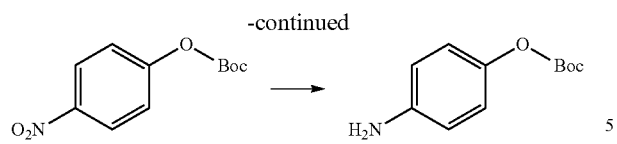

4-nitrophenol (2 g, 14.37 mmol) was dissolved in dichloromethane (25 ml), added with di-t-butyl dicarbonate (3.76 g, 17.25 mmol) and 4-dimethylaminopyridine (2.28 g, 18.68 mmol). The resulting mixture was stirred for 10 hours at room temperature and poured into water. After extraction with chloroform, the organic layer was washed with brine, dried over anhydrous magnesium sulfate, and concentrated under reduced pressure. The residue was dissolved in ethyl acetate (30 ml), and 10%-palladium (Pd) (300 mg) was added. The mixture was then stirred under hydrogen gas for one day at room temperature. Once the reaction was completed, 10%-palladium (Pd) was removed by celite-filter and the filtrate was concentrated to dryness. The residue was purified by flash column chromatography (hexane:ethyl acetate=3:1) to obtain title compound (2.7 g, yield: 90%, white solid).

$^1$H NMR (400 MHz, CDCl$_3$) δ 6.94 (d, J=4.4 Hz, 2H), 6.64 (d, J=4.4 Hz, 2H) 3.62 (br, 2H), 1.54 (s, 9H)

Step 2: Synthesis of t-Butyl 4-(chloro nicotine amino)phenyl carbonate

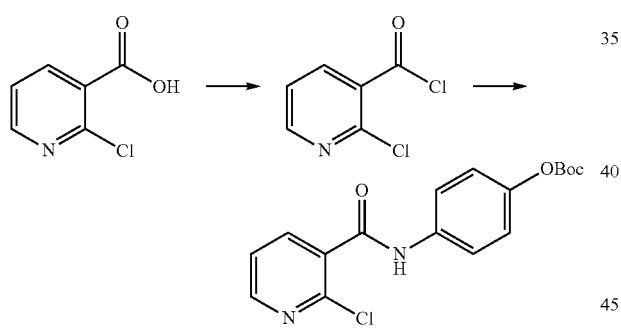

To a stirred solution of 2-chloronicotinic acid (1 g, 6.35 mmol) in dichloromethane were added dropwise oxalyl chloride and a catalytic amount of N,N-dimethylformamide at 0° C. The resulting mixture was refluxed for 3 hours and concentrated in vacuo. The residue was then dissolved in dichloromethane, added with the compound of 4-aminophenyl t-butyl carbonate (1.46 g, 7 mmol) prepared in step 1 and triethylamine at 0° C. The mixture was stirred for 12 hours at room temperature and extracted with chloroform. The organic layer was dried over anhydrous magnesium sulfate and concentrated to dryness. The residue was then purified by flash column chromatography (chloroform:methanol=10:1) to obtain the title compound (2.05 g, yield: 93%, whiute solid).

$^1$H NMR (400 MHz, CDCl$_3$); δ 8.54-8.52 (m, 1H), 8.21-8.19 (m, 1H) 8.17 (br, 1H), 7.57 (d, J=4.2 Hz, 2H), 7.42-7.39 (m, 1H), 7.24 (d, J=4.2 Hz, 2H), 1.54 (s, 9H)

Step 3: Synthesis of t-Butyl 4-[2-chloro-N-(methoxymethyl)nicotine amino]phenyl carbonate

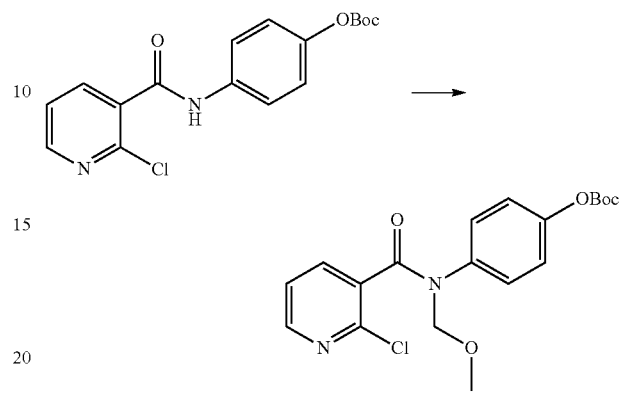

The compound (2 g, 5.09 mmol) prepared in step 2 was dissolved in N,N-dimethylformamide, added with sodium hydride (407 mg, 10.02 mmol) slowly at 0° C. After stirring for 30 minutes, chloromethyl methyl ether was added dropwise and the stirring was continued for 1 hour at room temperature. Once the reaction was completed, chloroform and water were added and the mixture was extracted. The organic layer was washed with brine, dried over anhydrous magnesium sulfate, and concentrated to dryness. The residue was then purified by flash column chromathography (hexane:ethyl acetate=2:1) to obtain the title compound (1.16 g, yield: 52%, yellow solid).

$^1$H NMR (400 MHz, CDCl$_3$); δ 8.24-8.22 (m, 1H), 7.47-7.45 (m, 1H), 7.12-7.04 (m, 5H), 5.26 (s, 3H), 3.59 (s, 3H), 1.54 (s, 9H).

Step 4: Synthesis of t-Butyl 6-(methoxymethyl)-5-oxo-5,6-dihydrobenzo[h][1,6]naphthyridine-9yl carbonate

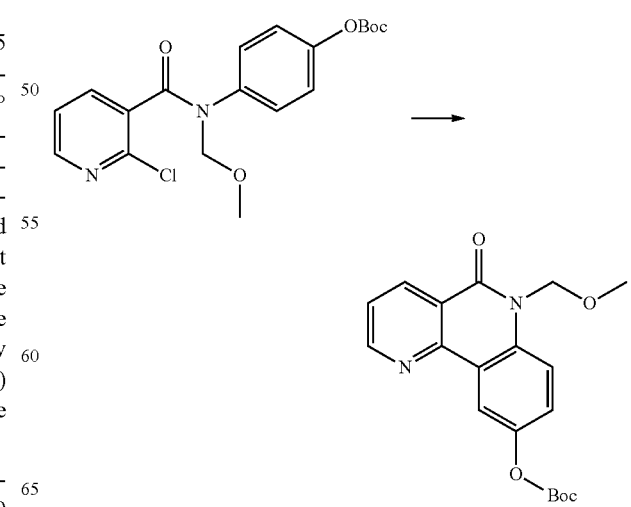

The compound (1.16 g, 3.23 mmol) prepared in step 3 was dissolved in N,N-dimethylformamide, sequentially added with palladium(II) acetate (218 mg, 0.97 mmol), 1,3-bis(dephenylphosphino)propane (400 mg, 0.97 mmol), tributylphosphine (0.80 ml, 3.23 mmol), and potassium carbonate (894 mg, 6.47 mmol). The resulting mixture was refluxed for 5 hours and cooled to room temperature. Water and dichloromethane were added and the mixture was extracted. The organic layer was dried over anhydrous magnesium sulfate and concentrated to dryness. The residue was then purified by flash column chromatography (hexane:ethyl acetate=3:1) to obtain the title compound (580 mg, yield: 55%, yellow solid).

¹H NMR (400 MHz, CDCl₃); δ 9.01-9.00 (m, 1H), 8.78-8.75 (m, 1H), 8.36 (d, J=1.4 Hz, 1H), 7.58-7.52 (m, 2H), 7.29-7.26 (m, 2H), 5.82 (s, 2H), 3.47 (s, 3H), 1.54 (s, 3H).

Step 5: Synthesis of 9-Hydroxy-6-(methoxymethyl)benzo[h][1,6]naphthyridine-5(6H)-one

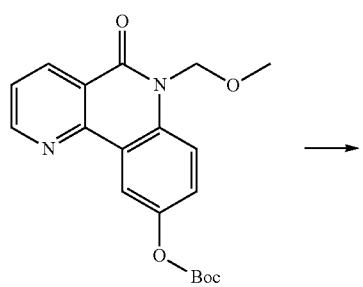

The compound (580 mg, 1.627 mmol) prepared in step 4 was dissolved in 1,4-dioxane (10 ml), added with 3.7 N hydrochloric acid 1,4-dioxane solution (6 ml). The resulting mixture was stirred for one day at room temperature and the precipitate was collected by filtration to obtain the title compound (410 mg, yield: 98%, yellow solid).

¹H NMR (400 MHz, DMSO-d₆); δ 9.60-9.15 (br, 1H), 9.07-9.05 (s, 1H), 8.66-8.64 (m, 1H), 8.14 (s, 1H), 7.70-7.67 (m, 1H), 7.47 (d, J=4.6 Hz, 1H), 7.15-7.12 (m, 1H), 5.71 (s, 2H), 3.32 (s, 3H).

Step 6: Synthesis of 9-[2-(Dimethylamino)ethoxy]-6-(methoxymethyl)benzo[h][1,6]naphthyridine-5(6H)-one

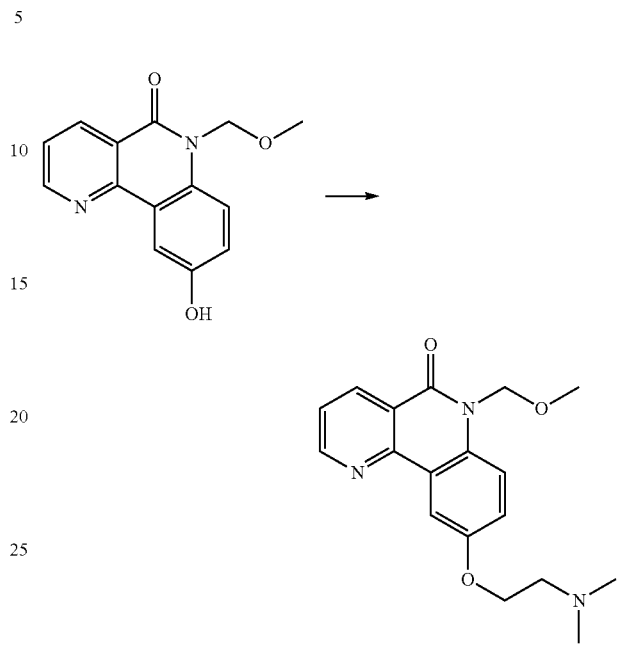

The compound (60 mg, 0.234 mmol) prepared in step 5 was dissolved in N,N-dimethylformamide (5 ml), added with potassium carbonate (161 mg, 1.17 mmol) and potassium iodide (8 mg, 0.047 mmol). After stirring for 30 minutes, N,N-dimethylaminoethyl chloride hydrochloride was added at room temperature and the resulting mixture was stirred for one more day at 70° C. The mixture was extracted chloroform, dried over anhydrous magnesium sulfate, concentrated to dryness. The residue was then purified by flash column chromatography (chloroform:methanol=10:1) to obtain the title compound (40 mg, yield: 53%, white solid).

¹H NMR (400 MHz, CDCl₃); δ 9.01-9.00 (m, 1H), 8.78-8.75 (m, 1H), 8.36 (d, J=1.4 Hz, 1H), 7.57-7.52 (m, 2H), 7.29-7.26 (m, 2H), 5.82 (s, 2H), 4.26 (t, J=5.6 Hz, 2H), 3.47 (s, 3H), 2.81 (t, J=5.2 Hz, 2H), 2.38 (s, 6H).

Step 7: Synthesis of 9-[2-(Dimethylamino)ethoxy]-6-(methoxymethyl)-1,2,3,4-tetrahydrobenzo[h][1,6]naphthyridine-5(6H)-one

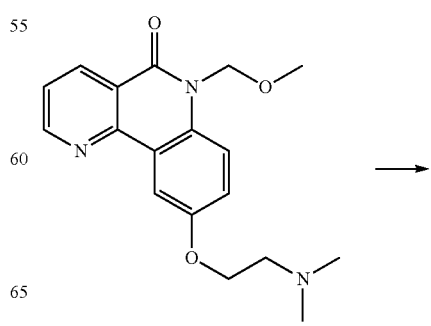

-continued

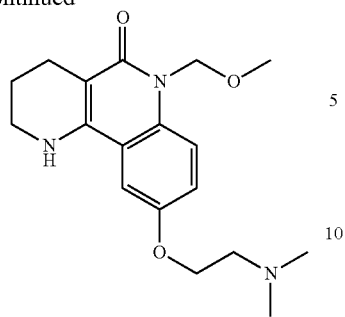

The compound (40 mg, 0.122 mmol) prepared in step 6 was dissolved in dichloromethane/methanol (5 ml), added with 10%-palladium (Pd) (4 mg). The resulting mixture was stirred under hydrogen gas for one day at room temperature. Once the reaction was completed, the solution was filtered with celite and the filtrate was concentrated to dryness. The residue was then purified by flash column chromatography (chloroform:methanol=10:1) to obtain the title compound (40 mg, yield: 99%, white solid).

$^1$H NMR (400 MHz, CDCl$_3$); δ 7.47-7.44 (m, 2H), 7.08-7.06 (m, 1H), 5.75 (br, 1H), 5.71 (s, 2H), 4.53 (t, J=5.6 Hz, 2H), 3.48 (m, 2H), 3.40 (s, 3H), 3.22 (t, J=5.6 Hz, 2H), 2.78 (s, 6H), 2.69 (t, J=6.4 Hz, 2H), 1.95 (m, 2H).

Step 8: Synthesis of 9-[2-(Dimethylamino)ethoxy]-1,2,3,4-tetrahydrobenzo[h][1,6]naphthyridine-5(6H)-one hydrochloride

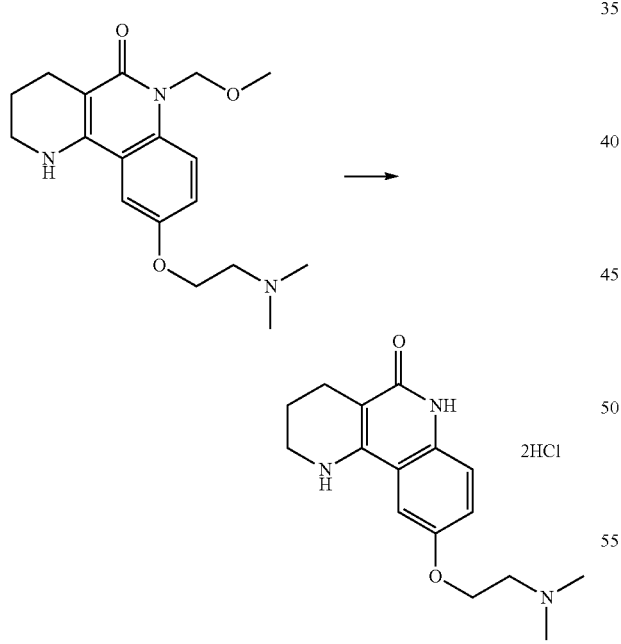

The compound (40 mg, 0.120 mmol) prepared in step 7 was dissolved in ethanol (3 ml), added with 12 N hydrochloric acid (2 ml). The resulting mixture was refluxed for 12 hours at 90° C. Once the reaction was completed, the mixture was concentrated under reduced pressure and the residue was washed ethyl acetate to obtain the title compound (36 mg, yield: 84%, yellow solid).

$^1$H NMR (400 MHz, DMSO-d$_6$): δ 11.70 (s, 1H), 10.61 (br, 1H), 7.99-7.80 (br, 1H), 7.69 (s, 1H), 7.38 (d, J=4.4 Hz, 1H), 7.24 (d, J=4.8 Hz, 1H), 4.43 (t, J=4.4 Hz, 2H), 3.54-3.53 (m, 2H), 3.38 (m, 1H), 2.86 (s, 3H), 2.85 (s, 3H), 2.56-2.51 (m, 2H), 1.82 (m, 2H)

By the reaction of Example 16, compounds were prepared as follows.

Example 17

9-[2-(Piperidine-1yl)ethoxy]-1,2,3,4-tetrahydrobenzo[h][1,6]naphthyridine-5(6H)-one dihydrochloride Example 18

9-(2-Methoxyethoxy)-1,2,3,4-tetrahydrobenzo[h][1,6]naphthyridine-5(6H)-one hydrochloride Example 19

9-[2-(Piperazine-1yl)ethoxy]-1,2,3,4-tetrahydrobenzo[h][1,6]naphthyridine-5(6H)-one trihydrochloride Example 20

9-Ethoxy-1,2,3,4-tetrahydrobenzo[h][1,6]naphthyridine-5(6H)-one hydrochloride

Example 21

9-[3-(Piperidine-1yl)propoxy]-1,2,3,4-tetrahydrobenzo[h][1,6]naphthyridine-5(6H)-one dihydrochloride Example 22

9-(2-Aminoethoxy)-1,2,3,4-tetrahydrobenzo[h][1,6]naphthyridine-5(6H)-one dihydrochloride Example 23

9-[2-(4-Phenylpiperidine-1yl)ethoxy]-1,2,3,4-tetrahydrobenzo[h][1,6]naphthyridine-5(6H)-one dihydrochloride Example 24

9-(2-Hydroxyethoxy)-1,2,3,4-tetrahydrobenzo[h][1,6]naphthyridine-5(6H)-one hydrochloride Example 25

9-Penethoxy-1,2,3,4-tetrahydrobenzo[h][1,6]naphthyridine-5(6H)-one dihydrochloride

Example 26

9-[2-(Diethylamino)ethoxy]-1,2,3,4-tetrahydrobenzo[h][1,6]naphthyridine-5(6H)-one dihydrochloride

Example 27

9-(2-Morpholinoethoxy)-1,2,3,4-tetrahydrobenzo[h][1,6]naphthyridine-5(6H)-one dihydrochloride

Example 28

1,1-Diethyl-4-[2-(5-oxo-1,2,3,4,5,6-hexahydro benzo[h][1,6]naphthyridine-9-yloxy]ethyl)piperazine-1-ium chloride

Example 29

9-[4-(Piperidine-1yl)butoxy]-1,2,3,4-tetrahydrobenzo[h][1,6]naphthyridine-5(6H)-one dihydrochloride

| Ex. | Chemical Structure | NMR spectrum data |
| --- | --- | --- |
| 17 | ·2HCl | $^1$H NMR (400 MHz, DMSO-$d_6$); δ 12.03 (s, 1H), 10.87 (br, 1H), 7.78 (s, 1H), 7.45 (m, 1H), 7.28 (m, 1H), 4.53 (m, 2H), 3.56-3.39 (m, 6H), 3.01 (m, 2H), 2.57 (m, 2H), 1.80-1.71 (m, 7H), 1.38 (m, 1H) |
| 18 | HCl | $^1$H NMR (400 MHz, DMSO-$d_6$); δ 11.73 (m, 1H), 7.75 (br, 1H), 7.51 (s, 1H), 7.35 (d, J = 4.8 Hz, 1H), 7.21 (d, J = 6.0 Hz, 1H), 4.14 (t, J = 3.6 Hz, 2H), 3.69 (t, J = 5.2 Hz, 2H), 3.38-3.37 (m, 2H), 3.32 (s, 3H), 2.55-2.53 (m, 2H), 1.84-1.81 (m, 2H) |
| 19 | ·3HCl | $^1$H NMR (400 MHz, CD$_3$OD); δ 7.70 (s, 1H), 7.53 (m, 2H), 4.58 (s, 2H), 3.79-3.48 (m, 6H), 2.71 (m, 2H), 2.01 (t, J = 7.6 Hz, 2H) |
| 20 | ·HCl | $^1$H NMR (400 MHz, DMSO-$d_6$); δ 11.93 (s, 1H), 7.97 (br, 2H), 7.52 (s, 1H), 7.38 (d, J = 8.8 Hz, 1H), 7.20 (d, J = 8.4 Hz, 1H), 4.06 (qt, J = 6.4 Hz, 2H), 3.37 (m, 2H), 2.54 (m, 2H), 1.81 (m, 2H), 1.33 (t, J = 6.4 Hz, 3H) |

-continued

| Ex. | Chmical Structure | NMR spectrum data |
|---|---|---|
| 21 | 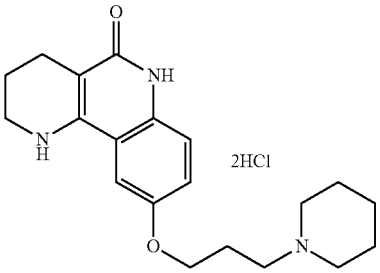 [SMILES: O=c1[nH]c2ccc(OCCCN3CCCCC3)cc2c2c1CCCN2 ; "2HCl"] 2HCl | $^1$H NMR (400 MHz, DMSO-d$_6$); δ 10.30 (brs, 1H), 7.23-7.20 (m, 2H), 6.87-6.94 (m, 1H), 5.06 (brs, 2H), 4.04 (t, J = 6.7 Hz, 2H), 3.47-3.43 (m, 2H), 2.76-2.72 (m, 2H), 2.64-2.56 (m, 6H), 2.07-2.02 (m, 4H), 1.69-1.63 (m, 4H), 1.47-1.42 (m, 2H) |
| 22 | 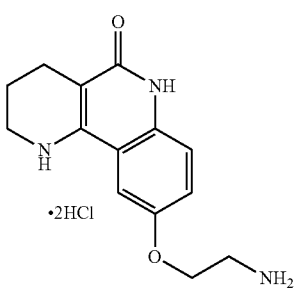 [SMILES: NCCOc1ccc2[nH]c(=O)c3c(c2c1)NCCC3 ; "·2HCl"] •2HCl | $^1$H NMR (400 MHz, DMSO-d$_6$); δ 12.02 (s, 1H), 8.13 (br, 3H), 7.79 (s, 1H), 7.47 (d, J = 8.8 Hz, 1H), 7.25 (m, 1H), 4.47 (m, 2H), 3.50 (m, 2H), 3.41 (m, 2H), 2.52 (m, 2H), 1.85 (m, 2H) |
| 23 | 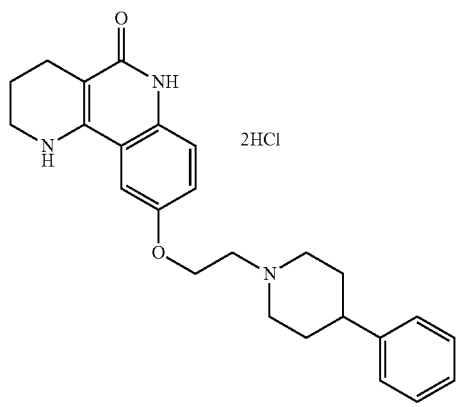 [SMILES: O=c1[nH]c2ccc(OCCN3CCC(c4ccccc4)CC3)cc2c2c1CCCN2 ; "2HCl"] 2HCl | $^1$H NMR (400 MHz, DMSO-d$_6$); δ 11.10 (s, 1H), 10.34 (br, 1H), 7.51 (s, 1H), 7.35-7.31 (m, 3H), 7.24-7.22 (m, 3H), 7.18-7.16 (m, 1H), 4.43 (s, 2H), 3.67-3.64 (m, 4H), 3.36-3.33 (m, 2H), 3.19-3.14 (m, 4H), 2.86-2.78 (m, 2H), 2.06-2.00 (m, 4H), 1.79-1.78 (m, 2H) |
| 24 | 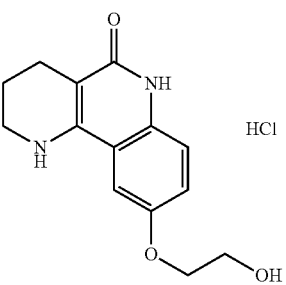 [SMILES: O=c1[nH]c2ccc(OCCO)cc2c2c1CCCN2 ; Cl] HCl | $^1$H NMR (400 MHz, DMSO-d$_6$); δ 11.54 (s, 1H), 7.72-7.46 (br, 1H), 7.46 (s, 1H), 7.31 (d, J = 4.0 Hz, 1H), 7.17 (d, J = 4.8 Hz, 1H), 4.02-4.01 (m, 2H), 3.74-3.73 (m, 2H), 3.36 (m, 2H), 2.54 (m, 2H), 1.82 (m, 2H) |
| 25 | 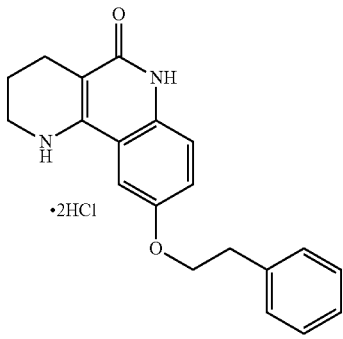 [SMILES: O=c1[nH]c2ccc(OCCc3ccccc3)cc2c2c1CCCN2 ; "·2HCl"] •2HCl | $^1$H NMR (400 MHz, DMSO-d$_6$); δ 12.08 (s, 1H), 8.07 (br, 2H), 7.57 (d, J = 2.4 Hz, 1H), 7.43 (d, J = 9.2 Hz, 1H), 7.36-7.29 (m, 4H), 7.25-7.16 (m, 2H), 4.22 (t, J = 6.8 Hz, 2H), 3.38-3.36 (m, 2H), 3.07 (t, J = 6.8 Hz, 2H), 2.57 (t, J = 6.0 Hz, 2H), 1.83-1.80 (m, 2H) |

| Ex. | Chmical Structure | NMR spectrum data |
|---|---|---|
| 26 | ·2HCl | $^1$H NMR (400 MHz, DMSO-d$_6$); δ 12.00 (s, 1H), 10.76 (s, 1H), 8.28 (br, 2H), 7.78 (d, J = 2.0 Hz, 1H), 7.45 (d, J = 8.8 Hz, 1H), 7.27 (dd, J = 8.8 Hz, 1.6 Hz, 1H), 4.48 (t, J = 4.8 Hz, 2H), 3.52 (m, 2H), 3.40 (m, 2H), 3.23-3.20 (m, 4H), 2.57 (t, J = 5.8 Hz, 2H), 1.83 (m, 2H), 1.26 (t, J = 7.2 Hz, 6H) |
| 27 | 2HCl | $^1$H NMR (400 MHz, DMSO-d$_6$); δ 11.78 (s, 1H), 11.40 (s, 1H), 7.69 (d, J = 2.4 Hz, 1H), 7.49 (d, J = 8.8 Hz, 1H), 7.25 (dd, J = 2.4 Hz, 8.8 Hz, 1H), 4.51 (t, J = 4.8 Hz, 2H), 3.97 (d, J = 12 Hz, 2H), 3.84 (t, J = 12 Hz, 2H), 3.57 (m, 2H), 3.51 (d, J = 12 Hz, 2H), 3.40-3.37 (m, 2H), 3.23-3.20 (m, 2H), 2.56-2.53 (m, 2H), 1.84-1.81 (m, 2H) |
| 28 | 2HCl | $^1$H NMR (400 MHz, DMSO-d$_6$); δ 11.86 (s, 1H), 7.75 (s, 1H), 7.40 (d, J = 8.8 Hz, 1H), 7.26 (d, J = 7.6 Hz, 1H), 4.51 (s, 2H), 3.79 (s, 8H), 3.71 (s, 2H), 3.54 (br s, 4H), 3.39 (t, J = 7.2 Hz, 2H), 2.54 (s, 2H), 1.81 (s, 2H), 1.21 (t, J = 6.4 Hz, 6H) |
| 29 | 2HCl | $^1$H NMR (400 MHz, DMSO-d$_6$); δ 11.56 (m, 1H), 10.03 (d, J = 17.6 Hz, 1H), 8.57 (br, 1H), 7.75 (br, 1H), 7.53 (d, J = 7.4 Hz, 1H), 7.32 (d, J = 4.8 Hz, 1H), 7.17 (d, J = 4.4 Hz, 1H), 4.06-4.04 (m, 2H), 3.43-3.37 (m, 6H), 3.11-3.04 (m, 1H), 3.01-2.94 (m, 1H), 2.88-2.75 (m, 2H), 1.81-1.70 (m, 10H), 1.5 (m, 2H) |

Example 30

Synthesis of 1-Methyl-9-[2-(piperidine-1-yl)ethoxy]-1,2,3,4-tetrahydrobenzo[h][1,6]naphthyridine-5(6H)-one dihydrochloride Step 1: Synthesis of 9-Methoxy-6-(4-methoxybenzyl)-1-methyl-1,2,3,4-tetrahydrobenzo[h][1,6]naphthyridine-5(6H)-one

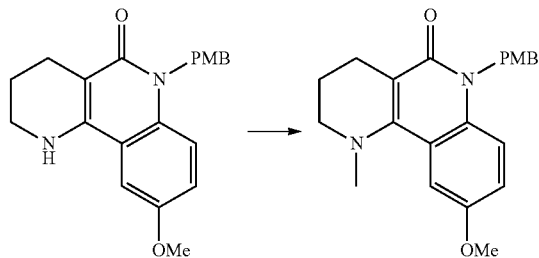

9-methoxy-6-(4-methoxybenzyl)-1,2,3,4-tetrahydrobenzo[h][1,6]naphthyridine-5(6H)-one (500 mg, 1.36 mmol) was dissolved in N,N-dimethylformamide (10 ml), added with sodium hydride (140 mg, 2.04 mmol) at 0° C. After stirring for 30 minutes, iodomethane (0.13 ml, 2.04 mmol) was added and the resulting mixture was stirred for 3 hours at 0° C. After completion, the mixture was poured into ice water and extracted with ethyl acetate. The combined organic layer was washed with brine, dried over anhydrous sodium sulfate, and concentrated to dryness. The residue was then purified by flash column chromatography (hexane:ethyl acetate=1:1) to obtain the title compound (445 mg, yield: 90%, white solid).

$^1$H NMR (400 MHz, CDCl$_3$); δ7.32~7.31 (m, 1H), 7.22~7.20 (m, 1H), 7.17 (d, J=8.8 Hz, 2H), 6.98~6.95 (m, 1H), 6.83 (d, J=8.8 Hz, 1H), 3.84 (s, 3H), 3.75 (s, 3H), 3.18~3.15 (m, 2H), 2.97 (s, 3H), 2.71 (t, J=6.6 Hz, 2H), 1.93 (m, 2H)

Step 2: Synthesis of 9-Methoxy-1-methyl-1,2,3,4-tetrahydrobenzo[h][1,6]naphthyridine-5(6H)-one

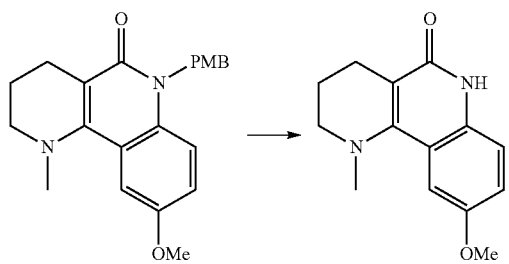

The compound (440 mg, 1.20 mmol) prepared in step 1 was dissolved in excess trifluoroacetic acid (3 ml), and the resulting mixture was heated at 100° C. for 18 hours in sealed-tube. The mixture was poured into ice water and acidified with 2 N sodium hydroxide aqueous solution. After neutralizing with 2 N hydrochloric acid aqueous solution, the crude solution was extracted with dichloromethane and washed with brine. The organic layer was dried over anhydrous sodium sulfate and concentrated to dryness. The residue was then purified by flash column chromatography (dichloromethane:methanol=10:1) to obtain the title compound (260 mg, yield: 88%, white solid).

$^1$H NMR (400 MHz, CDCl$_3$); δ 9.89 (brs, 1H), 7.24~7.21 (m, 1H), 7.15 (d, J=8.8 Hz, 1H), 7.06~7.03 (m, 1H), 3.87 (s, 3H), 3.18~3.15 (m, 2H), 3.00 (s, 3H), 2.67 (t, J=6.4 Hz, 2H), 1.91~1.85 (m, 2H)

Step 3: Synthesis of 1-Methyl-9-[2-(piperidine-1yl)ethoxy]-1,2,3,4-tetrahydrobenzo[h][1,6]naphthyridine-5(6H)-one dihydrochloride

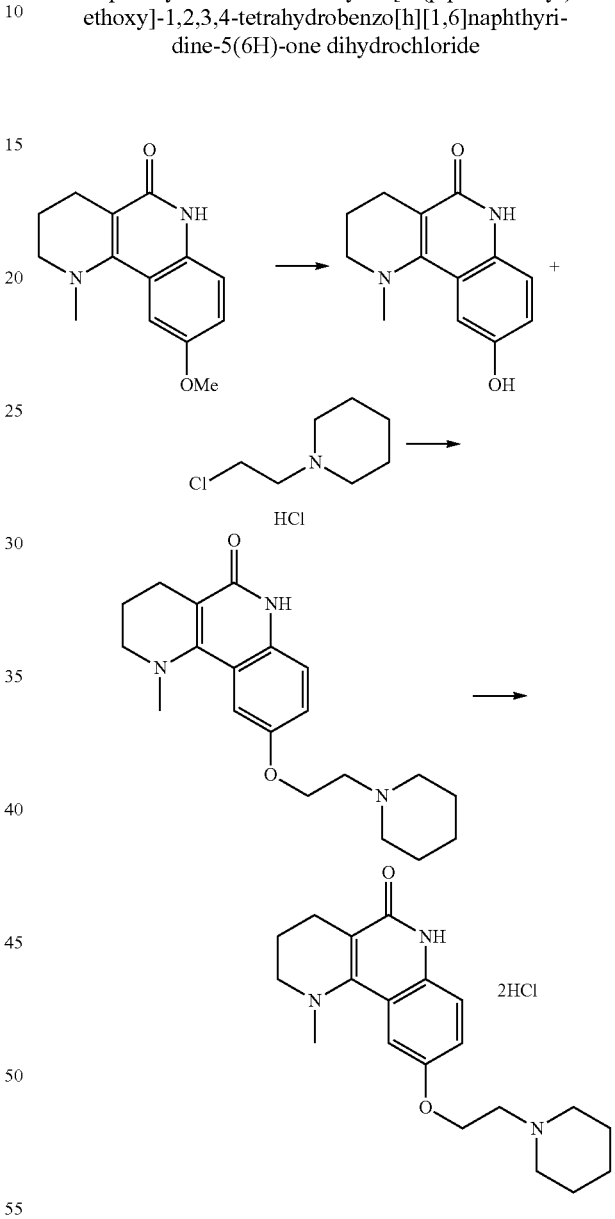

The compound (50 mg, 0.20 mmol) prepared in step 2 was dissolved in dichloromethane (3 ml), added with 1 M boron tribromide dichloromethane solution (0.61 ml, 0.61 mmol) at 0° C. The resulting mixture was stirred for 18 hours at room temperature and poured into cold sodium bicarbonate aqueous solution. The mixture was extracted with ethyl acetate, dried over anhydrous sodium sulfate and concentrated to dryness. And then, the residue was dissolved in N,N-dimethylformamide (10 ml), added with potassium carbonate (72 mg, 0.52 mmol) and 1-(2-chloroethyl)piperidine (48 mg, 0.26 mmol). The resulting mixture was stirred for 18 hours at 90°

C. and cooled to room temperature. The mixture was extracted with chloroform, dried over anhydrous sodium sulfate, and concentrated to dryness. The residue was purified by flash column chromatography (chloroform:methanol=7:1) to obtain the title compound (24.7 mg, yield: 34%, white solid). The obtained compound (23 mg, 0.067 mmol) was reacted in the same manner as in step 5 of Example 5 to obtain the title compound (21 mg, yield: 73%, yellow solid).

$^1$H NMR (400 MHz, DMSO-$d_6$); δ 11.41 (brs, 1H), 10.42 (brs, salt), 7.27~7.22 (m, 2H), 7.16~7.14 (m, 1H), 4.45~4.43 (m, 2H), 3.56~3.46 (m, 4H), 3.09~3.02 (m, 2H), 2.99~2.94 (m, 2H), 2.92 (s, 3H), 2.45~2.41 (m, 2H), 1.79~1.67 (m, 4H), 1.39~1.35 (m, 2H)

Example 31

Synthesis of 9-[2-(Dimethylamino)ethyl]-1,2,3,4-tetrahydrobenzo[h][1,6]naphthyridine-5(6H)-one dihydrochloride Step 1: Synthesis of t-Butyldimethyl(4-nitrophenethoxy)silane

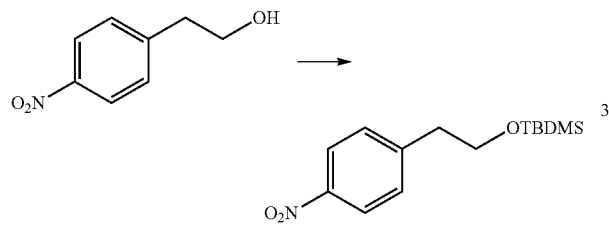

4-nitrophenethylalcohol (1.0 g, 5.98 mmol) was dissolved in tetrahydrofuran (20 ml), sequentially added with t-butyldimethylsilyl chloride (990 mg, 6.58 mmol) and imidazole (450 mg, 6.58 mmol). The resulting mixture was stirred for one day and extracted with ethyl acetate. The organic layer was washed with brine, dried over anhydrous sodium sulfate, and concentrated to dryness. The residue was then purified by flash column chromatography (ethylacetate:hexane=1:8) to obtain the title compound (1.65 g, yield: 98%, yellow oil).

$^1$H NMR (400 MHz, CDCl$_3$); δ 8.19 (d, J=8.8 Hz, 2H), 7.43 (d, J=8.8 Hz, 2H), 3.90 (t, J=6.4 Hz, 2H), 2.96 (t, J=6.4 Hz, 2H), 0.89 (s, 9H), 0.00 (s, 6H)

Step 2: Synthesis of 4-[2-(t-Butyldimethylsilyloxy)ethyl]aniline

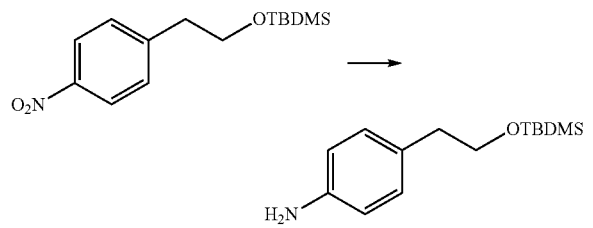

The compound (1.65 g, 5.86 mmol) prepared in step 1 was dissolved in ethyl acetate (20 ml), added with 10%-palladium (Pd) (165 mg) at room temperature. The reaction mixture was stirred for 3 days under hydrogen gas. 10%-palladium (Pd) was removed by using celite-filter and the filtrate was concentrated under reduced pressure. The residue was then purified by flash column chromatography (ethylacetate:hexane=1:4) to obtain the title compound (1.4 g, yield: 95%, colorless oil).

$^1$H NMR (400 MHz, CDCl$_3$); δ 7.00 (d, J=8.0 Hz, 2H), 6.63 (d, J=8.0 Hz, 2H), 3.74 (t, J=7.4 Hz, 2H), 3.57 (s, 2H), 2.72 (t, J=7.4 Hz, 2H), 0.89 (s, 9H), 0.00 (s, 6H)

Step 3: Synthesis of 9-[2-(t-Butylmethylsililoxy)ethyl]-6-(methoxymethyl)benzo[h][1,6]naphthyridine-5(6H)-one

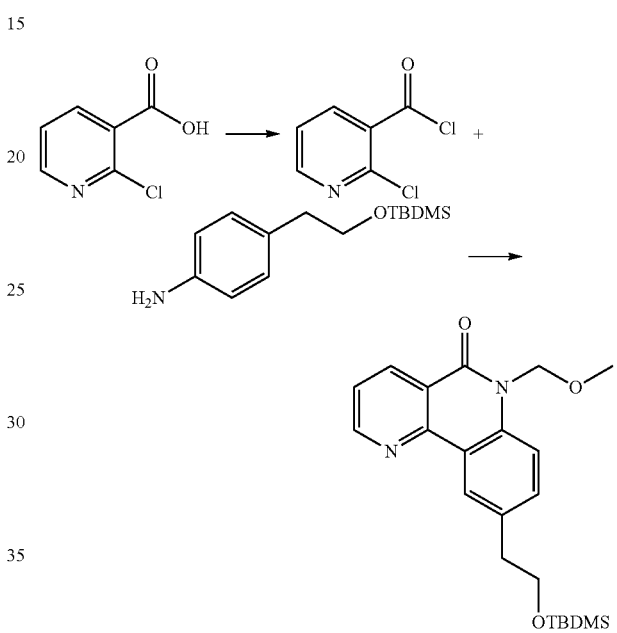

The same method as in steps 2~4 of Example 16 using 2-chloronicotinic acid (800 mg, 5.08 mmol) was performed to obtain the title compound (950 mg, yield (4 step): 47%, yellow oil).

$^1$H NMR (400 MHz, CDCl$_3$); δ 9.01 (dd, J=4.4 Hz, 2.0 Hz, 1H), 8.75 (dd, J=8.0 Hz, 2.0 Hz, 1H), 8.70 (d, J=2.0 Hz, 1H), 7.56-7.48 (m, 3H), 5.83 (s, 2H), 3.88 (t, J=6.8 Hz, 2H), 3.46 (s, 3H), 2.98 (t, J=6.8 Hz, 2H), 0.87 (s, 9H), 0.00 (s, 6H)

Step 4: Synthesis of 9-(2-Hydroxyethyl)-6-(methoxymethyl)benzo[h][1,6]naphthyridine-5(6H)-one

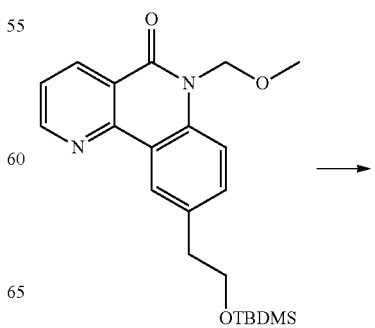

-continued

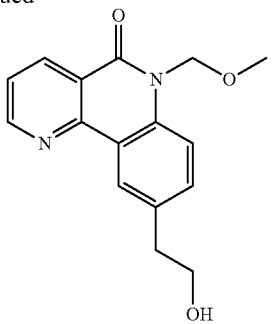

The compound (850 mg, 2.13 mmol) prepared in step 3 was dissolved in 3.7 N hydrochloric acid/1,4-dioxane solution and the solution was stirred overnight at room temperature. Once the reaction was completed, the precipitate was collected by filteration to obtain the title compound (540 mg, yield: 89%, yellow solid).

$^1$H NMR (400 MHz, DMSO-d$_6$+CDCl$_3$); δ 9.06-9.04 (m, 1H), 8.83-8.79 (m, 2H), 7.66 (dd, J=8.0 Hz, 4.8 Hz, 1H), 7.59-7.54 (m, 2H), 5.81 (s, 2H), 3.85 (t, J=6.8 Hz, 2H), 3.44 (s, 3H), 2.99 (t, J=6.8 Hz, 2H)

Step 5: Synthesis of 2-[6-(Methoxymethyl)-5-oxo-5,6-dihydrobenzo[h][1,6]naphthyridine-9yl]acetaldehyde

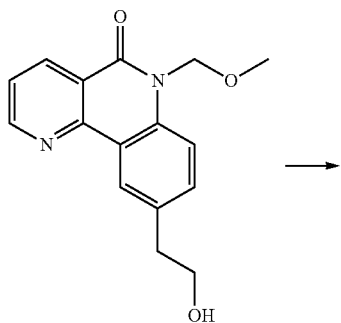

The compound (50 mg, 0.18 mmol) prepared in step 4 was dissolved in dichloromethane (10 ml), added with Dess-Martin periodinane (112 mg, 0.26 mmol) at 0° C. The resulting mixture was stirred for 90 minutes at room temperature and poured into saturated sodium bicarbonate aqueous solution. The mixture was extracted with dichloromethane and washed with brine. The organic layer was dried over anhydrous sodium sulfate and concentrated to dryness. The residue was then purified by flash column chromatography (ethylacetate:hexane=1:1) to obtain the title compound (25 mg, yield: 50%, white solid).

$^1$H NMR (400 MHz, CDCl$_3$); δ 9.85 (s, 1H), 9.01 (dd, J=4.4 Hz, 1.6 Hz, 1H), 8.78-8.74 (m, 2H), 7.64 (d, J=8.8 Hz, 1H), 7.55 (dd, J=8.0 Hz, 4.4 Hz, 1H), 7.46 (dd, J=8.8 Hz, 2.0 Hz, 1H), 5.84 (s, 2H), 3.88 (s, 2H), 3.47 (s, 3H)

Step 6: Synthesis of 9-([2-(Dimethylamino)ethyl]-6-(methoxymethyl)benzo[h][1,6]naphthyridine-5(6H)-one

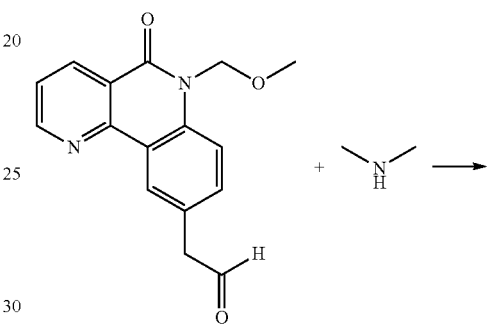

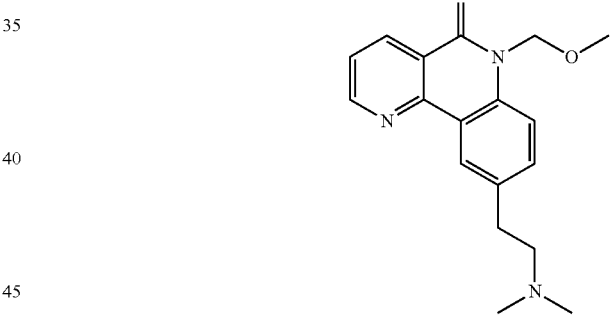

The compound (35 mg, 0.12 mmol) prepared in step 5 was dissolved in methanol (5 ml), sequentially added with dimethylamine (0.52 ml, 1.04 mmol), sodium cyanoborohydride (8 mg, 0.13 mmol), zinc chloride(II) (8 mg, 0.06 mmol) and 1.25 N hydrochloric acid methanol solution (0.58 ml, 0.72 mmol) at 0° C. The resulting mixture was stirred for one hour at 0° C. and poured into sodium bicarbonate aqueous solution. The mixture was extracted with chloroform and washed with brine. The organic layer was dried over anhydrous sodium sulfate and concentrated to dryness. The residue was then purified by flash column chromatography (chloroform:methanol=5:1) to obtain the title compound (22 mg, yield: 59%, white solid).

$^1$H NMR (400 MHz, CDCl$_3$); δ 9.02 (dd, J=4.4 Hz, 1.6 Hz, 1H), 8.76 (dd, J=8.0 Hz, 1.6 Hz, 1H), 8.69 (d, J=2.4 Hz, 1H), 7.58-7.47 (m, 3H), 5.83 (s, 2H), 3.47 (s, 3H), 2.97 (t, J=8.0 Hz, 2H), 2.67 (t, J=8.0 Hz, 2H), 2.36 (s, 6H)

Step 7: Synthesis of 9-[2-(Dimethylamino)ethyl]-6-(methoxymethyl)-1,2,3,4-tetrahydrobenzo[h][1,6]naphthyridine-5(6H)-one

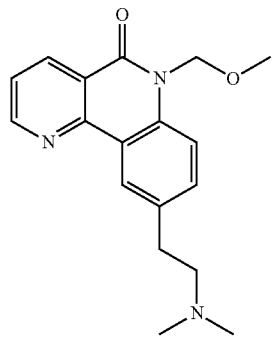 

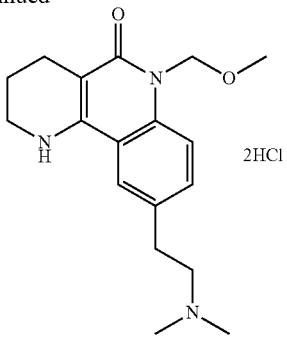

The compound (20 mg, 0.06 mmol) prepared in step 7 was dissolved in ethanol (4 ml) and added with conc. hydrochloric acid (0.5 ml). The resulting mixture was stirred for 8 hours at 80° C. and cooled to room temperature. The mixture was then concentrated under reduced pressure to obtain the title compound (18 mg, yield: 82%, yellow solid).

$^1$H NMR (400 MHz, DMSO-d$_6$); δ 11.91 (s, 1H), 10.97 (s, 1H), 8.12 (s, 1H), 7.46-7.43 (m, 2H), 3.37 (m, 4H), 3.09 (m, 2H), 2.79 (s, 6H), 2.55 (m, 2H), 1.81 (m, 2H)

Example 32

Synthesis of 8-[2-(Dimethylamino)ethyl]-1,2,3,4-tetrahydrobenzo[h][1,6]naphthyridine-5(6H)-one dihydrochloride

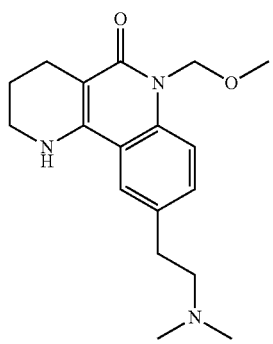

The compound (22 mg, 0.07 mmol) prepared in step 6 was dissolved in ethanol (4 ml)/dichloromethane (2 ml), added with 10%-palladium (Pd) (5 mg) at room temperature. The resulting mixture was stirred for one day under hydrogen gas and filtered using celite to remove 10%-palladium (Pd). The filtrate was then concentrated under reduced pressure to obtain the title compound (20 mg, yield: 90%, white solid).

$^1$H NMR (400 MHz, CDCl$_3$); δ 7.58 (s, 1H), 7.46 (d, J=8.8 Hz, 1H), 7.29 (dd, J=8.8 Hz, 1.6 Hz, 1H), 5.71 (s, 2H), 5.36 (s, 1H), 3.46 (m, 2H), 3.40 (s, 3H), 3.07 (m, 2H), 2.97 (m, 2H), 2.68 (t, J=6.4 Hz, 2H), 2.59 (s, 6H), 1.99-1.93 (m, 2H)

Step 8: Synthesis of 9-[2-(Dimethylamino)ethyl]-1,2,3,4-tetrahydrobenzo[h][1,6]naphthyridine-5(6H)-one dihydrochloride

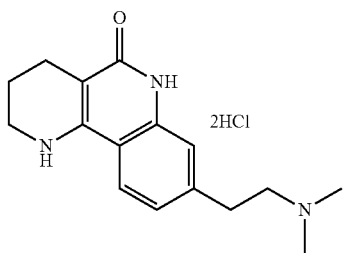 [SMILES: CN(C)CCc1ccc2c3c(c(=O)[nH]c2c1)CCCN3]

The same method as that of Example 31 was applied to obtain the title compound.

$^1$H NMR (400 MHz, DMSO-d$_6$); δ 10.99 (s, 1H), 10.76 (br, 1H), 8.79 (br, 1H), 7.83-7.81 (m, 1H), 7.22-7.19 (m, 1H), 6.92-6.80 (m, 1H), 4.37-4.35 (m, 2H), 3.37-3.34 (m, 2H), 3.06-3.02 (m, 2H), 2.82 (s. 6H), 2.46-2.43 (m, 2H), 1.79-1.78 (m. 2H)

Example 33

Synthesis of 9-[3-(Dimethylamino)propyl]-1,2,3,4-tetrahydrobenzo[h][1,6]naphthyridine-5(6H)-one dihydrochloride Step 1: Synthesis of ethyl 3-(4-aminophenyl)propanoate

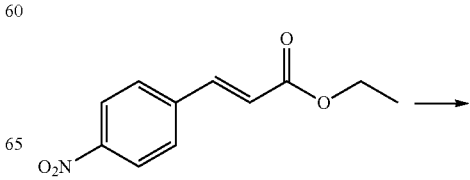

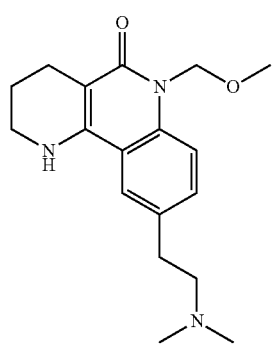 

-continued

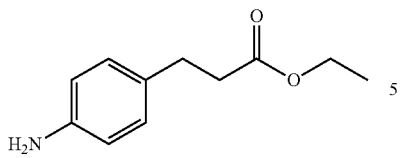

Ethyl 3-(4-nitrophenyl)acrylate (3 g, 13.56 mmol) was dissolved in methanol/tetrahydrofuran (20 ml), added with 10%-palladium (Pd) (300 mg). The resulting mixture was stirred for one day under hydrogen gas at room temperature and filtered using celite to remove 10%-palladium (Pd). The filtrate was then concentrated under reduced pressure. The residue was then purified by flash column chromatography (hexane:ethylacetate=3:1) to obtain the title compound (2.14 g, yield: 82%, colorless liquid).

$^1$H NMR (400 MHz, DMSO-$d_6$) δ 6.99 (d, J=4.0 Hz, 2H), 6.62 (d, J=4.2 Hz, 2H) 4.12 (q, J=3.6 Hz, 2H), 3.58 (br, 2H), 2.84 (t, J=8.0, 2H), 2.56 (t, J=7.6 Hz, 2H), 1.24 (t, J=6.4 Hz, 3H).

Step 2: Synthesis of ethyl 3-[4-(2-Chloronicotinamido)phenyl]propanoate

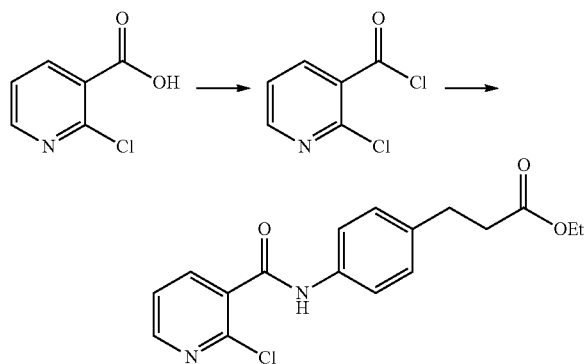

2-Chloronicotinic acid (1 g, 6.35 mmol) was dissolved in dichloromethane and added with oxalylchloride and a catalytic amount of N,N-dimethylformamide at 0° C. The resulting mixture was refluxed for 3 hours and concentrated under reduced pressure. And then, the obtained acid chloride was dissolved in dichloromethane and cooled to 0° C. Ethyl 3-(4-nitrophenyl)acrylate (1.35 g, 7 mmol) prepared in step 1 and triethylamine were added, and the reaction mixture was stirred at room temperature for 12 hours. The mixture was extracted with chloroform, dried over anhydrous magnesium sulfate, and concentrated to dryness. The residue then was purified by flash column chromatography (chloroform:methanol=10:1) to obtain the title compound (2.1 g, yield: 92%, colorless liquid).

$^1$H NMR (400 MHz, CDCl$_3$) δ 8.53-8.51 (m, 1H), 8.21-8.19 (m, 3H) 8.15 (br, 1H), 7.57 (d, J=3.4 Hz, 2H), 7.43-7.39 (m, 1H), 7.30-7.22 (m, 2H), 4.15-4.09 (m, 2H), 2.96 (t, J=8.0 Hz, 2H), 2.62 (t, J=8.0 Hz, 2H), 1.25 (m, 3H).

Step 3: Synthesis of ethyl 3-{4-[2-Chloro-N-(methoxymethyl)nicotinamido]phenyl}propanoate

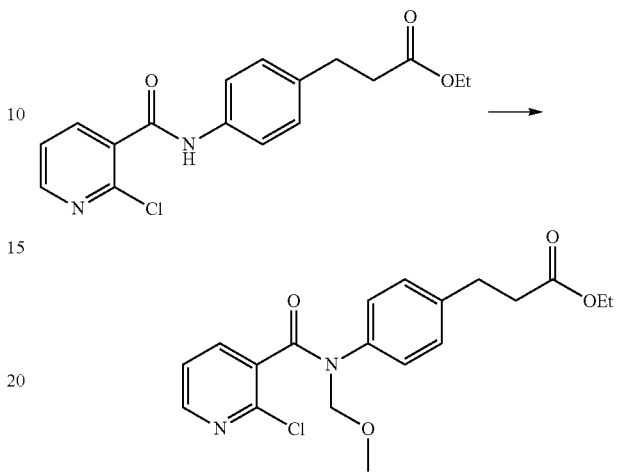

The compound (100 mg, 0.31 mmol) prepared in step 2 was dissolved in N,N-dimethylformamide (3 ml), added with sodium hydride (407 mg, 10.02 mmol) at 0° C. After stirring for 30 minutes, chloromethyl methyl ether was added dropwise and the resulting mixture was stirred for 8 hours. The mixture was poured into ice water and extracted with chloroform. The organic layer was washed with brine, dried over anhydrous magnesium sulfate, and concentrated to dryness. The residue was then purified by flash column chromatography (hexane:ethyl acetate=2:1) to obtain title compound (57 mg, yield: 50%, yellow liquid).

$^1$H NMR (400 MHz, CDCl$_3$) δ 8.24 (m, 1H), 7.47-7.45 (m, 1H), 7.12-7.04 (m, 5H), 5.26 (s, 2H), 4.09 (q, J=3.6 Hz, 2H), 3.59 (s, 3H), 2.83 (t, J=8.4 Hz, 2H), 2.51 (t, J=7.6 Hz, 2H), 1.21 (t, J=7.2 Hz, 3H).

Step 4: Synthesis of ethyl 3-[6-(Methoxymethyl)-5-oxo-5,6-dihydrobenzo[h][1,6]naphthyridine-9yl]propanoate

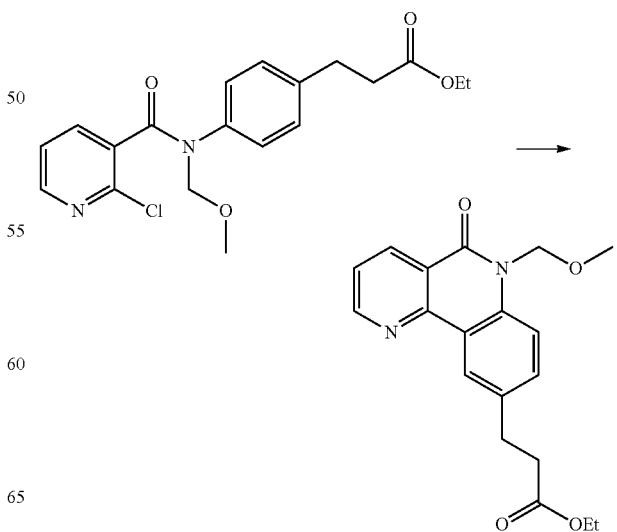

The compound (55 mg, 0.146 mmol) prepared in step 3 was dissolved in N,N-dimethylformamide (3 ml), sequentially added with palladium(II) acetate (9.83 mg, 0.0438 mmol), 1,3-bis(dephenylphosphino)propane (18 mg, 0.0438 mmol), tributylphosphine (0.036 ml, 0.146 mmol), and potassium carbonate (40 mg, 0.292 mmol). The resulting mixture was refluxed for 5 hours. Water was added to the above solution and the mixture was extracted with chloroform. The organic layer was dried over anhydrous magnesium sulfate and concentrated to dryness. The residue was then purified by flash column chromatography (hexane:ethyl acetate=3:1) to obtain title compound (31 mg, yield: 64%, white solid).

$^1$H NMR (400 MHz, CDCl$_3$); δ 9.02-9.00 (m, 1H), 8.77-8.71 (m, 2H), 7.57-7.48 (m, 3H), 5.83 (s, 2H), 4.15 (q, J=3.6 Hz, 2H), 3.47 (s, 3H), 3.11 (t, J=8.0 Hz, 2H), 2.73 (t, J=7.6 Hz, 2H), 1.26 (t, J=6.8 Hz, 3H).

Step 5: Synthesis of 3-[6-(Methoxymethyl)-5-oxo-5,6-dihydrobenzo[h][1,6]naphthyridine-9yl]propanone acid

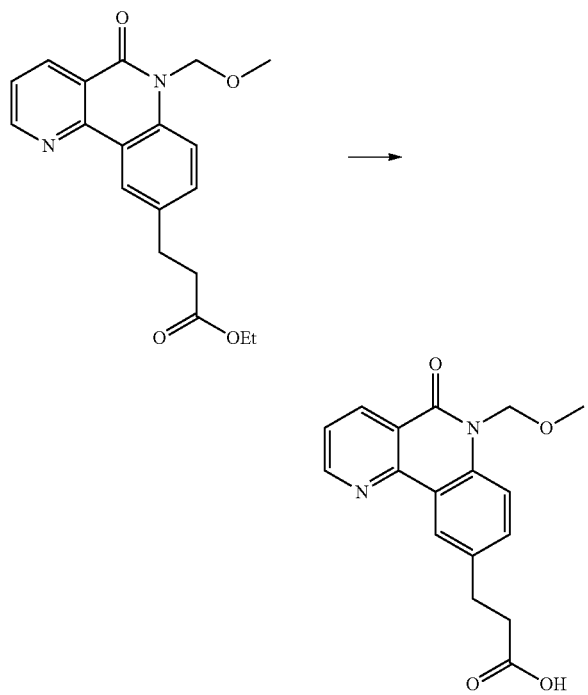

The compound (1.15 g, 3.38 mmol) prepared in step 4 was dissolved in dichloromethane/methanol (20 ml), added with 4 N sodium hydroxide aqueous solution at room temperature. The resulting mixture was stirred for 12 hours and acidified with 4 N hydrochloric acid. The precipitate was then collected by filtration to obtain the title compound (780 mg, yield: 74%, white solid).

$^1$H NMR (400 MHz, DMSO-d$_6$) δ 12.17 (s, 1H), 9.06-9.05 (m, 1H), 8.64-8.58 (m, 2H), 7.69-7.67 (m, 1H), 7.53 (m, 2H) 5.73 (s, 2H), 3.31 (s, 3H), 2.95 (t, J=7.6 Hz, 2H), 2.61 (t, J=7.6 Hz, 2H).

Step 6: Synthesis of 9-(3-Hydroxypropyl)-6-(methoxymethyl)benzo[h][1,6]naphthyridine-5(6H)-one

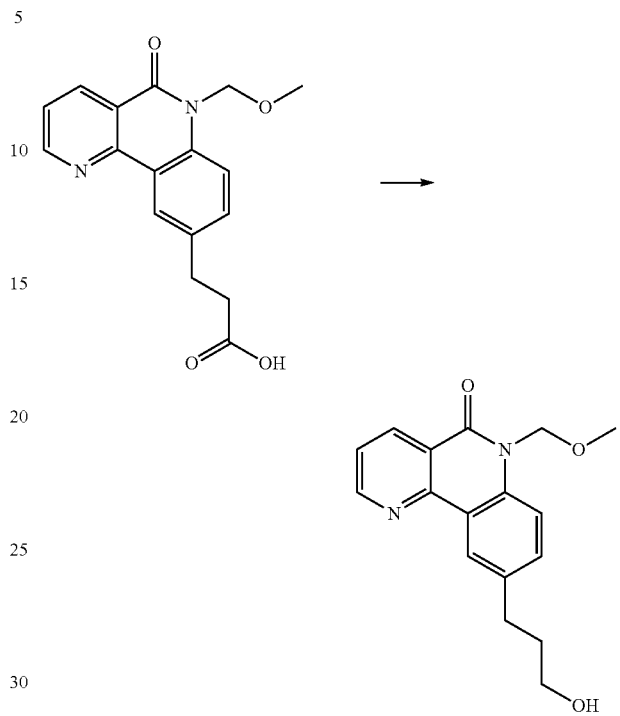

The compound (780 mg, 2.50 mmol) prepared in step 5 was dissolved in tetrahydrofuran, added dropwise with 2 M borane dimethyl sulfide tetrahydrofuran solution (6.24 ml, 12.49 mmol). The resulting mixture was stirred for 3 hours at room temperature and extracted with chloroform. The organic layer was dried over anhydrous magnesium sulfate and concentrated to dryness. The residue was then purified by flash column chromatography (chloroform:methanol=15:1) to obtain title compound (45 mg, yield: 75%, white solid).

$^1$H NMR (400 MHz, CDCl$_3$); δ 9.02-9.00 (m, 1H), 8.78-8.70 (m, 2H), 7.58-7.47 (m, 3H), 5.84 (s, 2H), 3.73 (t, J=6.4 Hz, 2H), 3.48 (s, 3H), 2.88 (t, J=7.6 Hz, 2H), 2.02-1.98 (m, 2H)

Step 7: Synthesis of 3-[6-(Methoxymethyl)-5-oxo-5,6-dihydrobenzo[h][1,6]naphthyridine-9yl]propanal

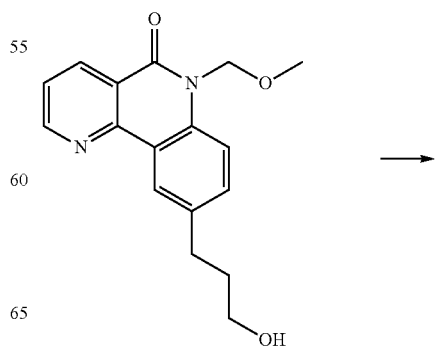

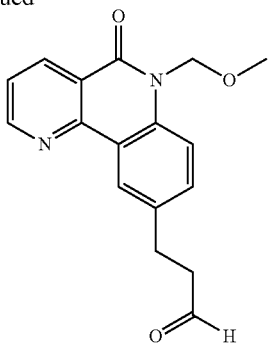

The compound (200 mg, 0.67 mmol) prepared in step 6 was dissolved in dichloromethane, added with pyridinium chlorochromate (289 mg, 1.34 mmol) and silica gel (289 mg) at room temperature. The resulting mixture was stirred for 2 hours at room temperature and filtered to remove silica gel. The filtrate was extracted with dichloromethane, dried over anhydrous magnesium sulfate and concentrated to dryness. The residue was then purified by flash column chromatography (chloroform:methanol=15:1) to obtain the title compound (151 mg, yield: 76%, white solid).

$^1$H NMR (400 MHz, CDCl$_3$); δ 9.87 (s, 1H), 9.02-9.00 (m, 1H), 8.77-8.70 (m, 2H), 7.58-7.46 (m, 3H), 5.83 (s, 2H), 3.47 (s, 3H), 3.14-3.10 (m, 2H), 2.93-2.89 (m, 2H)

Step 8: Synthesis of 9-[3-(Dimethylamino)propyl]-6-(methoxymethyl)benzo[h][1,6]naphthyridine-5(6H)-one

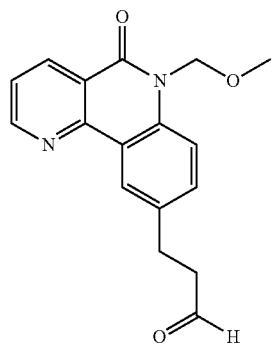

The compound (151 mg, 0.51 mmol) prepared in step 7 was dissolved in methanol, sequentially added with 2 M dimethylamine (2.18 ml, 4.38 mmol), sodium cyanoborohydride (35 mg, 0.56 mmol), zinc chloride(II) (35 mg, 0.255 mmol), and 1.25 M hydrochloric acid (2.44 ml, 3.06 mmol) at 0° C. The resulting mixture was stirred for one hour at room temperature. The mixture was poured into ice water and extracted with chloroform. The organic layer was dried over anhydrous magnesium sulfate and concentrated to dryness. The residue was then purified by flash column chromatography (chloroform:methanol=15:1) to obtain the title compound (152 mg, yield: 92%, white solid).

$^1$H NMR (400 MHz, CDCl$_3$); δ 9.03-9.01 (m, 1H), 8.76-8.75 (m, 1H), 8.69 (m, 1H), 7.57-7.48 (m, 3H), 5.83 (s, 2H), 3.48 (s, 3H), 2.80 (t, J=7.6 Hz, 2H), 2.58 (s, 6H), 2.36 (t, J=7.6 Hz, 2H), 1.92-1.87 (m, 2H).

Step 9: Synthesis of 9-[3-(Dimethylamino)propyl]-6-(methoxymethyl)-1,2,3,4-tetrahydrobenzo[h][1,6]naphthyridine-5(6H)-one

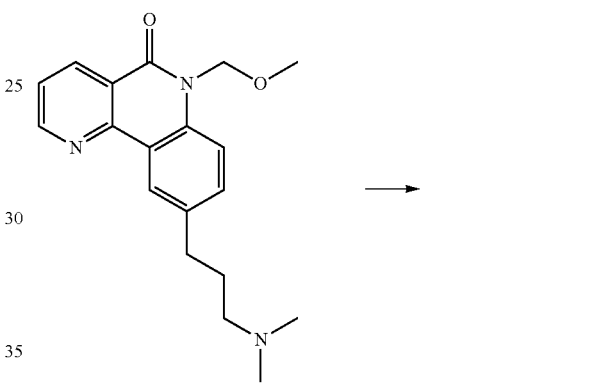

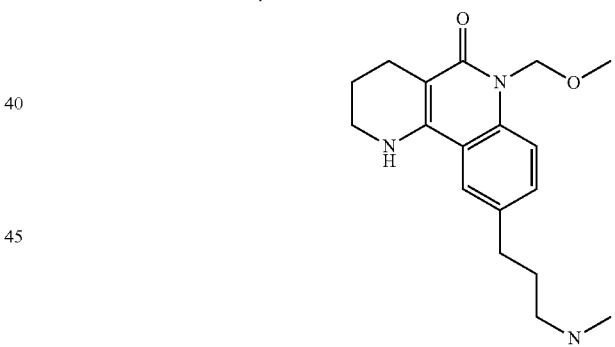

The compound (110 mg, 0.67 mmol) prepared in step 8 was dissolved in dichloromethane/methanol (10 ml), added with 10%-palladium (11 mg). The resulting mixture was stirred for one day at room temperature under hydrogen gas. Once the reaction was completed, the solution was celite-filtered and the filtrate was concentrated to dryness. The residue was then purified by flash column chromatography (chloroform:methanol=10:1) to obtain the title compound (112 mg, yield: 99%, white solid).

$^1$H NMR (400 MHz, CDCl$_3$); δ 7.87 (s, 1H), 7.44 (d, J=4.4 Hz, 1H), 7.23 (d, J=4.2 Hz, 2H), 6.42 (s, 1H), 5.72 (s, 2H), 3.49 (m, 2H), 3.41 (s, 3H), 2.93-2.89 (m, 4H), 2.77 (s, 6H), 2.68 (t, J=6.0 Hz, 2H), 2.39-2.36 (m, 2H), 1.95-1.93 (m, 2H)

Step 10: Synthesis of 9-[3-(Dimethylamino)propyl]-1,2,3,4-tetrahydrobenzo[h][1,6]naphthyridine-5(6H)-one dihydrochloride

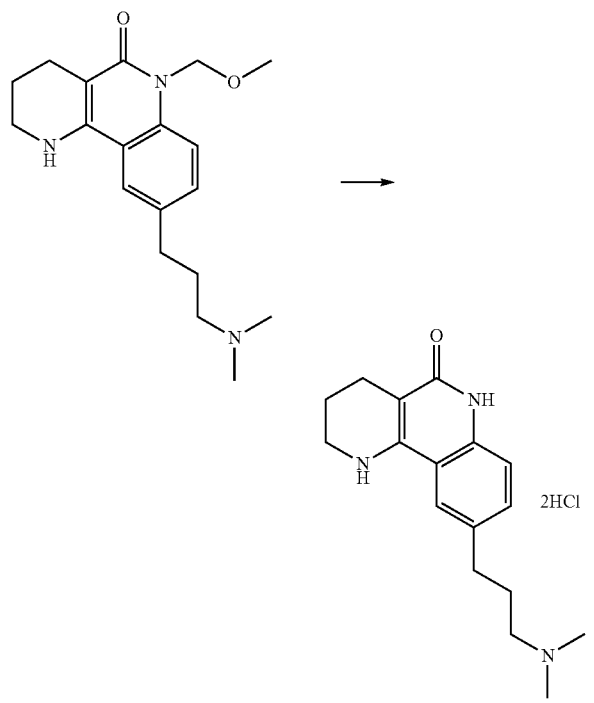

The compound (112 mg, 0.34 mmol) prepared in step 9 was dissolved in ethanol (3 ml) and added with 12 N hydrochloric acid (2 ml). The resulting mixture was refluxed for 12 hours. Once the reaction was completed, the mixture was concentrated and recrystallized from methanol/ethyl acetate to obtain the title compound (110 mg, yield: 90%, yellow solid).

$^1$H NMR (400 MHz, DMSO-$d_6$); δ 11.79 (s, 1H), 10.62 (s, 1H), 7.97 (s, 1H), 7.44 (d, J=4.2 Hz, 1H), 7.37 (d, J=4.2 Hz, 1H), 3.37 (m, 2H), 3.01 (m, 2H), 2.73 (s, 3H), 2.72 (s, 3H), 2.70-2.68 (m, 2H), 2.56-2.53 (m, 2H), 2.07-2.04 (m, 1H), 1.83-1.80 (m, 2H)

Example 34

Synthesis of 8-[2-(Dimethylamino)ethoxy]-1,2,3,4,5,6-hexahydrobenzo[h][1,6]naphthyridine-9-carboxamide dihydrochloride Step 1: Synthesis of 8-[2-(Dimethylamino)ethoxy]-6-(methoxymethyl)benzo[h][1,6]naphthyridine-5(6H)-one

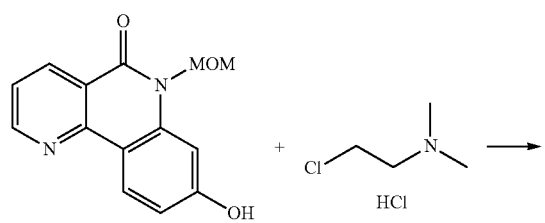

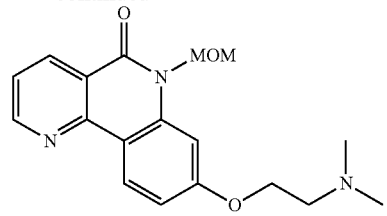

8-hydroxy-6-(methoxymethyl)benzo[h][1,6]naphthyridine-5(6H)-one (58 mg, 0.22 mmol) and potassium carbonate (94 mg, 0.67 mmol) were dissolved in N,N-dimethylformamide (5 ml) and added with 2-(dimethylamino)ethyl chloride (39 mg, 0.0.27 mmol). The resulting mixture was stirred for 2 hours at 90° C. and poured into ice water. The mixture was extracted with chloroform, dried over anhydrous sodium sulfate, and concentrated to dryness. The residue was then purified by flash column chromatography (chloroform:methanol=6:1) to obtain the title compound (53 mg, yield: 73%, white solid).

$^1$H NMR (400 MHz, CDCl$_3$); δ 8.97~8.82 (m, 1H), 8.77~8.72 (m, 1H), 8.70~8.67 (m, 1H), 7.46~7.42 (m, 1H), 7.18 (s, 1H), 7.02~6.98 (m, 1H), 5.79 (br, 2H), 4.22~4.17 (m, 2H), 3.43 (s, 3H), 2.83~2.78 (m, 2H), 2.38 (s, 6H)

Step 2: Synthesis of 8-[2-(Dimethylamino)ethoxy]-1,2,3,4,5,6-hexahydro benzo[h][1,6]naphthyridine-9-carboxamide dihydrochloride

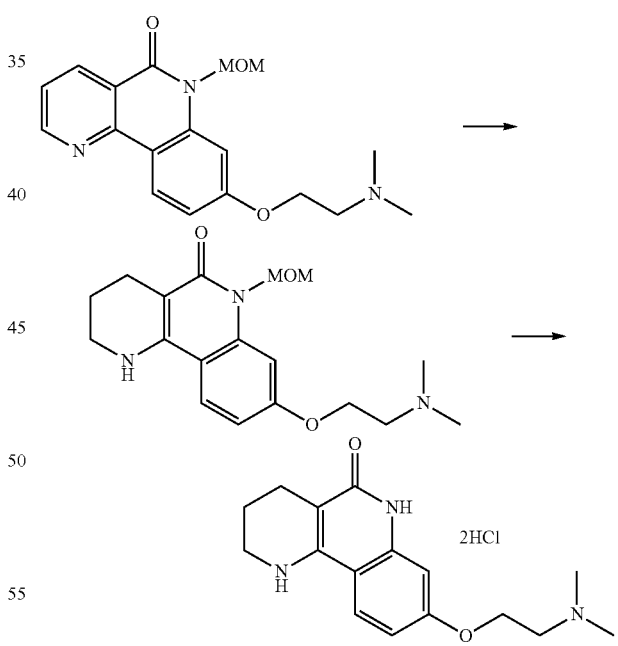

By using compound (50 mg, 0.15 mmol) prepared in step 1, the same manner as in step 4 of Example 6 was applied to obtain intermediate product. The intermediate was dissolved in ethanol (5 ml) and added with conc. hydrochloric acid (1 ml). The resulting mixture was refluxed for 18 hours and cooled to room temperature. The mixture was concentrated under reduced pressure and recrystallized from methanol/ethyl acetate to obtain the title compound (51 mg, yield: 94%, yellow solid).

¹H NMR (400 MHz, DMSO-d₆); δ 11.09 (s, 1H), 10.21 (brs, salt), 7.83 (d, J=9.1 Hz, 1H), 6.85 (d, J=8.8 Hz, 1H), 6.80 (s, 1H), 4.37-4.35 (m, 2H), 3.59-3.44 (m, 2H), 3.32-3.29 (m, 2H), 2.85 (s, 3H), 2.84 (s, 3H), 2.46-2.43 (m, 2H), 1.79-1.78 (m, 2H)

By the reaction of Example 34, the following compounds were prepared.

Example 35

8-[2-(Piperidine-1yl)ethoxy]-1,2,3,4-tetrahydrobenzo[h][1,6]naphthyridine-5(6H)-one dihydrochloride

Example 36

8-[3-(Dimethylamino)propoxy]-1,2,3,4-tetrahydrobenzo[h][1,6]naphthyridine-5(6H)-one dihydrochloride

| Ex. | Chemical structure | NMR spectrum data |
|---|---|---|
| 35 | 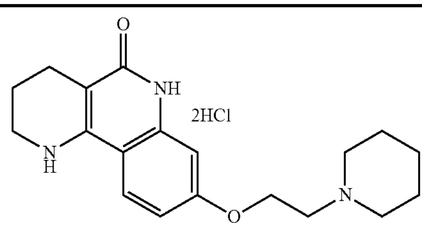 | ¹H NMR (400 MHz, DMSO-d₆); δ 11.29 (s, 1H), 10.41 (s, 1H), 7.87 (d, J = 8.8 Hz, 1H), 6.86-6.84 (m, 2H), 4.43 (t, J = 4.6 Hz, 2H), 3.50-3.49 (m, 4H), 3.32 (m, 2H), 3.04-2.95 (m, 2H), 2.47 (m, 2H), 1.79 (m, 6H), 1.71-1.67 (m, 1H), 1.38 (m, 1H) |
| 36 | 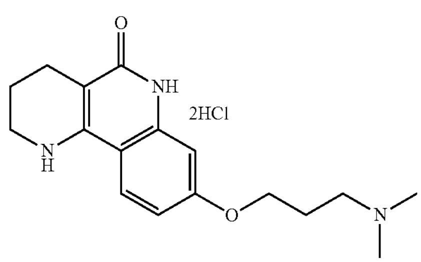 [SMILES: CN(C)CCCOc1ccc2c3c(c(=O)[nH]c2c1)CCCN3] | ¹H NMR (400 MHz, DMSO-d₆); δ 11.65 (s, 1H), 10.59 (s, 1H), 7.94 (d, J = 4.4 Hz, 1H), 7.90-7.61 (br, 1H), 6.90-6.88 (m, 2H), 4.11 (t, J = 6.0 Hz, 2H), 3.34 (m, 2H), 3.25-3.18 (m, 2H), 2.78 (s, 3H), 2.77 (s, 3H), 2.53-2.51 (m, 2H), 2.20-2.16 (m, 2H), 1.82-1.79 (m, 2H) |

Example 37

Synthesis of 8-(Dimethylamino)-1,2,3,4-tetrahydrobenzo[h][1,6]naphthyridine-5(6H)-one hydrochloride Step 1: Synthesis of N,N-Dimethyl-3-nitroaniline

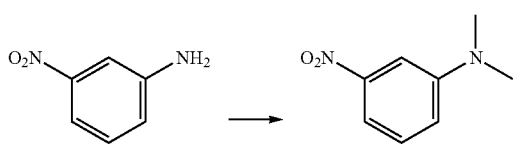

3-nitroaniline (1.0 g, 7.25 mmol) was dissolved in N,N-dimethylformamide (50 ml), added with sodium hydride (1.7 g, 21.7 mmol) and iodomethane (2.7 ml, 21.7 mmol) at 0° C. The resulting mixture was stirred for 4 hours at room temperature and poured into ice water. The mixture was extracted with ethyl acetate, dried over anhydrous magnesium sulfate, and concentrated to dryness. The residue was then purified by flash column chromatography (hexane:ethyl acetate=1:1) to obtain the title compound (2.0 g, yield: 86%, yellow solid).

¹H NMR (400 MHz, CDCl₃); δ 7.53-7.48 (m, 1H), 7.33 (t, J=8.0 Hz, 1H), 6.96 (d, J=8.0 Hz, 1H), 3.04 (s, 6H)

Step 2: Synthesis of N',N'-Dimethylbenzene-1,3-diamine

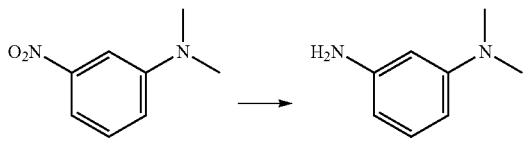

The compound (1.0 g, 6.08 mmol) prepared in step 1 was dissolved in methanol (25 ml) and added with 10%-palladium (Pd) (100 mg). The mixture was hydrogenated for 15 hours at room temperature under hydrogen gas. Once the reaction was completed, 10%-palladium (Pd) was removed by using celite-filter and the filtrate was concentrated to dryness. The residue was then purified by flash column chromatography (hexane:ethyl acetate=1:1) to obtain the title compound (700 mg, yield: 90%, colorless liquid).

¹H NMR (400 MHz, CDCl₃); δ 7.04 (t, J=7.6 Hz, 1H), 6.2 (d, J=8.0 Hz, 1H), 6.11-6.08 (m, 1H), 3.60 (br s, 2H), 2.92 (s, 6H)

Step 3: Synthesis of 8-(Dimethylamino)-6-(methoxymethyl)-1,2,3,4-tetrahydrobenzo[h][1,6]naphthyridine-5(6H)-one

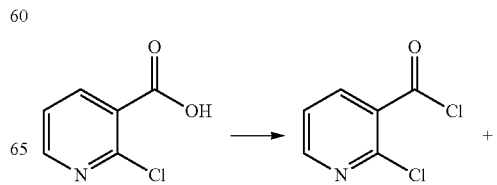

-continued

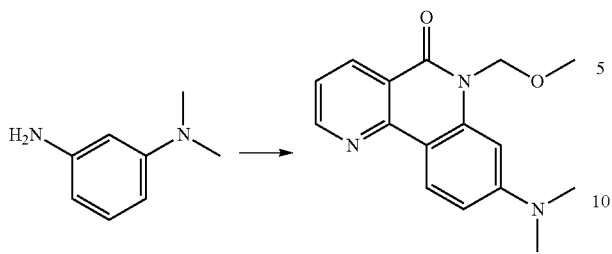

By using 2-chloronicotinic acid (700 mg, 8.9 mmol), the same manner as in steps 2-4 of Example 16 was performed to obtain the title compound (1.08 g, yield (4 step): 43%, yellow solid).

$^1$H NMR (400 MHz, CDCl$_3$); δ 7.64 (d, J=9.2 Hz, 1H), 6.90 (s, 1H), 6.63 (d, J=8.8 Hz, 1H), 6.50 (s, 1H), 5.54 (s, 2H), 3.25 (s, 2H), 3.21 (s, 3H), 2.96 (s, 6H), 2.42 (t, J=6.0 Hz, 2H), 1.76 (t, J=5.2 Hz, 2H)

Step 4: Synthesis of 8-(Dimethylamino)-1,2,3,4-tetrahydrobenzo[h][1,6]naphthyridine-5(6H)-one hydrochloride

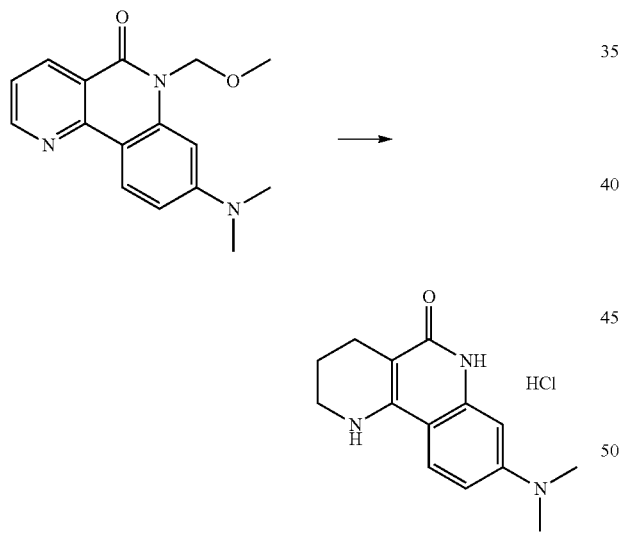

The compound (100 mg, 0.34 mmol) prepared in step 3 was dissolved in ethanol (5 ml) and added with conc. hydrochloric acid (1.0 ml). The mixture was stirred overnight at 80° C., cooled to room temperature, and concentrated under reduced pressure to obtain the title compound (89.6 mg, yield: 92%, yellow solid).

$^1$H NMR (400 MHz, DMSO-d$_6$); δ 12.22 (s, 1H), 7.99 (d, J=9.6 Hz, 1H), 6.95 (d, J=9.6 Hz, 1H), 6.65 (s, 1H), 3.38 (t, J=5.2 Hz, 2H), 3.01 (s, 6H), 2.58 (t, J=6.4 Hz, 2H), 1.81 (t, J=5.2 Hz, 2H)

Example 38

Synthesis of 8-[1-(Dimethylamino)ethyl]-1,2,3,4-tetrahydrobenzo[h][1,6]naphthyridine-5(6H)-one dihydrochloride Step 1: Synthesis of 1-(3-aminophenyl)ethanol

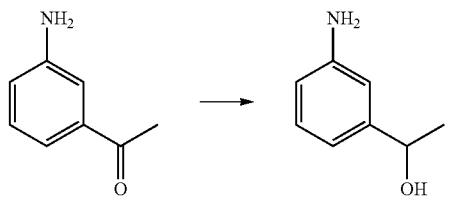

3-aminoacetophenon (2.0 g, 14.80 mmol) was dissolved in ethanol (25 ml) and added with sodium borohydride (1.4 g, 36.99 mmol) at 0° C. The resulting mixture was stirred for 3 hours and poured into ice water. The mixture was neutralized with 2 N hydrochloric acid aqueous solution and extracted with chloroform. The organic layer was washed with brine, dried over anhydrous sodium sulfate, and concentrated under reduced pressure to obtain the title compound (1.7 g, yield: 84%, white solid).

$^1$H NMR (400 MHz, CDCl$_3$); δ 7.13 (t, J=8.0 Hz, 1H), 6.76-6.72 (m, 2H), 6.60 (dd, J=8.0 Hz, 2.4 Hz, 1H), 4.81 (m, 1H), 1.46 (d, J=6.8 Hz, 3H)

Step 2: Synthesis of 3-[1-(t-Butyldimethylsililoxy)ethyl]aniline

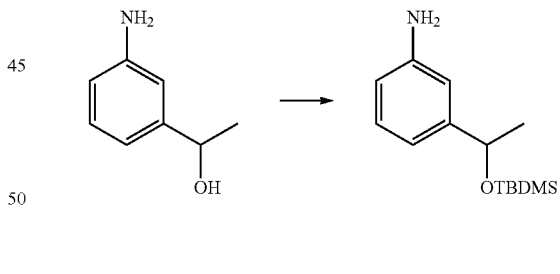

The compound (1.7 g, 12.39 mmol) prepared in step 1 was dissolved in tetrahydrofuran (30 ml), sequentially added with t-butyldimethylsilyl chloride (2.8 g, 18.59 mmol) and imidazole (1.26 g, 18.59 mmol). The resulting mixture was stirred overnight and extracted with chloroform. The organic layer was washed with brine, dried over anhydrous sodium sulfate, concentrated to dryness. The residue was then purified by flash column chromatography (hexane:ethyl acetate=4:1) to obtain the title compound (2.2 g, yield: 72%, yellow oil).

$^1$H NMR (400 MHz, CDCl$_3$); δ 7.08 (t, J=7.8 Hz, 1H), 6.71-6.69 (m, 2H), 6.55 (dd, J=7.8 Hz, 2.4 Hz, 1H), 4.77 (qt, J=6.4 Hz, 1H), 3.63 (br, 2H), 1.37 (d, J=6.0 Hz, 3H), 0.90 (s, 9H), 0.04 (s, 3H), 0.01 (s, 3H)

Step 3: Synthesis of 8-[1-(t-Butyldimethylsililoxy)ethyl]-6-(methoxymethyl)benzo[h][1,6]naphthyridine-5(6H)-one

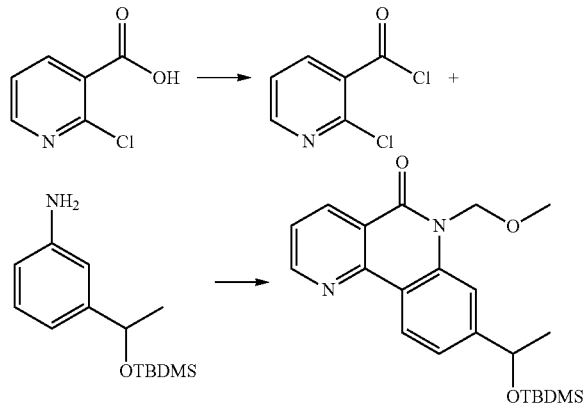

By using 2-chloronicotinic acid (1.0 g, 6.35 mmol), the same manner as in steps 2-4 of Example 16 was performed to obtain the title compound (1.06 g, yield (4 step): 42%, yellow oil).

$^1$H NMR (400 MHz, CDCl$_3$); δ 8.99 (dd, J=4.4 Hz, 2.0 Hz, 1H), 8.79 (d, J=8.4 Hz, 1H), 8.74 (dd, J=8.0 Hz, 2.0 Hz, 1H), 7.67 (s, 1H), 7.49 (dd, J=8.0 Hz, 4.4 Hz, 1H), 7.34 (d, J=8.4 Hz, 1H) 5.89-5.79 (m, 2H), 5.02 (qt, J=6.4 Hz, 1H), 3.47 (s, 3H), 1.49 (d, J=7.dHz, 3H), 0.93 (s, 9H), 0.09 (s, 3H), 0.02 (s, 3H)

Step 4: Synthesis of 8-(1-Hydroxyethyl)-6-(methoxymethyl)benzo[h][1,6]naphthyridine-5(6H)-one

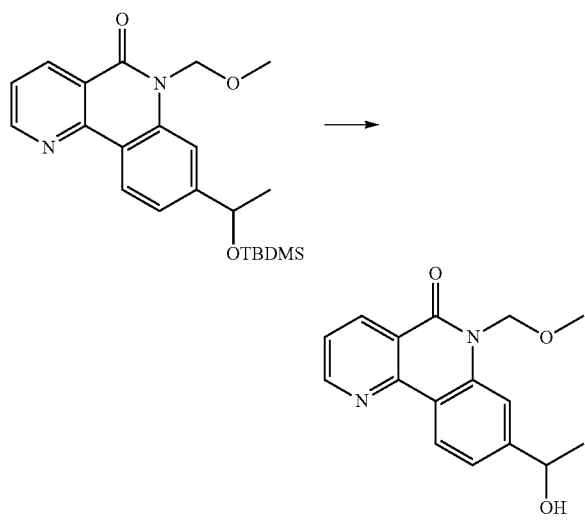

The compound (1.04 g, 2.61 mmol) prepared in step 3 was dissolved in 3.7 N hydrochloric acid 1,4-dioxane solution and stirred overnight at room temperature. Once the reaction was completed, the precipitate was collected by filtration and dried in vacuo to obtain the title compound (760 mg, yield: 100%, yellow solid).

$^1$H NMR (400 MHz, CDCl$_3$); δ 9.33 (dd, J=8.0 Hz, 1.6 Hz, 1H), 9.26-9.22 (m, 2H), 8.02 (dd, J=8.0 Hz, 5.6 Hz, 1H), 7.76 (s, 1H), 7.56 (d, J=8.8 Hz, 1H) 5.85 (s, 2H), 5.04 (m, 1H), 3.50 (s, 3H), 1.54 (d, J=6.8 Hz, 3H)

Step 5: Synthesis of 8-(1-Hydroxyethyl)-6-(methoxymethyl)-1,2,3,4-tetrahydrobenzo[h][1,6]naphthyridine-5(6H)-one

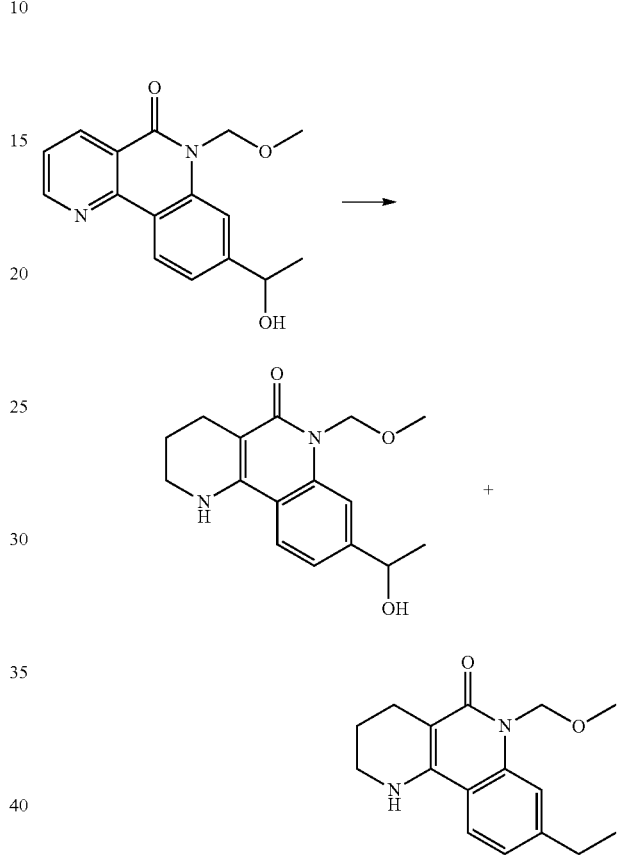

The compound (650 mg, 2.29 mmol) prepared in step 4 was dissolved in ethanol (10 ml)/dichloromethane (10 ml) and added with 10%-palladium (Pd) (200 mg) at room temperature. The resulting mixture was stirred for one day under hydrogen gas and 10%-palladium was removed by using celite-filter. The filtrate was concentrated under reduced pressure and the residue was purified by flash column chromatography (chloroform:methanol=30:1) to obtain the title compound (320 mg, yield: 49%, white solid).

$^1$H NMR (400 MHz, CDCl$_3$); δ 7.48 (s, 1H), 7.41 (d, J=8.4 Hz, 1H), 7.26-7.23 (m, 1H), 5.69 (s, 2H), 4.99 (m, 1H), 4.86 (s, 1H), 3.45 (m, 2H), 3.40 (s, 3H), 2.68 (t, J=6.4 Hz, 2H), 1.97 (m, 2H), 1.53 (d, J=6.4 Hz, 3H)

Further, in the reaction, 8-ethyl-6-(methoxymethyl)-1,2,3,4-tetrahydrobenzo[h][1,6]naphthyridine-5(6H)-one (140 mg, yield: 22%, whiute solid) was obtained.

$^1$H NMR (400 MHz, CDCl$_3$); δ 7.36-7.33 (m, 2H), 7.06 (d, J=8.4 Hz, 1H), 5.73 (s, 2H), 4.85 (s, 1H), 3.44 (m, 2H), 3.42 (s, 3H), 2.75 (qt, J=7.6 Hz, 2H), 2.69 (d, J=6.4 Hz, 2H), 1.97 (m, 2H), 1.28 (t, J=7.6 Hz, 3H)

Step 6: Synthesis of 8-[1-(Dimethylamino)ethyl]-6-(methoxymethyl)-1,2,3,4-tetrahydrobenzo[h][1,6]naphthyridine-5(6H)-one

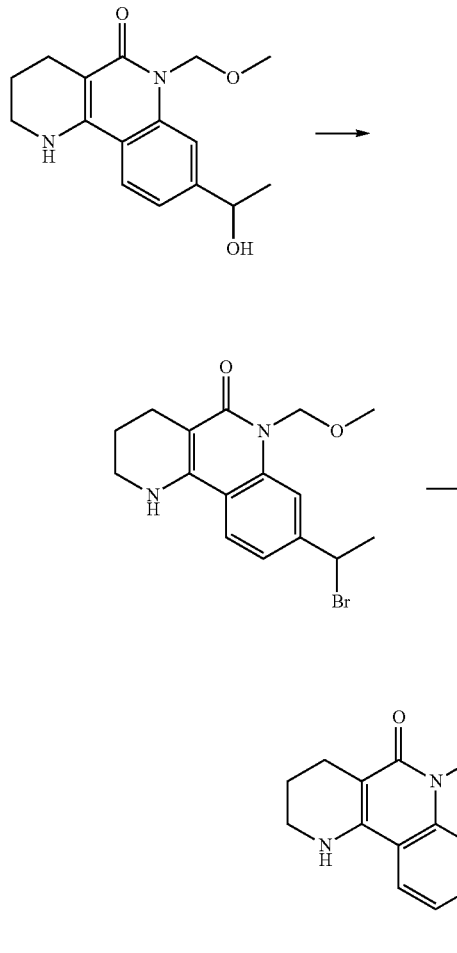

The compound (50 mg, 0.17 mmol) prepared in step 5 was dissolved in tetrahydrofuran (5 ml), sequentially added with pyridine (56 μl, 0.69 mmol) and phosphorus tribromide (33 μl, 0.35 mmol) at room temperature. The resulting mixture was stirred for 3 hours and poured into cold saturated sodium bicarbonate aqueous solution. The mixture was extracted with dichloromethane, washed with brine, dried over anhydrous sodium sulfate, and concentrated to dryness. The residue was then dissolved in tetrahydrofuran (4 ml), and 2.0 M dimethylamine tetrahydrofuran solution (1.7 ml, 3.47 mmol) was added dropwise. The resulting mixture was stirred overnight at room temperature and concentrated to dryness. The residue was purified by flash column chromatography (chloroform:methanol=10:1) to obtain the title compound (15 mg, yield (2 step): 27%, colorless oil).

$^1$H NMR (400 MHz, CDCl$_3$); δ 7.44 (s, 1H), 7.41 (d, J=8.4 Hz, 1H), 7.24 (d, J=8.4 Hz, 1H), 5.74 (s, 2H), 4.88 (s, 1H), 3.45 (m, 2H), 3.42 (s, 3H), 2.69 (t, J=6.4 Hz, 2H), 2.24 (s, 6H), 1.97 (m, 2H), 1.42 (d, J=6.0 Hz, 3H)

Step 7: Synthesis of 8-[1-(Dimethylamino)ethyl])-1,2,3,4-tetrahydrobenzo[h][1,6]naphthyridine-5(6H)-one dihydrochloride

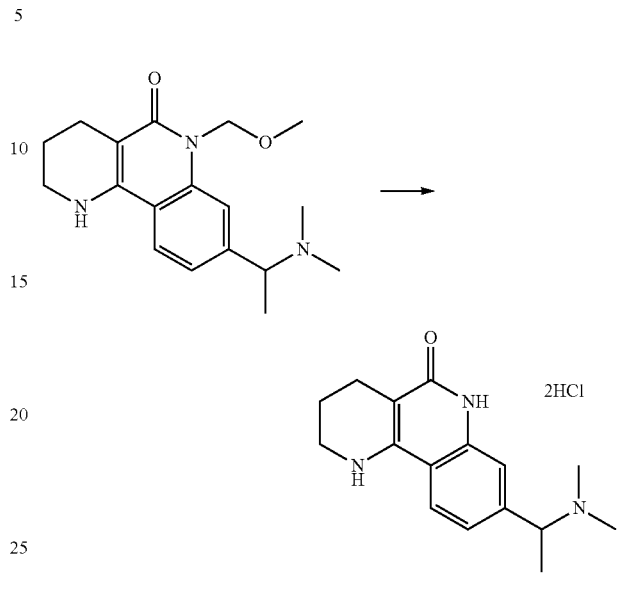

The compound (15 mg, 0.05 mmol) prepared in step 6 was dissolved in ethanol (4 ml) and added with conc. hydrochloric acid (0.5 ml). The mixture was stirred overnight at 80° C. and the precipitate was collected by filteration to obtain the title compound (14 mg, yield: 86%, yellow solid).

$^1$H NMR (400 MHz, DMSO-d$_6$); δ 11.28 (s, 1H), 10.85 (s, 1H), 7.95 (d, J=8.8 Hz, 1H), 7.45 (d, J=8.8 Hz, 1H), 7.30 (s, 1H), 4.48 (m, 1H), 3.32 (m, 2H), 2.74 (s, 3H), 2.50 (m, 5H), 1.79 (m, 2H), 1.63 (d, J=6.8 Hz, 3H)

Example 39

Synthesis of 8-[1-(Methylamino)ethyl]-1,2,3,4-tetrahydrobenzo[h][1,6]naphthyridine-5(6H)-one dihydrochloride

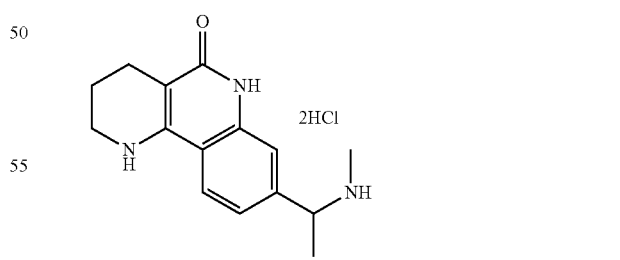

The title compound was obtained using the same manner as in Example 38.

$^1$H NMR (400 MHz, DMSO-d$_6$); δ 11.10 (s, 1H), 9.41 (s, 1H), 9.05 (s, 1H), 7.88 (d, J=8.0 Hz, 1H), 7.29 (d, J=8.0 Hz, 1H), 7.21 (s, 1H), 4.29 (m, 1H), 3.29 (m, 2H), 2.43-2.38 (m, 5H), 1.76-1.73 (m, 2H), 1.53 (d, J=6.4 Hz, 3H)

Example 40

Synthesis of 8-Ethyl-1,2,3,4-tetrahydrobenzo[h][1,6]naphthyridine-5(6H)-one hydrochloride

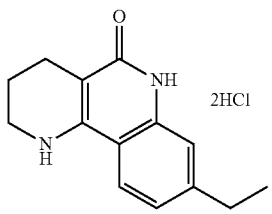 [SMILES: CCc1ccc2c3c(c(=O)[nH]c2c1)CCCN3]

8-ethyl-6-(methoxymethyl)-1,2,3,4-tetrahydrobenzo[h][1,6]naphthyridine-5(6H)-one (130 mg, 0.48 mmol) prepared in step 5 of Example 38 was dissolved in ethanol (8 ml) and added with conc. hydrochloric acid solution (2.5 ml). The mixture was stirred overnight at 80° C. and the precipitate was collected by filteration to obtain the title compound (120 mg, yield: 95%, yellow solid).

$^1$H NMR (400 MHz, DMSO-$d_6$); δ 11.88 (s, 1H), 8.18 (br, 2H), 7.95 (d, J=8.4 Hz, 1H), 7.26 (s, 1H), 7.17 (d, J=8.4 Hz, 1H), 3.37 (t, J=5.6 Hz, 2H), 2.68 (qt, J=7.8 Hz, 2H), 2.55 (t, J=6.0 Hz, 2H), 1.82 (m, 2H), 1.20 (t, J=7.8 Hz, 3H)

Example 41

Synthesis of 8-[(Dimethylamino)methyl]-1,2,3,4-tetrahydrobenzo[h][1,6]naphthyridine-5(6H)-one dihydrochloride

Step 1: Synthesis of Ethyl 3-(2-chloronicotineamido)benzoate

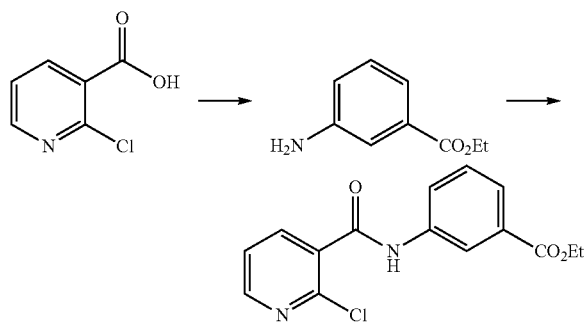

To a stirred solution of 2-chloronicotinic acid (500 mg, 3.17 mmol) in anhydrous dichloromethane (10 ml) were added oxalyl chloride (0.407 ml, 4.76 mmol) and a drop of anhydrous N,N-dimethylformamid at room temperature. The resulting mixture was stirred at room temperature for 2.5 hours and concentrated in vacuo. The residue was then dissolved in anhydrous dichloromethane (10 ml), and ethyl 3-aminobenzoate (0.521 ml, 3.49 mmol) in anhydrous dichloromethane (5 ml) and triethylamine (0.885 ml, 6.337 mmol) were added dropwise at 0° C. The mixture was stirred for 1 hour at room temperature and extracted with dichloromethane. The organic layer was dried over anhydrous magnesium sulfate and concentrated under reduced pressure to obtain the title compound (1.16 g, yield: quant. yield, ivory oil).

$^1$H NMR (400 MHz, CDCl$_3$); δ 8.53 (dd, J=1.6 Hz, 4.4 Hz, 1H), 8.41 (s, 1H), 8.21 (dd, J=2.0 Hz, 8.0 Hz, 1H), 8.14 (s, 1H), 8.08-8.05 (m, 1H), 7.89-7.87 (m, 1H), 7.49 (t, J=8.0 Hz, 1H), 7.42 (dd, J=4.8 Hz, 7.2 Hz, 1H), 4.37 (q, J=6.8 Hz, 2H), 1.38 (t, J=6.8 Hz, 3H)

Step 2: Synthesis of Ethyl 3-[2-chloro-N-(methoxymethyl)nicotineamido]benzoate

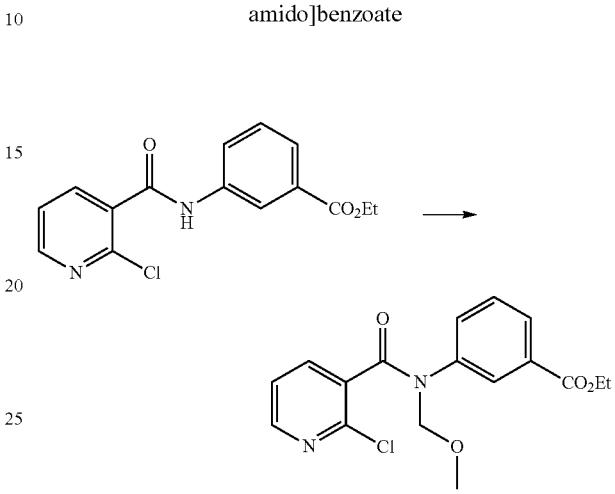

The compound (1.017 g, 3.337 mmol) prepared in step 1 was dissolved in anhydrous tetrahydrofuran (10 ml), added with potassium t-butoxide (749 mg, 6.674 mmol) slowly at 0° C. After stirring for 30 minutes, chloromethyl methyl ether (0.379 ml, 4.995 mmol) was added and the stirring was continued for 1 hour at room temperature. Once the reaction was completed, ethyl acetate and water were added and the mixture was extracted. The organic layer was dried over anhydrous magnesium sulfate and concentrated to dryness. The residue was then purified by flash column chromatography (dichloromethane:ethyl acetate=9:1) to obtain the title compound (981 mg, yield: 84%, colorless oil).

$^1$H NMR (400 MHz, CDCl$_3$); δ 8.24 (d, J=4.8 Hz 1H), 7.87-7.85 (m, 2H), 7.53-7.41 (m, 2H), 7.31 (t, J=8.0 Hz, 1H), 7.12-7.09 (m, 1H), 5.30 (s, 2H), 4.34 (q, J=6.8 Hz, 2H), 3.55 (s, 3H), 1.38 (t, J=6.8 Hz, 3H)

Step 3: Synthesis of Ethyl 6-(methoxymethyl)-5-oxo-5,6-dihydrobenzo[h][1,6]naphthyridine-8-carboxylate

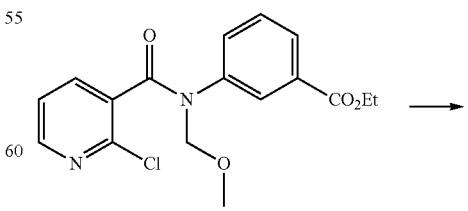

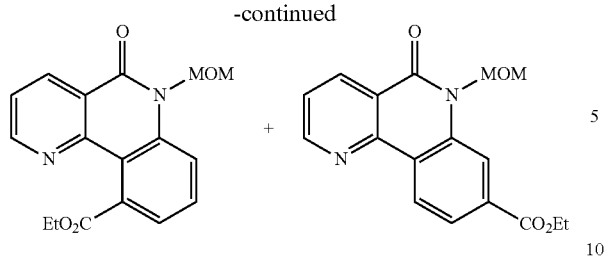

The compound (981 mg, 2.81 mmol) prepared in step 2 was dissolved in N,N-dimethylformamide (10.0 ml), added with palladium (II) acetate (206 mg, 0.844 mmol), 1,3-bis(diphenylphosphino)propane (348 mg, 0.844 mmol), tributylphosphine (0.693 ml, 2.81 mmol), and potassium carbonate (777 mg, 5.62 mmol). The resulting mixture was refluxed for 5 hours at 120° C. and cooled to room temperature. The mixture was extracted with dichloromethane, dried over anhydrous magnesium sulfate, and concentrated to dryness. The residue was then purified by flash column chromatography (dichloromethane:ethyl acetate=5:1) to obtain the title compound (657.3 mg, yield: 75%, white solid).

$^1$H NMR (400 MHz, CDCl$_3$); δ 9.05 (dd, J=2.0 Hz, 4.4 Hz, 1H), 8.93-8.91 (m, 1H), 8.78-8.74 (m, 1H), 8.30 (s, 1H), 8.05-8.03 (m, 1H), 7.59 (dd, J=4.4 Hz, 8.0 Hz, 1H), 5.88 (s, 2H), 4.46 (q, J=6.8 Hz, 2H), 3.50 (s, 3H), 1.46 (t, J=6.8 Hz, 1H)

Further, Ethyl 6-(methoxymethyl)-5-oxo-5,6-dihydrobenzo[h][1,6]naphthyridine-10-carboxylate was obtained in the above reaction.

$^1$H NMR (400 MHz, CDCl$_3$); δ 8.93-8.91 (m, 1H), 8.78-8.74 (m, 1H), 7.72 (d, J=8.8 Hz, 1H), 7.64 (t, J=7.6 Hz, 1H), 7.53 (dd, J=4.8 Hz, 8.0 Hz, 1H), 7.34 (d, J=7.6 Hz, 1H), 5.85 (s, 2H), 4.52 (q, J=6.8 Hz, 2H), 3.46 (s, 3H), 1.40 (t, J=6.8 Hz, 3H)

Step 4: Synthesis of Ethyl 6-(methoxymethyl)-5-oxo-1,2,3,4,5,6-hexahydrobenzo[h][1,6]naphthyridine-8-carboxylate

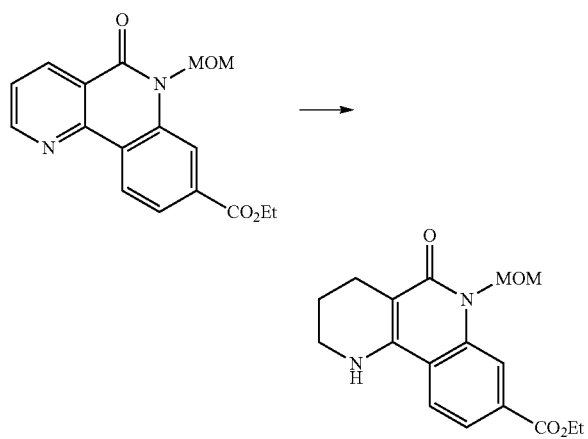

The compound (639 mg, 2.047 mmol) prepared in step 3 was dissolved in dichloromethane and methanol, added with 10%-palladium (Pd) (70.0 mg). The resulting mixture was stirred at room temperature for 20 hours under hydrogen gas. After completion, 10%-palladium (Pd) was removed by celite-filter and the solvent was concentrated under reduced pressure. The residue was then purified by flash column chromatography (dichloromethane:ethyl acetate=3:1) to obtain the title compound (423 mg, yield: 65.3%, white solid).

$^1$H NMR (400 MHz, CDCl$_3$); δ 8.22 (d, J=1.2 Hz, 1H), 7.86 (dd, J=1.2 Hz, 8.4 Hz, 1H), 7.49 (d, J=8.4 Hz, 1H), 5.78 (s, 2H), 4.42 (q, J=7.2 Hz, 2H), 3.49-3.46 (m, 1H), 3.43 (s, 3H), 2.72 (t, J=6.4 Hz, 1H), 2.00-1.98 (m, 1H), 1.43 (t, J=7.2 Hz, 3H)

Step 5: Synthesis of 8-(Hydroxymethyl)-6-(methoxymethyl)-1,2,3,4-tetrahydrobenzo[h][1,6]naphthyridine-5-(6H)-one

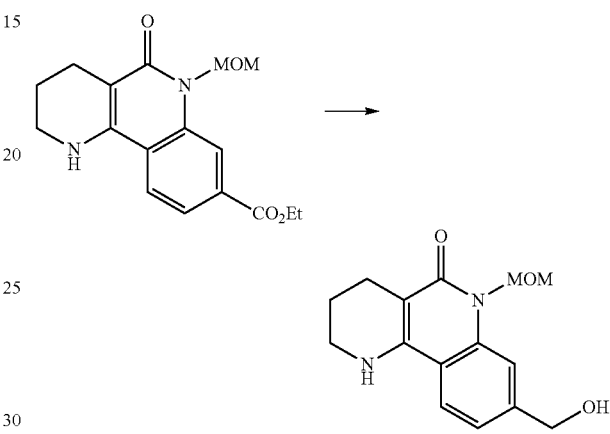

To a stirred solution of lithium aluminum hydride (72.9 mg, 1.92 mmol) in anhydrous tetrahydrofuran (5 ml) was added the compound prepared (405 mg, 1.28 mmol) in step 4 at 0° C. The resulting mixture was stirred at 0° C. for 1 hour and quenched with ammonium chloride aqueous solution. The mixture was extacted with ethyl cetate, dried over anhydrous magnesium sulfate, and concentrated to dryness. The residue was then purified by flash column chromatography (dichloromethane:methanol=7:1) to obtain the title compound (339 mg, yield: 94%, ivory solid).

$^1$H NMR (400 MHz, CDCl$_3$+CD$_3$OD); δ 7.73 (d, J=8.0 Hz, 1H), 7.55 (d, J=1.6 Hz, 1H), 7.26 (dd, J=1.6 Hz, 8.0 Hz, 1H), 5.74 (s, 2H), 4.75 (s, 2H), 3.46-3.41 (m, 1H), 3.40 (s, 3H), 2.65 (t, J=6.4 Hz, 1H), 1.98-1.95 (m, 1H)

Step 6: Synthesis of 8-(Chloromethyl)-6-(methoxymethyl)-1,2,3,4-tetrahydrobenzo[h][1,6]naphthyridine-5-(6H)-one

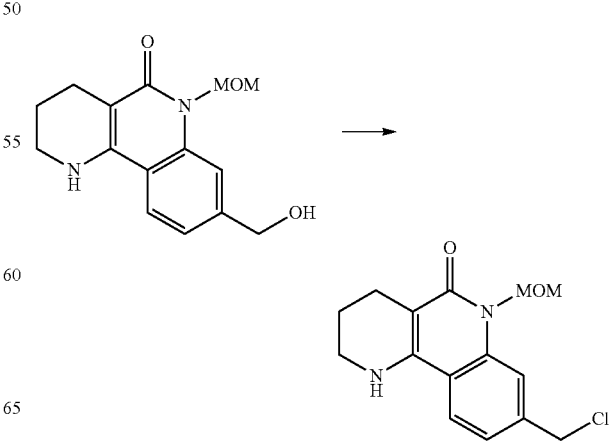

Anhydrous dichloromethane (10 ml) was added to the compound (50.0 mg, 0.182 mmol) prepared in step 5, and thionyl chloride (0.016 ml, 0.219 mmol) was added dropwise at room temperature. The resulting mixture was stirred at room temperature for 2 hours and poured into sodium bicarbonate aqueous solution. The mixture was extracted with dichloromethane, dried over anhydrous magnesium sulfate, and concentrated under reduced pressure to obtain the title compound (51.4 mg, yield: 96%, white solid). The compound was used in the following reaction without further purification.

$^1$H NMR (400 MHz, CDCl$_3$); δ 7.54 (s, 1H), 7.43 (d, J=8.4 Hz, 1H), 7.25 (d, J=8.4 Hz, 1H), 5.74 (s, 2H), 4.68 (s, 2H), 3.47-3.45 (m, 2H), 3.43 (s, 3H), 2.70 (t, J=6.4 Hz, 2H), 1.99-1.95 (m, 2H)

Step 7: Synthesis of 8-[(Dimethylamino)methyl]-6-(methoxymethyl)-1,2,3,4-tetrahydrobenzo[h][1,6]naphthyridine-5-(6H)-one

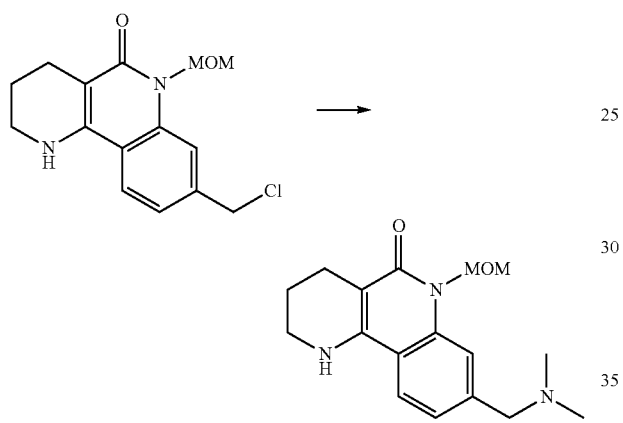

The compound (25.3 mg, 0.0864 mmol) prepared in step was dissolved in methanol (3.0 ml), added with 2.0 M dimethylamine (0.864 ml, methanol solution). The resulting mixture was stirred at room temperature for 19 hours and concentrated under reduced pressure. Sodium bicarbonate aqueous solution was added to the concentrated residue and the mixture was extracted with dichloromethane. The organic layer was dried over anhydrous magnesium sulfate and concentrated to dryness. The residue was then purified by flash column chromatography (dichloromethane:methanol=7:1) to obtain the title compound (17.8 mg, yield: 68%, white solid).

$^1$H NMR (400 MHz, CDCl$_3$); δ 7.46 (s, 1H), 7.39 (d, J=8.0 Hz, 1H), 7.22 (d, J=8.0 Hz, 1H), 5.75 (s, 2H), 4.96 (s, 1H), 3.54 (s, 2H), 3.47-3.44 (m, 2H), 3.42 (s, 3H), 2.70 (t, J=6.8 Hz, 2H), 2.28 (s, 6H), 1.99-1.96 (m, 2H)

Step 8: Synthesis of 8-[(Dimethylamino)methyl]-1,2,3,4-tetrahydrobenzo[h][1,6]naphthyridine-5-(6H)-one dihydrochloride

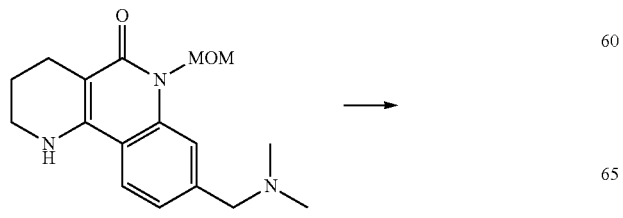

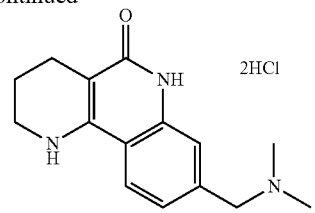

The compound (57.8 mg, 0.192 mmol) prepared in step 7 was dissolved in ethanol (3 ml), added with 12 N hydrochloric acid aqueous solution (3.0 ml). The resulting mixture was heated to 90° C. and stirred for 3 hours. The mixture was concentrated to dryness and dissolved in ethyl acetate. After stirring for 30 minutes, the precipitate was filtered and washed with diethyl ether to obtain the title compound (53.5 mg, yield: 84.5%, ivory solid).

$^1$H NMR (400 MHz, DMSO); δ 11.50 (s, 1H), 10.80 (s, 1H), 7.98 (d, J=8.4 Hz, 1H), 7.43 (d, J=8.4 Hz, 1H), 7.36 (s, 1H), 4.31 (d, J=5.2 Hz, 1H), 3.35-3.33 (m, 1H), 2.69 (s, 3H), 2.68 (s, 3H), 1.82-1.79 (m, 1H)

The following compound was prepared using the reaction of Example 41.

Example 42

8-[(Diethylamino)methyl]-1,2,3,4-tetrahydrobenzo[h][1,6]naphthyridine-5(6H)-one dihydrochloride Example 43

8-[(Ethylamino)methyl]-1,2,3,4-tetrahydrobenzo[h][1,6]naphthyridine-5(6H)-one dihydrochloride Example 44

8-(Pyrrolidine-1-ylmethyl)-1,2,3,4-tetrahydrobenzo[h][1,6]naphthyridine-5(6H)-one dihydrochloride Example 45

8-[(Isopropylamino)methyl]-1,2,3,4-tetrahydrobenzo[h][1,6]naphthyridine-5(6H)-one dihydrochloride Example 46

8-[(Propylamino)methyl]-1,2,3,4-tetrahydrobenzo[h][1,6]naphthyridine-5(6H)-one dihydrochloride Example 47

8-{[Ethyl(methyl)amino]methyl}-1,2,3,4-tetrahydrobenzo[h][1,6]naphthyridine-5(6H)-one dihydrochloride

Example 48

8-(Piperidine-1-ylmethyl)-1,2,3,4-tetrahydrobenzo[h][1,6]naphthyridine-5(6H)-one dihydrochloride

Example 49

8-(Morpholinomethyl)-1,2,3,4-tetrahydrobenzo[h][1,6]naphthyridine-5(6H)-one dihydrochloride

Example 50

9-[(Dimethylamino)methyl]-1,2,3,4-tetrahydrobenzo[h][1,6]naphthyridine-5(6H)-one dihydrochloride

Example 51

8-{[Benzyl(methyl)amino]methyl}-1,2,3,4-tetrahydrobenzo[h][1,6]naphthyridine-5(6H)-one dihydrochloride

Example 52

8-[(Methylamino)methyl]-1,2,3,4-tetrahydrobenzo[h][1,6]naphthyridine-5(6H)-one dihydrochloride

Example 53

8-{[(2-Hydroxyethyl)(methyl)amino]methyl}-1,2,3,4-tetrahydrobenzo[h][1,6]naphthyridine-5(6H)-one dihydrochloride

Example 54

8-{[(2-(Dimethylaminoethyl)(methyl)amino]methyl}-1,2,3,4-tetrahydrobenzo[h][1,6]naphthyridine-5(6H)-one trihydrochloride

Example 55

8-[(4-Methylpiperazine-1-yl)methyl]-1,2,3,4-tetrahydrobenzo[h][1,6]naphthyridine-5(6H)-one trihydrochloride

Example 56

8-[(Methyl(propyl)amino)methyl]-1,2,3,4-tetrahydrobenzo[h][1,6]naphthyridine-5(6H)-one dihydrochloride

Example 57

Ethyl-3-{methyl[(5-oxo-1,2,3,4,5,6-hexahydrobenzo-[h][1,6]naphthyridine-8-yl)methyl]-amino}propanoate dihydrochloride

Example 58

3-{Methyl[(5-oxo-1,2,3,4,5,6-hexahydrobenzo[h][1,6]naphthyridine-8-yl)methyl]amino}propanoic acid dihydrochloride

Example 59

8-{[Isopropyl(methyl)amino]methyl}-1,2,3,4-tetrahydrobenzo[h][1,6]naphthyridine-5(6H)-one dihydrochloride

Example 60

8-{[(2-Methoxyethyl)(methyl)amino]methyl}-1,2,3,4-tetrahydrobenzo[h][1,6]naphthyridine-5(6H)-one dihydrochloride

Example 61

Ethyl-3-[(5-oxo-1,2,3,4,5,6-hexahydrobenzo[h][1,6]naphthyridine-8-yl)methyl amino]propanoate dihydrochloride

Example 62

8-[(2,2,2-Trifuloroethylamino)methyl]-1,2,3,4-tetrahydrobenzo[h][1,6]naphthyridine-5(6H)-one dihydrochloride

Example 63

2-[(5-Oxo-1,2,3,4,5,6-hexahydrobenzo[h][1,6]naphthyridine-8-yl)methylamino]acetonitrile dihydrochloride

Example 64

8-[(1H-Imidazole-1-yl)methyl]-1,2,3,4-tetrahydrobenzo[h][1,6]naphthyridine-5(6H)-one hydrochloride

Example 65

8-[(1H-Pyrrole-1-yl)methyl]-1,2,3,4-tetrahydrobenzo[h][1,6]naphthyridine-5(6H)-one hydrochloride

| Ex. | Chmical Structure | NMR spectrum data |
|---|---|---|
| 42 | 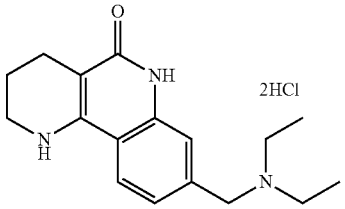 [SMILES: CCN(CC)Cc1ccc2c3c(c(=O)[nH]c2c1)CCCN3] 2HCl | ¹H NMR (400 MHz, DMSO-d₆); δ 11.49 (s, 1H), 9.61 (brs, 1H), 7.88 (d, J = 8.4 Hz, 1H), 7.27 (s, 1H), 7.14 (brs, 1H), 4.32~4.30 (m, 2H), 3.34~3.31 (m, 2H), 3.07~3.03 (m, 4H), 1.90~1.79 (m, 2H), 1.22 (t, J = 6.9 Hz, 6H) |
| 43 | 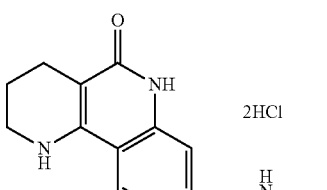 2HCl | ¹H NMR (400 MHz, DMSO-d₆); δ 11.20 (s, 1H), 9.12 (brs, 1H), 7.88 (d, J = 8.0 Hz, 1H), 7.32 (d, J = 8.4 Hz, 1H), 7.27 (s, 1H), 4.13 (t, J = 6.0 Hz, 2H), 3.32 (brs, 2H), 2.98~2.94 (m, 2H), 2.46~2.44 (m, 2H), 1.79~brs, 2H), 1.22 (t, J = 7.1 Hz, 3H) |
| 44 | 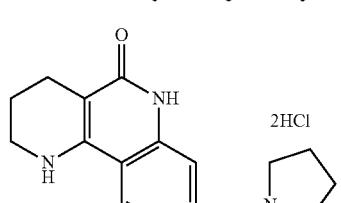 2HCl | ¹H NMR (400 MHz, DMSO-d₆); δ 11.33 (s, 1H), 10.82 (s, 1H), 7.93 (d, J = 4.2 Hz, 1H), 7.43 (d, J = 3.6 Hz, 1H), 7.33 (s, 1H), 6.20-5.80 (brs, 1H), 4.37 (d, J = 3.0 Hz, 2H), 3.34-3.32 (m, 4H), 3.06-3.02 (m, 2H), 2.51-2.47 (m, 2H), 2.03-2.01 (m, 2H), 1.88 (m, 4H) |
| 45 | 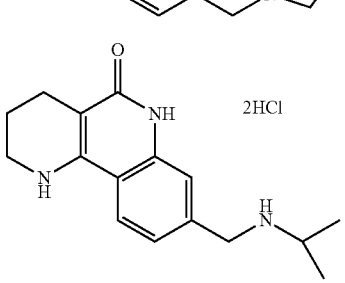 2HCl | ¹H NMR (400 MHz, DMSO-d₆); δ 11.17 (s, 1H), 9.02 (s, 1H), 8.54 (br, 1H), 7.89 (d, J = 4.2 Hz, 1H), 7.32 (d, J = 4.0 Hz, 1H), 7.28 (s, 1H), 7.22-7.03 (br, 1H), 4.15 (m, 2H), 3.32 (m, 2H), 2.53-2.52 (m, 2H), 2.46-2.45 (m, 1H), 1.80 (m, 2H), 1.3 (s, 3H), 1.29 (s, 3H) |
| 46 | 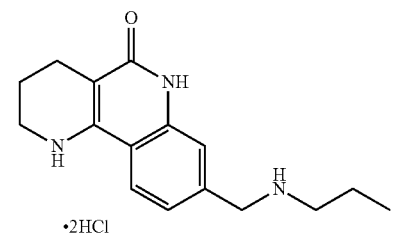 [SMILES: CCCNCc1ccc2c3c(c(=O)[nH]c2c1)CCCN3] •2HCl | ¹H NMR (400 MHz, DMSO-d₆); δ 11.41 (s, 1H), 9.28 (s, 2H), 7.94 (d, J = 8.4 Hz, 1H), 7.38 (d, J = 8.4 Hz, 1H), 7.33 (s, 1H), 4.14 (t, J = 5.4 Hz, 2H), 3.33 (t, J = 5.0 Hz, 2H), 2.84 (m, 2H), 2.48 (m, 2H), 1.80 (t, J = 5.4 Hz, 2H), 1.69-1.63 (m, 2H), 0.89 (t, J = 7.4 Hz, 3H) |
| 47 | 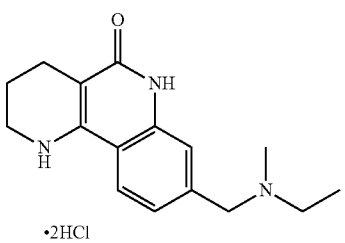 [SMILES: CCN(C)Cc1ccc2c3c(c(=O)[nH]c2c1)CCCN3] •2HCl | ¹H NMR (400 MHz, DMSO-d₆); δ 11.48 (s, 1H), 10.74 (s, 1H), 7.98 (d, J = 8.0 Hz, 1H), 7.47 (d, J = 8.0 Hz, 1H), 7.38 (s, 1H), 4.39 (m, 1H), 4.23 (m, 1H), 3.16-3.10 (m, 1H), 3.34 (t, J = 5.2 Hz, 2H), 3.04-2.98 (m, 1H), 2.60 (d, J = 4.8 Hz, 3H), 2.50-2.49 (m, 2H), 1.80 (t, J = 5.2 Hz, 2H), 1.27 (t, J = 7.0 Hz, 3H) |
| 48 | 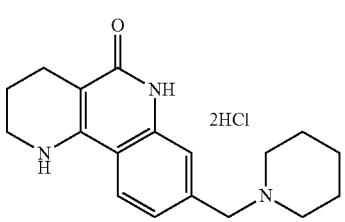 [SMILES: O=c1[nH]c2cc(CN3CCCCC3)ccc2c2c1CCCN2] 2HCl | ¹H NMR (400 MHz, DMSO-d₆); δ 7.47 (s, 1H), 7.38 (d, J = 8.4 Hz, 1H), 7.32 (d, J = 8.4 Hz, 1H), 5.74 (s, 2H), 4.87 (s, 1H), 3.58 (s, 2H), 3.46-3.43 (m, 2H), 3.42 (s, 3H), 2.69 (t, J = 6.4 Hz, 2H), 2.41 (br, 4H), 1.98-1.95 (m, 2H), 1.60-1.56 (m, 4H), 1.42-1.44 (m, 2H) |

-continued

| Ex. | Chmical Structure | NMR spectrum data |
|---|---|---|
| 49 | (structure) 2HCl | $^1$H NMR (400 MHz, DMSO-d$_6$); δ 7.49 (s, 1H), 7.40 (d, J = 8.0 Hz, 1H), 7.27-7.21 (m, 1H), 5.74 (s, 2H), 4.94 (s, 1H), 3.72 (t, J = 4.4 Hz, 4H), 3.60 (s, 2H), 3.48-3.44 (m, 2H), 3.42 (s, 3H), 2.69 (t, J = 4.6 Hz, 2H), 2.47 (br, 4H), 2.00-1.94 (m, 2H) |
| 50 | (structure) 2HCl | $^1$H NMR (400 MHz, DMSO-d$_6$); δ 11.09 (s, 1H), 10.98 (brs, salt), 8.00 (s, 1H), 7.58 (d, J = 8.4 Hz, 1H), 7.27 (d, J = 8.4 Hz, 1H), 4.22~4.20 (m, 2H), 3.33~3.30 (m, 2H), 2.70~s, 3H), 2.69 (s, 3H), 2.46~2.44 (m, 2H), 1.98~1.79 (m, 2H) |
| 51 | (structure) 2HCl | $^1$H NMR (400 MHz, DMSO-d$_6$); δ 11.22 (s, 1H), 10.70 (br, 1H), 7.92 (d, J = 8.4 Hz, 1H), 7.61~7.58 (m, 2H), 7.48-7.46 (m, 3H), 7.39 (d, J = 8.4 Hz, 1H), 7.32 (s, 1H), 4.42-4.39 (m, 2H), 4.26-4.21 (m, 2H), 3.32 (br, 2H), 2.47-2.45 (m, 2H), 1.79 (br, 2H) |
| 52 | (structure) 2HCl | $^1$H NMR (400 MHz, DMSO-d$_6$); δ 11.45 (s, 1H), 9.30 (s, 1H), 7.95 (d, J = 8.4 Hz, 1H), 7.35 (d, J = 8.4 Hz, 1H), 7.33 (s, 1H), 4.14 (t, J = 5.6 Hz, 2H), 3.35-3.32 (m, 2H), 2.55-2.47 (m, 5H), 1.81-1.79 (m, 2H) |
| 53 | (structure) •2HCl | $^1$H NMR (400 MHz, DMSO-d$_6$); δ 11.55 (s, 1H), 10.45 (s, 1H), 8.01 (d, J = 8.4 Hz, 1H), 7.45 (d, J = 8.4 Hz, 1H), 7.41 (s, 1H), 4.46-4.41 (m, 1H), 4.36-4.31 (m, 1H), 3.77 (m, 2H), 3.34 (t, J = 5.2 Hz, 2H), 3.10 (m, 2H), 2.71 (d, J = 4.8 Hz, 3H), 2.52 (m, 2H), 1.80 (m, 2H) |
| 54 | (structure) 3HCl | $^1$H NMR (400 MHz, DMSO-d$_6$); δ 11.37 (s, 1H), 11.29 (br, 1H), 11.02 (br, 1H), 7.97 (d, J = 4.2 Hz, 1H), 7.51 (d, J = 4.4 Hz, 1H), 7.38 (s, 1H), 4.61-4.58 (m, 1H), 4.34-4.31 (m, 1H), 3.64-3.52 (m, 4H), 3.34 (s, 2H), 2.83 (s, 6H), 2.68 (s, 3H), 2.48 (s, 2H), 1.80 (s, 2H) |

| Ex. | Chmical Structure | NMR spectrum data |
|---|---|---|
| 55 | 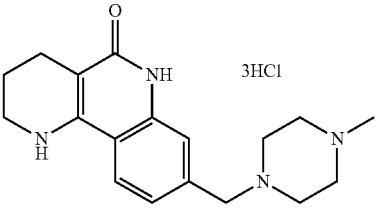 [SMILES: CN1CCN(Cc2ccc3c4c(c(=O)[nH]c3c2)CCCN4)CC1] 3HCl | $^1$H NMR (400 MHz, DMSO-d$_6$); δ 11.70 (br, 1H), 11.31 (s, 1H), 7.93 (d, J = 8.4 Hz, 1H), 7.44 (d, J = 8.4 Hz, 1H), 7.34 (s, 1H), 4.39 (br, 2H), 3.63-3.33 (m, 10H), 2.79 (br, 3H), 2.48-2.46 (m, 2H), 1.82-1.79 (m, 2H) |
| 56 | 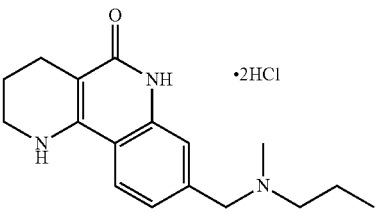 [SMILES: CCCN(C)Cc1ccc2c3c(c(=O)[nH]c2c1)CCCN3] ·2HCl | $^1$H NMR (400 MHz, DMSO-d$_6$); δ 11.20 (s, 1H), 10.36 (s, 1H), 7.89 (d, J = 8.0 Hz, 1H), 7.35 (d, J = 8.0 Hz, 1H), 7.28 (s, 1H), 4.39-4.34 (m, 1H), 4.24-4.19 (m, 1H), 3.30 (m, 2H), 2.97-2.80 (m, 2H), 2.61 (d, J = 4.8 Hz, 3H), 2.45 (m, 2H), 1.77 (m, 2H), 1.70 (m, 2H), 0.85 (t, J = 7.6 Hz, 3H) |
| 57 | 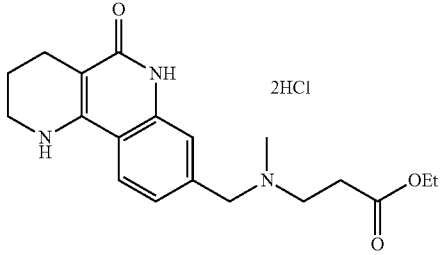 [SMILES: CCOC(=O)CCN(C)Cc1ccc2c3c(c(=O)[nH]c2c1)CCCN3] 2HCl | $^1$H NMR (400 MHz, DMSO-d$_6$); δ 11.32 (s, 1H), 10.70 (br, 1H), 7.93 (d, J = 4.0 Hz, 1H), 7.41 (d, J = 4.0 Hz, 1H), 7.33 (s, 1H), 4.46-4.28 (m, 2H), 4.11-4.06 (m, 2H), 3.37-3.32 (m, 4H), 2.94 (t, J = 7.2 Hz, 2H), 2.65 (d, J = 2.2 Hz, 3H), 2.48 (m, 2H), 1.80 (m, 2H), 1.22-1.15 (m, 3H) |
| 58 | 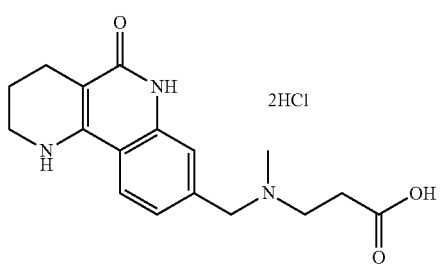 [SMILES: CN(CCC(=O)O)Cc1ccc2c3c(c(=O)[nH]c2c1)CCCN3] 2HCl | $^1$H NMR (400 MHz, DMSO-d$_6$); δ 11.37 (s, 1H), 10.58 (br, 1H), 7.95 ((d, J = 4.2 Hz, 1H), 7.41 (d, J = 4.2 Hz, 1H), 7.34 (s, 1H), 4.45-4.28 (m, 2H), 3.33 (br, 3H), 3.23-3.20 (m, 1H), 2.85 (t, J = 7.6 Hz, 2H), 2.65 (d, J = 2.0 Hz, 3H), 2.53 (m, 2H), 1.82 (br, 2H) |
| 59 | 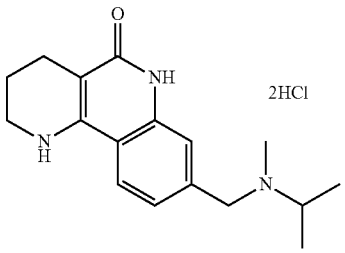 [SMILES: CC(C)N(C)Cc1ccc2c3c(c(=O)[nH]c2c1)CCCN3] 2HCl | $^1$H NMR (400 MHz, DMSO-d$_6$); δ 11.47 (s, 1H), 10.44 (br, 1H), 7.99 (d, J = 4.2 Hz, 1H), 7.52 (d, J = 3.8 Hz, 1H), 7.41 (s, 1H), 4.42-4.17 (m, 2H), 3.47-3.42 (m, 1H), 3.35-3.33 (m, 2H), 2.54 (d, J = 2.6 Hz, 3H), 1.80 (t, J = 4.8 Hz, 2H), 1.32-1.28 (m, 6H) |
| 60 | 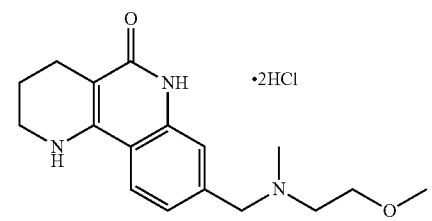 [SMILES: COCCN(C)Cc1ccc2c3c(c(=O)[nH]c2c1)CCCN3] ·2HCl | $^1$H NMR (400 MHz, DMSO-d$_6$); δ 11.57 (s, 1H), 10.69 (s, 1H), 8.01 (d, J = 7.6 Hz, 1H), 7.46 (d, J = 7.6 Hz, 1H), 7.41 (s, 1H), 4.44-4.40 (m, 1H), 4.33-4.28 (m, 1H), 3.72 (m, 2H), 3.34 (m, 2H), 3.27 (s, 3H), 3.22 (m, 2H), 2.68 (s, 3H), 2.51 (m, 3H), 1.80 (m, 2H) |

-continued
| Ex. | Chmical Structure | NMR spectrum data |
|---|---|---|
| 61 | 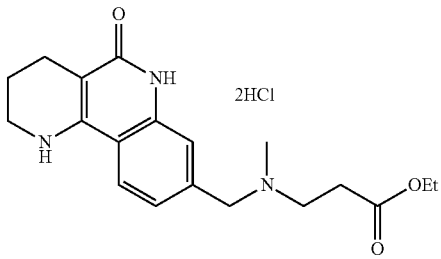 [SMILES: CCOC(=O)CCN(C)Cc1ccc2c3c(c(=O)[nH]c2c1)CCCN3] 2HCl | $^1$H NMR (400 MHz, DMSO-d$_6$); δ 11.57 (s, 1H), 9.56 (s, 2H), 7.96 (s, 1H), 7.39 (s, 1H), 7.35 (s, 1H), 4.16 (s, 2H), 4.05 (s, 2H), 3.31 (s, 2H), 3.11 (s, 2H), 2.80 (s, 2H), 1.77 (s, 2H), 1.15 (s, 3H) |
| 62 | 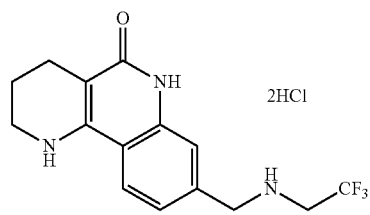 [SMILES: O=c1[nH]c2cc(CNCC(F)(F)F)ccc2c2c1CCCN2] 2HCl | $^1$H NMR (400 MHz, DMSO-d$_6$); δ 11.35 (s, 1H), 10.09 (br, 1H), 7.93 (d, J = 4.0 Hz, 1H), 7.38-7.35 (m, 2H), 4.25 (s, 2H), 4.01 (d, J = 4.6 Hz, 2H), 3.33 (m, 2H), 1.80 (m, 2H) |
| 63 | 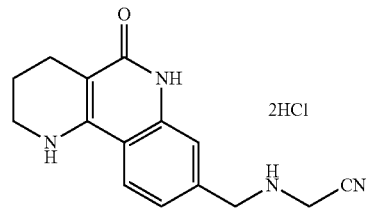 [SMILES: N#CCNCc1ccc2c3c(c(=O)[nH]c2c1)CCCN3] 2HCl | $^1$H NMR (400 MHz, DMSO-d$_6$); δ 11.43 (s, 1H), 7.83 (d, J = 4.0 Hz, 1H), 7.30 (s, 1H), 7.09 (d, J = 4.0 Hz, 1H), 4.54 (s, 2H), 3.36 (s, 2H), 3.32 (m, 2H), 2.53 (m, 2H), 1.79 (m, 2H) |
| 64 | 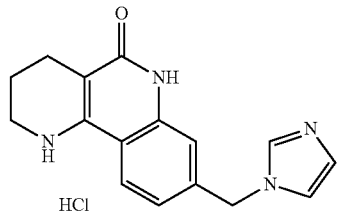 [SMILES: O=c1[nH]c2cc(Cn3ccnc3)ccc2c2c1CCCN2 ; Cl] HCl | $^1$H NMR (400 MHz, DMSO-d$_6$); δ 11.58 (s, 1H), 9.36 (s, 1H), 8.02 (d, J = 8.4 Hz, 1H), 7.80 (s, 1H), 7.74 (s, 1H), 7.22 (s, 1H), 7.16 (d, J = 1.6 Hz, 1H), 5.53 (s, 2H), 3.32 (s, 2H), 2.49 (s, 2H), 1.78 (s, 2H) |
| 65 | 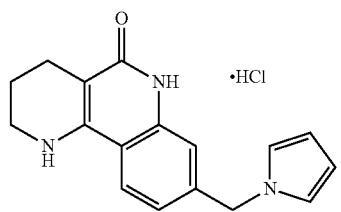 [SMILES: O=c1[nH]c2cc(Cn3cccc3)ccc2c2c1CCCN2 ; Cl] ·HCl | $^1$H NMR (400 MHz, DMSO-d$_6$); δ 11.49 (s, 1H), 7.86 (d, J = 7.6 Hz, 1H), 7.09 (s, 1H), 6.94 (d, J = 8.4 Hz, 1H), 6.78 (m, 2H), 6.01 (m, 2H), 5.15 (s, 2H), 3.30 (m, 2H), 2.47 (m, 2H), 1.77 (m, 2H) |

Example 66

Synthesis of 8-[(Dimethylamino)methyl]-1-methyl-1,2,3,4-tetrahydrobenzo[h][1,6]naphthyridine-5(6H)-one dihydrochloride Step 1: Synthesis of 8-[(Dimethylamino)methyl]-6-(methoxymethyl)-1-methyl-1,2,3,4-tetrahydrobenzo[h][1,6]naphthyridine-5(6H)-one

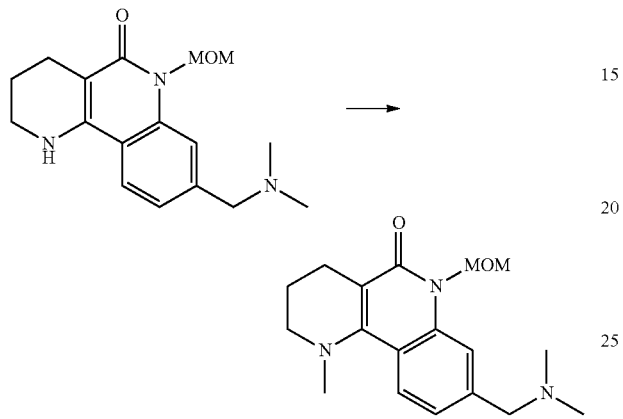

Title compound (16 mg, yield: 56%, yellow solid) was obtained by performing a reaction of 8-[(dimethylamino)methyl]-6-(methoxymethyl)-1,2,3,4-tetrahydrobenzo[h][1,6]naphthyridine-5-(6H)-one (30 mg, 0.09 mmol) in the same manner as step 1 of Example 30.

$^1$H NMR (400 MHz, CDCl$_3$); δ 7.80 (d, J=8.4 Hz, 1H), 7.47 (s, 1H), 7.24~7.22 (m, 1H), 5.75 (brs, 2H), 3.57 (s, 2H), 3.43 (s, 3H), 3.17~3.14 (m, 2H), 2.99 (s, 3H), 2.63 (t, J=6.6 Hz, 2H), 2.31 (s, 6H), 1.89~1.86 (m, 2H)

Step 2: Synthesis of 8-[(Dimethylamino)methyl]-1-methyl-1,2,3,4-tetrahydrobenzo[h][1,6]naphthyridine-5(6H)-one hydrochloride

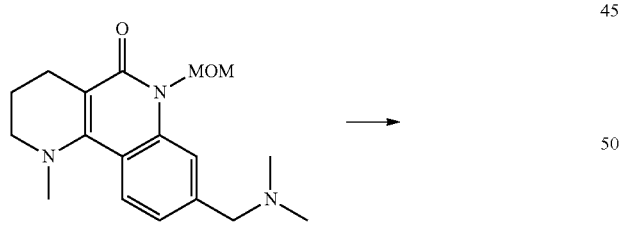

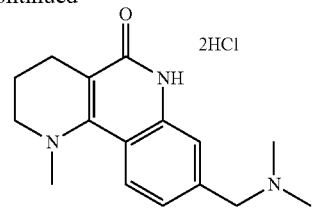

The reaction of the compound (16 mg, 0.05 mmol) prepared in step 1 was carried out in the same manner as in step 2 of Example 34 to obtain the title compound (18 mg, yield: 99%, yellow solid).

$^1$H NMR (400 MHz, DMSO-d$_6$); δ 11.71 (s, 1H), 10.70 (brs, 1H), 10.62 (s, 1H), 8.01 (d, J=8.0 Hz, 1H), 7.41 (d, J=8.0 Hz, 1H), 7.34 (s, 1H), 4.33~4.32 (m, 2H), 2.69 (s, 9H), 1.78~1.71 (m, 2H)

The following compounds were prepared using the reaction of Example 66.

Example 67

8-(Pyrrolidine-1-ylmethyl)-1,2,3,4-tetrahydrobenzo[h][1,6]naphthyridine-5(6H)-one dihydrochloride

Example 68

8-[(Diethylamino)methyl]-1-methyl-1,2,3,4-tetrahydrobenzo[h][1,6]naphthyridine-5(6H)-one dihydrochloride

Example 69

1-Methyl-8-(piperidine-1-ylmethyl)-1,2,3,4-tetrahydrobenzo[h][1,6]naphthyridine-5(6H)-one dihydrochloride

Example 70

1-Methyl-8-(morpholinomethyl)-1,2,3,4-tetrahydrobenzo[h][1,6]naphthyridine-5(6H)-one dihydrochloride

Example 71

8-{[Ethyl(methyl)amino]methyl}-1-methyl-1,2,3,4-tetrahydrobenzo[h][1,6]naphthyridine-5(6H)-one dihydrochloride

| Ex. | Chmical Structure | | NMR spectrum data |
|---|---|---|---|
| 67 | (structure) | 2HCl | $^1$H NMR (400 MHz, DMSO-d$_6$); δ 11.69 (s, 1H), 11.09 (br, 1H), 10.60 (br, 1H), 7.99 (d, J = 4.0 Hz, 1H), 7.47 (d, J = 4.2 Hz, 1H), 7.36-7.34 (m, 1H), 3.33 (br, 2H), 3.16 (br, 2H), 2.85 (br, 2H), 2.66-2.64 (m, 2H), 2.44-2.43 (m,2H), 2.00 (br, 2H), 1.87-1.77 (m, 4H) |

-continued

| Ex. | Chmical Structure | NMR spectrum data |
|---|---|---|
| 68 | 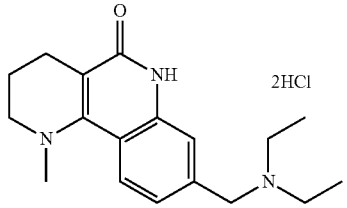 [SMILES: CCN(CC)Cc1ccc2c3c(c(=O)[nH]c2c1)CCCN3C] | $^1$H NMR (400 MHz, DMSO-d$_6$); δ 11.67 (s, 1H), 10.62 (brs, 1H), 8.78 (br s, 1H), 7.99 (d, J = 8.4 Hz, 1H), 7.49 (d, J = 8.3 Hz, 1H), 7.39 (s, 1H), 5.76 (s, 1H), 4.35~4.33 (m, 2H), 3.03~2.91 (m, 4H), 2.85 (br s, 2H), 2.67~2.64 (m, 2H), 1.79~1.77 (m, 2H), 1.26~1.23 (m, 6H) |
| 69 | 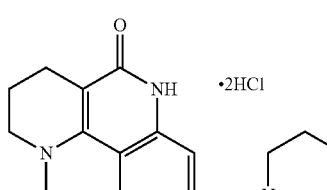 | $^1$H NMR (400 MHz, DMSO-d$_6$); δ 11.69 (s, 1H), 10.61 (m, 2H), 7.99 (d, J = 8.4 Hz, 1H), 7.47 (d, J = 8.4 Hz, 1H), 7.35 (s, 1H), 4.29 (m, 2H), 3.24 (m, 2H), 2.91-2.84 (m, 4H), 2.66 (t, J = 6.8 Hz, 2H), 2.50 (m, 3H), 1.76 (m, 6H), 1.69-1.65 (m, 1H), 1.33 (m, 1H) |
| 70 | 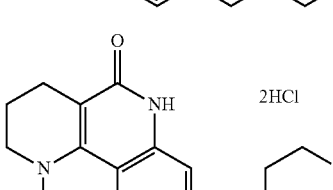 | $^1$H NMR (400 MHz, DMSO-d$_6$); δ 11.60 (s, 1H), 11.14 (s, 1H), 7.78 (d, J = 8.4 Hz, 1H), 7.44 (d, J = 8.4 Hz, 1H), 7.36 (s, 1H), 4.37 (d, J = 4.8 Hz, 2H), 3.94-3.77 (m, 4H), 3.24-3.09 (m, 6H), 2.92 (s, 3H), 2.43 (t, J = 6.4 Hz, 2H), 1.77 (m, 2H) |
| 71 | 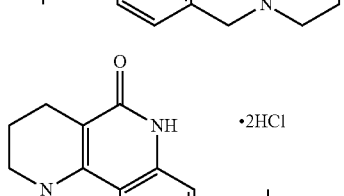 | $^1$H NMR (400 MHz, DMSO-d$_6$); δ 11.69 (s, 1H), 10.68 (s, 1H), 10.62 (s, 1H), 8.00 (d, J = 8.4 Hz, 1H), 7.45 (d, J = 8.4 Hz, 1H), 7.36 (s, 1H), 4.43-4.38 (m, 1H), 4.27-4.22 (m, 1H), 3.13-3.00 (m, 2H), 2.84 (m, 2H), 2.66 (t, J = 6.8 Hz, 2H), 2.60 (s, 3H), 2.52 (m, 3H), 1.80-1.77 (m, 2H) |

Example 72

Synthesis of 8-[(Dimethylamino)methyl]-10-methoxy-1,2,3,4-tetrahydrobenzo[h][1,6]naphthyridine-5(6H)-one dihydrochloride

Step 1: Synthesis of 3-Methoxy-5-nitrobenzoic acid

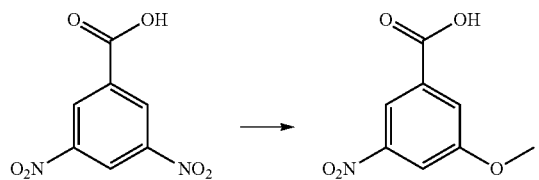

To a stirred solution of 3,5-dinitrobenzoic acid (2.0 g, 9.42 mmol) in 2,6-dimethylcyclohexanone (20.0 ml) was added lithium methoxide (1.43 g, 37.8 mol). The resulting mixture was stirred at room temperature for 20 hours and poured into cold diluted sulfuric acid aqueous solution. The mixture was extracted with diethylether, dried over anhydrous magnesium sulfate, and concentrated under reduced pressure to obtain the title compound (1.31 g, yield: 70.25%, reddish brown solid).

$^1$H NMR (400 MHz, CDCl$_3$); δ 8.36 (s, 1H), 7.97 (s, 1H), 7.90 (s, 1H), 4.03 (s, 3H)

Step 2: Synthesis of ethyl 3-Methoxy-5-nitrobenzoate

The compound (5.33 g, 27.0 mmol) prepared in step 1 was dissolved in absolute ethanol (55.0 ml), added dropwise with thionyl chloride (2.96 ml, 40.55 mmol) at 0° C. The resulting mixture was refluxed for 6 hours. After completion, the reaction mixture was concentrated under reduced pressure and mixed with sodium bicarbonate aqueous solution. The mixture was extracted with dichloromethan, dried over anhydrous magnesium sulfate, and concentrated to dryness. The residue was then purified by flash column chromatography (dichloromethane:hexane=4:1) to obtain the title compound (5.1 g, yield: 85.6%, ivory solid).

$^1$H NMR (400 MHz, CDCl$_3$); δ 8.45 (s, 1H), 7.91 (s, 1H), 7.88 (s, 1H), 4.43 (t, J=7.2 Hz, 2H), 3.95 (s, 3H), 1.44 (t, J=7.2 Hz, 3H)

Step 3: Synthesis of Ethyl 3-amino-5-methoxybenzoate

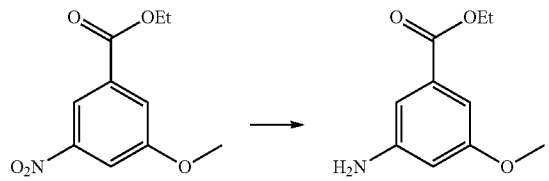 [SMILES: CCOC(=O)c1cc(OC)cc([N+](=O)[O-])c1 ; CCOC(=O)c1cc(N)cc(OC)c1]

The compound (5.1 g, 23.1 mmol) prepared in step 2 was dissolved in ethyl acetate (50.0 ml), added with 10%-palladium (Pd) (100 mg). The resulting mixture was then stirred at room temperature for 24 hours in presence of hydrogen gas. After completion, 10%-palladium (Pd) was removed by celite-filter and the filtrate concentrated to dryness. The residue was purified by flash column chromatography (hexane:ethyl acetate=2:1) to obtain the title compound (4.36 g, yield: 96.8%, white solid).

$^1$H NMR (400 MHz, CDCl$_3$); δ 6.99 (m, 2H), 6.41 (s, 1H), 4.34 (q, J=7.2 Hz, 2H), 3.79 (s, 3H), 1.37 (t, J=7.2 Hz, 3H)

Step 4: Synthesis of ethyl 3-(2-Chloronicotine amido)-5-methoxybenzoate

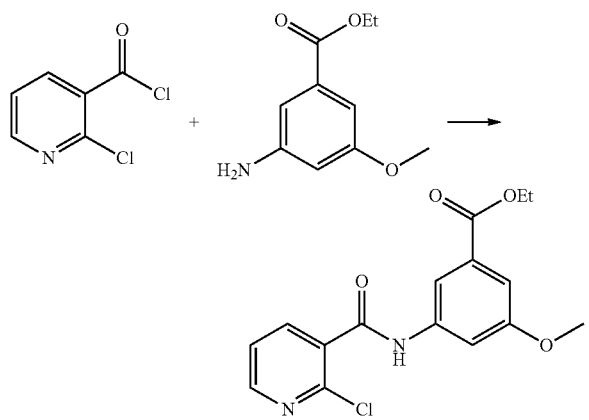

To a stirred solution of 2-chloronicotinic acid (410 mg, 2.60 mmol) in anhydrous dichloromethane (10 ml) were added oxalyl chloride (0.667 ml, 7.80 mmol) and a drop of anhydrous N,N-dimethylformamide at room temperature. The resulting mixture was stirred at room temperature for 2 hours. After completion, the mixture was concentrated under reduced pressure and dried in vacuo. Anhydrous dichloromethane (5 ml) solution of the compound (760 mg, 3.90 mmol) prepared in step 3 was added dropwise at 0° C. and then triethylamine (1.36 ml, 9.75 mmol) was sequentially added. The stirring was continued for 1 hour at 0° C. and the mixture was extracted with dichloromethane. The organic layer was dried over anhydrous magnesium sulfate and concentrated under reduced pressure to obtain the title compound (1.24 g, yield: 95.3%, ivory solid).

$^1$H NMR (400 MHz, CDCl$_3$); δ 8.53 (s, 1H), 8.49 (d, J=4.8 Hz, 1H), 8.14 (d, J=7.6 Hz, 1H), 7.78 (s, 1H), 7.66 (s, 1H), 7.40-7.37 (m, 2H), 4.33 (qt, J=7.6 Hz, 2H), 3.88 (s, 3H), 1.38 (t, J=7.6 Hz, 3H)

Step 5: Synthesis of Ethyl 3-[2-chloro-N-(methoxymethyl)nicotinamido]-5-methoxybenzoate

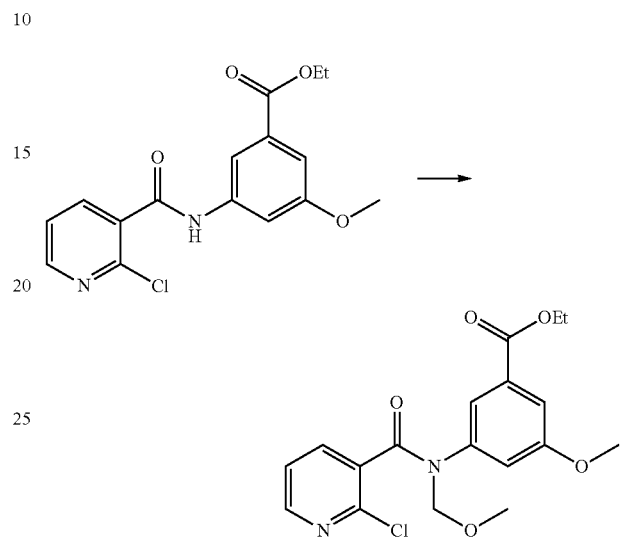

The compound (1.24 g, 3.72 mmol) prepared in step 4 was dissolved in anhydrous tetrahydrofuran (20 ml), added with potassium t-butoxide (834 mg, 7.43 mmol) slowly at 0° C. After stirring for 30 minutes, bromomethyl methyl ether (0.455 ml, 5.57 mmol) was added and the stirring was continued for 1 hour at room temperature. Once the reaction was completed, dichloromethane and water were added and the mixture was extracted. The organic layer was dried over anhydrous magnesium sulfate and concentrated to dryness. The residue was then purified by flash column chromathography (dichloromethane:ethyl acetate=10:1) to obtain the title compound (1.11 g, yield: 79.0%, ivory oil).

$^1$H NMR (400 MHz, CDCl$_3$); δ 8.25 (d, J=4.0 Hz, 1H), 8.14 (d, J=7.6 Hz, 1H), 7.42 (s, 1H), 7.36 (s, 1H), 7.10 (dd, J=4.0 Hz, 7.6 Hz, 1H), 6.98 (s, 1H), 5.29 (s, 2H), 4.30 (qt, J=7.2 Hz, 2H), 3.75 (s, 3H), 3.56 (s, 3H), 1.36 (t, J=7.6 Hz, 3H)

Step 6: Synthesis of Ethyl 10-methoxy-6-(methoxymethyl)-5-oxo-5,6-dihydrobenzo[h][1,6]naphthyridine-8-carboxylate

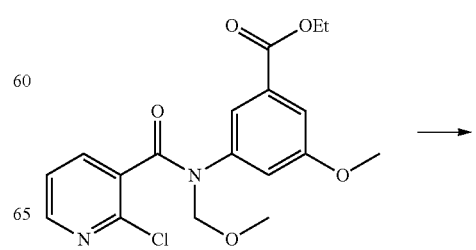

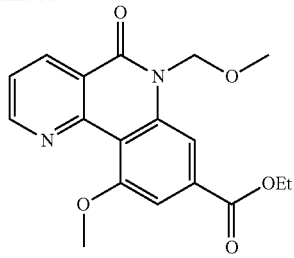

The compound (1.11 g, 2.94 mmol) prepared in step 5 was dissolved in N,N-dimethylformamide (10.0 ml), added with palladium(II) acetate (215 mg, 0.881 mmol), 1,3-bis(dephenylphosphino)propane (363 mg, 0.881 mmol), tributylphosphine (0.724 ml, 2.94 mmol), and potassium carbonate (812 mg, 5.87 mmol). The resulting mixture was refluxed for 3 hours and cooled to room temperature. Water and dichloromethane were added and the mixture was extracted. The organic layer was dried over anhydrous magnesium sulfate and concentrated to dryness. The residue was then purified by flash column chromatography (dichloromethane:ethyl acetate=4:1) to obtain the title compound (776.5 mg, yield: 77.3%, white solid).

$^1$H NMR (400 MHz, CDCl$_3$); δ 9.17-9.15 (m, 1H), 8.83 (td, J=2.0 Hz, 8.0 Hz, 1H), 8.00 (s, 1H), 7.63 (s, 1H), 7.57-7.54 (m, 1H), 5.87 (s, 2H), 4.46 (qt, J=6.8 Hz, 2H), 4.17 (s, 3H), 3.51 (s, 3H), 1.46 (t, J=6.8 Hz, 3H)

Step 7: Synthesis of Ethyl 10-methoxy-6-(methoxymethyl)-5-oxo-1,2,3,4,5,6-hexahydrobenzo[h][1,6]naphthyridine-8-carboxylate

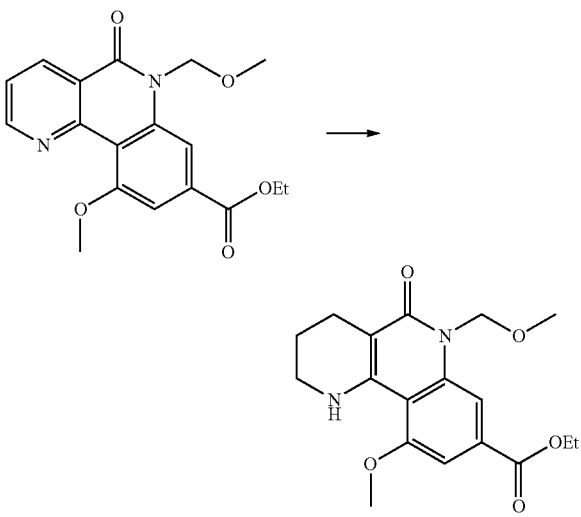

The compound (776.5 mg, 2.27 mmol) prepared in step 6 was dissolved in dichloromethane and methanol, added with 10%-palladium (Pd) (80.0 mg). The resulting mixture was stirred at room temperature for 20 hours under hydrogen gas. After completion, 10%-palladium (Pd) was removed by celite-filter and the solvent was concentrated under reduced pressure. The residue was then purified by flash column chromatography (dichloromethane:ethyl acetate=3:1) to obtain the title compound (458 mg, yield: 58.2%, white solid).

$^1$H NMR (400 MHz, CDCl$_3$); δ 7.89 (s, 1H), 7.34 (s, 1H), 5.76 (s, 2H), 4.42 (q, J=7.2 Hz, 2H), 4.04 (s, 3H), 3.44 (s, 3H), 3.44-3.41 (m, 2H), 2.75 (t, J=6.0 Hz, 2H), 1.94-1.91 (m, 2H), 1.43 (t, J=7.2 Hz, 3H)

Step 8: Synthesis of 8-(Hydroxymethyl)-10-methoxy-6-(methoxymethyl)-1,2,3,4-tetrahydrobenzo[h][1,6]naphthyridine-5-(6H)-one

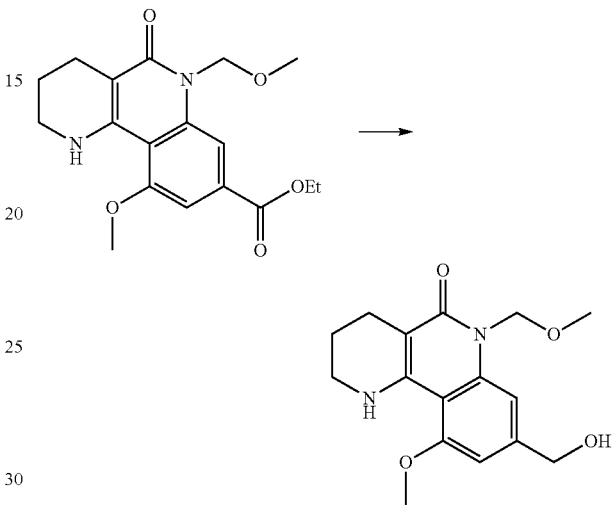

Tetrahydrofuran (10.0 ml) was added to lithium aluminum hydride (125 mg, 3.30 mmol) and cooled to 0° C. The compound (457 mg, 1.32 mmol) prepared in step 7 was dissolved in tetrahydrofuran (10.0 ml) was added dropwise slowly at 0° C. and the resulting mixture was stirred at the same temperature for 1 hour. After completion, ammonium chloride aqueous solution was added and the mixture was extracted with ethyl acetate. The organic layer was washed with brine, dried over anhydrous magnesium sulfate, and concentrated to dryness. The residue was then purified by flash column chromatography (dichloromethane:methanol=10:1) to obtain the title compound (399 mg, yield: 99.2%, ivory solid).

$^1$H NMR (400 MHz, CDCl$_3$); δ 7.47 (s, 1H), 6.97 (s, 1H), 6.77 (s, 1H), 5.70 (s, 2H), 4.70 (s, 2H), 3.97 (s, 3H), 3.40-3.36 (m, 2H), 3.35 (s, 3H), 2.66 (t, J=6.0 Hz, 2H), 1.93-1.87 (m, 2H)

Step 9: Synthesis of 8-[(Dimethylamino)methyl]-10-methoxy-1,2,3,4-tetrahydrobenzo[h][1,6]naphthyridine-5-(6H)-one dihydrochloride

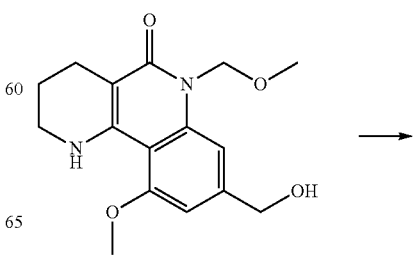

-continued

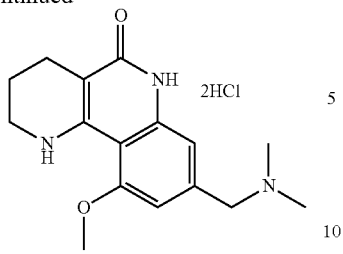

The compound prepared in step 8 was reacted in the same manner as in steps 6 to 8 of Example 41 to obtain the title compound (30.5 mg, yield: 96.1%, ivory solid).

$^1$H NMR (400 MHz, DMSO-d$_6$); δ 11.37 (s, 1H), 10.75 (s, 1H), 7.14 (s, 1H), 6.90 (s, 1H), 4.26 (d, J=4.8 Hz, 2H), 3.95 (s, 3H), 3.34 (m, 2H), 2.70 (s, 3H), 2.69 (s, 3H), 2.50-2.46 (m, 2H), 1.77-1.75 (m, 2H)

The following compounds were prepared using the reaction of Example 72.

Example 73

10-Methoxy-8-[(methylamino)methyl]-1,2,3,4-tetrahydrobenzo[h][1,6]naphthyridine-5(6H)-one dihydrochloride

Example 74

10-Methoxy-8-(morpholinomethyl)-1,2,3,4-tetrahydrobenzo[h][1,6]naphthyridine-5(6H)-one dihydrochloride

Example 75

8-[(Ethylamino)methyl]-10-methoxy-1,2,3,4-tetrahydrobenzo[h][1,6]naphthyridine-5(6H)-one dihydrochloride

Example 76

8-{[Ethyl(methyl)amino]methyl}-10-methoxy-1,2,3,4-tetrahydrobenzo[h][1,6]naphthyridine-5(6H)-one

Example 77

10-Methoxy-8-(pyrrolidine-1-ylmethyl)-1,2,3,4-tetrahydrobenzo[h][1,6]naphthyridine-5(6H)-one dihydrochloride

Example 78

10-Methoxy-8-[(4-oxopiperidine-1-yl)methyl]-1,2,3,4-tetrahydrobenzo[h][1,6]naphthyridine-5(6H)-one dihydrochloride

Example 79

8-{[4-(Hydroxyimino)piperidine-1-yl]methyl}-10-methoxy-1,2,3,4-tetrahydrobenzo[h][1,6]naphthyridine-5(6H)-one trihydrochloride

Example 80

10-Methoxy-8-[(4-(methoxyimino)piperidine-1-yl)methyl]-1,2,3,4-tetrahydrobenzo[h][1,6]naphthyridine-5(6H)-one trihydrochloride

Example 81

10-Methoxy-8-{[(2-methoxyethyl)(methyl)amino]methyl}-1,2,3,4-tetrahydrobenzo[h][1,6]naphthyridine-5(6H)-one dihydrochloride

Example 82

8-[(2,5-Dihydro-1H-pyrrole-1-yl)methyl]-10-methoxy-1,2,3,4-tetrahydrobenzo[h][1,6]naphthyridine-5(6H)-one dihydrochloride

Example 83

8-{[(2-Isopropoxyethyl)(methyl)amino]methyl}-10-methoxy-1,2,3,4-tetrahydrobenzo[h][1,6]naphthyridine-5(6H)-one dihydrochloride

Example 84

10-Methoxy-8-(piperidine-1-ylmethyl)-1,2,3,4-tetrahydrobenzo[h][1,6]naphthyridine-5(6H)-one dihydrochloride

Example 85

8-{[(2-Chloroethyl)(methyl)amino]methyl}-10-methoxy-1,2,3,4-tetrahydrobenzo[h][1,6]naphthyridine-5(6H)-one dihydrochloride

Example 86

8-[(Diethylamino)methyl]-10-methoxy-1,2,3,4-tetrahydrobenzo[h][1,6]naphthyridine-5(6H)-one dihydrochloride

Example 87

8-[(t-Butylamino)methyl]-10-methoxy-1,2,3,4-tetrahydrobenzo[h][1,6]naphthyridine-5(6H)-one dihydrochloride

Example 88

8-[(Isopropylamino)methyl]-10-methoxy-1,2,3,4-tetrahydrobenzo[h][1,6]naphthyridine-5 (6H)-one dihydrochloride

Example 89

8-[(Cyclopentylamino)methyl]-10-methoxy-1,2,3,4-tetrahydrobenzo[h][1,6]naphthyridine-5(6H)-one dihydrochloride

Example 90

8-[(2,6-Dimethylmorpholino)methyl]-10-methoxy-1,2,3,4-tetrahydrobenzo[h][1,6]naphthyridine-5(6H)-one dihydrochloride

Example 91

N-[(10-Methoxy-5-oxo-1,2,3,4,5,6-hexahydrobenzo[h][1,6]naphthyridine-8-yl)methyl]-N,N-dimethylcyclopentene aminium chloride hydrochloride

Example 92

8-{[Cyclopentyl(methyl)amino]methyl}-10-methoxy-1,2,3,4-tetrahydrobenzo[h][1,6]naphthyridine-5 (6H)-one dihydrochloride

Example 93

8-{[Isopropyl(methyl)amino]methyl}-10-methoxy-1,2,3,4-tetrahydrobenzo[h][1,6]naphthyridine-5(6H)-one dihydrochloride

Example 94

8-{[(2-Fluoroethyl)(methyl)amino]methyl}-10-methoxy-1,2,3,4-tetrahydrobenzo[h][1,6]naphthyridine-5 (6H)-one dihydrochloride

| Ex. | Chmical Structure | NMR spectrum data |
|---|---|---|
| 73 | | $^1$H NMR (400 MHz, DMSO-d$_6$); δ 11.35 (s, 1H), 8.42 (s, 2H), 6.96 (s, 1H), 6.86 (s, 1H), 3.97 (m, 2H), 3.91 (s, 3H), 3.32 (m, 2H), 2.53-2.43 (m, 5H), 1.73 (m, 2H) |
| 74 | | $^1$H NMR (400 MHz, DMSO-d$_6$); δ 11.40 (s, 1H), 11.38 (br, 1H), 7.81 (br, 1H), 7.24 (s, 1H), 6.92 (s, 1H), 4.31 (m, 2H), 3.96 (s, 3H), 3.93-3.81 (m, 4H), 3.34 (m, 2H), 3.22-3.09 (m, 4H), 2.47 (m, 2H), 1.75 (m, 2H) |
| 75 | | $^1$H NMR (400 MHz, DMSO-d$_6$); δ 11.33 (s, 1H), 9.206 (s, 1H), 7.07 (s, 1H), 6.90 (s, 1H), 4.10-4.07 (m, 2H), 3.95 (s, 3H), 3.34 (m, 2H), 2.99-2.95 (m, 2H), 2.49-2.45 (m, 2H), 1.75 (m, 2H), 1.23 (t, J = 7.6 Hz, 3H) |
| 76 | | $^1$H NMR (400 MHz, CDCl$_3$); δ 10.82 (br, 1H), 7.34 (s, 1H), 6.85 (s, 1H), 6.79 (br, 1H), 3.97 (s, 3H), 3.59 (s, 2H), 3.40 (s, 2H), 2.72 (m, 2H), 2.57 (m, 2H), 2.29 (s, 3H), 1.94-1.90 (m, 1H), 1.18-1.15 (m, 3H) |

| Ex. | Chmical Structure | NMR spectrum data |
| --- | --- | --- |
| 77 | 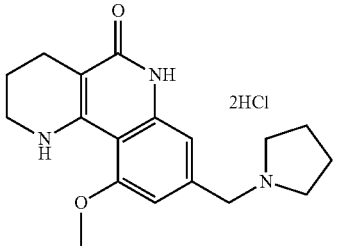 [SMILES: COc1cc(CN2CCCC2)cc2[nH]c(=O)c3c(c12)NCCC3] | ¹H NMR (400 MHz, DMSO-d₆); δ 11.82 (s, 1H), 11.47 (s, 1H), 7.35 (s, 1H), 7.01 (s, 1H), 3.97 (s, 3H), 3.37-3.32 (m, 4H), 3.00 (t, J = 8.4 Hz, 2H), 2.52 (s, 2H), 1.99-1.74 (m, 6H) |
| 78 | 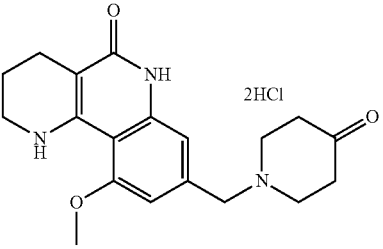 [SMILES: COc1cc(CN2CCC(=O)CC2)cc2[nH]c(=O)c3c(c12)NCCC3] | ¹H NMR (400 MHz, DMSO-d₆); δ 11.88 & 11.17 (s, 1H), 11.50 (d, J = 13.2 Hz, 1H), 7.34 (s, 1H), 6.96 (s, 1H), 4.41 & 4.32 (s, 2H), 3.98 (d, J = 7.6 Hz, 3H), 3.53-3.11 (m, 4H), 3.41-3.36 (m, 2H), 2.96-2.94 (m, 2H), 1.76 (m, 2H), 1.17-1.01 (m, 4H) |
| 79 | 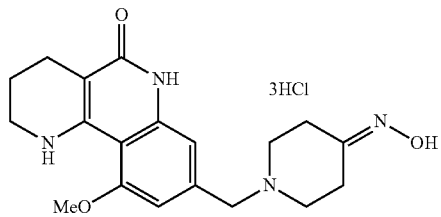 [SMILES: COc1cc(CN2CCC(=NO)CC2)cc2[nH]c(=O)c3c(c12)NCCC3] | ¹H NMR (400 MHz, DMSO-d₆); δ 11.38 (br, salt), 7.77 (br s, 1H), 7.23 (br s, 1H), 6.86 (br, 1H), 4.38 (br, 2H), 3.33-3.22 (m, 4H), 3.18~2.93 (m, 4H), 1.76~1.74 (m, 2H) |
| 80 | 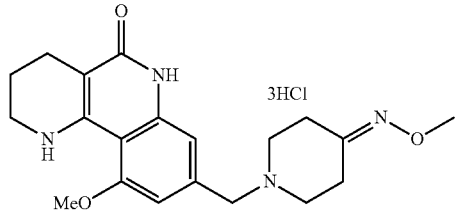 [SMILES: CON=C1CCN(Cc2cc(OC)c3c4c(c(=O)[nH]c3c2)CCCN4)CC1] | ¹H NMR (400 MHz, DMSO-d₆); δ 11.38 (br, salt), 7.79 (br, 1H), 7.26 (br, 1H), 6.97 (br, 1H), 4.31~4.28 (m, 2H), 3.97 (s, 3H), 3.76 (s, 3H), 3.40~3.34 (m, 4H), 3.15-2.93 (m, 4H), 1.76-1.74 (m, 2H) |
| 81 | 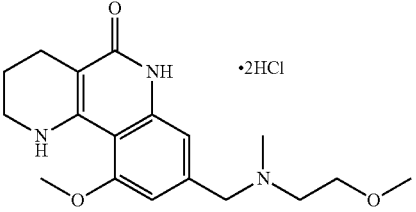 [SMILES: COCCN(C)Cc1cc(OC)c2c3c(c(=O)[nH]c2c1)CCCN3] | ¹H NMR (400 MHz, DMSO-d₆); δ 11.67 (s, 1H), 11.00 (s, 1H), 7.28 (s, 1H), 6.99 (s, 1H), 4.41-4.36 (m, 1H), 4.28-4.25 (m, 1H), 3.96 (s, 3H), 3.75 (m, 2H), 3.36 (m, 2H), 3.28 (s, 3H), 3.23 (m, 2H), 2.69 (s, 3H), 2.49 (m, 2H), 1.76 (m, 2H) |
| 82 | 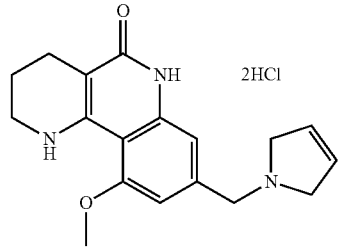 [SMILES: COc1cc(CN2CC=CC2)cc2[nH]c(=O)c3c(c12)NCCC3] | ¹H NMR (400 MHz, DMSO-d₆); δ 11.59 (br, 1H), 11.30 (s, 1H), 7.78 (br, 1H), 7.19 (s, 1H), 6.93 (s, 1H), 5.92 (s, 2H), 4.46 (d, J = 2.8 Hz, 2H), 4.11-4.05 (m, 2H), 3.96 (s, 3H), 3.91-3.90 (m, 2H), 1.77-1.74 (m, 2H) |

-continued

| Ex. | Chmical Structure | NMR spectrum data |
|---|---|---|
| 83 | 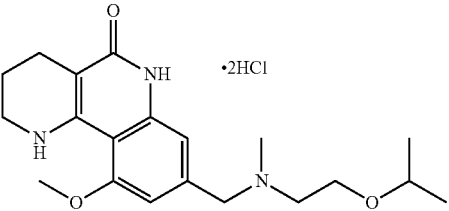 [SMILES: COc1cc(CN(C)CCOC(C)C)cc2[nH]c(=O)c3c(c12)NCCC3] ·2HCl | ¹H NMR (400 MHz, CD₃OD); δ 7.35 (s, 1H), 7.26 (s, 1H), 4.60 (m, 1H), 4.51 (m, 1H), 4.15 (s, 3H), 3.85 (m, 2H), 3.72 (m, 1H), 3.59 (m, 2H), 3.41 (m, 2H), 2.94 (s, 3H), 2.71 (m, 2H), 1.98 (m, 2H), 1.21 (s, 6H) |
| 84 | 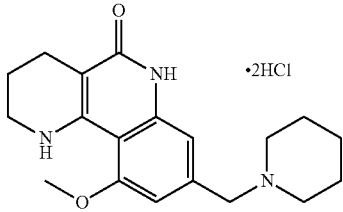 [SMILES: COc1cc(CN2CCCCC2)cc2[nH]c(=O)c3c(c12)NCCC3] ·2HCl | ¹H NMR (400 MHz, DMSO-d₆); δ 12.15 (s, 1H), 11.26 (s, 1H), 7.52 (s, 1H), 7.09 (s, 1H), 4.27 (m, 2H), 4.00 (s, 3H), 3.40 (m, 2H), 3.22 (m, 2H), 2.92-2.84 (m, 2H), 2.55 (m, 2H), 1.90-1.86 (m, 2H), 1.75-1.67 (m, 5H), 1.35-1.32 (m, 1H) |
| 85 | 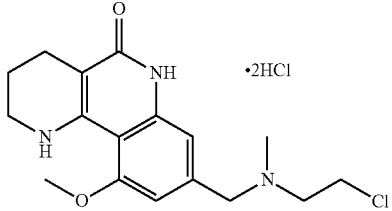 [SMILES: COc1cc(CN(C)CCCl)cc2[nH]c(=O)c3c(c12)NCCC3] ·2HCl | ¹H NMR (400 MHz, DMSO-d₆); δ 11.82 (s, 1H), 11.56 (s, 1H), 7.36 (s, 1H), 7.03 (s, 1H), 4.50-4.47 (m, 1H), 4.31-4.26 (m, 1H), 4.11 (t, J = 6.8 Hz, 2H), 3.98 (s, 3H), 3.45 (m, 2H), 3.38 (m, 2H), 2.71 (s, 3H), 2.52 (m, 2H), 1.77 (m, 2H) |
| 86 | 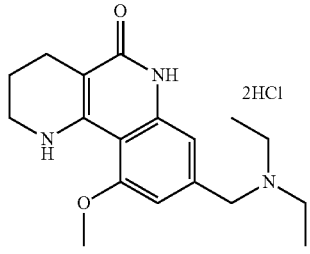 [SMILES: CCN(CC)Cc1cc(OC)c2c3c(c(=O)[nH]c2c1)CCCN3] 2HCl | ¹H NMR (400 MHz, DMSO-d₆); δ 11.74 (s, 1H), 11.07 (s, 1H), 7.40 (s, 1H), 7.02 (s, 1H), 4.28 (d, J = 5.6 Hz, 2H), 3.97 (s, 3H), 3.36 (t, J = 4.8 Hz, 2H), 3.04-2.98 (m, 2H), 2.51 (s, 2H), 1.75 (t, J = 5.6 Hz, 2H), 1.23 (t, J = 7.6 hz, 6H) |
| 87 | 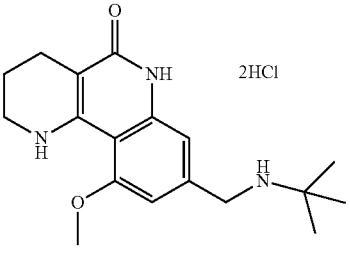 [SMILES: COc1cc(CNC(C)(C)C)cc2[nH]c(=O)c3c(c12)NCCC3] 2HCl | ¹H NMR (400 MHz, DMSO-d₆); δ 11.23 (s, 1H), 9.05 (br, 2H), 7.10 (s, 1H), 6.91 (s, 1H), 4.07-4.05 (m, 2H), 3.96 (s, 3H), 3.33 (m, 2H), 2.50-2.44 (m, 2H), 1.75 (m, 2H) |
| 88 | 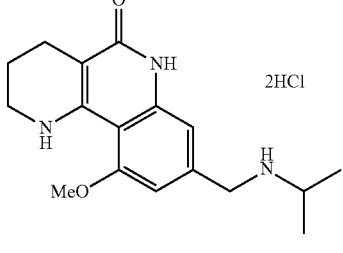 2HCl | ¹H NMR (400 MHz, DMSO-d₆); δ 11.41 (s, 1H), 9.23 (br s, 1H), 7.16 (s, 1H), 6.94 (s, 1H), 4.12-4.09 (m, 2H), 3.96 (s, 3H), 3.36-3.28 (m, 3H), 2.47~2.45 (m, 2H), 1.77-1.74 (m, 2H), 1.31 (s, 3H), 1.29 (s, 3H) |

-continued

| Ex. | Chmical Structure | NMR spectrum data |
|---|---|---|
| 89 | 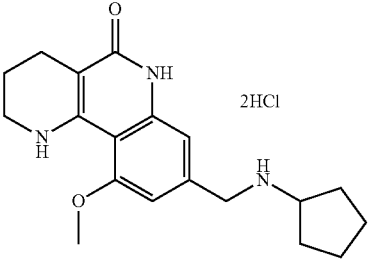 [SMILES: COc1cc(CNC2CCCC2)cc2[nH]c(=O)c3c(c12)NCCC3] | $^1$H NMR (400 MHz, DMSO-d$_6$); δ 11.54 (s, 1H), 9.45 (s, 2H), 7.19 (s, 1H), 6.96 (s, 1H), 4.09 (t, J = 5.2 Hz, 2H), 3.95 (s, 3H), 3.43 (s, 1H), 3.34 (t, J = 4.8 Hz, 2H), 2.48 (s, 2H), 1.97 (s, 2H), 1.76-1.71 (m, 6H), 1.50 (s, 2H) |
| 90 | 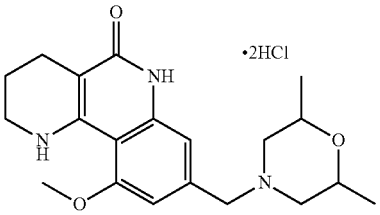 [SMILES: COc1cc(CN2CC(C)OC(C)C2)cc2[nH]c(=O)c3c(c12)NCCC3] | $^1$H NMR (400 MHz, DMSO-d$_6$); δ 11.99 (s, 1H), 11.77 (s, 1H), 7.44 (s, 1H), 7.00 (s, 1H), 4.37 (m, 2H), 4.27-4.26 (m, 1H), 4.10-4.04 (m, 1H), 3.99 (s, 3H), 3.37 (m, 2H), 3.21-3.18 (m, 2H), 2.71-2.63 (m, 2H), 2.53 (m, 2H), 1.76 (m, 2H), 1.09 (s, 3H), 1.08 (s, 3H) |
| 91 | 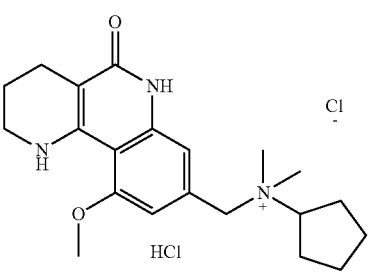 | $^1$H NMR (400 MHz, DMSO-d$_6$); δ 11.35 (s, 1H), 7.06 (s, 1H), 6.92 (s, 1H), 4.47 (s, 2H), 3.94 (s, 3H), 3.87 (t, J = 7.6 Hz, 1H), 3.33 (s, 2H), 2.90 (s, 6H), 2.48 (s, 2H), 1.99 (s, 4H), 1.73 (s, 4H), 1.56 (s, 2H) |
| 92 | 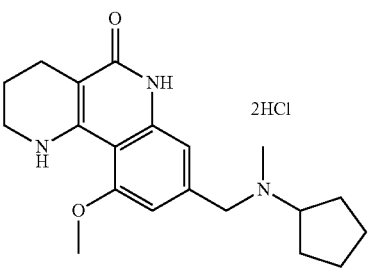 [SMILES: COc1cc(CN(C)C2CCCC2)cc2[nH]c(=O)c3c(c12)NCCC3] | $^1$H NMR (400 MHz, DMSO-d$_6$); δ 11.51 (s, 1H), 11.06 (s, 1H), 7.27 (s, 1H), 6.96 (s, 1H), 4.44 (d, J = 9.6 Hz, 2H), 3.96 (s, 3H), 3.55 (q, J = 7.6 Hz, 1H), 3.34 (t, J = 4.8 Hz, 2H), 2.52 (d, J = 4.8 Hz, 3H), 2.48 (s, 2H), 2.08-2.06 (m, 2H), 1.94-1.89 (m, 2H), 1.73 (s, 4H), 1.57-1.49 (m, 2H) |
| 93 | 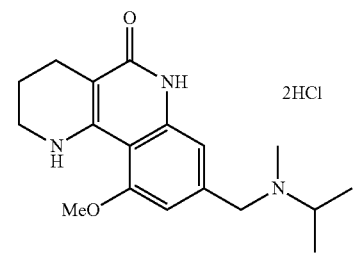 [SMILES: COc1cc(CN(C)C(C)C)cc2[nH]c(=O)c3c(c12)NCCC3] | $^1$H NMR (400 MHz, DMSO-d$_6$); δ 11.61 (brs, 1H), 10.84 (brs, 1H), 7.38 (s, 2H), 7.02 (s, 2H), 4.37-4.33 (m, 1H), 4.18-4.13 (m, 1H), 3.98 (s, 3H), 3.38-3.34 (m, 4H), 2.53 (s, 3H), 1.77-1.75 (m, 2H), 1.34 (s, 3H), 1.29 (s, 3H), 1.22-1.19 (m, 1H) |
| 94 | 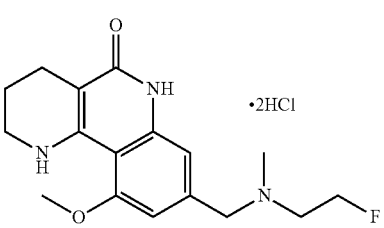 [SMILES: COc1cc(CN(C)CCF)cc2[nH]c(=O)c3c(c12)NCCC3] | $^1$H NMR (400 MHz, DMSO-d$_6$); δ 11.46 (s, 1H), 11.21 (s, 1H), 7.20 (s, 1H), 6.93 (s, 1H), 4.98-4.82 (m, 2H), 4.42-4.21 (m, 2H), 3.94 (s, 3H), 3.48-3.40 (m, 2H), 3.33 (m, 2H), 2.70 (s, 3H), 2.46 (m, 2H), 1.74 (m, 2H) |

Example 95

Synthesis of 8-[(1H-tetrazole-5-yl)methyl]-1,2,3,4-tetrahydrobenzo[h][1,6]naphthyridine-5(6H)-one hydrochloride

Step 1: Synthesis of 2-[6-(Methoxymethyl)-5-oxo-1,2,3,4,5,6-hexahydrobenzo[h][1,6]naphthyridine-8-yl]acetonitrile

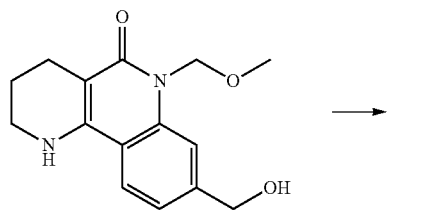

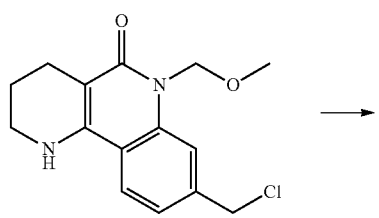

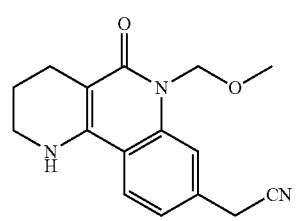

8-(hydroxymethyl)-6-(methoxymethyl)-1,2,3,4-tetrahydrobenzo[h][1,6]naphthyridine-5-(6H)-one (100 mg, 0.36 mmol) prepared in step 5 of Example 41 was dissolved in dichloromethane (10 ml), added dropwise with thionylchloride (66 μl, 0.91 mmol) at 0° C. The resulting mixture was stirred at room temperature for 4 hours and poured into saturated sodium bicarbonate aqueous solution. The mixture was extracted with dichloromethane, washed with brine, dried over anhydrous sodium sulfate, and concentrated to dryness. The residue was then dissolved in N,N-dimethylformamide (5 ml) and sodium cyanide (55 mg, 1.09 mmol) was added. The resulting mixture was stirred at room temperature overnight and poured into ice water. The mixture was extracted with chloroform and the organic layer was washed with brine. The solution was dried over anhydrous sodium sulfate and the solvent was removed under reduced pressure. The residue was then purified by flash column chromatography (chloroform:methanol=30:1) to obtain the title compound (70 mg, yield: 69%, white solid).

$^1$H NMR (400 MHz, CDCl$_3$); δ 7.46-7.44 (m, 2H), 7.22 (d, J=8.4 Hz, 1H), 5.72 (s, 2H), 4.87 (s, 1H), 3.86 (s, 2H), 3.47 (m, 2H), 3.42 (s, 3H), 2.69 (t, J=6.4 Hz, 2H), 1.98 (m, 2H)

Step 2: Synthesis of 8-[(1H-tetrazole-5-yl)methyl]-6-(methoxymethyl)-1,2,3,4-tetrahydrobenzo[h][1,6]naphthyridine-5(6H)-one

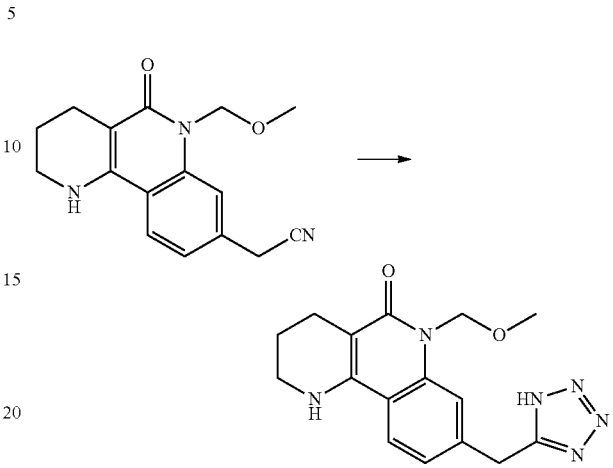

The compound (65 mg, 0.23 mmol) prepared in step 1 was dissolved in N,N-dimethylformamide (5 ml), sequentially added with sodium azide (75 mg, 1.15 mmol) and ammonium chloride (61 mg, 1.15 mmol). The resulting mixture was refluxed for 48 hours and cooled to room temperature. The mixture was washed with chloroform and the water layer was concentrated to dryness. The residue was then washend with methanol and filtered. The filtrate was purified by flash column chromatography (chloroform:methanol=5:1) to obtain the title compound (34 mg, yield: 45%, yellow solid).

$^1$H NMR (400 MHz, CDCl$_3$); δ 7.75 (d, J=8.0 Hz, 1H), 7.50 (s, 1H), 7.14 (d, J=8.4 Hz, 1H), 5.67 (s, 2H), 4.41 (s, 2H), 3.40 (m, 2H), 3.33 (s, 3H), 2.60 (t, J=6.4 Hz, 2H), 1.92 (m, 2H)

Step 3: Synthesis of 8-[(1H-tetrazole-5-yl)methyl]-1,2,3,4-tetrahydrobenzo[h][1,6]naphthyridine-5(6H)-one hydrochloride

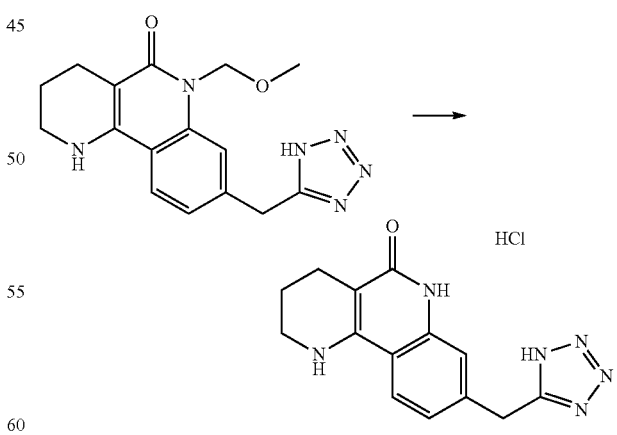

The compound (34 mg, 0.10 mmol) prepared in step 2 was dissolved in ethanol (5 ml), added with conc. hydrochloric acid (1.0 ml). The resulting mixture was stirred at 80° C. for 10 hours. Once the reaction was completed, the mixture concentrated under reduced pressure and filtered to obtain the title compound (28 mg, yield: 84%, yellow solid).

¹H NMR (400 MHz, DMSO-d₆); δ 11.09 (s, 1H), 7.80 (d, J=8.4 Hz, 1H), 7.10 (s, 1H), 7.03 (d, J=8.0 Hz, 1H), 4.33 (s, 2H), 3.30 (m, 2H), 2.45 (m, 2H), 1.78 (m, 2H)

Example 96

Synthesis of 10-Methoxy-8-[(morpholinoamino) methyl]-1,2,3,4-tetrahydrobenzo[h][1,6]naphthyridine-5(6H)-one trihydrochloride Step 1: Synthesis of 10-Methoxy-6-(methoxymethyl)-5-oxo-1,2,3,4,5,6-hexahydrobenzo[h][1,6]naphthyridine-8-carboaldehyde

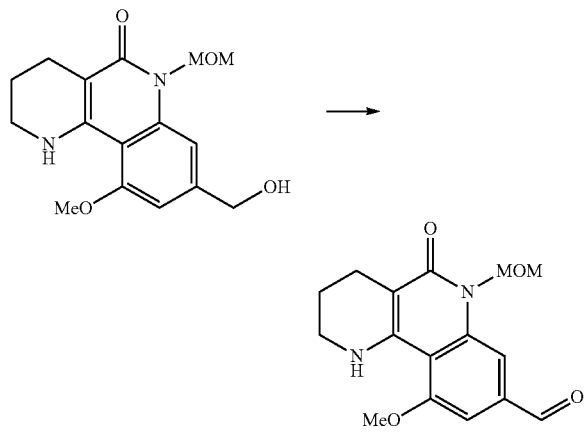

To a stirred solution of the compound prepared in step 8 of Example 73 (100 mg, 0.32 mmol) in anhydrous dichloromethane (5 ml) was added dropwise Dess-Martin periodinane (209 mg, 0.49 mmol) at 0° C. The resulting mixture was stirred at room temperature for 3 hours and poured into ice water. The mixture was extracted with dichloromethane, dried over anhydrous magnesium sulfate, and concentrated under reduced pressure to obtain the title compound (95 mg, yield: 96%, yellow solid). The obtained compound was used in the next reaction without further purification.

¹H NMR (400 MHz, CDCl₃); δ 10.02 (s, 1H), 7.68 (s, 1H), 7.47 (brs, 1H), 7.19 (s, 1H), 5.76 (brs, 2H), 4.04 (s, 3H), 3.44 (s, 3H), 3.43-3.40 (m, 2H), 2.70 (t, J=6.2 Hz, 2H), 1.92 (t, J=5.7 Hz, 2H)

Step 2: Synthesis of (E)-10-methoxy-6-(methoxymethyl)-8-[(morpholinoimino)methyl]-1,2,3,4-tetrahydrobenzo[h][1,6]naphthyridine-5(6H)-one

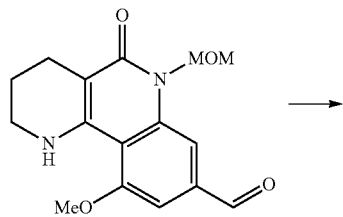

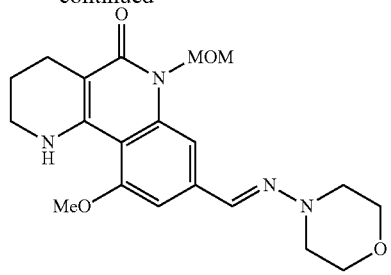

The compound (95 mg, 0.31 mmol) prepared in step 1 was dissolved in toluene (10 ml), added with 4-aminomorpholine (0.031 ml, 0.31 mmol) at room temperature. The resulting mixture was then heated and allowed to reflux under dean-stark condenser for 5 hours. After cooling to room temperature, the solivent was removed under reduced pressure and the residue was purified by flash column chromatography (dichloromethane:methanol=20:1) to obtain the title compound (109 mg, yield: 89%, yellow solid).

¹H NMR (400 MHz, CDCl₃); δ 7.58 (s, 1H), 7.45 (brs, 1H), 7.19 (s, 1H), 7.15 (s, 1H), 5.72 (brs, 2H), 4.00 (s, 3H), 3.91-3.89 (m, 4H), 3.43 (s, 3H), 3.40-3.38 (m, 2H), 3.24-3.21 (m, 4H), 2.68 (t, J=6.4 Hz, 2H), 1.94~1.88 (m, 2H)

Step 3: Synthesis of 10-Methoxy-6-(methoxymethyl)-8-[(morpholinoamino)methyl]-1,2,3,4-tetrahydrobenzo[h][1,6]naphthyridine-5(6H)-one

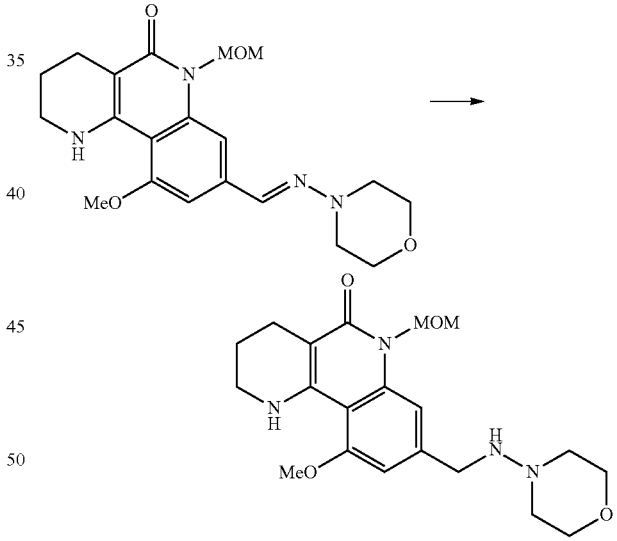

The compound (50 mg, 0.12 mmol) prepared in step 2 was dissolved in tetrahydrofuran (2 ml), added with sodium cyanoborohydride (4 mg, 0.06 mmol) and 1.25 N hydrochloric acid methanol solution (5 ml) slowly. The resulting mixture was stirred at room temperature for 2 hours and concentrated under reduced pressure to remove the solvent. The residue was basified with 1 N sodium hydroxide aqueous solution and extracted with chloroform. The organic layer was dried over anhydrous sodium sulfate and the solvent was concentrated to dryness. The residue was then purified by flash column chromatography (dichloromethane:methanol=20:1) to obtain the title compound (18 mg, yield: 38%, yellow solid).

$^1$H NMR (400 MHz, CDCl$_3$); δ 7.44 (brs, 1H), 7.16 (s, 1H), 6.76 (s, 1H), 5.69 (brs, 2H), 4.02 (s, 2H), 3.96 (s, 3H), 3.75-3.72 (m, 4H), 3.41 (s, 3H), 3.41-3.38 (m, 2H), 2.74-2.66 (m, 6H), 1.93-1.89 (m, 2H)

Step 4: Synthesis of 10-Methoxy-8-[(morpholinoamino)methyl]-1,2,3,4-tetrahydrobenzo[h][1,6]naphthyridine-5(6H)-one trihydrochloride

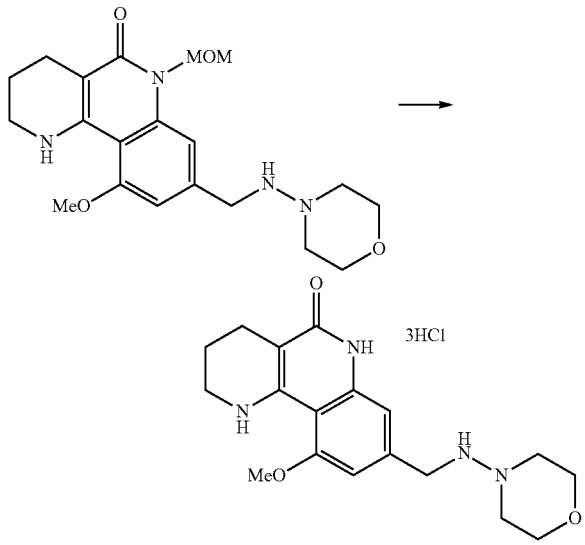

The compound (18 mg, 0.046 mmol) prepared in step 3 was dissolved in ethanol (1 ml), and added with 12 N aqueous solution of hydrochloric acid (1.5 ml). The reaction mixture was stirred at 75° C. for 2 hours. The solvent was concentrated under reduced pressure and the residue was dissolved in ethyl acetate. The precipitate was filtered, washed with ethyl acetate, and dried in vacuo to obtain the title compound (20.1 mg, yield: 96%, yellow solid).

$^1$H NMR (400 MHz, DMSO-d$_6$); δ 11.51 (brs, 1H), 11.05 (brs, 1H), 7.13 (s, 1H), 6.99 (s, 1H), 4.31 (s, 2H), 3.98-3.71 (m, 6H), 3.36-3.34 (m, 2H), 3.15 (brs, 2H), 2.48-2.46 (m, 2H), 1.77-1.76 (m, 2H)

Example 97

Synthesis of 10-Methoxy-8-{[methyl(morpholino)amino]methyl}-1,2,3,4-tetrahydrobenzo[h][1,6]naphthyridine-5(6H)-one trihydrochloride Step 1: Synthesis of 10-Methoxy-6-(methoxymethyl)-8-{[methyl(morpholino)amino]methyl}-1,2,3,4-tetrahydrobenzo[h][1,6]naphthyridine-5(6H)-one

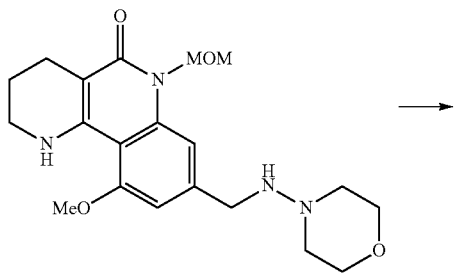

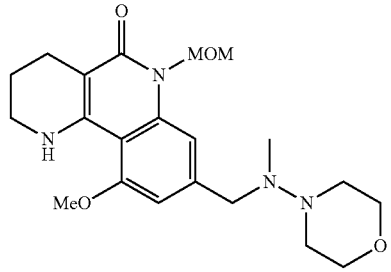

The compound (40 mg, 0.10 mmol) prepared in step 3 of Example 96 and potassium carbonate (22 mg, 0.15 mmol) were dissolved in acetonitrile (5 ml), added with iodo methane (0.008 ml, 0.12 mmol). The resulting mixture was heated to reflux temperature and stirred for 18 hours. The reaction mixture was poured into ice water and extracted with chloroform. The organic layer was dried over anhydrous magnesium sulfate and concentrated under reduced pressure. The residue was then purified by flash column chromatography (dichloromethane:methanol=15:1) to obtain the title compound (3 mg, yield: 8%, yellow solid).

$^1$H NMR (400 MHz, CDCl$_3$); δ 7.45 (brs, 1H), 7.11 (s, 1H), 6.74 (s, 1H), 5.69 (brs, 2H), 3.95 (s, 3H), 3.77 (s, 2H), 3.72-3.70 (m, 4H), 3.41 (s, 3H), 3.39-3.38 (m, 2H), 2.78-2.76 (m, 4H), 2.67 (t, J=6.4 Hz, 2H), 2.37 (s, 3H), 1.92-1.89 (m, 2H)

Step 2: Synthesis of 10-Methoxy-8-{[methyl(morpholino)amino]methyl}-1,2,3,4-tetrahydrobenzo[h][1,6]naphthyridine-5(6H)-one trihydrochloride

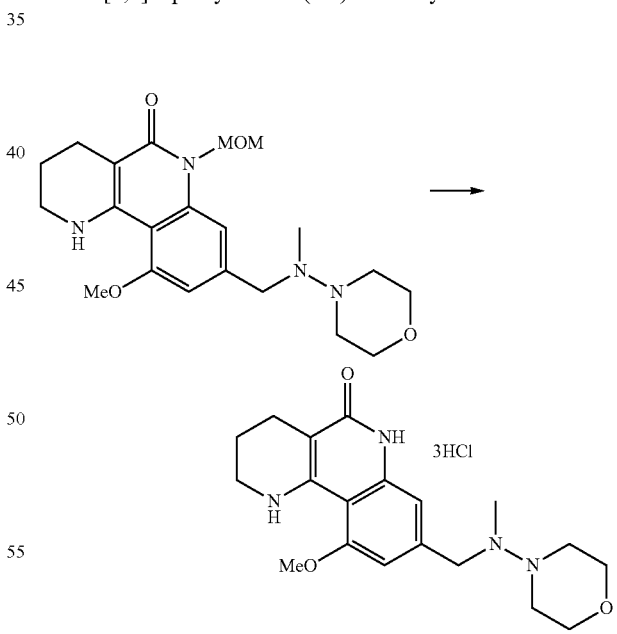

The compound (3 mg, 0.0075 mmol) prepared in step 1 was reacted in the same manner as in step 4 of Example 96 to obtain the title compound (2.6 mg, yield: 75%, yellow solid).

$^1$H NMR (400 MHz, DMSO-d$_6$); δ 11.05 (brs, 1H), 8.88 (brs, 1H), 7.36 (brs, 1H), 7.16 (s, 1H), 6.90 (s, 1H), 4.24 (brs, 2H), 3.98-3.71 (m, 6H), 3.36-3.34 (m, 2H), 3.15 (brs, 2H), 2.82-2.74 (m, 2H), 1.77-1.76 (m, 2H)

Example 98

Synthesis of (E)-10-methoxy-8-[(morpholinoimino) methyl]-1,2,3,4-tetrahydrobenzo[h][1,6]naphthyridine-5(6H)-one trihydrochloride

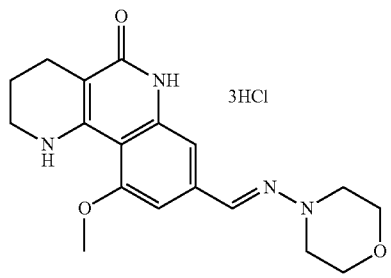 [SMILES: COc1cc(/C=N/N2CCOCC2)cc2[nH]c(=O)c3c(c12)NCCC3]

The compound (15 mg, 0.038 mmol) prepared in step 2 of Example 96 was reacted in the same manner as in step 4 of Example 96 to obtain the title compound (2.6 mg, yield: 75%, yellow solid).

$^1$H NMR (400 MHz, DMSO-$d_6$); δ 7.69 (s, 1H), 7.22 (brs, 1H), 7.08 (s, 1H), 4.02 (s, 3H), 3.89-3.87 (m, 4H), 3.42-3.37 (m, 2H), 3.20-3.17 (m, 4H), 2.66 (t, J=6.4 Hz, 2H), 1.90-1.89 (m, 2H)

Example 99

Synthesis of 8-[(Dimethylamino)methyl]-10-hydroxy-1,2,3,4-tetrahydrobenzo[h][1,6]naphthyridine-5-(6H)-one dihydrochloride Step 1: Synthesis of 8-[(Dimethylamino)methyl]-10-hydroxy-1,2,3,4-tetrahydrobenzo[h][1,6]naphthyridine-5-(6H)-one

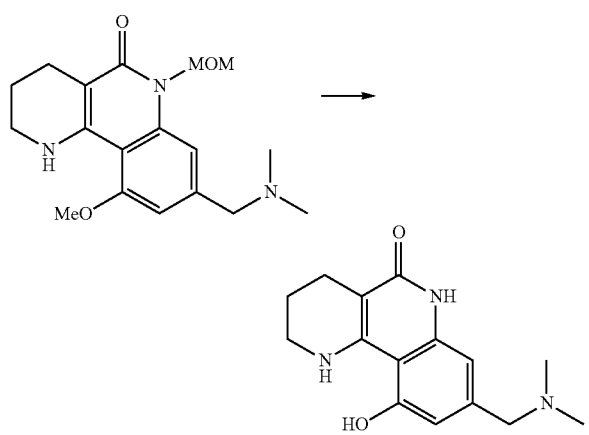

8-[(Dimethylamino)methyl]-10-methoxy-6-(methoxymethyl)-1,2,3,4-tetrahydrobenzo[h][1,6]naphthyridine-5-(6H)-one (28 mg, 0.084 mmol) prepared in Example 72 was dissolved in dichloromethane (10 ml), added dropwise with boron tribromide (0.6 mmol, 152 mg) at 0° C. The mixture was stirred at room temperature for 2 hours and then water was added carefully. The solution was washed with chloroform, the water layer was concentrated under reduced pressure, and the residue was purified by flash column chromatography (chloroform:ethanol=1:5) to obtain the title compound (14 mg, yield: 58%, white solid).

$^1$H NMR (400 MHz, CD$_3$OD); δ 6.53 (s, 1H), 6.41 (s, 1H), 3.40-3.36 (m, 2H), 2.55-2.53 (m, 4H), 2.26 (s, 6H), 1.87-1.84 (m, 2H)

Step 2: Synthesis of 8-[(Dimethylamino)methyl]-10-hydroxy-1,2,3,4-tetrahydrobenzo[h][1,6]naphthyridine-5-(6H)-one dihydrochloride

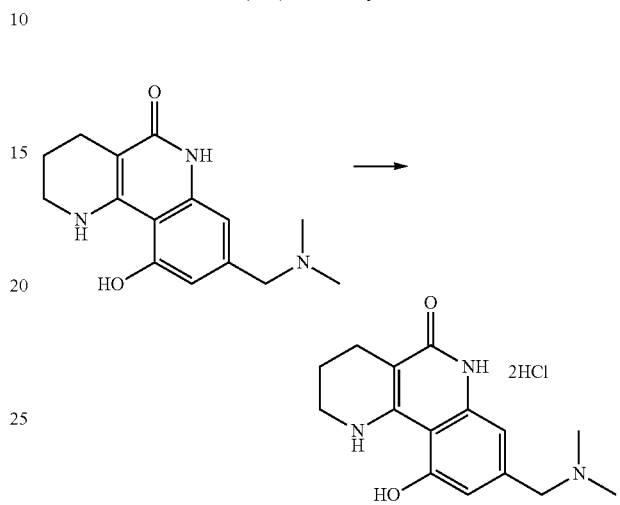

The title compound (13.6 mg, yield: 78%, yellow solid) was obtained using 8-[(dimethylamino)methyl]-10-hydroxy-1,2,3,4-tetrahydrobenzo[h][1,6]naphthyridine-5-(6H)-one (14 mg, 0.051 mol) prepared in step 1.

$^1$H NMR (400 MHz, DMSO-$d_6$); δ 11.71 (s, 1H), 11.25 (s, 1H), 10.88 (s, 1H), 8.01 (br, 1H), 6.83 (s, 2H), 4.17-4.16 (m, 2H), 3.36-3.34 (m, 2H), 2.67 (d, J=2.4 Hz, 6H), 2.47-2.45 (m, 2H), 1.76-1.74 (m, 2H)

Example 100

Synthesis of 8-[(Dimethylamino)methyl]-10-etoxy-1,2,3,4-tetrahydrobenzo[h][1,6]naphthyridine-5(6H)-one dihydrochloride Step 1: Synthesis of Ethyl 3-etoxy-5-nitrobenzoate

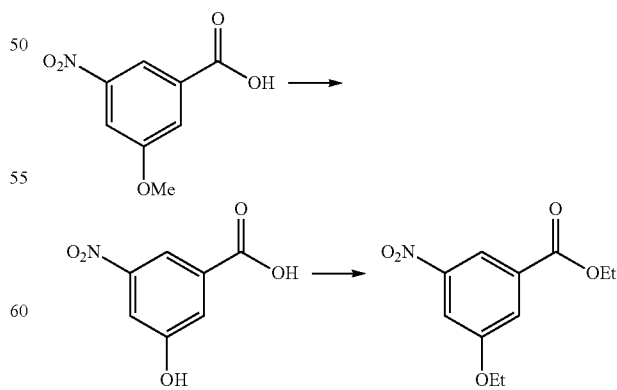

3-Methoxy-5-nitrobenzoic acid (10 g, 50.7 mmol) prepared in step 1 of Example 72 was dissolved in dichloromethane (200 ml), added with 1 M boron tribromide dichloromethane solution. The reaction mixture was stirred at room temperature for 8 hours. The mixture was poured into ice water and washed with dichloromethane. The water layer was concentrated under reduced pressure and dried in vacuo. The residue was dissolved in N,N-dimethylformamide (150 ml), added dropwise with potassium carbonate (42 g, 304 mmol) and iodoethane (20.2 ml, 253 mmol). The mixture was then stirred for one day at 60° C. and poured into ice water. The solution was extracted with ethyl acetate, washed with brine, and dried over anhydrous magnesium sulfate. The solvent was removed under reduced pressure and the residue was purified by flash column chromatography (hexane:ethyl acetate=5:1) to obtain the title compound (8.49 g, yield: 70%, yellow solid).

$^1$H NMR (400 MHz, CDCl$_3$) δ 8.44 (s, 1H), 7.90-7.88 (m, 2H), 4.43 (q, J=3.6 Hz, 2H), 4.16 (q, J=3.4 Hz, 2H) 1.48 (t, J=7.2 Hz, 3H), 1.43 (t, J=7.2 Hz, 3H).

Step 2: Synthesis of ethyl 3-Amino-5-etoxybenzoate

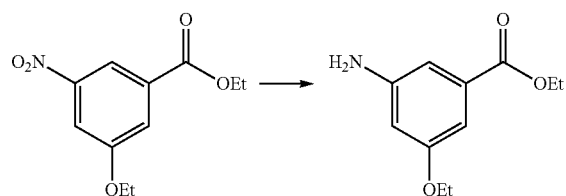 [SMILES: CCOC(=O)c1cc(OCC)cc([N+](=O)[O-])c1 ; CCOC(=O)c1cc(N)cc(OCC)c1]

The compound (8.49 g, 35.49 mmol) prepared in step 1 was dissolved in ethyl acetate, added with 10%-palladium (Pd) (900 mg). The reaction mixture was stirred at room temperature for one day under hydrogen gas. Once the reaction was completed, the solution was celite-filtered and the filtrate was concentrated under reduced pressure. The residue purified by flash column chromatography (hexane:ethyl acetate=3:1) to obtain the title compound (6.98 g, yield: 94%, yellow liquid).

$^1$H NMR (400 MHz, CDCl$_3$) δ 6.98 (m, 2H), 6.41 (m, 1H), 4.34 (q, J=3.6 Hz, 2H), 4.03 (q, J=3.6 Hz, 2H) 3.76 (br, 2H), 1.42-1.36 (m, 6H).

Step 3: Synthesis of 8-[(Dimethylamino)methyl]-10-etoxy-1,2,3,4-tetrahydrobenzo[h][1,6]naphthyridine-5(6H)-one dihydrochloride

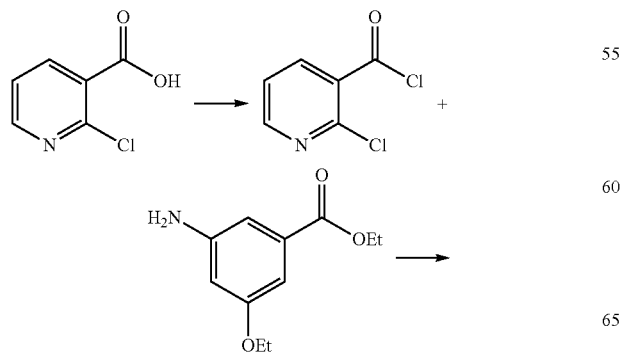

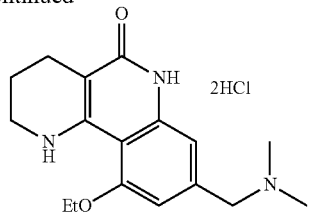

The title compound (85 mg, yield: 11.4% (total yield), yellow solid) was obtained in the same manner as in steps 4 to 9 of Example 72, using ethyl 3-amino-5-etoxybenzoate (415 mg, 1.98 mmol) synthesized in step 2.

$^1$H NMR (400 MHz, CDCl$_3$) δ 11.71 (s, 1H), 11.19 (s, 1H), 7.91 (br, 1H), 7.29 (s, 1H) 6.97 (s, 1H), 4.34-4.27 (m, 4H), 3.39 (m, 2H), 2.68 (d, J=2.0 Hz, 6H), 2.51-2.49 (m, 2H), 1.77 (m, 2H), 1.44 (t, J=6.8 Hz, 3H).

The following compounds were prepared using the reaction of Example 100.

Example 101

10-Ethoxy-8-(morpholinomethyl)-1,2,3,4-tetrahydrobenzo[h][1,6]naphthyridine-5(6H)-one dihydrochloride Example 102

10-Ethoxy-8-(piperidine-1-ylmethyl)-1,2,3,4-tetrahydrobenzo[h][1,6]naphthyridine-5(6H)-one dihydrochloride Example 103

10-Etoxy-8-[(methylamino)methyl]-1,2,3,4-tetrahydrobenzo[h][1,6]naphthyridine-5(6H)-one dihydrochloride Example 104

10-Etoxy-8-[(ethylamino)methyl]-1,2,3,4-tetrahydrobenzo[h][1,6]naphthyridine-5(6H)-one dihydrochloride Example 105

8-(Hydroxymethyl)-10-methoxy-1,2,3,4-tetrahydrobenzo[h][1,6]naphthyridine-5(6H)-one hydrochloride Example 106

10-Methoxy-8-(thiomorpholinomethyl)-1,2,3,4-tetrahydrobenzo[h][1,6]naphthyridine-5(6H)-one dihydrochloride

Example 107

10-Methoxy-8-[(2-morpholinoethylamino)methyl]-1,2,3,4-tetrahydrobenzo[h][1,6]naphthyridine-5(6H)-one trihydrochloride

Example 108

10-Methoxy-8-[(4-morpholinopiperidine-1-yl)methyl]-1,2,3,4-tetrahydrobenzo[h][1,6]naphthyridine-5(6H)-one trihydrochloride

Example 109

8-(Aminomethyl)-10-methoxy-1,2,3,4-tetrahydrobenzo[h][1,6]naphthyridine-5(6H)-one dihydrochloride

Example 110

8-[(Dimethylamino)methyl]-10-propoxy-1,2,3,4-tetrahydrobenzo[h][1,6]naphthyridine-5(6H)-one dihydrochloride

Example 111

8-(Morpholinomethyl)-10-propoxy-1,2,3,4-tetrahydrobenzo[h][1,6]naphthyridine-5(6H)-one dihydrochloride

Example 112

8-(Aminomethyl)-1,2,3,4-tetrahydrobenzo[h][1,6]-naphthyridine-5 (6H)-one dihydrochloride

Example 113

8-(Aminomethyl)-10-etoxy-1,2,3,4-tetrahydrobenzo[h][1,6]naphthyridine-5 (6H)-one dihydrochloride

Example 114

8-(Aminomethyl)-10-propoxy-1,2,3,4-tetrahydrobenzo[h][1,6]naphthyridine-5(6H)-one dihydrochloride

Example 115

10-Methoxy-8-{[methyl(tetrahydro-2H-pyran-4-yl)amino]methyl}-1,2,3,4-tetrahydrobenzo[h][1,6]naphthyridine-5(6H)-one dihydrochloride

Example 116

8-[(Dimethylamino)methyl]-10-(2-methoxyetoxy)-1,2,3,4-tetrahydrobenzo[h][1,6]naphthyridine-5(6H)-one dihydrochloride

Example 117

10-(2-Methoxyetoxy)-8-(morpholinomethyl)-1,2,3,4-tetrahydrobenzo[h][1,6]naphthyridine-5(6H)-one dihydrochloride

Example 118

1-[(10-Methoxy-5-oxo-1,2,3,4,5,6-hexahydrobenzo[h][1,6]naphthyridine-8-yl)methylamino]-1H-pyrrole-2,5-dione dihydrochloride

| Ex. | Chmical Structure | NMR spectrum data |
|---|---|---|
| 101 | 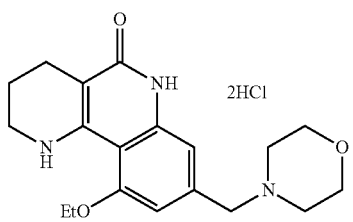 [SMILES: CCOc1cc(CN2CCOCC2)cc2[nH]c(=O)c3c(c12)NCCC3] | $^1$H NMR (400 MHz, DMSO-$d_6$) δ 11.39 (br, 1H), 11.35 (s, 1H), 7.64 (br, 1H), 7.26 (s, 1H), 6.91 (s, 1H) 4.32-4.26 (m, 4H), 3.97-3.82 (m, 4H), 3.39-3.34 (m, 2H), 3.22-3.08 (m, 4H), 2.47-2.45 (m, 2H), 1.78-1.75 (m, 2H), 1.44 (t, J = 7.2 Hz, 3H). |
| 102 | 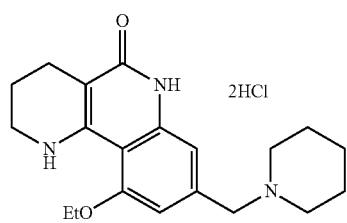 [SMILES: CCOc1cc(CN2CCCCC2)cc2[nH]c(=O)c3c(c12)NCCC3] | $^1$H NMR (400 MHz, DMSO-$d_6$) δ 11.41 (s, 1H), 10.74 (s, 1H), 7.78 (br, 1H), 7.28 (s, 1H), 6.91 (s, 1H) 4.29 (q, J = 6.8 Hz, 2H), 4.23-4.21 (m, 2H), 3.36 (m, 2H), 3.25-3.22 (m, 2H), 2.88-2.85 (m, 2H), 2.49-2.48 (m, 2H), 1.91-1.68 (m, 6H), 1.50 (t, J = 6.8 Hz, 3H), 1.36-1.33 (m, 2H) |

| Ex. | Chemical Structure | NMR spectrum data |
|---|---|---|
| 103 | 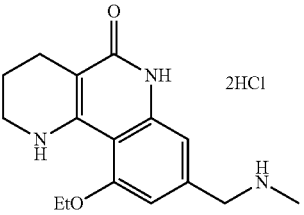 [SMILES: CCOc1cc(CNC)cc2[nH]c(=O)c3c(c12)NCCC3] | ¹H NMR (400 MHz, DMSO-d₆) δ 11.34 (s, 1H), 9.26 (s, 1H), 7.64 (br, 1H), 7.05 (s, 1H), 6.88 (s, 1H), 4.26 (q, J = 3.4 Hz, 2H), 4.09-4.06 (m, 2H), 3.37-3.34 (m, 2H), 2.60-2.57 (m, 3H), 2.49-2.45 (m, 2H), 1.78-1.75 (m, 2H), 1.50 (t, J = 5.2 Hz, 3H). |
| 104 | 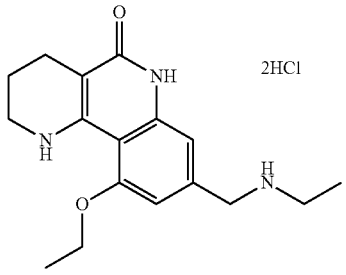 [SMILES: CCNCc1cc(OCC)c2c3c(c(=O)[nH]c2c1)CCCN3] | ¹H NMR (400 MHz, DMSO-d₆); δ 11.39 (s, 1H), 9.28 (Br, 1H), 7.70 (Br, 1H), 7.11 (s, 1H), 6.91 (s, 1H), 4.27 (q, J = 3.4 Hz, 2H), 4.08 (Br, 2H), 3.36 (Br, 1H), 2.95 (Br, 2H), 2.47 (Br, 2H), 1.77 (Br, 2H), 1.45 (t, J = 6.4 Hz, 3H), 1.23 (t, J = 7.6 Hz, 3H) |
| 105 | 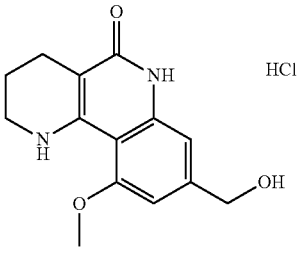 [SMILES: COc1cc(CO)cc2[nH]c(=O)c3c(c12)NCCC3 ; Cl] | ¹H NMR (400 MHz, DMSO-d₆); δ 11.77 (s, 1H), 8.23 (Br, 1H), 6.99 (s, 1H), 6.74 (s, 1H), 4.53 (s, 2H), 3.93 (s, 3H), 3.39 (t, J = 5.6 Hz, 2H), 2.54-2.52 (m, 2H), 1.78 (t, J = 5.2 Hz, 2H) |
| 106 | 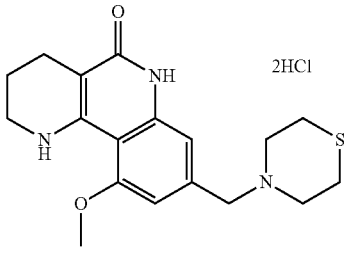 [SMILES: COc1cc(CN2CCSCC2)cc2[nH]c(=O)c3c(c12)NCCC3] | ¹H NMR (400 MHz, DMSO-d₆); δ 11.42 (s, 1H), 11.30 (Br, 1H), 7.82 (Br, 1H), 7.30 (s, 1H), 6.92 (s, 1H), 4.34-4.33 (m, 2H), 3.97 (s, 3H), 3.55-3.52 (m, 2H), 3.35-3.33 (m, 2H), 3.29-3.23 (m, 2H), 3.18-3.12 (m, 2H), 1.75 (t, J = 5.6 Hz, 2H) |
| 107 | 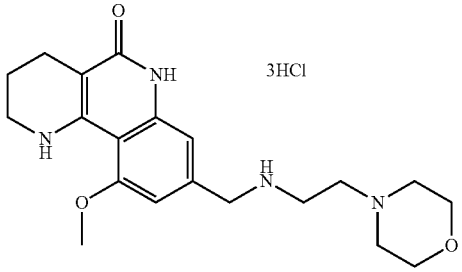 [SMILES: COc1cc(CNCCN2CCOCC2)cc2[nH]c(=O)c3c(c12)NCCC3] | ¹H NMR (400 MHz, DMSO-d₆); δ 11.83 (s, 1H), 11.39 (Br, 1H), 9.99 (Br, 1H), 7.28 (s, 1H), 7.03 (s, 1H), 4.22 (Br, 2H), 4.02-3.97 (m, 5H), 3.84-3.81 (m, 2H), 3.56-3.52 (m, 6H), 3.43-3.38 (m, 2H), 3.21-3.10 (m, 2H), 2.53-2.50 (m, 2H), 1.77 (t, J = 4.4 Hz, 2H) |
| 108 | 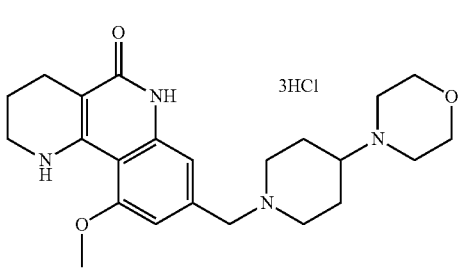 [SMILES: COc1cc(CN2CCC(N3CCOCC3)CC2)cc2[nH]c(=O)c3c(c12)NCCC3] | ¹H NMR (400 MHz, DMSO-d₆); δ 11.33 (Br, 1H), 11.29 (s, 1H), 11.14 (Br, 1H), 7.71 (Br, 1H), 7.19 (s, 1H), 6.89 (s, 1H), 4.27 (Br, 1H), 3.99-3.96 (m, 5H), 3.85-3.80 (m, 2H), 3.47-3.34 (m, 6H), 3.08-2.98 (m, 4H), 2.55 (m, 1H), 2.48-2.45 (m, 2H), 2.33-2.30 (m, 2H), 1.77-1.74 (m, 2H) |

| Ex. | Chmical Structure | NMR spectrum data |
| --- | --- | --- |
| 109 | (structure with 2HCl) | ¹H NMR (400 MHz, DMSO-d$_6$); δ 11.44 (s, 1H), 8.48 (Br, 3H), 7.01 (s, 1H), 6.90 (s, 1H), 4.00 (q, J = 3.2 Hz, 2H), 3.94 (s, 3H), 3.35 (Br, 2H), 2.48-2.46 (m, 2H), 1.76 (m, 2H) |
| 110 | (structure with 2HCl) | ¹H NMR (400 MHz, DMSO-d$_6$); δ 11.36 (s, 1H), 10.8 (Br, 1H), 7.62 (Br, 1H), 7.16 (s, 1H), 6.89 (s, 1H), 4.25 (d, J = 2.6 Hz, 2H), 4.17 (t, J = 6.8 Hz, 2H), 3.36 (Br, 2H), 2.70 (s, 3H), 2.69 (s, 3H), 2.48-2.46 (m, 2H), 1.86 (q, J = 3.6 Hz, 2H), 1.79-1.77 (m, 2H), 1.01 (t, J = 7.6 Hz, 3H) |
| 111 | (structure with 2HCl) | ¹H NMR (400 MHz, DMSO-d$_6$); δ 11.24 (m, 2H), 7.54 (Br, 1H), 7.21 (s, 1H), 6.89 (s, 1H), 4.30-4.29 (m, 2H), 4.19-4.16 (m, 2H), 3.94-3.91 (m, 2H), 3.84-3.78 (m, 2H), 3.38-3.34 (m, 2H), 3.22-3.19 (m, 2H), 3.14-3.10 (m, 2H), 2.49-2.46 (m, 2H), 1.89-1.83 (m, 2H), 1.76-1.75 (m, 2H), 1.01 (t, J = 7.2 Hz, 3H) |
| 112 | (structure with 2HCl) | ¹H NMR (400 MHz, DMSO-d$_6$); δ 11.45 (s, 1H), 8.52 (Br, 3H), 7.96 (s, 1H), 7.31 (s, 1H), 4.05 (d, J = 2.6 Hz, 2H), 3.34-3.32 (m, 2H), 2.53-2.48 (m, 2H), 1.81-1.79 (m, 2H) |
| 113 | (structure with 2HCl) | ¹H NMR (400 MHz, DMSO-d$_6$); δ 11.43 (s, 1H), 8.47 (Br, 3H), 7.72 (Br, 1H), 7.01 (s, 1H), 6.89 (s, 1H), 4.26 (q, J = 3.4 Hz, 2H), 3.99 (d, J = 2.8 Hz, 2H), 3.37 (m, 2H), 2.49-2.46 (m, 2H), 1.77 (m, 2H), 1.44 (t, J = 7.2 Hz, 3H) |
| 114 | (structure with 2HCl) | ¹H NMR (400 MHz, DMSO-d$_6$); δ 11.09 (s, 1H), 8.29 (Br, 3H), 7.45 (Br, 1H), 6.88 (s, 1H), 6.81 (s, 1H), 4.10 (t, J = 6.8 Hz, 2H), 3.97-3.95 (m, 2H), 3.32 (m, 2H), 2.46-2.41 (m, 2H), 1.86-1.83 (m, 2H), 1.74 (m, 2H), 0.99 (t, J = 7.2 Hz, 3H) |

| Ex. | Chmical Structure | NMR spectrum data |
|---|---|---|
| 115 | | ¹H NMR (400 MHz, DMSO-d₆); δ 11.25 (s, 1H), 10.76 (Br, 1H), 7.69 (Br, 1H), 7.19 (s, 1H), 6.93 (s, 1H), 4.49-4.45 (m, 1H), 4.20 (Br, 1H), 4.16-3.99 (m, 1H), 4.02-3.97 (m, 2H), 3.96 (s, 3H), 3.36-3.29 (m, 6H), 2.60-2.56 (m, 3H), 2.49-2.46 (m, 2H), 2.12-2.00 (m, 2H), 1.85-1.82 (m, 2H) |
| 116 | | ¹H NMR (400 MHz, DMSO-d₆); δ 11.43 (s, 2H), 10.94 (Br, 1H), 7.81 (Br, 1H), 7.23 (s, 1H), 6.93 (s, 1H), 4.32-4.30 (m, 2H), 4.30-4.25 (m, 2H), 3.79-3.77 (m, 2H), 3.38 (s, 3H), 3.35-3.33 (m, 2H), 2.69 (s, 3H), 2.68 (s, 3H), 2.49-2.47 (m, 2H), 1.79-1.77 (m, 2H) |
| 117 | | ¹H NMR (400 MHz, DMSO-d₆); δ 11.25 (Br, 2H), 7.71 (Br, 1H), 7.24 (s, 1H), 6.91 (s, 1H), 4.31-4.29 (m, 4H), 3.93-3.91 (m, 2H), 3.84-3.78 (m, 4H), 3.38 (s, 3H), 3.33 (Br, 2H), 3.23-3.20 (m, 2H), 3.12-3.09 (m, 2H), 2.49-2.45 (m, 2H), 1.76-1.75 (m, 2H) |
| 118 | | ¹H NMR (400 MHz, DMSO-d₆); δ 11.51-11.36 (m, 1H), 11.01 (Br, 1H), 8.12 (Br, 1H), 7.05-7.02 (m, 1H), 6.86-6.85 (m, 1H), 6.74-6.71 (m, 1H), 5.10 (t, J = 12.4 Hz, 2H), 3.91-3.88 (m, 3H), 3.36-3.30 (m, 2H), 2.49-2.46 (m, 2H), 2.09-2.05 (m, 3H), 1.76-1.75 (m, 2H) |

Example 119

Synthesis of 8-(Morpholinomethyl)-1,2,3,4-tetrahydrobenzo[h][1,6]naphthyridine-5(6H)-one

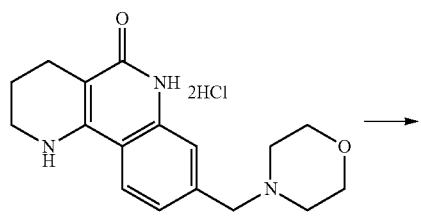

→

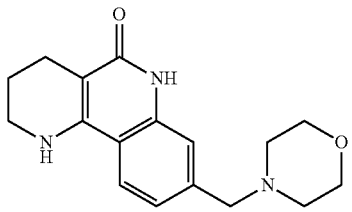

Dichloromethane (60 ml) and methanol (60 ml) were added to 8-(morpholinomethyl)-1,2,3,4-tetrahydrobenzo[h][1,6]naphthyridine-5(6H)-one dihydrochloride (13 g, 31.2 mmol) prepared in Example 49, and then triehylamine (13.05 ml, 93.6 mmol) was added dropwise at room temperature. After stirring at room temperature for 30 minutes, the precipitate was collected by filteration, washed with ethyl acetate (20 ml), and dried in vacuo to obtain the title compound (10 g, yield: 93%, white solid).

$^1$H NMR (400 MHz, DMSO-d$_6$); δ 10.77 (s, 1H), 7.72 (d, J=8.4 Hz, 1H), 7.14 (s, 1H), 7.00 (d, J=8.4 Hz, 1H), 6.91 (s, 1H), 3.57-3.55 (m, 4H), 3.44 (s, 2H), 3.28 (m, 2H), 2.43 (t, J=6.0 Hz, 2H), 2.33 (m, 4H), 1.77 (t, J=5.2 Hz, 2H)

The following compounds were prepared using the reaction of Example 119.

Example 120

8-[(Methylamino)methyl]-1,2,3,4-tetrahydrobenzo[h][1,6]naphthyridine-5(6H)-one

Example 121

8-[(Dimethylamino)methyl]-10-methoxy-1,2,3,4-tetrahydrobenzo[h][1,6]naphthyridine-5(6H)-one

Example 122

10-Methoxy-8-(morpholinomethyl)-1,2,3,4-tetrahydrobenzo[h][1,6]naphthyridine-5(6H)-one

Example 123

10-Etoxy-8-(morpholinomethyl)-1,2,3,4-tetrahydrobenzo[h][1,6]naphthyridine-5(6H)-one

| Ex. | Chmical Structure | NMR spectrum data |
| --- | --- | --- |
| 120 | (structure) | $^1$H NMR (400 MHz, DMSO-d6); δ 10.97 (s, 1H), 7.84 (d, J = 4.2 Hz, 1H), 7.26 (d, J = 4.0 Hz, 1H), 7.05 (s, 1H), 4.02 (s, 2H), 3.29 (Br, 2H), 2.47 (s, 3H), 2.49-2.42 (m, 2H), 1.78 (Br, 2H) |
| 121 | (structure) | $^1$H NMR (400 MHz, DMSO-d6); δ 10.92 (s, 1H), 7.45 (s, 1H), 7.07 (Br, 1H), 6.80 (s, 1H), 4.11 (Br, 2H), 3.93 (s, 3H), 3.30 (Br, 2H), 2.60 (Br, 6H), 2.42 (t, J = 6.4 Hz, 2H), 1.73 (Br, 2H) |
| 122 | (structure) | $^1$H NMR (400 MHz, DMSO-d$_6$); δ 10.68 (s, 1H), 7.41 (s, 1H), 6.77 (s, 1H), 6.57 (s, 1H), 3.87 (s, 3H), 3.58 (m, 4H), 3.41 (s, 2H), 3.29 (m, 2H), 2.41 (t, J = 6.0 Hz, 2H), 2.35 (m, 4H), 1.72t, J = 5.2 Hz, 2H) |
| 123 | (structure) | $^1$H NMR (400 MHz, CDCl$_3$); δ 10.68 (s, 1H), 7.36 (s, 1H), 6.76 (s, 1H), 6.59 (s, 1H), 4.17 (q, J = 3.6 Hz, 2H), 3.59-3.57 (m, 4H), 3.41 (s, 2H), 3.31 (br, 2H), 2.41 (t, J = 6.0 Hz, 2H), 2.35 (br, 4H), 1.76-1.73 (m, 2H), 1.41 (t, J = 6.8 Hz, 3H). |

Experiment Example 1

Poly(ADP-ribose)polymerase [PARP-1] Enzyme Inhibitory Activity

The activity of the compounds according to the present invention to inhibit the PARP-1 enzyme was examined using a PARP Assay kit (4671-096-K) purchased from Trevigen. The assay was performed following a modified previously reported method by Lee et al [Methods Find, Exp. Clin. Pharmacol., 27, 617-622, 2005].

Histone was coated on 384-well plate, which is a small volume PS plate (784101) of Greiner Bio-One, and left at 25° C. for 2 hours. After that, the plate was rinsed four times with PBS (7.5 mM $Na_2HPO_4$, 2.5 mM $NaH_2PO_4$, 145 mM NaCl, pH 7.4), and in order to prevent non-specific reaction, the Strep-diluent (provided from kit of Trevigen) was added and left at 25° C. for one hour. After one hour, the plate was again rinsed with PBS four times, and the compounds of the Examples in various concentrations were put into reactant containing PARP-1 enzyme (0.12 unit/well), 2×PARP cocktail (1.95 mM $NAD^+$, 50 uM biotinylated $NAD^+$, and activated DNA in 50 mM Tris pH 8.0, 25 mM $MgCl_2$) and allowed to react at 25° C. for 30 minutes. After 30 minutes, each well was rinsed with PBS four times, and in order to measure the amount of rybosylation by the PARP enzyme, strepavidin-linked peroxidase (Strep-HRP, 1:1000 diluted) was added and allowed to react at 37° C. for 30 minutes. The plate was rinsed with PBS four times, and TACS-Sapphire substrate was put and allowed to react at 25° C. for 10 minutes so that color reaction occurred. Finally, the reaction was terminated by the addition of 0.2 N HCl. The amount of histone ribosylation formed by PARP-1 enzyme was quantified at 450 nm using Wallac EnVision™ (PerkinElmer Oy, Turku, Finland). The results obtained according to various concentrations of the compounds of the present invention are average values obtained from three wells, and the result was analyzed by calculating the $IC_{50}$ data of the compounds using SigmaPlot 10 (Systat Software Inc., USA). Further, commercially-available DPQ (Sigma) was used as a control in the comparative experiment.

The results are listed in Table 1.

TABLE 1

| Ex. | PARP-1 Inhibitory activity $IC_{50}$ (μM) | Ex. | PARP-1 Inhibitory activity $IC_{50}$ (μM) | Ex. | PARP-1 Inhibitory activity $IC_{50}$ (μM) |
|---|---|---|---|---|---|
| 1 | >4 | 2 | 0.60 | 3 | 0.50 |
| 6 | >4 | 7 | >4 | 8 | >4 |
| 9 | >4 | 10 | >4 | 11 | 1.03 |
| 12 | 1.07 | 13 | 3.85 | 14 | >4 |
| 15 | 1.05 | 16 | 0.37 | 17 | 0.46 |
| 18 | 1.52 | 19 | 1.48 | 20 | 1.54 |
| 21 | >4 | 22 | 1.16 | 23 | 1.43 |
| 24 | 1.08 | 25 | >4 | 26 | 0.39 |
| 27 | 2.64 | 28 | >4 | 29 | 2.85 |
| 30 | 3.11 | 31 | 1.07 | 32 | 0.23 |
| 33 | 0.93 | 34 | 1.62 | 35 | 3.54 |
| 36 | 3.02 | 37 | >4 | 38 | 0.05 |
| 39 | 0.10 | 40 | >4 | 41 | 0.04 |
| 42 | 0.22 | 43 | 0.16 | 44 | 0.06 |
| 45 | 0.26 | 46 | 0.59 | 47 | 0.07 |
| 48 | 0.13 | 49 | 0.62 | 50 | 0.32 |
| 51 | 0.93 | 52 | 0.07 | 53 | 0.05 |
| 54 | 0.93 | 55 | 1.72 | 56 | 0.18 |
| 57 | 0.48 | 58 | 0.92 | 59 | 0.19 |
| 60 | 0.12 | 61 | 0.54 | 62 | >4 |
| 63 | 1.02 | 64 | 0.54 | 65 | 1.54 |
| 66 | 0.09 | 67 | 0.76 | 68 | 1.19 |
| 69 | >4 | 70 | 1.09 | 71 | 3.00 |
| 72 | 0.08 | 73 | 0.10 | 74 | 0.23 |
| 75 | 0.05 | 76 | 0.05 | 77 | 0.05 |
| 78 | 0.11 | 79 | 0.18 | 80 | 0.14 |
| 81 | 0.11 | 82 | 0.06 | 83 | 0.32 |
| 84 | 0.15 | 85 | 0.18 | 86 | 0.11 |
| 87 | 0.61 | 88 | 0.11 | 89 | 0.27 |
| 90 | 0.78 | 91 | 0.29 | 92 | 0.19 |
| 93 | 0.14 | 94 | 0.17 | 95 | 0.49 |
| 96 | 0.77 | 97 | 0.90 | 99 | 0.75 |
| 100 | 0.06 | 101 | 0.56 | 102 | 0.18 |
| 103 | 0.12 | 104 | 0.06 | 105 | 0.19 |
| 106 | 0.09 | 107 | 0.07 | 108 | 0.14 |
| 109 | 0.07 | 110 | 0.08 | 111 | 0.96 |
| 112 | 0.17 | 113 | 0.10 | 114 | 0.19 |
| 115 | 0.41 | 116 | 0.18 | 117 | 0.61 |
| Control (DPQ) | 2.51 | | | | |

As Table 1 above indicates, the compound according to the present invention exhibits PARP-1 inhibitory activity of 0.04~4 μM, and to be specific, the compounds of Examples 2, 3, 16, 17, 26, 32, 33, 38, 39, 41~54, 56~61, 64, 66, 67, 72~117 exhibit PARP-1 inhibitory activity lower than 1 μM. Accordingly, compared to the control (i.e., DPQ (2.51 μM)), the compounds of the present invention provide superior PARP-1 inhibitory activity. Accordingly, the compounds according to the present invention effectively inhibit PARP-1, and thus can be used effectively for prevention or treatment of diseases derived due to PARP over-activation, including, neuropathic pain, neurodegeneration diseases, cardiovascular diseases, diabetic neuropathy, inflammatory disease, osteoporosis, and cancer.

Experiment Example 2

Intracellular PARP Inhibitory Activity

In order to verify the ability of the compounds of the present invention to inhibit the PARP-1 enzyme activity, the amount of NAD(P)H accumulated on cell culture medium was measured.

The Chinese hamster ovary cells (CHO-K1) were cultured in RPMI1640 culture medium containing 10% fetal bovine serum (FBS). The cultured CHO-K1 cells were seeded into 96 well plate by $2.9 \times 10^3$ cells/well, and cultured for 16 hours under culture condition of 37° C., 5% $CO_2$. After the culture, the cells were treated with the compounds of the Examples at varying concentrations, and cultured at 37° C. for 2 hours. After that, methyl methanesulfonate (MMS) as DNA damaging substance was treated by 1.5 mM for each, and CCK-8 (Cell count kit-8) solution (CK01-13 of DOJINDO) was concurrently treated for the purpose of color development. The amount of NND(P)H released to the culture medium 3, 4, 5 hours after the treatment with MMS was quantified at 450 nm using Wallac EnVision™ (PerkinElmer Oy, Turku, Finland). The transference numbers of the compounds at varying concentrations according to the present invention are the average values obtained from four wells, and the results were calculated using regression analysis. Further, commercially-available DPQ (Sigma) was used as a control in the comparative experiment.

The Chinese hamster ovary cells (CHO-K1) were treated with the compounds at varying concentration according to the present invention, and the amount of NAD(P)H released into the culture medium 4 hours after the MMS treatment was quantified. The result is listed in Table 2 and FIG. 1.

TABLE 2

| Ex. | PARP-1 Inhibitory activity $IC_{50}$ (μM) | Ex. | PARP-1 Inhibitory activity $IC_{50}$ (μM) |
|---|---|---|---|
| 2 | 0.92 | 3 | 0.87 |
| 17 | 1.63 | 18 | 3.71 |
| 20 | 1.30 | 25 | 3.18 |
| 32 | 3.16 | 37 | 4.86 |
| 38 | 0.14 | 39 | 1.56 |
| 41 | 0.05 | 42 | 0.85 |
| 43 | 1.77 | 44 | 0.34 |
| 45 | 1.16 | 47 | 0.25 |
| 48 | 0.43 | 49 | 0.51 |
| 52 | 0.17 | 53 | 0.29 |
| 56 | 0.47 | 66 | 0.32 |
| 72 | 0.09 | 73 | 1.39 |
| 74 | 1.48 | 77 | 0.82 |
| 87 | 0.82 | 88 | 0.27 |
| 100 | 0.06 | 101 | 1.94 |
| 102 | 0.50 | 103 | 0.82 |
| 104 | 1.65 | 105 | 1.21 |
| 106 | 0.29 | 107 | 2.22 |
| 108 | 0.11 | 109 | 0.94 |
| 110 | 0.09 | 111 | 1.33 |
| 112 | 2.65 | 113 | 1.43 |
| 114 | 1.92 | 115 | 1.22 |
| 116 | 0.52 | 117 | 6.32 |
| Control (DPQ) | 12.40 | | |

As Table 2 and FIG. 1 indicate, the tricyclic derivatives according to the present invention exhibit PARP-1 inhibitory activity of 0.05~6.32 μM and thus provides superior PARP-1 inhibitory activity compared to the control compound (i.e., DPQ (12.40 μM)).

Experiment Example 3

Cell Growth Inhibition of Cancer Cell Lines

The following tests were performed to confirm the activity of the compounds of the present invention to inhibit cell growth of the cancer cell lines.

The tests on cell growth inhibitory activity were performed with respect to A549 (US, ATCC), SK-OV-3 (Korea Research Institute of Chemical Technology; KRICT), HT-29 (US, ATCC), MCF-7 cell (US, ATCC), using Sulforhodamin-B <SRB> Assay (1989, US National Cancer Institute (NCI)) which was developed to measure the in vitro anti-cancer activity of the drug. The cells to be used in the tests were separated from the attached surface with 0.25% trypsin-EDTA solution, prepared into $1.5 \times 10^4 \sim 7 \times 10^4$ cell/ml cell suspension, added to 96 well plates by 200 μl per well, and cultured in 37° C., 5% $CO_2$ culture medium for 24 hours. The samples of the compounds of the Examples according to the present invention were used for the tests, and before the tests, the samples were dissolved in dimethylsulfoxide and diluted with the culture medium (RPMI 1640) to be used. The final concentration of the sample was varied in the range of 0.3~100 μM. After the culture medium was removed from the 96 well plates, the diluted sample solution was added by 100 μl, and cultured in 37° C., 5% $CO_2$ culture medium for 72 hours. The time zero (Tz) plates were collected at the time point of adding the sample. Upon completing the culture, the medium was removed from each well along with Tz plate, then cold 10% trichloroacetic acid (TCA) was added by 100 μl per well. The wells were left at 4° C. for 1 hour, so that the cells were fixed into the bottom of the plates. After the cells were fixed, the plates were rinsed with water five to six times to remove the remaining trichloroacetic acid solution, and moisture was completely dried at room temperature. The cells were dyed for 30 minutes by adding the dye solution in which 0.4% sulforhodamine-B was dissolved in 1% acetic acid solution, by 100 μl per dried wells. The above was rinsed again with 1% acetic acid solution five to six times to ensure that sulforhodamine-B which had not attached to the cells was removed. The plates were again dried at room temperature. 100 μl of 10 mM tris-buffer was then added to dissolve the dye, and the optical density (OD) at 520 nm was measured with the microplate reader. $GI_{50}$ of the sample regarding cancer cell was calculated as explained below. Time zero (Tz), control value (C) and test value (T) were obtained, in which Tz corresponds to OD value of time at which the sample is applied and culture is started, C corresponds to OD value of the well which is cultured without treatment with the sample, and T corresponds to OD value of the well which is treated with the sample and then cultured. The degree of cell growth inhibition of the sample was measured using:

If $T \leq Tz$, $(T-Tz)/(C-Tz) \times 100$

If $T \geq Tz$, $(T-Tz)/Tz \times 100$ [Mathematical Formula 1]

Based on the result of calculation by Mathematical Formula 1, the growth inhibition concentration (GI50), which represents the concentration of a drug for inhibiting growth of cancel cell by 50%, was calculated by using a regression analysis of Lotus program. Further, the ability of Examples 2, 42, 49, 52, 72, 74, 101 to increase growth inhibition effect of temozolomide and SN-38 at 2 μM was determined.

$PF_{50}$ was calculated by:

$GI_{50}$ with (temozolomide) or (SN-38) treated alone/
GI50 with (temozolomide) or (SN-38)+2 μM
compound treated [Mathematical Formula 2]

The result of calculation is shown in Tables 3 to 6.

TABLE 3

| A549 cell line | | | |
|---|---|---|---|
| Ex. | $GI_{50}$ (μM) | Temozolomide $PF_{50}$ | SN-38 $PF_{50}$ |
| 2 | 59 | 2.4 | 2.2 |
| 42 | >100 | 2.3 | 1.6 |
| 29 | >100 | 2.0 | 1.5 |
| 52 | >100 | 1.5 | 2.2 |
| 72 | >100 | 3.4 | 3.8 |
| 74 | 75 | 3.2 | 2.2 |
| 101 | 55 | 3.2 | 2.6 |

TABLE 4

| SK-OV-3 Cell line | | | |
|---|---|---|---|
| Ex. | $GI_{50}$ (μM) | Temozolomide $PF_{50}$ | SN-38 $PF_{50}$ |
| 2 | 50 | >3.2 | 1.2 |
| 42 | >100 | >2.1 | 1.6 |
| 29 | >100 | >1.7 | 1.5 |
| 52 | >100 | >2.2 | 1.4 |
| 72 | >100 | >10.2 | 1.8 |
| 74 | 52 | >5.0 | 2.2 |
| 101 | 19 | >3.9 | 2.8 |

TABLE 5

HT-29 Cell line

| Ex. | $GI_{50}$ (μM) | Temozolomide $PF_{50}$ | SN-38 $PF_{50}$ |
|---|---|---|---|
| 2 | 70 | >1.5 | 1.4 |
| 42 | 81 | >1.4 | 2.1 |
| 29 | 91 | >1.2 | 1.5 |
| 52 | 90 | >1.3 | 1.4 |
| 72 | >100 | >5.2 | 2.2 |
| 74 | 30 | >2.8 | 3.5 |
| 101 | 20 | >1.9 | 4.0 |

TABLE 6

MCF-7 Cell line

| Ex. | $GI_{50}$ (μM) | Temozolomide $PF_{50}$ | SN-38 $PF_{50}$ |
|---|---|---|---|
| 2 | 51 | 1.7 | 1.4 |
| 42 | 75 | 1.6 | 1.6 |
| 29 | >100 | 2.1 | 2.2 |
| 52 | >100 | 1.5 | 1.1 |
| 72 | 54 | 1.7 | 2.6 |
| 74 | 45 | 6.3 | 3.0 |
| 101 | 11 | 5.9 | 3.0 |

As indicated in Tables 3 to 6, when 2 μM of tricyclic derivative according to the present invention was added, the $GI_{50}$ value of temozolomide or SN-38 decreased to be 1.5 to 3.8 times lower in A549 cell line, 1.2 to 10.2 times lower in SK-OV-3 cell line, 1.2 to 5.2 times lower in HT-29 cell line, and 1.1 to 6.3 times lower in MCF-7 cell line.

Experiment Example 4

Neuroprotective Effect in Rat Middle Cerebral Artery Occlusion (MCAO) Animal Model The present inventors performed the following test to confirm the neuroprotective ability of the compounds according to the present invention.

Animal test was performed on male Sprague Dawley rats (KOATECH Co., Ltd., South Korea) weighing 280 to 340 g. Animals were given food and water ad libitum and adapted to the test environment for 1 week. The modified intraluminal filament technique as described by Zea Longa et al. (Stroke, 20:84-91, 1989) was used to induce MCAO. The rats were developed ischemic regions due to insufficient blood flow in striatum and temporal lobe which are the domain regions of the middle cerebral artery and depletion of oxygen and energy sources after the middle cerebral artery occlusion. In order to occlude the middle cerebral artery with the intraluminal suture method, 4-0 nylon suture was cut to 22 mm, and 2 mm of the terminal end was rounded by flame heating. In order to increase the effect of damage preventing and occlusion in the lumen, a probe was coated with silicon to 0.3 mm.

Rats were anaesthetized with isoflurane (3% for induction and 2% for surgical procedure) in a mixture of oxygen/nitrous oxide (30%/70%). The left common carotid artery (CCA) was exposed through a ventral midline incision in the neck. The external carotid artery (ECA), internal carotid artery (ICA), and CCA were carefully isolated and maintained in a Y-shape by use of silk suture. The upper external carotid artery was blocked by a thread, and a minute hole is bored 1 mm below the spot at which the external and internal carotid arteries bifurcate from the common carotid. The probe was inserted in the minute hole and fixed by a thread. The neck wound was closed and each animal was allowed to recover from anesthesia. 120 min after MCA occlusion, each animal was re-anesthetized, and the neck wound was re-opened to remove the thread. Along with the reperfusion, the compound of Example 74 was injected intravenously. 22 hours after the reperfusion, the animals were sacrificed by $CO_2$ suffocation, decapitated, and 2 mm thick six coronal sections were obtained using rodent brain matrix. The coronal slices were incubated in phosphate-buffered saline (PBS) containing 2% 2,3,5-triphenyl tetrazolium chloride (TTC, Sigma) at 37° C. for 30 min, and then fixed in 4% phosphate-buffered formalin. After fixation these brain sections were scanned using a flat-bed scanner. The infarct area was determined by image J (NIH image version 1.59), and the total infarct volume was calculated by:

$$\text{Infarct volume (mm}^3\text{)} = \text{infarct volume (mm}^2\text{)} \times \text{thickness of slice (2 mm)} \qquad \text{[Mathematical formula 3]}$$

The statistical analysis of the decrease of infarct volume was performed by Mann Whitney test (*:p<0.05, **:p<0.01). The result of the test is shown in Table 7 and FIG. 2.

TABLE 7

| Group | Number of mice | Dose (mg/kg) | Infarct volume (mm³) | Percent of infraction decrease (%) | p |
|---|---|---|---|---|---|
| 1 | 10 | — (Control group) | 263.23 | — | — |
| 2 | 10 | 10 | 252.38 | 4 | 0.65 |
| 3 | 12 | 20 | 124.68 | 53 | 0.003** |
| 4 | 11 | 30 | 162.88 | 38 | 0.024* |

Figure 2:
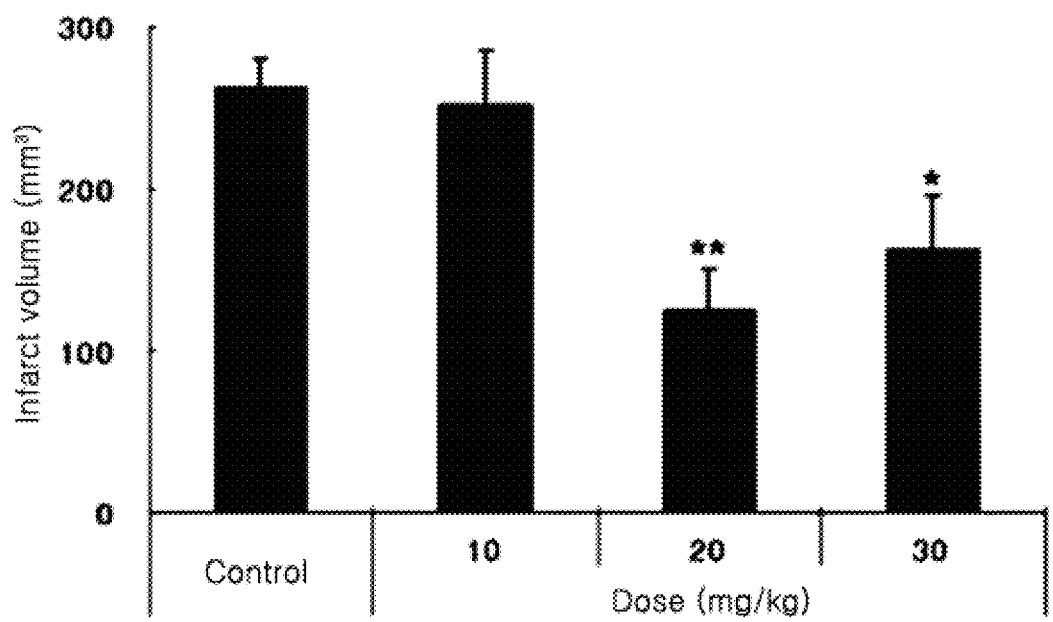
FIG. 2 is a graphical representation of infarct volume according to a dose of compound of an embodiment of the present invention.

As shown in Table 7 and FIG. 2, in comparison with the control group, the group administered with the compound of the present invention by 10 mg/kg did not exhibit meaningful reduction of infarct volume. However, the group administered with the compound of the present invention by 20 mg/kg and 30 mg/kg, respectively, exhibited meaningful decrease of infarct area, by 53% and 38%, respectively, when compared with the control group.

Accordingly, the tricyclic derivatives according to the present invention show superior inhibitory activity on the Poly(ADP-ribose)polymerase, in particularly, superior PARP-1 inhibitory activity when compared with DPQ as the conventional Poly(ADP-ribose)polymerase inhibitor, increase cancer cell growth inhibition effect of temozolomide or SN-38, and exhibit prevention effect in the focal ischemia of white mice using Middle Cerebral Artery Occlusion (MCAO), and thus can be used effectively for prevention or treatment of the diseases induced by over-activation of PARP, including, in particular, neuropathic pain, neurodegeneration diseases, cardiovascular diseases, diabetic neuropathy, inflammatory disease, osteoporosis, and cancer.

Meanwhile, the tricyclic derivatives according to the present invention can be formulated into a variety of forms depending on purposes. Accordingly, the concept of the present invention is not limited to a few examples of formulations containing the derivatives as effective components disclosed herein.

Exemplary Formulation 1

Preparation of Pharmaceutical Medicine

1. Formulation of Tablet

| | | |
|---|---|---|
| | Compound of chemical formula 1 | 100 mg |
| | Corn starchy | 100 mg |
| | Lactose | 100 mg |
| | Magnesium stearate | 2 mg |

The above-mentioned components were mixed with each other, and the tablet was made using compression according to conventional method for making tablets.

2. Formulation of Capsule

| | | |
|---|---|---|
| | Compound of chemical formula 1 | 100 mg |
| | Corn starchy | 100 mg |
| | Lactose | 100 mg |
| | Magnesium stearate | 2 mg |

The above-mentioned components were mixed, and the capsule was made by filling the mixture into gelatin captures according to conventional methods for making capsules.

We claim:

1. A tricyclic compound represented by chemical formula 1 or pharmaceutically acceptable salts thereof:

[Chemical formula 1]

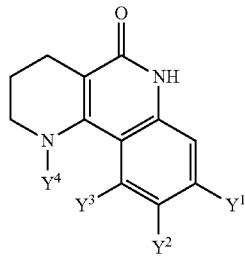

wherein $Y^1$ and $Y^2$ are independently H, methyl, ethyl, methoxy, ethoxy, hydroxy, $COOR^1$, $-NR^2R^3$ or -A-B;

$Y^3$ is H, hydroxy, methoxy, ethoxy, propoxy, or methoxyethoxy, provided that at least one of $Y^1$ and $Y^2$ is methoxy, ethoxy, hydroxy, $-COOR^1$, $-NR^2R^3$ or -A-B;

wherein

A is $-O-$, $-CH_2-$, $-CH(CH_3)-$, $-CH=N-$ or $-CONH-$;

B is $-(CH_2)n_1-Z$, $-(CH_2)n_2-NR^2R^3$ or $-(CH_2)n_3-OR^1$;

Z is one base selected from the group consisting of the below structural formulae;

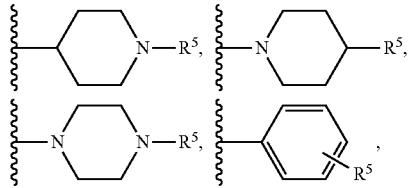

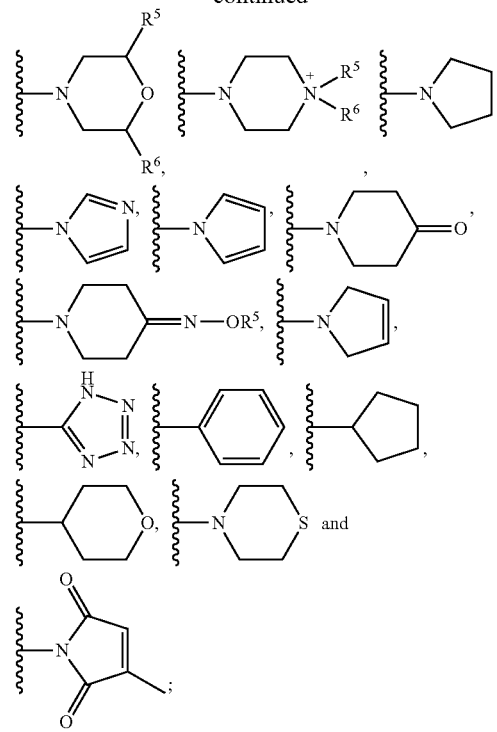

wherein $R^1$ is H, methyl, ethyl or isopropyl;

$R^2$ and $R^3$ are independently H, methyl, ethyl, propyl, isopropyl, t-butyl or $-(CH_2)n_4R^7$;

$R^5$ is H, compound, methyl, ethyl, propyl, phenyl or morpholino;

$R^6$ is H, methyl or ethyl;

$R^7$ is $-NR^8R^9$, $-COOR^1$, $-OR^1$, $-CF_3$, $-CN$, F, Cl or Z;

$R^8$ and $R^9$ are independently H or methyl;

$n_1$ to $n_4$ are respectively integers between 0 and 5; and $Y^4$ is H, methyl, ethyl or propyl.

2. The tricyclic compound represented by chemical formula 1 or pharmaceutically acceptable salts thereof according to claim 1, selected from a group consisting of:

1) 8-Methoxy-1,2,3,4-tetrahydrobenzo[h][1,6]naphthyridine-5(6H)-one;

2) 10-Methoxy-1,2,3,4-tetrahydrobenzo[h][1,6]naphthyridine-5(6H)-one;

3) 9-Methoxy-1,2,3,4-tetrahydrobenzo[h][1,6]naphthyridine-5(6H)-one;

5) Ethyl 5-oxo-1,2,3,4,5,6-hexahydro benzo[h][1,6]naphthyridine-9-carboxylate;

6) 9-Methoxy-1-propyl-1,2,3,4-tetrahydrobenzo[h][1,6]naphthyridine-5(6H)-one;

8) 9-Methoxy-1-methyl-1,2,3,4-tetrahydrobenzo[h][1,6]naphthyridine-5(6H)-one;

9) 1-Ethyl-9-methoxy-1,2,3,4-tetrahydrobenzo[h][1,6]naphthyridine-5(6H)-one;

10) 1-Methyl-9-hydroxy-1,2,3,4-tetrahydrobenzo[h][1,6]naphthyridine-5(6H)-one;

11) 9-(1-Propylpiperidine-4-yloxy)-1,2,3,4-tetrahydrobenzo[h][1,6]naphthyridine-5(6H)-one;

12) 9-(1-Methylpiperidine-4-yloxy)-1,2,3,4-tetrahydrobenzo[h][1,6]naphthyridine-5(6H)-one;

13) 1-Methyl-9-(piperidine-4-yloxy)-1,2,3,4-tetrahydrobenzo[h][1,6]naphthyridine-5(6H)-one;

14) 1-Methyl-9-(1-methylpiperidine-4-yloxy)-1,2,3,4-tetrahydrobenzo[h][1,6]naphthyridine-5(6H)-one;
15) 5-Oxo-N-[2-(piperidine-1-yl)ethyl]-1,2,3,4,5,6-hexahydro benzo[h][1,6]naphthyridine-9-carboxamide;
16) 9-[2-(Dimethylamino)ethoxy]-1,2,3,4-tetrahydrobenzo[h][1,6]naphthyridine-5(6H)-one;
17) 9-[2-(Piperidine-1-yl)ethoxy]-1,2,3,4-tetrahydrobenzo[h][1,6]naphthyridine-5(6H)-one;
18) 9-(2-Methoxyethoxy)-1,2,3,4-tetrahydrobenzo[h][1,6]naphthyridine-5(6H)-one;
19) 9-[2-(Piperazine-1-yl)ethoxy]-1,2,3,4-tetrahydrobenzo[h][1,6]naphthyridine-5(6H)-one;
20) 9-Ethoxy-1,2,3,4-tetrahydrobenzo[h][1,6]naphthyridine-5(6H)-one;
21) 9-[3-(Piperidine-1-yl)propoxy]-1,2,3,4-tetrahydrobenzo[h][1,6]naphthyridine-5(6H)-one;
22) 9-(2-Aminoethoxy)-1,2,3,4-tetrahydrobenzo[h][1,6]naphthyridine-5(6H)-one;
23) 9-[2-(4-Phenylpiperidine-1-yl)ethoxy]-1,2,3,4-tetrahydrobenzo[h][1,6]naphthyridine-5(6H)-one;
24) 9-(2-Hydroxyethoxy)-1,2,3,4-tetrahydrobenzo[h][1,6]naphthyridine-5(6H)-one;
25) 9-Penethoxy-1,2,3,4-tetrahydrobenzo[h][1,6]naphthyridine-5(6H)-one;
26) 9-[2-(Diethylamino)ethoxy]-1,2,3,4-tetrahydrobenzo[h][1,6]naphthyridine-5(6H)-one;
27) 9-(2-Morpholinoethoxy)-1,2,3,4-tetrahydrobenzo[h][1,6]naphthyridine-5(6H)-one;
28) 1,1-Diethyl-4-[2-(5-oxo-1,2,3,4,5,6-hexahydrobenzo[h][1,6]naphthyridine-9-yloxy]ethyl)piperazine-1-ium;
29) 9-[4-(Piperidine-1-yl)butoxy]-1,2,3,4-tetrahydrobenzo[h][1,6]naphthyridine-5(6H)-one;
30) 1-Methyl-9-[2-(piperidine-1-yl)ethoxy]-1,2,3,4-tetrahydrobenzo[h][1,6]naphthyridine-5(6H)-one
31) 9-[2-(Dimethylamino)ethyl]-1,2,3,4-tetrahydrobenzo[h][1,6]naphthyridine-5(6H)-one;
32) 8-[2-(Dimethylamino)ethoxy]-1,2,3,4,-tetrahydrobenzo[h][1,6]naphthyridine-5(6H)-one;
33) 9-[3-(Dimethylamino)propyl]-1,2,3,4-tetrahydrobenzo[h][1,6]naphthyridine-5(6H)-one;
34) 8-[2-(Dimethylamino)ethoxy]-1,2,3,4,5,6-hexahydrobenzo[h][1,6]naphthyridine-9-carboxamide;
35) 8-[2-(Piperidine-1-yl)ethoxy]-1,2,3,4-tetrahydrobenzo[h][1,6]naphthyridine-5(6H)-one;
36) 8-[3-(Dimethylamino)propoxy]-1,2,3,4-tetrahydrobenzo[h][1,6]naphthyridine-5(6H)-one;
37) 8-(Dimethylamino)-1,2,3,4-tetrahydrobenzo[h][1,6]naphthyridine-5(6H)-one;
38) 8-[1-(Dimethylamino)ethyl]-1,2,3,4-tetrahydrobenzo[h][1,6]naphthyridine-5(6H)-one;
39) 8-[1-(Methylamino)ethyl]-1,2,3,4-tetrahydrobenzo[h][1,6]naphthyridine-5(6H)-one;
41) 8-[(Dimethylamino)methyl]-1,2,3,4-tetrahydrobenzo[h][1,6]naphthyridine-5(6H)-one;
42) 8-[(Diethylamino)methyl]-1,2,3,4-tetrahydrobenzo[h][1,6]naphthyridine-5(6H)-one;
43) 8-[(Ethylamino)methyl]-1,2,3,4-tetrahydrobenzo[h][1,6]naphthyridine-5(6H)-one;
44) 8-(Pyrrolidine-1-ylmethyl)-1,2,3,4-tetrahydrobenzo[h][1,6]naphthyridine-5(6H)-one;
45) 8-[(Isopropylamino)methyl]-1,2,3,4-tetrahydrobenzo[h][1,6]naphthyridine-5(6H)-one;
46) 8-[(Propylamino)methyl]-1,2,3,4-tetrahydrobenzo[h][1,6]naphthyridine-5(6H)-one;
47) 8-{[Ethyl(methyl)amino]methyl}-1,2,3,4-tetrahydrobenzo[h][1,6]naphthyridine-5(6H)-one;
48) 8-(Piperidine-1-ylmethyl)-1,2,3,4-tetrahydrobenzo[h][1,6]naphthyridine-5(6H)-one;
49) 8-(Morpholinomethyl)-1,2,3,4-tetrahydrobenzo[h][1,6]naphthyridine-5(6H)-one;
50) 9-[(Dimethylamino)methyl]-1,2,3,4-tetrahydrobenzo[h][1,6]naphthyridine-5(6H)-one;
51) 8-{[Benzyl(methyl)amino]methyl}-1,2,3,4-tetrahydrobenzo[h][1,6]naphthyridine-5(6H)-one;
52) 8-[(Methylamino)methyl]-1,2,3,4-tetrahydrobenzo[h][1,6]naphthyridine-5(6H)-one;
53) 8-{[(2-Hydroxyethyl)(methyl)amino]methyl}-1,2,3,4-tetrahydrobenzo[h][1,6]naphthyridine-5(6H)-one;
54) 8-{[(2-(Dimethylaminoethyl)(methyl)amino]methyl}-1,2,3,4-tetrahydrobenzo[h][1,6]naphthyridine-5(6H)-one;
55) 8-[(4-Methylpiperazine-1-yl)methyl]-1,2,3,4-tetrahydrobenzo[h][1,6]naphthyridine-5(6H)-one;
56) 8-[(Methyl(propyl)amino]methyl]-1,2,3,4-tetrahydrobenzo[h][1,6]naphthyridine-5(6H)-one;
57) Ethyl-3-{methyl[(5-oxo-1,2,3,4,5,6-hexahydrobenzo[h][1,6]naphthyridine-8-yl)methyl]amino}propanoate;
58) 3-{Methyl[(5-oxo-1,2,3,4,5,6-hexahydrobenzo[h][1,6]naphthyridine-8-yl)methyl]amino}propanoic acid;
59) 8-{[Isopropyl(methyl)amino]methyl}-1,2,3,4-tetrahydrobenzo[h][1,6]naphthyridine-5(6H)-one;
60) 8-{[(2-Methoxyethyl)(methyl)amino]methyl}-1,2,3,4-tetrahydrobenzo[h][1,6]naphthyridine-5(6H)-one;
61) Ethyl-3-[(5-oxo-1,2,3,4,5,6-hexahydrobenzo[h][1,6]naphthyridine-8-yl)methylamino]propanoate;
62) 8-[(2,2,2-Trifluoroethylamino)methyl]-1,2,3,4-tetrahydrobenzo[h][1,6]naphthyridine-5(6H)-one;
63) 2-[(5-oxo-1,2,3,4,5,6-hexahydrobenzo[h][1,6]naphthyridine-8-yl)methylamino]acetonitrile;
64) 8-[(1H-Imidazole-1-yl)methyl]-1,2,3,4-tetrahydrobenzo[h][1,6]naphthyridine-5(6H)-one;
65) 8-[(1H-Pyrrole-1-yl)methyl]-1,2,3,4-tetrahydrobenzo[h][1,6]naphthyridine-5(6H)-one;
66) 8-[(Dimethylamino)methyl]-1-methyl-1,2,3,4-tetrahydrobenzo[h][1,6]naphthyridine-5(6H)-one;
67) 1-Methyl-8-(pyrrolidine-1ylmethyl)-1,2,3,4-tetrahydrobenzo[h][1,6]naphthyridine-5(6H)-one;
68) 8-[(Diethylamino)methyl]-1-methyl-1,2,3,4-tetrahydrobenzo[h][1,6]naphthyridine-5(6H)-one;
69) 1-Methyl-8-(piperidine-1-ylmethyl)-1,2,3,4-tetrahydrobenzo[h][1,6]naphthyridine-5(6H)-one;
70) 1-Methyl-8-(morpholinomethyl)-1,2,3,4-tetrahydrobenzo[h][1,6]naphthyridine-5(6H)-one;
71) 8-{[Ethyl(methyl)amino]methyl}-1-methyl-1,2,3,4-tetrahydrobenzo[h][1,6]naphthyridine-5(6H)-one;
72) 8-[(Dimethylamino)methyl]-10-methoxy-1,2,3,4-tetrahydrobenzo[h][1,6]naphthyridine-5(6H)-one;
73) 10-Methoxy-8-[(methylamino)methyl]-1,2,3,4-tetrahydrobenzo[h][1,6]naphthyridine-5(6H)-one;
74) 10-Methoxy-8-(morpholinomethyl)-1,2,3,4-tetrahydrobenzo[h][1,6]naphthyridine-5(6H)-one;
75) 8-[(Ethylamino)methyl]-10-methoxy-1,2,3,4-tetrahydrobenzo[h][1,6]naphthyridine-5(6H)-one;
76) 8-{[Ethyl(methyl)amino]methyl}-10-methoxy-1,2,3,4-tetrahydrobenzo[h][1,6]naphthyridine-5(6H)-one;
77) 10-Methoxy-8-(pyrrolidine-1-ylmethyl)-1,2,3,4-tetrahydrobenzo[h][1,6]naphthyridine-5(6H)-one;
78) 10-Methoxy-8-[(4-oxopiperidine-1-yl)methyl]-1,2,3,4-tetrahydrobenzo[h][1,6]naphthyridine-5 (6H)-one;
79) 8-{[4-(Hydroxyimino)piperidine-1-yl]methyl}-10-methoxy-1,2,3,4-tetrahydrobenzo[h][1,6]naphthyridine-5(6H)-one;

80) 10-Methoxy-8-[(4-(methoxyimino)piperidine-1-yl) methyl]-1,2,3,4-tetrahydrobenzo[h][1,6]naphthyridine-5(6H)-one;
81) 10-Methoxy-8-{[(2-methoxyethyl)(methyl)amino] methyl}-1,2,3,4-tetrahydrobenzo[h][1,6]naphthyridine-5(6H)-one;
82) 8-[(2,5-Dehydro-1H-pyrrole-1-yl)methyl]-10-methoxy-1,2,3,4-tetrahydrobenzo[h][1,6]naphthyridine-5(6H)-one;
83) 8-{[(2-Isopropoxyethyl)(methyl)amino]methyl}-10-methoxy-1,2,3,4-tetrahydrobenzo[h][1,6]naphthyridine-5(6H)-one;
84) 10-Methoxy-8-(piperidine-1-ylmethyl)-1,2,3,4-tetrahydrobenzo[h][1,6]naphthyridine-5(6H)-one;
85) 8-{[(2-Chloroethyl)(methyl)amino]methyl}-10-methoxy-1,2,3,4-tetrahydrobenzo[h][1,6]naphthyridine-5(6H)-one;
86) 8-[(Diethylamino)methyl]-10-methoxy-1,2,3,4-tetrahydrobenzo[h][1,6]naphthyridine-5(6H)-one;
87) 8-[(t-Butylamino)methyl]-10-methoxy-1,2,3,4-tetrahydrobenzo[h][1,6]naphthyridine-5(6H)-one;
88) 8-[(Isopropylamino)methyl]-10-methoxy-1,2,3,4-tetrahydrobenzo[h][1,6]naphthyridine-5(6H)-one;
89) 8-[(Cyclopentylamino)methyl]-10-methoxy-1,2,3,4-tetrahydrobenzo[h][1,6]naphthyridine-5(6H)-one;
90) 8-[(2,6-Dimethylmorpholino)methyl]-10-methoxy-1,2,3,4-tetrahydrobenzo[h][1,6]naphthyridine-5(6H)-one;
91) N-[(10-Methoxy-5-oxo-1,2,3,4,5,6-hexahydrobenzo[h][1,6]naphthyridine-8-yl)methyl]-N,N-dimethylcyclopentane aminium chloride;
92) 8-{[Cyclopentyl(methyl)amino]methyl}-10-methoxy-1,2,3,4-tetrahydrobenzo[h][1,6]naphthyridine-5(6H)-one;
93) 8-{[Isopropyl(methyl)amino]methyl}-10-methoxy-1,2,3,4-tetrahydrobenzo[h][1,6]naphthyridine-5(6H)-one;
94) 8-{[(2-Fluoroethyl)(methyl)amino]methyl}-10-methoxy-1,2,3,4-tetrahydrobenzo[h][1,6]naphthyridine-5(6H)-one;
95) 8-[(1H-Tetrazol-5-yl)methyl]-1,2,3,4-tetrahydrobenzo[h][1,6]naphthyridine-5(6H)-one;
96) 10-Methoxy-8-[(morpholinoamino)methyl]-1,2,3,4-tetrahydrobenzo[h][1,6]naphthyridine-5(6H)-one;
97) 10-Methoxy-8-{[methyl(morpholino)amino]methyl}-1,2,3,4-tetrahydrobenzo[h][1,6]naphthyridine-5(6H)-one;
98) (E)-10-Methoxy-8-[(morpholinoimino)methyl]-1,2,3,4-tetrahydrobenzo[h][1,6]naphthyridine-5(6H)-one;
99) 8-[(Dimethylamino)methyl]-10-hydroxy-1,2,3,4-tetrahydrobenzo[h][1,6]naphthyridine-5-(6H)-one;
100) 8-[(Dimethylamino)methyl]-10-ethoxy-1,2,3,4-tetrahydrobenzo[h][1,6]naphthyridine-5(6H)-one;
101) 10-Ethoxy-8-(morpholinomethyl)-1,2,3,4-tetrahydrobenzo[h][1,6]naphthyridine-5(6H)-one;
102) 10-Ethoxy-8-(piperidine-1-ylmethyl)-1,2,3,4-tetrahydrobenzo[h][1,6]naphthyridine-5(6H)-one;
103) 10-Ethoxy-8-[(methylamino)methyl]-1,2,3,4-tetrahydrobenzo[h][1,6]naphthyridine-5(6H)-one;
104) 10-Ethoxy-8-[(ethylamino)methyl]-1,2,3,4-tetrahydrobenzo[h][1,6]naphthyridine-5(6H)-one;
105) 8-(Hydroxymethyl)-10-methoxy-1,2,3,4-tetrahydrobenzo[h][1,6]naphthyridine-5(6H)-one;
106) 10-Methoxy-8-(thiomorpholinomethyl)-1,2,3,4-tetrahydrobenzo[h][1,6]naphthyridine-5(6H)-one;
107) 10-Methoxy-8-[(2-morpholinoethylamino)methyl)-1,2,3,4-tetrahydrobenzo[h][1,6]naphthyridine-5(6H)-one;
108) 10-Methoxy-8-[(4-morpholinopiperidine-1-yl)methyl]-1,2,3,4-tetrahydrobenzo[h][1,6]naphthyridine-5(6H)-one;
109) 8-(Aminomethyl)-10-methoxy-1,2,3,4-tetrahydrobenzo[h][1,6]naphthyridine-5(6H)-one;
110) 8-[(Dimethylamino)methyl)]-10-propoxy-1,2,3,4-tetrahydrobenzo[h][1,6]naphthyridine-5(6H)-one;
111) 8-(Morpholinomethyl)-10-propoxy-1,2,3,4-tetrahydrobenzo[h][1,6]naphthyridine-5(6H)-one;
112) 8-(Aminomethyl)-1,2,3,4-tetrahydrobenzo[h][1,6]naphthyridine-5(6H)-one;
113) 8-(Aminomethyl)-10-ethoxy-1,2,3,4-tetrahydrobenzo[h][1,6]naphthyridine-5(6H)-one;
114) 8-(Aminomethyl)-10-propoxy-1,2,3,4-tetrahydrobenzo[h][1,6]naphthyridine-5(6H)-one;
115) 10-Methoxy-8-{[methyl(tetrahydro-2H-pyran-4-yl)amino]methyl}-1,2,3,4-tetrahydrobenzo[h][1,6]naphthyridine-5(6H)-one;
116) 8-[(Dimethylamino)methyl]-10-(2-methoxyethoxy)-1,2,3,4-tetrahydrobenzo[h][1,6]naphthyridin e-5(6H)-one;
117) 10-(2-Methoxyethoxy)-8-(morpholinomethyl)-1,2,3,4-tetrahydrobenzo[h][1,6]naphthyridine-5(6H)-one;
118) 1-[(10-Methoxy-5-oxo-1,2,3,4,5,6-hexahydrobenzo[h][1,6]naphthyridine-8-yl)methylamino]-1H-pyrrole-2,5-dione;
119) 8-Methoxy-1,2,3,4-tetrahydrobenzo[h][1,6]naphthyridine-5(6H)-one hydrochloride;
120) 10-Methoxy-1,2,3,4-tetrahydrobenzo[h][1,6]naphthyridine-5(6H)-one hydrochloride;
121) 9-Methoxy-1,2,3,4-tetrahydrobenzo[h][1,6]naphthyridine-5(6H)-one hydrochloride;
123) Ethyl 5-oxo-1,2,3,4,5,6-hexahydro benzo[h][1,6]naphthyridine-9-carboxylate hydrochloride;
124) 9-Methoxy-1-propyl-1,2,3,4-tetrahydrobenzo[h][1,6]naphthyridine-5(6H)-one hydrochloride;
126) 9-Methoxy-1-methyl-1,2,3,4-tetrahydrobenzo[h][1,6]naphthyridine-5(6H)-one hydrochloride;
127) 1-Ethyl-9-methoxy-1,2,3,4-tetrahydrobenzo[h][1,6]naphthyridine-5(6H)-one hydrochloride;
128) 1-Methyl-9-hydroxy-1,2,3,4-tetrahydrobenzo[h][1,6]naphthyridine-5(6H)-one hydrochloride;
129) 9-(1-Propylpiperidine-4-yloxy)-1,2,3,4-tetrahydrobenzo[h][1,6]naphthyridine-5(6H)-one dihydrochloride;
130) 9-(1-Methylpiperidine-4-yloxy)-1,2,3,4-tetrahydrobenzo[h][1,6]naphthyridine-5(6H)-one dihydrochloride;
131) 1-Methyl-9-(piperidine-4-yloxy)-1,2,3,4-tetrahydrobenzo[h][1,6]naphthyridine-5(6H)-one dihydrochloride;
132) 1-Methyl-9-(1-methylpiperidine-4-yloxy)-1,2,3,4-tetrahydrobenzo[h][1,6]naphthyridine-5(6H)-one dihydrochloride;
133) 5-Oxo-N-[2-(piperidine-1-yl)ethyl]-1,2,3,4,5,6-hexahydrobenzo[h][1,6]naphthyridine-9-carboxamide dihydrochloride;
134) 9-[2-(Dimethylamino)ethoxy]-1,2,3,4-tetrahydrobenzo[h][1,6]naphthyridine-5(6H)-one dihydrochloride;
135) 9-[2-(Piperidine-1-yl)ethoxy]-1,2,3,4-tetrahydrobenzo[h][1,6]naphthyridine-5(6H)-one dihydrochloride;

136) 9-(2-Methoxyethoxy)-1,2,3,4-tetrahydrobenzo[h][1,6]naphthyridine-5(6H)-one hydrochloride;
137) 9-[2-(piperazine-1-yl)ethoxy]-1,2,3,4-tetrahydrobenzo[h][1,6]naphthyridine-5(6H)-one trihydrochloride;
138) 9-Ethoxy-1,2,3,4-tetrahydrobenzo[h][1,6]naphthyridine-5(6H)-one hydrochloride;
139) 9-[3-(Piperidine-1-yl)propoxy]-1,2,3,4-tetrahydrobenzo[h][1,6]naphthyridine-5(6H)-one dihydrochloride;
140) 9-(2-Aminoethoxy)-1,2,3,4-tetrahydrobenzo[h][1,6]naphthyridine-5(6H)-one dihydrochloride;
141) 9-[2-(4-Phenylpiperidine-1-yl)ethoxy]-1,2,3,4-tetrahydrobenzo[h][1,6]naphthyridine-5(6H)-one dihydrochloride;
142) 9-(2-Hydroxyethoxy)-1,2,3,4-tetrahydrobenzo[h][1,6]naphthyridine-5(6H)-one hydrochloride;
143) 9-Penethoxy-1,2,3,4-tetrahydrobenzo[h][1,6]naphthyridine-5(6H)-one hydrochloride;
144) 9-[2-(Diethylamino)ethoxy]-1,2,3,4-tetrahydrobenzo[h][1,6]naphthyridine-5(6H)-one dihydrochloride;
145) 9-(2-Morpholinoethoxy)-1,2,3,4-tetrahydrobenzo[h][1,6]naphthyridine-5(6H)-one dihydrochloride;
146) 1,1-Diethyl-4-[2-(5-oxo-1,2,3,4,5,6-hexahydrobenzo[h][1,6]naphthyridine-9-yloxy]ethyl)piperazine-1-ium dihydrochloride;
147) 9-[4-(Piperidine-1-yl)butoxy]-1,2,3,4-tetrahydrobenzo[h][1,6]naphthyridine-5(6H)-one dihydrochloride;
148) 1-Methyl-9-[2-(piperidine-1yl)ethoxy]-1,2,3,4-tetrahydrobenzo[h][1,6]naphthyridine-5(6H)-one dihydrochloride;
149) 9-[2-(Dimethylamino)ethyl]-1,2,3,4-tetrahydrobenzo[h][1,6]naphthyridine-5(6H)-one dihydrochloride;
150) 8-[2-(Dimethylamino)ethoxy]-1,2,3,4,-tetrahydrobenzo[h][1,6]naphthyridine-5(6H)-one dihydrochloride;
151) 9-[3-(Dimethylamino)propyl]-1,2,3,4-tetrahydrobenzo[h][1,6]naphthyridine-5(6H)-one dihydrochloride;
152) 8-[2-(Dimethylamino)ethoxy]-1,2,3,4,5,6-hexahydrobenzo[h][1,6]naphthyridine-9-carboxamide dihydrochloride;
153) 8-[2-(Piperidine-1-yl)ethoxy]-1,2,3,4-tetrahydrobenzo[h][1,6]naphthyridine-5(6H)-one dihydrochloride;
154) 8-[3-(Dimethylamino)propoxy]-1,2,3,4-tetrahydrobenzo[h][1,6]naphthyridine-5(6H)-one dihydrochloride;
155) 8-(Dimethylamino)-1,2,3,4-tetrahydrobenzo[h][1,6]naphthyridine-5(6H)-one hydrochloride;
156) 8-[1-(Dimethylamino)ethyl]-1,2,3,4-tetrahydrobenzo[h][1,6]naphthyridine-5(6H)-one dihydrochloride;
157) 8-[1-(Methylamino)ethyl]-1,2,3,4-tetrahydrobenzo[h][1,6]naphthyridine-5(6H)-one dihydrochloride;
159) 8-[(Dimethylamino)methyl]-1,2,3,4-tetrahydrobenzo[h][1,6]naphthyridine-5(6H)-one dihydrochloride;
160) 8-[(Diethylamino)methyl]-1,2,3,4-tetrahydrobenzo[h][1,6]naphthyridine-5(6H)-one dihydrochloride;
161) 8-[(Ethylamino)methyl]-1,2,3,4-tetrahydrobenzo[h][1,6]naphthyridine-5(6H)-one dihydrochloride;
162) 8-(Pyrrolidine-1-ylmethyl)-1,2,3,4-tetrahydrobenzo[h][1,6]naphthyridine-5(6H)-one dihydrochloride;
163) 8-[(Isopropylamino)methyl]-1,2,3,4-tetrahydrobenzo[h][1,6]naphthyridine-5(6H)-one dihydrochloride;
164) 8-[(Propylamino)methyl]-1,2,3,4-tetrahydrobenzo[h][1,6]naphthyridine-5(6H)-one dihydrochloride;
165) 8-{[Ethyl(methyl)amino]methyl}-1,2,3,4-tetrahydrobenzo[h][1,6]naphthyridine-5(6H)-one dihydrochloride;
166) 8-(Piperidine-1-ylmethyl)-1,2,3,4-tetrahydrobenzo[h][1,6]naphthyridine-5(6H)-one dihydrochloride;
167) 8-(Morpholinomethyl)-1,2,3,4-tetrahydrobenzo[h][1,6]naphthyridine-5(6H)-one dihydrochloride;
168) 9-[(Dimethylamino)methyl]-1,2,3,4-tetrahydrobenzo[h][1,6]naphthyridine-5(6H)-one dihydrochloride;
169) 8-{[Benzyl(methyl)amino]methyl}-1,2,3,4-tetrahydrobenzo[h][1,6]naphthyridine-5(6H)-one dihydrochloride;
170) 8-[(Methylamino)methyl]-1,2,3,4-tetrahydrobenzo[h][1,6]naphthyridine-5(6H)-one dihydrochloride;
171) 8-{[(2-Hydroxyethyl)(methyl)amino]methyl}-1,2,3,4-tetrahydrobenzo[h][1,6]naphthyridine-5(6H)-one dihydrochloride;
172) 8-{[(2-(Dimethylaminoethyl)(methyl)amino]methyl}-1,2,3,4-tetrahydrobenzo[h][1,6]naphthyridine-5(6H)-one trihydrochloride;
173) 8-[(4-Methylpiperazine-1-yl)methyl]-1,2,3,4-tetrahydrobenzo[h][1,6]naphthyridine-5(6H)-one trihydrochloride;
174) 8-[(Methyl(propyl)amino)methyl]-1,2,3,4-tetrahydrobenzo[h][1,6]naphthyridine-5(6H)-one dihydrochloride;
175) Ethyl-3-{methyl[(5-oxo-1,2,3,4,5,6-hexahydrobenzo[h][1,6]naphthyridine-8-yl)methyl]amino}propanoate dihydrochloride;
176) 3-{Methyl[(5-oxo-1,2,3,4,5,6-hexahydrobenzo[h][1,6]naphthyridine-8-yl)methyl]amino}propanoic acid dihydrochloride;
177) 8-{[Isopropyl(methyl)amino]methyl}-1,2,3,4-tetrahydrobenzo[h][1,6]naphthyridine-5(6H)-one dihydrochloride;
178) 8-{[(2-Methoxyethyl)(methyl)amino]methyl}-1,2,3,4-tetrahydrobenzo[h][1,6]naphthyridine-5(6H)-one dihydrochloride;
179) Ethyl-3-[(5-oxo-1,2,3,4,5,6-hexahydrobenzo[h][1,6]naphthyridine-8-yl)methylamino]propanoate dihydrochloride;
180) 8-[(2,2,2-Trifluoroethylamino)methyl]-1,2,3,4-tetrahydrobenzo[h][1,6]naphthyridine-5(6H)-one dihydrochloride;
181) 2-[(5-Oxo-1,2,3,4,5,6-hexahydrobenzo[h][1,6]naphthyridine-8-yl)methylamino]acetonitrile dihydrochloride;
182) 8-[(1H-Imidazole-1-yl)methyl]-1,2,3,4-tetrahydrobenzo[h][1,6]naphthyridine-5(6H)-one hydrochloride;
183) 8-[(1H-Pyrrole-1-yl)methyl]-1,2,3,4-tetrahydrobenzo[h][1,6]naphthyridine-5(6H)-one hydrochloride;
184) 8-[(Dimethylamino)methyl]-1-methyl-1,2,3,4-tetrahydrobenzo[h][1,6]naphthyridine-5(6H)-one dihydrochloride;
185) 1-Methyl-8-(pyrrolidine-lylmethyl)-1,2,3,4-tetrahydrobenzo[h][1,6]naphthyridine-5(6H)-one dihydrochloride;

186) 8-[(Diethylamino)methyl]-1-methyl-1,2,3,4-tetrahydrobenzo[h][1,6]naphthyridine-5(6H)-one dihydrochloride;
187) 1-Methyl-8-(piperidine-1-ylmethyl)-1,2,3,4-tetrahydrobenzo[h][1,6]naphthyridine-5(6H)-one dihydrochloride;
188) 1-Methyl-8-(morpholinomethyl)-1,2,3,4-tetrahydrobenzo[h][1,6]naphthyridine-5(6H)-one dihydrochloride;
189) 8-{[Ethyl(methyl)amino]methyl}-1-methyl-1,2,3,4-tetrahydrobenzo[h][1,6]naphthyridine-5(6H)-one dihydrochloride;
190) 8-[(Dimethylamino)methyl]-10-methoxy-1,2,3,4-tetrahydrobenzo[h][1,6]naphthyridine-5(6H)-one dihydrochloride;
191) 10-Methoxy-8-[(methylamino)methyl]-1,2,3,4-tetrahydrobenzo[h][1,6]naphthyridine-5(6H)-one dihydrochloride;
192) 10-Methoxy-8-(morpholinomethyl)-1,2,3,4-tetrahydrobenzo[h][1,6]naphthyridine-5(6H)-one dihydrochloride;
193) 8-[(Ethylamino)methyl]-10-methoxy-1,2,3,4-tetrahydrobenzo[h][1,6]naphthyridine-5(6H)-one dihydrochloride;
194) 8-{[Ethyl(methyl)amino]methyl}-10-methoxy-1,2,3,4-tetrahydrobenzo[h][1,6]naphthyridine-5(6H)-one;
195) 10-Methoxy-8-(pyrrolidine-1-ylmethyl)-1,2,3,4-tetrahydrobenzo[h][1,6]naphthyridine-5(6H)-one dihydrochloride;
196) 10-Methoxy-8-[(4-oxopiperidine-1-yl)methyl]-1,2,3,4-tetrahydrobenzo[h][1,6]naphthyridine-5 (6H)-one dihydrochloride;
197) 8-{[4-(Hydroxyimino)piperidine-1-yl]methyl}-10-methoxy-1,2,3,4-tetrahydrobenzo[h][1,6]naphthyridine-5(6H)-one trihydrochloride;
198) 10-Methoxy-8-[(4-(methoxyimino)piperidine-1-yl)methyl]-1,2,3,4-tetrahydrobenzo[h][1,6]naphthyridine-5(6H)-one trihydrochloride;
199) 10-Methoxy-8-{[(2-methoxyethyl)(methyl)amino]methyl}-1,2,3,4-tetrahydrobenzo[h][1,6]naphthyridine-5(6H)-one dihydrochloride;
200) 8-[(2,5-Dehydro-1H-pyrrole-1-yl)methyl]-10-methoxy-1,2,3,4-tetrahydrobenzo[h][1,6]naphthyridine-5 (6H)-one dihydrochloride;
201) 8-{[(2-Isopropoxyethyl)(methyl)amino]methyl}-10-methoxy-1,2,3,4-tetrahydrobenzo[h][1,6]naphthyridine-5(6H)-one dihydrochloride;
202) 10-Methoxy-8-(piperidine-1-ylmethyl)-1,2,3,4-tetrahydrobenzo[h][1,6]naphthyridine-5(6H)-one dihydrochloride;
203) 8-{[(2-Chloroethyl)(methyl)amino]methyl}-10-methoxy-1,2,3,4-tetrahydrobenzo[h][1,6]naphthyridine-5(6H)-one dihydrochloride;
204) 8-[(Diethylamino)methyl]-10-methoxy-1,2,3,4-tetrahydrobenzo[h][1,6]naphthyridine-5(6H)-one dihydrochloride;
205) 8-[(t-Butylamino)methyl]-10-methoxy-1,2,3,4-tetrahydrobenzo[h][1,6]naphthyridine-5(6H)-one dihydrochloride;
206) 8-[(Isopropylamino)methyl]-10-methoxy-1,2,3,4-tetrahydrobenzo[h][1,6]naphthyridine-5(6H)-one dihydrochloride;
207) 8-[(Cyclopentylamino)methyl]-10-methoxy-1,2,3,4-tetrahydrobenzo[h][1,6]naphthyridine-5(6H)-one dihydrochloride;
208) 8-[(2,6-Dimethylmorpholino)methyl]-10-methoxy-1,2,3,4-tetrahydrobenzo[h][1,6]naphthyridine-5(6H)-one dihydrochloride;
209) N-[(10-Methoxy-5-oxo-1,2,3,4,5,6-hexahydrobenzo[h][1,6]naphthyridine-8-yl)methyl]-N,N-dimethylcyclopentane aminium chloride hydrochloride;
210) 8-{[Cyclopentyl(methyl)amino]methyl}-10-methoxy-1,2,3,4-tetrahydrobenzo[h][1,6]naphthyridine-5(6H)-one dihydrochloride;
211) 8-{[Isopropyl(methyl)amino]methyl}-10-methoxy-1,2,3,4-tetrahydrobenzo[h][1,6]naphthyridine-5(6H)-one dihydrochloride;
212) 8-{[(2-Fluoroethyl)(methyl)amino]methyl}-10-methoxy-1,2,3,4-tetrahydrobenzo[h][1,6]naphthyridine-5(6H)-one dihydrochloride;
213) 8-[(1H-Tetrazol-5-yl)methyl]-1,2,3,4-tetrahydrobenzo[h][1,6]naphthyridine-5(6H)-one hydrochloride;
214) 10-Methoxy-8-[(morpholinoamino)methyl]-1,2,3,4-tetrahydrobenzo[h][1,6]naphthyridine-5(6H)-one trihydrochloride;
215) 10-Methoxy-8-{[methyl(morpholino)amino]methyl}-1,2,3,4-tetrahydrobenzo[h][1,6]naphthyridine-5(6H)-one trihydrochloride;
216) (E)-10-Methoxy-8-[(morpholinoimino)methyl]-1,2,3,4-tetrahydrobenzo[h][1,6]naphthyridine-5(6H)-one trihydrochloride;
217) 8-[(Dimethylamino)methyl]-10-hydroxy-1,2,3,4-tetrahydrobenzo[h][1,6]naphthyridine-5-(6H)-one dihydrochloride;
218) 8-[(Dimethylamino)methyl]-10-ethoxy-1,2,3,4-tetrahydrobenzo[h][1,6]naphthyridine-5(6H)-one dihydrochloride;
219) 10-Ethoxy-8-(morpholinomethyl)-1,2,3,4-tetrahydrobenzo[h][1,6]naphthyridine-5(6H)-one dihydrochloride;
220) 10-Ethoxy-8-(piperidine-1-ylmethyl)-1,2,3,4-tetrahydrobenzo[h][1,6]naphthyridine-5(6H)-one dihydrochloride;
221) 10-Ethoxy-8-[(methylamino)methyl]-1,2,3,4-tetrahydrobenzo[h][1,6]naphthyridine-5(6H)-one dihydrochloride;
222) 10-Ethoxy-8-[(ethylamino)methyl]-1,2,3,4-tetrahydrobenzo[h][1,6]naphthyridine-5(6H)-one dihydrochloride;
223) 8-(Hydroxymethyl)-10-methoxy-1,2,3,4-tetrahydrobenzo[h][1,6]naphthyridine-5(6H)-one hydrochloride;
224) 10-Methoxy-8-(thiomorpholinomethyl)-1,2,3,4-tetrahydrobenzo[h][1,6]naphthyridine-5(6H)-one dihydrochloride;
225) 10-Methoxy-8-[(2-morpholinoethylamino)methyl]-1,2,3,4-tetrahydrobenzo[h][1,6]naphthyridine-5(6H)-one trihydrochloride;
226) 10-Methoxy-8-[(4-morpholinopiperidine-lyl)methyl]-1,2,3,4-tetrahydrobenzo[h][1,6]naphthyridine-5 (6H)-one trihydrochloride;
227) 8-(Aminomethyl)-10-methoxy-1,2,3,4-tetrahydrobenzo[h][1,6]naphthyridine-5(6H)-one dihydrochloride;
228) 8-[(Dimethylamino)methyl)]-10-propoxy-1,2,3,4-tetrahydrobenzo[h][1,6]naphthyridine-5(6H)-one dihydrochloride;
229) 8-(Morpholinomethyl)-10-propoxy-1,2,3,4-tetrahydrobenzo[h][1,6]naphthyridine-5(6H)-one dihydrochloride;

230) 8-(Aminomethyl)-1,2,3,4-tetrahydrobenzo[h][1,6]naphthyridine-5(6H)-one dihydrochloride;

231) 8-(Aminomethyl)-10-ethoxy-1,2,3,4-tetrahydrobenzo[h][1,6]naphthyridine-5(6H)-one dihydrochloride;

232) 8-(Aminomethyl)-10-propoxy-1,2,3,4-tetrahydrobenzo[h][1,6]naphthyridine-5(6H)-one dihydrochloride;

233) 10-Methoxy-8-{[methyl(tetrahydro-2H-pyran-4-yl)amino]methyl}-1,2,3,4-tetrahydrobenzo[h][1,6]naphthyridine-5(6H)-one dihydrochloride;

234) 8-[(Dimethylamino)methyl]-10-(2-methoxyethoxy)-1,2,3,4-tetrahydrobenzo[h][1,6]naphthyridin e-5(6H)-one dihydrochloride;

235) 10-(2-Methoxyethoxy)-8-(morpholinomethyl)-1,2,3,4-tetrahydrobenzo[h][1,6]naphthyridine-5(6H)-one dihydrochloride; and 236) 1-[(10-Methoxy-5-oxo-1,2,3,4,5,6-hexahydrobenzo[h][1,6]naphthyridine-8-yl)methylamino]-1H-pyrrole-2,5-dione dihydrochloride.

3. A method for preparing the tricyclic compound derivative represented by chemical formula 1 or pharmaceutically acceptable salts thereof according to claim 1, the method represented by reaction formula 1 below and comprising steps of:

1) converting carboxylic acid of 2-chloronicotinic acid expressed by chemical formula 2 into carboxylic acid chloride expressed by chemical formula 3 (step 1);

2) preparing compound of chemical formula 5 by amidation reaction of carboxylic acid chloride of chemical formula 3 prepared in step 1 with aniline of chemical formula 4 substituted at meta and/or para position (step 2);

3) introducing protection group in the compound of chemical formula 5 prepared in step 2 to obtain N-protected compound of chemical formula 6 (step 3);

4) preparing compound of chemical formula 7 by cyclization of the compound of chemical formula 6 prepared in step 3 under metal-catalyst (step 4);

5) preparing compound of chemical formula 8 by aromatic ring reduction of compound of chemical formula 7 prepared in step 4 under hydrogen-palladium (Pd) catalyst, or by aromatic ring reduction of compound of chemical formula 7 prepared in step 4 under hydrogen-palladium (Pd) catalyst and then by reaction of alkyl halide compound or aryl halide compound and a base (step 5); and 6) deprotecting the compound of chemical formula 8 prepared in step 5 to obtain tricyclic compound of chemical formula 1 (step 6),

[Reaction formula 1]

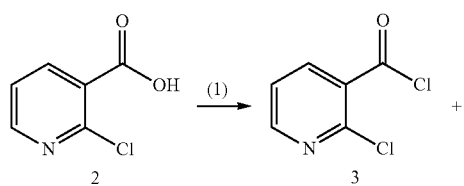

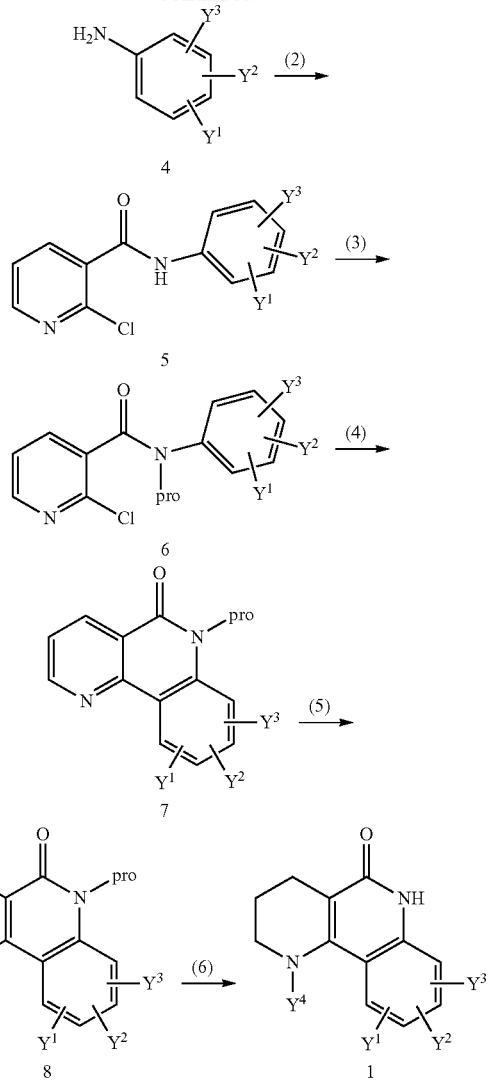

wherein, 'pro' represents protection group selected from the group consisting of aryl group, benzyl group, benzyloxymethyl group, para-methoxybenzyl group, and methoxymethyl group.

4. A method for preparing the tricyclic compound represented by chemical formula 1 or pharmaceutically acceptable salts thereof according to claim 1, the method represented by reaction formula 2 below and comprising steps of:

1) demethylating the compound (7a) with boron tribromide to obtain hydroxyl compound (7a-1) (step 1);

2) reacting the hydroxyl compound (7a-1) prepared in step 1 with alkyl halide compound in the presence of a base and a catalytic amount of sodium iodide to obtain alkoxy compound (7a-2) (step 2);

3) preparing piperidine-lactam (8a) by aromatic ring reduction of the pyridine-lactam compound (7a-2) prepared in step 2 under hydrogen gas and palladium (Pd) catalyst (step 3); and 4) deprotecting the compound (8a) prepared in step 3 under acidic condition such as hydrochloric acid to obtain compound of chemical formula (1a) (step 4),

[Reaction formula 2]

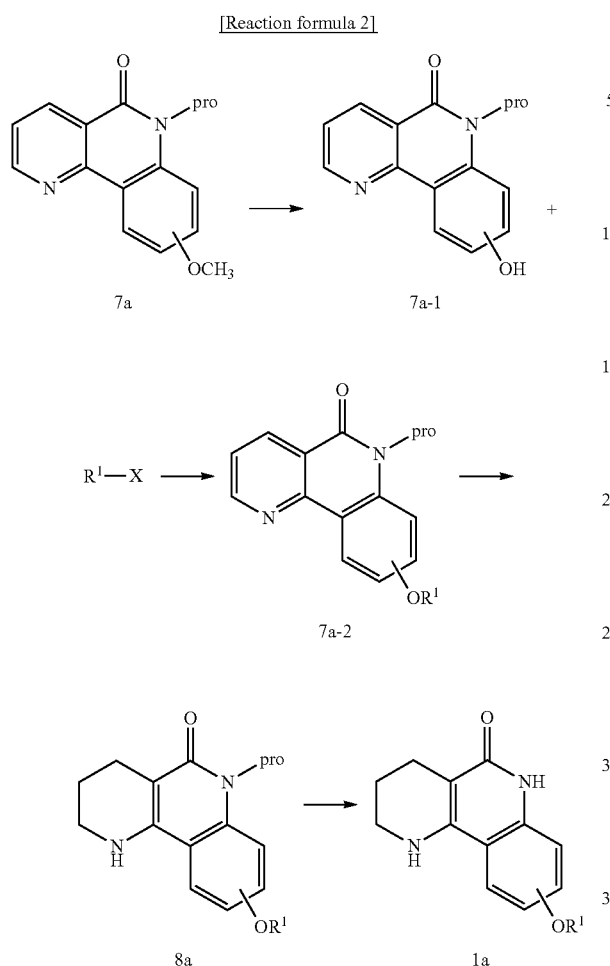

wherein, 'pro' represents methoxymethyl(MOM) group, benzyl group, or para-methoxybenzyl(PMB) group; and X denotes leaving group including halogen, methanesulfonyl group.

5. A method for preparing the tricyclic compound derivative represented by chemical formula 1 or pharmaceutically acceptable salts thereof according to claim 1, the method represented by reaction formula 3 below and comprising steps of:

1) hydrolyzing the compound (7b) by slowly dropwise adding potassium hydroxide or sodium hydroxide aqueous solution into the compound (7b) to obtain the carboxyl acid compound (7b-1) (step 1);

2) amidating the carboxyl acid compound (7b-1) prepared in step 1 with amines using coupling reagent to obtain the compound of chemical formula (7b-2) (step 2);

3) preparing piperidine-lactam (8b) by aromatic ring reduction of pyridine-lactam (7b-2) prepared in step 2 under hydrogen gas and palladium (Pd) catalyst (step 3); and 4) deprotecting the compound (8b) prepared in step 3 under acidic condition such as hydrochloric acid to obtain the compound of chemical formula (1b) (step 4),

[Reaction formula 3]

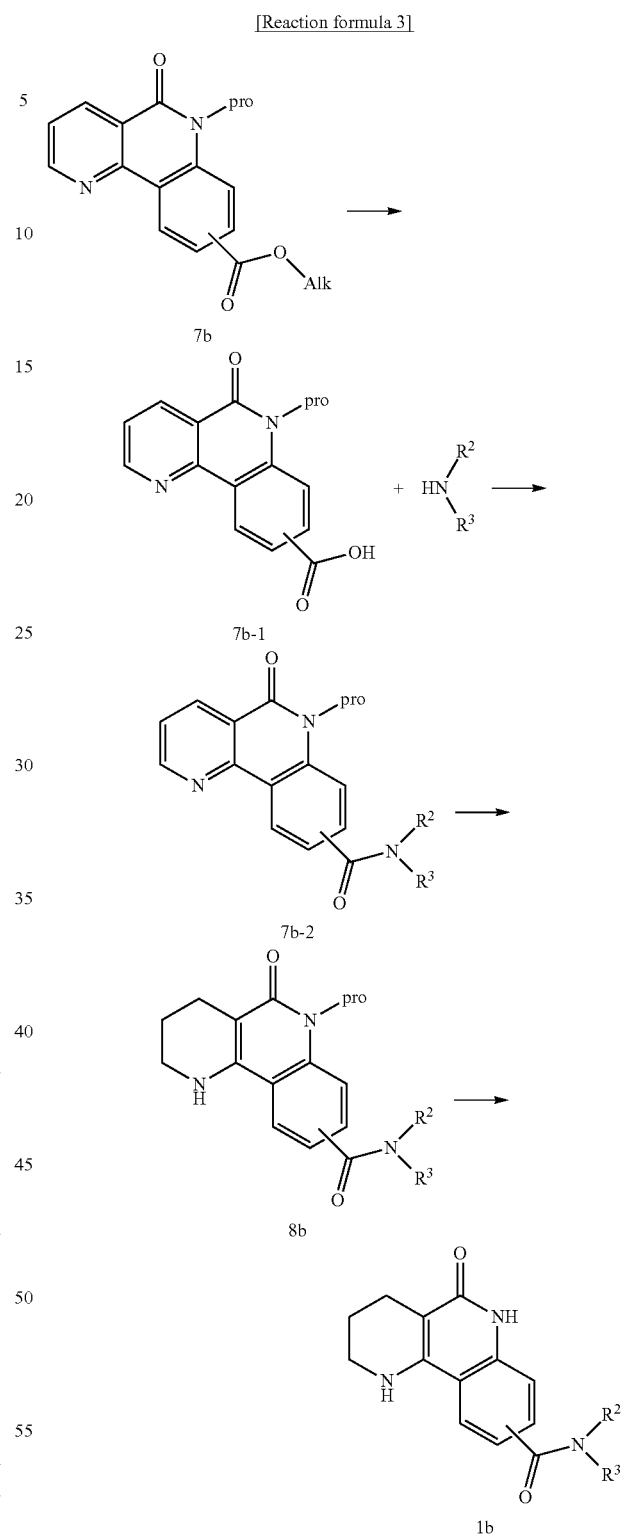

wherein, 'Alk' represents $C_1$~$C_{10}$ straight or branched chain alkyl; and 'pro' represents methoxymethyl (MOM) group, benzyl group, or para-methoxybenzyl (PMB) group.

6. A method for preparing the tricyclic compound represented by chemical formula 1 or pharmaceutically acceptable salts thereof according to claim 1, the method represented by reaction formula 4 below and comprising steps of:

1) reducing the lactam compound (8c) into corresponding alcohol (8c-1) by using a reducing agent (step 1);
2) preparing diamino-lactam compound (8c-2) by halogenation and amination of the alcohol compound (8c-1) prepared in step 1 (step 2); and
3) deprotecting the compound (8c-2) prepared in step 2 under acidic condition such as hydrochloric acid to obtain tricyclic compound of chemical formula (1c) (step 3),

[Reaction formula 4]

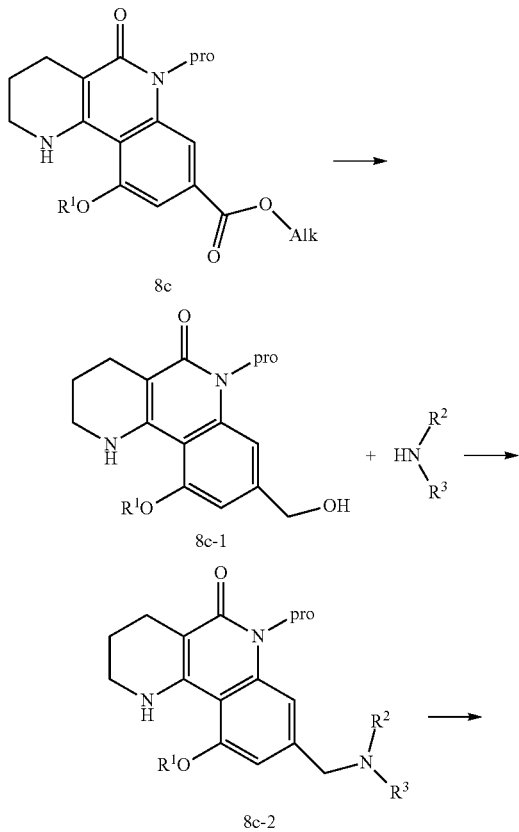

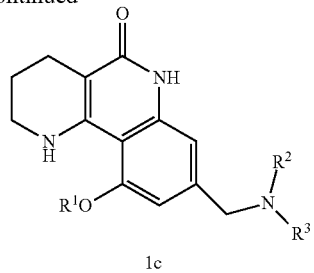

wherein, 'Alk' represents $C_1$~$C_{10}$ straight or branched chain alkyl; and 'pro' is methoxymethyl(MOM) group, benzyl group, or para-methoxybenzyl(PMB) group.

7. A composition comprising the tricyclic compound represented by chemical formula 1 or pharmaceutically acceptable salts thereof according to claim 1 as an effective ingredient, the composition for inhibiting PARP overexpression in a patient with a disease selected from the group consisting of neuropathic pain, epilepsy, stroke, Alzheimer's disease, Parkinson's disease, amyotrophic lateral sclerosis (ALS), Huntington's disease, schizophrenia, chronic and acute pain, ischemia, neuron damage after hypoxia, external injury, and neural damage.

8. A composition comprising the tricyclic compound represented by chemical formula 1 or pharmaceutically acceptable salts thereof according to claim 1 as an effective ingredient, the composition for inhibiting PARP overexpression in a patient with a disease selected from the group consisting of atherosclerosis, hyperlipidemia, cadiac tissue damage, coronary-artery disease, myocardial infarction, angina, and cardiogenic shock.

9. A composition comprising the tricyclic compound represented by chemical formula 1 or pharmaceutically acceptable salts thereof according to claim 1 as an effective ingredient, the composition for inhibiting PARP overexpression in a patient with a disease selected from the group consisting of: diabetic neuropathy, osteotarthritis, and osteoporosis.

10. A composition comprising the tricyclic compound represented by chemical formula 1 or pharmaceutically acceptable salts thereof according to claim 1 as an effective ingredient, the composition for inhibiting PARP overexpression in a patient with a diabetic neuropathy.

11. A composition comprising the tricyclic compound represented by chemical formula 1 or pharmaceutically acceptable salts thereof according to claim 1 as an effective ingredient, the composition for inhibiting PARP overexpression in a patient with a cancer.

* * * * *